US012691111B2

(12) United States Patent
Raimondi et al.

(10) Patent No.: US 12,691,111 B2
(45) Date of Patent: Jul. 28, 2026

(54) SETD2 INHIBITORS AND RELATED METHODS AND USES, INCLUDING COMBINATION THERAPIES

(71) Applicant: EPIZYME, INC., Cambridge, MA (US)

(72) Inventors: Maria Alejandra Raimondi, Jamaica Plain, MA (US); Jennifer Anne Totman, Berlin, MA (US); Vinny Motwani, Boston, MA (US); Katherine Louise Cosmopoulos, Medford, MA (US); John Lampe, Norfolk, MA (US)

(73) Assignee: Epizyme, Inc., Cambridge, MA (US)

( * ) Notice: Subject to any disclaimer, the term of this patent is extended or adjusted under 35 U.S.C. 154(b) by 897 days.

(21) Appl. No.: 17/904,570

(22) PCT Filed: Feb. 19, 2021

(86) PCT No.: PCT/US2021/018863
§ 371 (c)(1),
(2) Date: Aug. 18, 2022

(87) PCT Pub. No.: WO2021/168313
PCT Pub. Date: Aug. 26, 2021

(65) Prior Publication Data

US 2023/0133671 A1 May 4, 2023

Related U.S. Application Data

(60) Provisional application No. 62/978,692, filed on Feb. 19, 2020.

(51) Int. Cl.
*A61K 31/496* (2006.01)
*A61K 31/407* (2006.01)
*A61K 45/06* (2006.01)

(52) U.S. Cl.
CPC .......... *A61K 31/496* (2013.01); *A61K 31/407* (2013.01); *A61K 45/06* (2013.01)

(58) Field of Classification Search
CPC ..... A61K 31/496; A61K 31/407; A61K 45/06
See application file for complete search history.

(56) References Cited

U.S. PATENT DOCUMENTS

| | | | |
|---|---|---|---|
| 4,582,788 | A | 4/1986 | Erlich |
| 4,595,766 | A | 6/1986 | Roloff et al. |
| 4,683,194 | A | 7/1987 | Saiki et al. |
| 4,683,202 | A | 7/1987 | Mullis |
| 4,769,461 | A | 9/1988 | Musser et al. |
| 5,519,048 | A | 5/1996 | Salituro et al. |
| 5,602,136 | A | 2/1997 | Rühter et al. |
| 5,922,752 | A | 7/1999 | Harrison et al. |
| 9,045,477 | B2 | 6/2015 | Campbell et al. |
| 9,446,064 | B2 | 9/2016 | Klaus et al. |
| 10,266,526 | B2 | 4/2019 | Foley et al. |
| 11,952,572 | B2 | 4/2024 | Grassian et al. |
| 12,116,358 | B2 * | 10/2024 | Foley ................. C07D 491/107 |
| 2003/0203909 | A1 | 10/2003 | Ushio et al. |
| 2003/0225053 | A1 | 12/2003 | Gao et al. |
| 2004/0186114 | A1 | 9/2004 | Cirillo et al. |
| 2004/0220229 | A1 | 11/2004 | Bussolotti et al. |
| 2005/0020661 | A1 | 1/2005 | Gammill |
| 2005/0107362 | A1 | 5/2005 | Whittamore et al. |
| 2006/0111338 | A1 | 5/2006 | Sher et al. |
| 2006/0111415 | A1 | 5/2006 | Meng et al. |
| 2006/0173024 | A1 | 8/2006 | Malik et al. |
| 2006/0270686 | A1 | 11/2006 | Kelly et al. |
| 2007/0299070 | A1 | 12/2007 | Suzuki et al. |
| 2008/0280891 | A1 | 11/2008 | Kelly et al. |
| 2009/0069565 | A1 | 3/2009 | Nazare et al. |
| 2009/0082560 | A1 | 3/2009 | Kobayashi et al. |
| 2011/0021362 | A1 | 1/2011 | Trojer et al. |
| 2011/0136807 | A1 | 6/2011 | Hangauer, Jr. |
| 2011/0178074 | A1 | 7/2011 | Burli et al. |
| 2013/0053370 | A1 | 2/2013 | Son et al. |
| 2013/0137748 | A1 | 5/2013 | Hamamoto et al. |
| 2014/0213790 | A1 | 7/2014 | Lim et al. |

(Continued)

FOREIGN PATENT DOCUMENTS

| | | | |
|---|---|---|---|
| CN | 106317043 | A | 1/2017 |
| EP | 0050424 | A1 | 4/1982 |

(Continued)

OTHER PUBLICATIONS

Gura et al., Systems for Identifying New Drugs are Often Faulty. Science, New Series, (1997), 278(5340), 1041-1042 (Year: 1997).*
Johnson et al., Relationships between drug activity in NCI preclinical in vitro and in vivo models and early clinical trials. British Journal of Cancer, (2001), 84(10), 1424-1431 (Year: 2001).*
Kumar et al., Impact of dexamethasone responsiveness on long term outcome in patients with newly diagnosed multiple myeloma. British Journal of Haematology, (2010), 148(6), 853-858 (Year: 2010).*
Barwick et al., "Multiple myeloma immunoglobulin lambda translocations portend poor prognosis", Nature Communications, 2019, 10(1):1911, pp. 1-13.

(Continued)

*Primary Examiner* — Renee Claytor
*Assistant Examiner* — Christopher Lindsay Johnson
(74) *Attorney, Agent, or Firm* — COOLEY LLP; Andrea Reid; Nicholas Pace

(57) ABSTRACT

The present disclosure provides SETD2 protein inhibitors, and methods, compositions, and kits for treating diseases, disorders, or conditions in a subject with a SETD2 protein inhibitor and, optionally, a second therapeutic agent, wherein the second therapeutic agent comprises one or more glucocorticoid receptor agonists, one or more immunomodulatory drugs, one or more proteasome inhibitors, one or more Bcl-2 inhibitors, one or more pleiotropic pathway modulators, one or more XPO1 inhibitors, one or more histone deacetylase inhibitors, or one or more EZH2 inhibitors, or a combination thereof.

19 Claims, 4 Drawing Sheets

(56) References Cited

U.S. PATENT DOCUMENTS

| | | | |
|---|---|---|---|
| 2014/0294767 | A1 | 10/2014 | Waugh et al. |
| 2014/0303106 | A1 | 10/2014 | Zheng et al. |
| 2015/0289512 | A1 | 10/2015 | Mukumoto et al. |
| 2015/0353539 | A1 | 12/2015 | Cheve et al. |
| 2017/0044100 | A1 | 2/2017 | Bishai et al. |
| 2017/0216252 | A1 | 8/2017 | Young et al. |
| 2017/0232030 | A1 | 8/2017 | Klaus et al. |
| 2017/0275279 | A1 | 9/2017 | Buckner et al. |
| 2017/0281810 | A1 | 10/2017 | He |
| 2017/0355695 | A1 | 12/2017 | Foley et al. |
| 2018/0339060 | A1 | 11/2018 | Maderna et al. |
| 2019/0127337 | A1 | 5/2019 | Ma et al. |
| 2021/0002645 | A1 | 1/2021 | Grassian et al. |
| 2023/0049113 | A1 | 2/2023 | Thomenius et al. |
| 2023/0075198 | A1 | 3/2023 | Lampe et al. |
| 2024/0299352 | A1 | 9/2024 | Raimondi et al. |
| 2025/0000856 | A1 | 1/2025 | Connors et al. |

FOREIGN PATENT DOCUMENTS

| | | | | |
|---|---|---|---|---|
| EP | 0084796 | A2 | 8/1983 | |
| EP | 00201184 | A2 | 11/1986 | |
| EP | 00237362 | A1 | 9/1987 | |
| EP | 00258017 | A2 | 3/1988 | |
| EP | 1880994 | A1 | 1/2008 | |
| EP | 1942105 | A1 | 7/2008 | |
| JP | 2012-107001 | A | 6/2012 | |
| WO | 1994017075 | A1 | 8/1994 | |
| WO | 1994027964 | A1 | 12/1994 | |
| WO | 1998008818 | A1 | 3/1998 | |
| WO | 1998014427 | A1 | 4/1998 | |
| WO | 1999047511 | A1 | 9/1999 | |
| WO | WO-2002080926 | A1 | 10/2002 | |
| WO | 2003091213 | A1 | 11/2003 | |
| WO | WO-2004018428 | A1 | 3/2004 | |
| WO | WO-2004018461 | A2 | 3/2004 | |
| WO | 2005072457 | A2 | 8/2005 | |
| WO | 2007049532 | A1 | 5/2007 | |
| WO | WO-2009158375 | A1 | 12/2009 | |
| WO | WO-2010028192 | A1 | 3/2010 | |
| WO | WO-2011079102 | A1 | 6/2011 | |
| WO | WO-2015143424 | A2 | 9/2015 | |
| WO | WO-2015150097 | A1 | 10/2015 | |
| WO | WO-2015164482 | A1 | 10/2015 | |
| WO | WO-2016010950 | A1 | 1/2016 | |
| WO | WO-2016040505 | A1 * | 3/2016 | ........... A61K 31/404 |
| WO | WO-2016079321 | A1 | 5/2016 | |
| WO | WO-2017106259 | A1 | 6/2017 | |
| WO | 2017156177 | A1 | 9/2017 | |
| WO | 2017156181 | A1 | 9/2017 | |
| WO | 2018073828 | A1 | 4/2018 | |
| WO | 2018165611 | A1 | 9/2018 | |
| WO | 2018219281 | A1 | 12/2018 | |
| WO | 2019005841 | A1 | 1/2019 | |
| WO | WO-2019036466 | A1 | 2/2019 | |
| WO | 2019222349 | A1 | 11/2019 | |
| WO | WO-2020037079 | A1 | 2/2020 | |
| WO | WO-2020112872 | A1 | 6/2020 | |
| WO | 2021168313 | A1 | 8/2021 | |
| WO | WO-2022261243 | A1 | 12/2022 | |
| WO | WO-2023077117 | A1 | 5/2023 | |

OTHER PUBLICATIONS

Brito et al., "MMSET deregulation affects cell cycle progression and adhesion regulons in t(4;14) myeloma plasma cells", Haematologica, 2009, 94(1):78-86.

Carvalho et al., "SETD2 is required for DNA double-strand break repair and activation of the p53-mediated checkpoint", eLife, 2014, 3:e02482, pp. 1-19.

Chesi et al., "Frequent translocation t(4;14)(p16.3;q32.3) in multiple myeloma is associated with increased expression and activating mutations of fibroblast growth factor receptor 3", Nature Genetics, Jul. 1997, 16(3):260-264.

Database Registry [online], CAS Registry No. 1787856-87-4, Jun. 24, 2015, 1 page.

Database Registry [online], CAS Registry No. 1795289-64-3, Jul. 6, 2015, 1 page.

Database Registry [online], CAS Registry No. 1795337-47-1, Jul. 6, 2015, 1 page.

Diagouraga et al., "PRDM9 Methyltransferase Activity Is Essential for Meiotic DNA Double-Strand Break Formation at Its Binding Sites", Molecular Cell, Mar. 1, 2018, 69(5):853-865.

Grey et al., "In vivo binding of PRDM9 reveals interactions with noncanonical genomic sites", Genome Research, 2017, 27(4):580-590.

Hart et al., "High-Resolution CRISPR Screens Reveal Fitness Genes and Genotype-Specific Cancer Liabilities", Cell, Dec. 3, 2015, 163(6):1515-1526.

Keats et al., "In multiple myeloma, t(4;14)(p16;q32) is an adverse prognostic factor irrespective of FGFR3 expression", Blood, Feb. 15, 2003, 101(4):1520-1529.

Kumar et al., "Multiple myeloma", Nature Reviews Disease Primers, 2017, 3(17046):1-20.

Lauring et al., "The multiple myeloma-associated MMSET gene contributes to cellular adhesion, clonogenic growth, and tumorigenicity", Blood, Jan. 15, 2008, 111(2):856-864.

Licht, "SETD2: a complex role in blood malignancy", Blood, Dec. 14, 2017, 130(24):2576-2578.

Marango et al., "The MMSET protein is a histone methyltransferase with characteristics of a transcriptional corepressor", Blood, Mar. 15, 2008, 111(6):3145-3154.

Martinez-Garcia et al., "The MMSET histone methyl transferase switches global histone methylation and alters gene expression in t(4;14) multiple myeloma cells", Blood, Jan. 6, 2011, 117(1):211-220.

Park et al., "Dual Chromatin and Cytoskeletal Remodeling by SETD2", Cell, Aug. 11, 2016, 166(4):950-962.

Reddy et al., "Genetic and Functional Drivers of Diffuse Large B Cell Lymphoma", Cell, Oct. 5, 2017, 171 (2):481-494.

Richelda et al., "A Novel Chromosomal Translocation t(4; 14)(p16. 3; q32) in Multiple Myeloma Involves the Fibroblast Growth-Factor Receptor 3 gene", Blood, Nov. 15, 1997, 90(10):4062-4070.

Shi et al., "Transcriptional profiling of mouse B cell terminal differentiation defines a signature for antibody-secreting plasma cells", Nature Immunology, Jun. 2015, 16(6):663-673.

Skucha et al., "Roles of SETD2 in Leukemia-Transcription, DNA-Damage, and Beyond", International Journal of Molecular Sciences, 2019, 20(1029):1-11.

Sun et al., "Identification and Characterization of a Novel Human Histone H3 Lysine 36-specific Methyltransferase", The Journal of Biological Chemistry, Oct. 21, 2005, 280(42):35261-35271.

Tzelepis et al., "A CRISPR Dropout Screen Identifies Genetic Vulnerabilities and Therapeutic Targets in Acute Myeloid Leukemia", Cell Reports, Oct. 18, 2016, 17:1193-1205.

Wang et al., "Identification and characterization of essential genes in the human genome", Science, Nov. 27, 2015, 350(6264):1096-1101.

Yusufova et al., "Histone H1 loss drives lymphoma by disrupting 3D chromatin architecture", Nature, Jan. 2021, 589(7841):299-305.

U.S. Appl. No. 18/757,878 of Lampe et al., filed on Jun. 28, 2024.

U.S. Appl. No. 18/919,587 of Grassian et al., filed on Oct. 18, 2024.

U.S. Appl. No. 18/956,447 of Thomenius et al., filed on Nov. 22, 2024.

U.S. Appl. No. 19/022,493 of Lampe et al., filed on Jan. 15, 2025.

U.S. Appl. No. 19/215,718 of Grassian et al., filed on May 22, 2025.

Alford et al., "Conformational-Design-Driven Discovery of EZM0414: A Selective, Potent SETD2 Inhibitor for Clinical Studies," ACS Med. Chem. Lett., 2022, 13:1137-1143.

Chng et al., "Genomics in multiple myeloma: biology and clinical implications", Pharmacogenomics, Sep. 2005, 6(6):563-573.

Lampe et al., "Discovery of a First-in-Class Inhibitor of the Histone Methyltransferase SETD2 Suitable for Preclinical Studies," ACS Med Chem Lett., 2021, 12(10):1539-1545.

Registry (STN) [online]; 2023; RN 2105115-46-4, 1 page.

Richardson et al., "A Phase 1/1b Open-Label, Multicenter, Two-Part Study of SETD2 Inhibitor EZM0414 in Patients with Relapsed/

(56) References Cited

OTHER PUBLICATIONS

Refractory Multiple Myeloma or Diffuse Large B-Cell Lymphoma", Blood, 2021, 138(Supplement 1):1679 (6 pages).
Shi et al., "Discovery of cancer drug targets by CRISPR-Cas9 screening of protein domains", Nature Biotechnology, 33(6):661-667.
Vardiman et al., "The 2008 revision of the World Health Organization (WHO) classification of myeloid neoplasms and acute leukemia: rationale and important changes", Blood, 2009, 114(5):937-951.
Zugazagoitia et al., "Current Challenges in Cancer Treatment", Clinical Therapeutics, Jul. 2016, 38(7):1551-1566.
Altschul and Gish, "Local alignment statistics," Methods in Enzymology. 1996;266:460-480.
Altschul et al., "Gapped BLAST and PSI-BLAST: a new generation of protein database search programs," Nucleic Acids Res. 1997;25:3389-3402.
Bingham et al., "Over one hundred solvates of sulfathiazole," Chemical Communications. 2001;7(7):603-604.
Caira et al., "Preparation and crystal characterization of a polymorph, a monohydrate, and an ethyl acetate solvate of the antifungal fluconazole," 2003;93(3):601-11.
Chang et al., "Investigation of the inhibitors of histone-lysine N-methyltransferase SETD2 for acute lymphoblastic leukaemia from traditional Chinese medicine," SAR QSAR Environ Res. 2016;27(7):589-608.
Chavda et al., "A novel achiral seco-cyclopropylpyrido[e]indolone (CPyl) analog of CC-1065 and the duocarmycins: synthesis, DNA interactions, in vivo anticancer and anti-parasitic evaluation," Bioorg Med Chem. 2010;18(14):5016-24.
Chen et al., "CRISPR-Cas9: from Genome Editing to Cancer Research," Int. J Biol. Sci. 2016;12:1427-1436.
Chen et. al., "Histone methyltransferase SETD2: a potential tumor suppressor in solid cancers," J Cancer. 2020; 1(11):3349-3356.
Chesi et al., "The t(4;14) Translocation in Myeloma Dysregulates Both FGFR3and a Novel Gene, MMSET, Resulting in IgH/MMSET Hybrid Transcripts," Blood. 1998;92(9):3025-34.
"CID 108791761 Compound Summary: 7-Chloro-N-pyridin-2-yl-1H-indole-2-carboxamide," PubChem. Created Jan. 15, 2016: https://pubchem.ncbi.nlm.nih.gov/compound/108791761.
"CID 110853847 Compound Summary: ethyl 4-[(7-methyl-1H-indole-2-carbonyl)amino]piperidine-1-carboxylate," PubChem. Created Jan. 18, 2016: https://pubchem.ncbi.nlm.nih.gov/compound/110853847.
"CID 131900417 Compound Summary: (6-Methoxy-3,4-dihydro-1H-isoquinolin-2-yl)-(3,4,7-trimethyl-1H-indol-2-yl)methanone," PubChem. Created Dec. 12, 2017: https://pubchem.ncbi.nlm.nih.gov/compound/131900417.
Daigle et al., "Selective Killing of Mixed Lineage Leukemia Cells by a Potent Small-Molecule DOT1L Inhibitor" Cancer Cell. 2011;20:53-65.
Edmunds et al., "Dynamic histone H3 methylation during gene induction: HYPB/Setd2 mediates all H3K36 trimethylation," The EMBO Journal. 2008;27:406-420.
Engelhardt et al., "Detailed structure-activity relationship of indolecarboxamides as H4 receptor ligands," Eur J Med Chem. 2012;54:660-8.
Fahey and Davis, "SETting the Stage for Cancer Development: SETD2 and the Consequences of Lost Methylation," Cold Spring Harb Perspect Med. May 1, 2017;7(5):a026468.
Fonfara et al., "The CRISPR-associated DNA-cleaving enzyme Cpf1 also processes precursor CRISPR RNA," Nature. 2016;532:517-521.
Fontebasso et al., "Mutations in SETD2 and genes affecting histone H3K36 methylation target hemispheric high-grade gliomas," Acta Neuropathol. 2013;125(5):659-69.
Gaj et al., "ZFN, Talen, and CRISPR/Cas-based methods for genome engineering," Trends Biotechnol. 2013;31:397-405.
Goossens et al., "Cancer biomarker discovery and validation," Transl Cancer Res. 2015;4(3):256-269.
Gupta and Zhang, "Angiogenesis: a curse or cure?," Postgrad Med J. 2005;81:236-242.
Gura, "Systems for Identifying New Drugs are Often Faulty," Science. 1997;278:1041-1042.
Hadjipavlou-Litina et al., "2D-QSAR and 3D-QSAR/CoMFA analyses of the N-terminal substituted anthranilic acid based CCK(1) receptor antagonists: 'Hic Rhodus, hic saltus'," Bioorg Med Chem. 2009;17(14):5198-206.
Herzog et al., "Trabectedin Followed by Irinotecan Can Stabilize Disease in Advanced Translocation-Positive Sarcomas with Acceptable Toxicity," 2016;2016:7461783.
Hudlebusch et al., "The Histone Methyltransferase and Putative Oncoprotein MMSET Is Overexpressed in a Large Variety of Human Tumors," Clin Cancer Res. 2011;17(9):2919-29.
Jin and Zhou, "Crucial role of the pentose phosphate pathway in malignant tumors," Oncology Letters. 2019;17(5):4213-4221.
Johnson et al., "End points and United States Food and Drug Administration approval of oncology drugs," J Clin. Oncol. 2003;21:1404-11.
Johnson et al., "Relationships between drug activity in NCI preclinical in vitro and in vivo models and early clinical trials," British Journal of Cancer. 2001;84(10):1424-1431.
Kalff and Spencer, "The t(4;14) translocation and FGFR3 overexpression in multiple myeloma: prognostic implications and current clinical strategies," Blood Cancer Journal. 2012;2:89.
Kamel et al., "Exploitation of Gene Expression and Cancer Biomarkers in Paving the Path to Era of Personalized Medicine," Genomics Proteomics Bioinformatics. 2017;15(4):220-235.
Karlin et al., "Applications and statistics for multiple high-scoring segments in molecular sequences" Proc. Natl. Acad Sci. 1993;90:5873-77.
Karlin et al., "Methods for assessing the statistical significance of molecular sequence features by using general scoring schemes," Proc. Natl. Acad Sci. 1990;87:2264-68.
Kassambara, et al., "MMSET is overexpressed in cancers: link with tumor aggressiveness," Biochemical and Biophysical Research Communications. 2009;379(4):840-845.
Konikova and Kusenda, "Altered expression of p53 and MDM2 proteins in hematological malignancies," Neoplasma. 2003;50(1):31-40.
Kuo et al., "NSD2 links dimethylation of histone H3 at lysine 36 to oncogenic programming," Molecular Cell. 2011;44:609-20.
Kwak et. al. "Structure-activity relationship of indoline-2-carboxylic acid N-(substituted)phenylamide derivatives," Bioorg Med Chem Lett. Aug. 1, 2010;20(15):4620-3.
Larkin et al., "Epigenetic regulation in RCC: opportunities for therapeutic intervention?," Nat Rev Urol. 2012;9(3):147-55.
Li et al., "SETD2: an epigenetic modifier with tumor suppressor functionality," Oncotarget. 2016;7:50719-34.
Maeda and Khatami, "Analyses of repeated failures in cancer therapy for solid tumors: poor tumor-selective drug delivery, low therapeutic efficacy and unsustainable costs," Clin Trans Med. 2018;7:11.
Maeder and Gersbach, "Genome-editing Technologies for Gene and Cell Therapy," Mol. Ther. 2016;24:430-46.
Morera et. al., "Targeting histone methyltransferases and demethylases in clinical trials for cancer therapy," Clinical Epigenetics. 2016;8(57):1-16.
Mullis et al., "Specific enzymatic amplification of DNA in vitro: the polymerase chain reaction," Cold Spring Harb Symp Quant Biol. 1986;51 Pt 1:263-73.
Myers and Miller, "Optimal alignments in linear space," Cabios. 1988;4:11-17.
NCBI GenBank, "*Homo sapiens* SET domain containing 2, histone lysine methyltransferase (SETD2), transcript variant 1, mRNA," ncbi.nlm.nih.gov, Accession No. NM_014159.6, accessed at URL:[https://www.ncbi.nlm.nih.gov/nuccore/NM_014159.6] on Dec. 23, 2021, 12 pages.
NCBI Gene, "SETD2 Set domain containing 2, histone lysine methyltransferase [ *Homo sapiens* (human) ]," ncbi.nlm.nih.gov, Gene ID: 29072, HGNC: 18420, accessed at URL:[https://www.ncbi.nlm.nih.gov/gene?Db=gene&Cmd=DetailsSearch&Term=29072] on Dec. 23, 2021, 12 pages (Dec. 2021).

(56) References Cited

OTHER PUBLICATIONS

Needleman and Wunsch, "A General Method Applicable to the Search for Similiarities in the Amino Acid Sequence of Two Proteins," J Mol. Biol. 1970;48:443-53.
Newbold, "Evidence for a tumour suppressor function of SETD2 in human breast cancer: a new hypothesis," Anticancer Res. 2010;30(9):3309-11.
Ohri et al., "Tumour necrosis factor-alpha expression in tumour islets confers a survival advantage in non-small cell lung cancer," BMC Cancer. 2010;10:323.
Park et al., "Metabolism of fluorine-containing drugs," Annu Rev Pharmacol Toxicol. 2001;41:443-70.
Park et al.,"Methylation of Aurora kinase A by MMSET reduces p53 stability and regulates cell proliferation and apoptosis," Oncogne. 2018;37:6212-24.
Pawlyn and Morgan, "Evolutionary biology of high-risk multiple myeloma," Nature Reviews. Cancer. 2017;17(9):543-56.
PCT International Search Report and Written Opinion from PCT/US2018/046698, dated Oct. 19, 2018.
PCT International Search Report and Written Opinion from PCT/US2019/046569, dated Nov. 5, 2019.
PCT International Search Report and Written Opinion from PCT/US2019/063405, dated Apr. 21, 2021.
PCT International Search Report and Written Opinion from PCT/US2021/018863, dated Jul. 20, 2021.
PCT International Search Report and Written Opinion from PCT/US2022/032718, dated Sep. 12, 2022.
PCT International Search Report and Written Opinion from PCT/US2022/078962, dated Jan. 26, 2023.
Perez-Pinera et al., "Advances in targeted genome editing," Curr Opin Chem Biol. 2012;16:268-77.
Prideaux et al., "The genetic architecture of multiple myeloma," Advances in Hematology. 2014:1-16.
Sanchez-Rivera and Jacks, "Applications of the CRISPR-Cas9 System in Cancer Biology," Nat Rev Cancer. 2015;15:387-95.
Slagle et al., "Expression of ras, c-myc, and p53 proteins in cervical intraepithelial neoplasia," Cancer. 1998;83(7):1401-8.
Smith and Waterman, "Comparison of biosequences," Advances in Applied Mathematics. 1981;2:482-89.
Thomenius, et al., "Identification of a First-in-Class SETD2 Inhibitor That Shows Potent and Selective Anti-Proliferative Activity in t(4;14) Multiple Myeloma: T(4;14) Multiple Myeloma Cells Are Dependent on Both H3K36 Di and Tri-Methylation," Blood. 2018;132(Supplement1):3207.
Tisi et al., "Structure of the Epigenetic Oncogene MMSET and Inhibition by N-Alkyl Sinefungin Derivatives," ACS Biol. 2016;11(11):3093-3105.
van Tonder et al., "Preparation and physicochemical characterization of 5 niclosamide solvates and 1 hemisolvate," AAPS PharmSciTech. 2004;5(1):E12.
Xie et al., "MMSET regulates expression of IRF4 in t(4;14) myeloma and its silencing potentiates the effect of bortezomib," Leukemia. 2015;29:2347-54.
Zetsche et al., "Cpf1 Is a Single RNA-Guided Endonuclease of a Class 2 CRISPR-Cas System," Cell. 2015;163:759-71.
Zheng et al., "Sinefungin derivatives as inhibitors and structure probes of protein lysine methyltransferase SETD2," J Am Chem Soc. 2012;134(43):18004-14.
Zhu et al., "Identification of functional cooperative mutations of SETD2 in human acute leukemia," Nature Genetics. 2014;46:287-293.
Zips et al., "New Anticancer Agents: In Vitro and in Vivo Evaluation," in vivo. 2005;19:1-8.
CID 24967599 Compound Summary: Avadomide, PubChem., Created Oct. 20, 2008: https://pubchem.ncbi.nlm.nih.gov/compound/Avadomide#section=Springer-Nature-References, 37 pages.
Database Registry [online], CAS Registry No. 1795381-89-3, 1795172-12-1, Jul. 6, 2015, 2 pages.
Witzig et al., "A comprehensive review of lenalidomide therapy for B-cell non-Hodgkin lymphoma", Annals of Oncology, Aug. 3, 2015, 26(8):1667-1677.
U.S. National Library of Medicine, "Drugs, Herbs and Supplements", Medline Plus, 2025, 2 pages.
U.S. Appl. No. 19/319,006 of Lampe et al., filed on Sep. 4, 2025.

* cited by examiner

SETD2 INHIBITORS AND RELATED METHODS AND USES, INCLUDING COMBINATION THERAPIES

BACKGROUND OF THE INVENTION

Field of the Invention

The present disclosure provides SETD2 protein inhibitors, and methods, compositions, and kits for treating diseases, disorders, or conditions in a subject with a SETD2 protein inhibitor. In some embodiments, the methods, compositions, and kits for treating diseases, disorders, or conditions further comprise a second therapeutic agent, wherein the second therapeutic agent comprises one or more glucocorticoid receptor agonists, one or more immunomodulatory drugs, one or more proteasome inhibitors, one or more Bcl-2 inhibitors, one or more pleiotropic pathway modulators, one or more XPO1 inhibitors, one or more histone deacetylase inhibitors, or one or more EZH2 inhibitors, or a combination thereof.

Background

The selective addition of methyl groups to specific amino acid sites on histones is controlled by the action of a family of enzymes known as histone methyltransferases (HMTs). The level of expression of a particular gene is influenced by the presence or absence of one or more methyl groups at a relevant histone site. The specific effect of a methyl group at a particular histone site persists until the methyl group is removed by a histone demethylase, or until the modified histone is replaced through nucleosome turnover. In a like manner, other enzyme classes can decorate DNA and histones with other chemical species, and still other enzymes can remove these species to provide control of gene expression.

SETD2 is a human histone methyltransferase located at the cytogenic band p21.31 of chromosome 3 (3p21.31). The acronym "SETD2" stands for Suppressor of variegation, Enhancer of zeste, and Trithorax domain containing 2. The SETD2 protein comprises three conserved functional domains: (1) the triplicate AWS-SET-PostSET domain; (2) a WW domain; and (3) a Set2-Rbp1 interacting ("SRI") domain. These three functional domains define the biological function of SETD2. See, Li, J. et al., *Oncotarget* 7:50719-50734 (2016). SETD2 is believed to be the single human gene responsible for the trimethylation of lysine 36 (Lys-36) of histone H3 (H3K36me3) using dimethylated Lys-36 (H3K36me2) as substrate. Edmunds, J. W. et al., *The EMBO Journal* 27:406-420 (2008).

Human SETD2 has been shown to have tumor suppressor functionality. Li, J. et al., *Oncotarget* 7:50719-50734 (2016). For example, inactivation of human SETD2 has been reported in renal cell carcinoma (RCC). Larkin, J., et al., *Nature Reviews* 9:147-155 (2012). Also, expression levels of SETD2 in breast cancer samples have been reported as significantly lower than in adjacent non-cancerous tissue (ANCT) samples. Newbold, R. F. and Mokbel, K., *Anticancer Research* 30: 3309-3311 (2010). Additionally, biallelic mutations and loss-of-function point mutations in SETD2 were reported in patients with acute leukemia. Zhu, X. et al., *Nature Genetics* 46: 287-293 (2014). Mutations in SETD2 have also been reported in pediatric high-grade gliomas. Fontebasso, A. M. et al., *Acta Neuropathol.* 125: 659-669 (2013).

BRIEF SUMMARY OF THE INVENTION

The present disclosure generally provides SETD2 protein inhibitors, and methods, compositions, and kits for treating diseases, disorders, or conditions in a subject with a SETD2 protein inhibitor and, optionally, a second therapeutic agent, wherein the second therapeutic agent comprises glucocorticoid receptor agonists, immunomodulatory drugs, proteasome inhibitors, Bcl-2 inhibitors, pleiotropic pathway modulators, XPO1 inhibitors, histone deacetylase inhibitors, or EZH2 inhibitors, or a combination thereof.

In one aspect, the present disclosure provides methods of treating diseases, disorders, or conditions, e.g., cancer, in a subject in need thereof with:

(1) a therapeutically effective amount of a substituted indole represented by any one of Formulae I, II, II-A, III, III-A, IV, IV-A, IV-B, IV-C, IV-D, V, V-A, V-B, VI, VII, VII-A, VII-B, VII-C, VII-D, VII-E, VII-F, VII-G, VII-H, VIII, VIII-A, or VIII-B, or a compound of Table 1, or a compound of Table 1B, below, and the pharmaceutically acceptable salts and solvates thereof, collectively referred to herein as a "Compounds of the Disclosure;" and (2) a therapeutically effective amount of a second therapeutic agent, wherein the second therapeutic agent comprises one or more glucocorticoid receptor agonists, one or more immunomodulatory drugs, one or more proteasome inhibitors, one or more Bcl-2 inhibitors, one or more pleiotropic pathway modulators, one or more XPO1 inhibitors, one or more histone deacetylase inhibitors, or one or more EZH2 inhibitors, or a combination thereof.

In another aspect, the present disclosure provides a Compound of the Disclosure for use in treating cancer, e.g., multiple myeloma, in a subject in need thereof, wherein the Compound of the Disclosure is to be administered to the subject in combination with a Second Therapeutic Agent.

In another aspect, the present disclosure provides a Compound of the Disclosure for use in the manufacture of a medicament for treating cancer in a mammal, wherein the Compound of the Disclosure is to be administered to the subject in combination with a Second Therapeutic Agent.

In another aspect, the present disclosure provides a kit comprising a Compound of the Disclosure and a Second Therapeutic Agent.

In another aspect, the present disclosure provides a Compound of the Disclosure, i.e., substituted indole represented by any one of Formulae I, II, II-A, III, III-A, IV, IV-A, IV-B, IV-C, IV-D, V, V-A, V-B, VI, VII, VII-A, VII-B, VII-C, VII-D, VII-E, VII-F, VII-G, VII-H, VIII, VIII-A, or VIII-B, or a compound of Table 1, or a compound of Table 1B.

In another aspect, the present disclosure provides a pharmaceutical composition comprising a Compound of the Disclosure and a pharmaceutically acceptable carrier.

In one aspect, the present disclosure provides methods of treating diseases, disorders, or conditions, e.g., cancer, in a subject in need thereof, comprising administering to the subject a therapeutically effective amount of a Compound of the Disclosure.

In another aspect, the present disclosure provides a Compound of the Disclosure for use in treating cancer, e.g., multiple myeloma, in a subject in need thereof.

In another aspect, the present disclosure provides a Compound of the Disclosure for use in the manufacture of a medicament for treating cancer in a subject.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the invention as claimed.

DETAILED DESCRIPTION OF THE INVENTION

I. Compounds of the Disclosure

Figure 1:
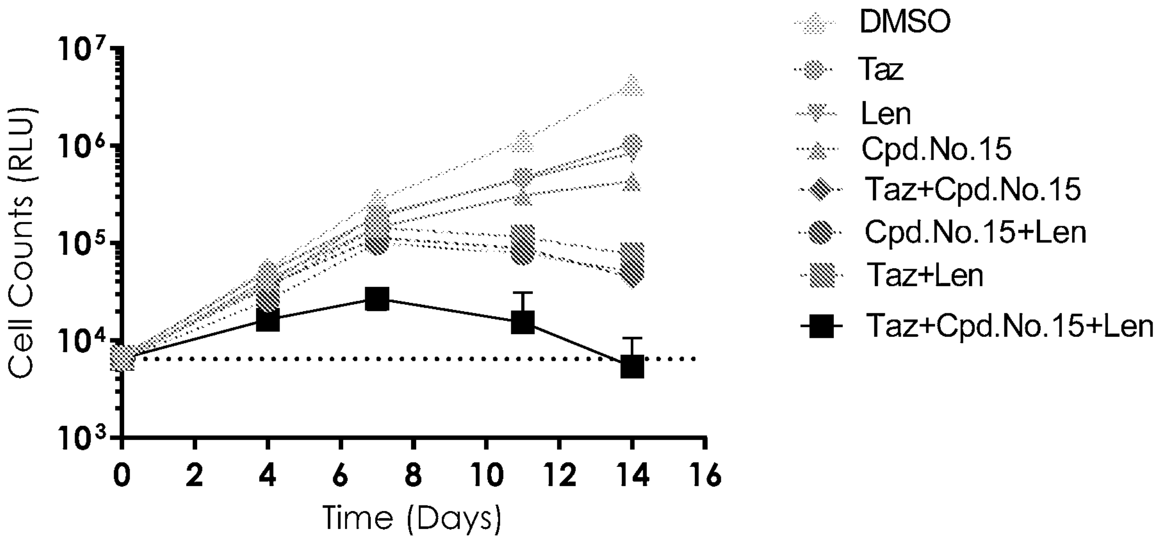
FIG. 1 is a line graph showing the anti-proliferative activity of Cpd. No. 15, tazemetostat (Taz), and lenalidomide (Len), and combinations thereof, in KMS-11 cells over the course of a 14-day co-treatment study.

Certain Compounds of the Disclosure are disclosed in PCT/US2019/046569 as SETD2 inhibitors. PCT/US2019/046569 is fully incorporated by reference herein in its entirety. Certain other Compounds of the Disclosure are an embodiment of the disclosure as set forth herein.

In one embodiment, Compounds of the Disclosure are compounds having Formula I:

I

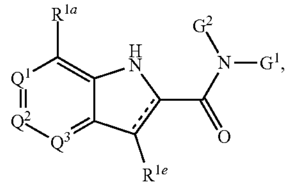

wherein:

$R^{1a}$ is selected from the group consisting of halogen, alkyl, alkoxy, cycloalkyl, (hydroxy)alkyl, and (cycloalkyl)alkyl;

$Q^1$ is selected from the group consisting of —C($R^{1b}$)═ and —N═;

$Q^2$ is selected from the group consisting of —C($R^{1c}$)═ and —N═;

$Q^3$ is selected from the group consisting of —C($R^{1d}$)═ and —N═;

provided that at least one of $Q^1$, $Q^2$, or $Q^3$ is —C($R^{1b}$)═, —C($R^{1c}$)═, or —C($R^{1d}$)═, respectively;

$R^{1b}$, $R^{1c}$ and $R^{1d}$ are each independently selected from the group consisting of hydrogen, halogen, alkyl, alkenyl, (hydroxy)alkyl, and alkoxy;

$R^{1e}$ is selected from the group consisting of hydrogen, halogen, alkyl, cycloalkyl, (hydroxy)alkyl, and (cycloalkyl)alkyl;

⎓ is a single or double bond;

$G^1$ is selected from the group consisting of optionally substituted aryl, optionally substituted heteroaryl, optionally substituted heterocyclo, optionally substituted cycloalkyl, (aryl)alkyl, (heteroaryl)alkyl, (heterocyclo)alkyl, (amino)(aryl)alkyl, (heteroaryl)(aryl)alkyl, (heteroaryl)(heterocyclo)alkyl, (heteroaryl)(carboxamido)alkyl, (heteroaryl)(cycloalkyl)alkyl, (aryl)(alkoxycarbonyl)alkyl, (cycloalkyl)alkyl, (heteroaryl)(amino)alkyl, (cycloalkyl)(alkoxycarbonyl)alkyl, (heteroaryl)(alkoxycarbonyl)alkyl, (heterocyclo)(cycloalkyl)alkyl, (aryl)(cycloalkyl)alkyl, (aryl)(hydroxy)alkyl, (cycloalkyl)(hydroxy)alkyl, (hydroxy)alkyl, optionally substituted alkyl, (aryl)(haloalkyl)alkyl, (cycloalkyl)(haloalkyl)alkyl, (hydroxy)(haloalkyl)alkyl, and (alkoxycarbonyl)(haloalkyl)alkyl; and $G^2$ is selected from the group consisting of hydrogen and alkyl; or $G^1$ and $G^2$ taken together with the nitrogen atom to which they are attached form an optionally substituted heterocyclo, or a pharmaceutically acceptable salt or solvate thereof.

In another embodiment, the compound having Formula I is not N-(1-(1-(L-alanyl)piperidin-4-yl)ethyl)-7-methyl-1H-indole-2-carboxamide, N-((1r,4r)-4-(3-aminopropanamido)cyclohexyl)-7-methyl-1H-indole-2-carboxamide, or N-((1r,4r)-4-aminocyclohexyl)-7-methyl-1H-indole-2-carboxamide.

In another embodiment, Compounds of the Disclosure are compounds having Formula I, wherein:

$R^{1a}$ is selected from the group consisting of halogen, $C_1$-$C_6$ alkyl, $C_1$-$C_6$ alkoxy, $C_3$-$C_8$ cycloalkyl, (hydroxy)$C_{1-6}$ alkyl, and ($C_3$-$C_6$ cycloalkyl)$C_{1-6}$ alkyl;

$R^{1b}$, $R^{1c}$, and $R^{1d}$ are each independently selected from the group consisting of hydrogen, halogen, $C_1$-$C_6$ alkyl, $C_2$-$C_6$ alkenyl, (hydroxy)$C_1$-$C_6$ alkyl, and $C_1$-$C_6$ alkoxy;

$R^{1e}$ is selected from the group consisting of hydrogen and $C_1$-$C_6$ alkyl;

$G^1$ is selected from the group consisting of optionally substituted $C_6$-$C_{10}$ aryl, optionally substituted 5- to 10-membered heteroaryl, optionally substituted 3- to 10-membered heterocyclo, optionally substituted $C_3$-$C_8$ cycloalkyl, ($C_6$-$C_{10}$ aryl)$C_1$-$C_6$ alkyl, (5- to 10-membered heteroaryl)$C_1$-$C_6$ alkyl, (3- to 10-membered heterocyclo)$C_1$-$C_6$ alkyl, (amino)($C_6$-$C_{10}$ aryl)$C_1$-$C_6$ alkyl, (5- to 14-membered heteroaryl)($C_6$-$C_{10}$ aryl)$C_1$-$C_6$ alkyl, (5- to 10-membered heteroaryl)(3- to 10-membered heterocyclo)$C_1$-$C_6$ alkyl, (5- to 10-membered heteroaryl)(carboxamido)$C_1$-$C_6$ alkyl, (5- to 10-membered heteroaryl)($C_3$-$C_6$ cycloalkyl)$C_1$-$C_6$ alkyl, ($C_6$-$C_{10}$ aryl)(alkoxycarbonyl)$C_1$-$C_6$ alkyl, ($C_3$-$C_6$ cycloalkyl)$C_1$-$C_6$ alkyl, (5- to 10-membered heteroaryl)(amino)$C_1$-$C_6$ alkyl, ($C_3$-$C_6$ cycloalkyl)(alkoxycarbonyl)$C_1$-$C_6$ alkyl, (5- to 14-membered heteroaryl)(alkoxycarbonyl)$C_1$-$C_6$ alkyl, (3- to 14-membered heterocyclo)($C_3$-$C_6$ cycloalkyl)$C_1$-$C_6$ alkyl, ($C_{6-10}$ aryl)($C_3$-$C_8$ cycloalkyl)$C_1$-$C_6$ alkyl, ($C_6$-$C_{10}$ aryl)(hydroxy)$C_1$-$C_6$ alkyl, ($C_3$-$C_6$ cycloalkyl)(hydroxy)$C_1$-$C_6$ alkyl, (hydroxy)$C_1$-$C_6$ alkyl, optionally substituted $C_1$-$C_6$ alkyl, ($C_6$-$C_{10}$ aryl)($C_1$-$C_6$ haloalkyl)$C_1$-$C_6$ alkyl, ($C_3$-$C_6$ cycloalkyl)($C_1$-$C_6$ haloalkyl)$C_1$-$C_6$ alkyl, (hydroxy)($C_1$-$C_6$ haloalkyl)$C_1$-$C_6$ alkyl; and (alkoxycarbonyl)($C_1$-$C_6$ haloalkyl)$C_1$-$C_6$ alkyl; and $G^2$ is selected from the group consisting of hydrogen and $C_1$-$C_6$ alkyl; or $G^1$ and $G^2$ taken together with the nitrogen atom to which they are attached form a 5- to 10-membered optionally substituted heterocyclo, or a pharmaceutically acceptable salt or solvate thereof.

In another embodiment, Compounds of the Disclosure are compounds having Formula I, wherein:

$R^{1a}$ is selected from the group consisting of halogen, $C_1$-$C_3$ alkyl, $C_1$-$C_3$ alkoxy, $C_3$-$C_6$ cycloalkyl, (hydroxy)$C_1$-$C_4$ alkyl, and ($C_3$-$C_6$ cycloalkyl)$C_1$-$C_4$ alkyl;

$R^{1b}$, $R^{1c}$, and $R^{1d}$ are each independently selected from the group consisting of hydrogen, halogen, $C_1$-$C_3$ alkyl, $C_2$-$C_4$ alkenyl, (hydroxy)$C_1$-$C_4$ alkyl, and $C_1$-$C_3$ alkoxy;

$R^{1e}$ is selected from the group consisting of hydrogen and $C_1$-$C_3$ alkyl;

$G^1$ is selected from the group consisting of optionally substituted $C_6$-$C_{10}$ aryl, optionally substituted 5- to 10-membered heteroaryl, optionally substituted 3- to 10-membered heterocyclo, optionally substituted $C_3$-$C_8$ cycloalkyl, ($C_6$-$C_{10}$ aryl)$C_1$-$C_4$ alkyl, (5- to 10-membered heteroaryl)$C_1$-$C_6$ alkyl, (3- to 10-membered heterocyclo)$C_1$-$C_4$ alkyl, (amino)($C_6$-$C_{10}$ aryl)$C_1$-$C_6$ alkyl, (5- to 14-membered heteroaryl)($C_6$-$C_{10}$ aryl)$C_1$-$C_4$ alkyl, (5- to 10-membered heteroaryl)(3- to 10-membered heterocyclo)$C_1$-$C_4$ alkyl, (5- to 10-membered heteroaryl)(carboxamido)$C_1$-$C_4$ alkyl, (5- to 10-membered heteroaryl)($C_3$-$C_6$ cycloalkyl)$C_1$-$C_4$ alkyl, ($C_6$-$C_{10}$ aryl)(alkoxycarbonyl)$C_1$-$C_4$ alkyl, ($C_3$-$C_6$ cycloalkyl)$C_1$-$C_4$ alkyl, (5- to 10-membered heteroaryl)(amino)$C_1$-$C_4$ alkyl, ($C_3$-$C_6$ cycloalkyl)(alkoxycarbonyl)$C_1$-$C_4$ alkyl, (5- to 14-membered heteroaryl)(alkoxycarbonyl)$C_1$-$C_4$ alkyl, (3- to 14-membered heterocyclo)($C_3$-$C_6$ cycloalkyl)$C_1$-$C_4$ alkyl, ($C_{6-10}$ aryl)($C_3$-$C_6$ cycloalkyl)$C_1$-$C_4$ alkyl, ($C_6$-$C_{10}$ aryl)(hydroxy)$C_1$-$C_4$ alkyl, ($C_3$-$C_6$ cycloalkyl)(hydroxy)$C_1$-$C_4$ alkyl, (hydroxy)$C_1$-$C_4$ alkyl, optionally substituted $C_1$-$C_4$ alkyl, ($C_6$-$C_{10}$ aryl)($C_1$-$C_4$ haloalkyl)$C_1$-$C_4$ alkyl, ($C_3$-$C_6$ cycloalkyl)($C_1$-$C_4$ haloalkyl)$C_1$-$C_4$ alkyl, (hydroxy)($C_1$-$C_4$ haloalkyl)$C_1$-$C_4$ alkyl, and (alkoxycarbonyl)($C_1$-$C_4$ haloalkyl)$C_1$-$C_4$ alkyl; and $G^2$ is selected from the group consisting of hydrogen and $C_1$-$C_4$ alkyl; or $G^1$ and $G^2$ taken together with the nitrogen atom to which they are attached form a 5- to 10-membered optionally substituted heterocyclo, or a pharmaceutically acceptable salt or solvate thereof.

In another embodiment, Compounds of the Disclosure are compounds having Formula I, wherein ⎓ is a double bond, or a pharmaceutically acceptable salt or solvate thereof.

In another embodiment, Compounds of the Disclosure are compounds having Formula I, wherein $Q^1$ and $Q^2$ are —C(H)═, or a pharmaceutically acceptable salt or solvate thereof.

In another embodiment, Compounds of the Disclosure are compounds having Formula I, wherein $Q^3$ is —C($R^{1d}$)═; and $R^{1d}$ is selected from the group consisting of hydrogen and halo, or a pharmaceutically acceptable salt or solvate thereof.

In another embodiment, Compounds of the Disclosure are compounds having Formula I, wherein $R^{1e}$ is hydrogen, or a pharmaceutically acceptable salt or solvate thereof.

In another embodiment, Compounds of the Disclosure are compounds having Formula I, wherein $R^{1a}$ is $C_1$-$C_3$ alkyl, or a pharmaceutically acceptable salt or solvate thereof.

In another embodiment, Compounds of the Disclosure are compounds having Formula I, wherein $G^2$ is hydrogen, or a pharmaceutically acceptable salt or solvate thereof.

In another embodiment, Compounds of the Disclosure are compounds having Formula II:

II

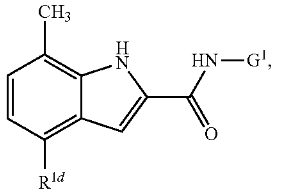

or a pharmaceutically acceptable salt or solvate thereof, wherein $R^{1d}$ and $G^1$ are as defined in connection with Formula I.

In another embodiment, Compounds of the Disclosure are compounds having Formulae I or II, wherein $R^{1d}$ is selected from the group consisting of hydrogen and fluoro, or a pharmaceutically acceptable salt or solvate thereof.

In another embodiment, Compounds of the Disclosure are compounds having Formula II-A:

II-A

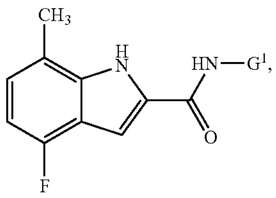

or a pharmaceutically acceptable salt or solvate thereof, wherein $G^1$ is as defined in connection with Formula II.

In another embodiment, Compounds of the Disclosure are compounds having Formulae I, II, or II-A, wherein $G^1$ is selected from the group consisting of optionally substituted $C_6$-$C_{10}$ aryl, optionally substituted 5- to 9-membered heteroaryl, optionally substituted 3- to 10-membered heterocyclo, optionally substituted $C_6$-$C_8$ cycloalkyl, (5- to 9-membered heteroaryl)$C_1$-$C_6$ alkyl, (5- to 9-membered heteroaryl)($C_{6-10}$ aryl)$C_1$-$C_4$ alkyl, (5- to 9-membered heteroaryl heteroaryl)($C_3$-$C_6$ cycloalkyl)$C_1$-$C_4$ alkyl, and ($C_3$-$C_6$ cycloalkyl)$C_1$-$C_4$ alkyl, or a pharmaceutically acceptable salt or solvate thereof.

In another embodiment, Compounds of the Disclosure are compounds having Formula III:

III

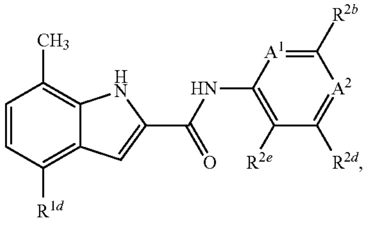

wherein:

$A^1$ is selected from the group consisting of —N═ and —C($R^{2a}$)═;

$R^{2a}$ is selected from the group consisting of hydrogen, alkyl, halogen, and haloalkyl;

$R^{2b}$ is selected from the group consisting of optionally substituted alkyl, optionally substituted heterocyclo, optionally substituted cycloalkyl, optionally substituted heteroaryl, optionally substituted aryl, (carboxamido)alkyl, —$OR^{10c}$, amino, (heterocyclo)alkyl, (amino)alkyl, (hydroxy)alkyl, carboxamido, (heteroaryl)alkyl, —S(═O)$R^{9b}$, —S(═O)$_2$ $R^{9b}$, and —C(═O)$R^{9c}$;

$A^2$ is selected from the group consisting of —N═ and —C($R^{2c}$)═;

$R^{2c}$ is selected from the group consisting of hydrogen, alkyl, halogen, and haloalkyl;

$R^{2d}$ is selected from the group consisting of hydrogen, alkyl, halogen, cyano, and haloalkyl;

$R^{2e}$ is selected from the group consisting of hydrogen, alkyl, halogen, and haloalkyl;

$R^{9b}$ is selected from the group consisting of amino, alkyl, optionally substituted cycloalkyl, optionally substituted aryl, optionally substituted heterocyclo, and optionally substituted heteroaryl;

$R^{9c}$ is selected from the group consisting of amino, alkyl, optionally substituted cycloalkyl, optionally substituted aryl, optionally substituted heterocyclo, and optionally substituted heteroaryl; and $R^{10c}$ is selected from the group consisting of alkyl, (hydroxy)alkyl, and (amino)alkyl; and $R^{1d}$ is as defined in connection with Formula I, or a pharmaceutically acceptable salt or solvate thereof.

In another embodiment, Compounds of the Disclosure are compounds having Formula III-A:

III-A

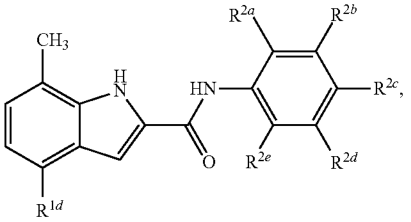

wherein $R^{1d}$, $R^{2a}$, $R^{2b}$, $R^{2c}$, $R^{2d}$, and $R^{2e}$ are as defined in connection with Formula III, or a pharmaceutically acceptable salt or solvate thereof.

In another embodiment, Compounds of the Disclosure are compounds having Formula III or Formula III-A, wherein:

$R^{2a}$ is selected from the group consisting of hydrogen, $C_1$-$C_4$ alkyl, halogen, and $C_1$-$C_4$ haloalkyl;

$R^{2b}$ is selected from the group consisting of:

(A) unsubstituted 4- to 10-membered heterocyclo;

(B) substituted 4- to 10-membered heterocyclo having one, two, three, or four substituents independently selected from the group consisting of (i) —N($R^{3a}$)C(═O)$R^{4a}$; (ii) —$NR^{5a}R^{5b}$; (iii) unsubstituted 4- to 10-membered heterocyclo; (iv) substituted 4- to 10-membered heterocyclo having one, two, or three substituents independently selected from the group consisting of hydroxy, —$NR^{5c}R^{5d}$, $C_1$-$C_4$ alkyl, $C_1$-$C_6$ alkoxy, —C($R^{6a}$)($R^{6b}$)C(═O)$NR^{5e}R^{5f}$, —C(═O)$R^{4b}$, (hydroxy)$C_1$-$C_4$ alkyl, and halo; (v) unsubstituted $C_3$-$C_6$ cycloalkyl; (vi) (hydroxy)$C_1$-$C_4$ alkyl; (vii) $C_1$-$C_6$ alkyl; (viii) —C(═O)$NR^{5g}R^{5h}$; (ix) halo; (x) —C(═O)$R^{4c}$; (xi) $C_1$-$C_6$ haloalkyl; (xii) hydroxy; (xiii) (amino)$C_1$-$C_4$ alkyl; (xiv) ($C_1$-$C_4$ alkoxy)$C_1$-$C_4$ alkyl; (xv) —S(═O)$_2R^{9a}$; (xvi) (3- to 8-membered heterocyclo)$C_1$-$C_4$ alkyl; (xvii) $C_1$-$C_6$ alkoxy; (xviii) ($C_3$-$C_6$ cycloalkyl)$C_1$-$C_4$ alkyl; (xix) ($C_{6-10}$ aryl)$C_1$-$C_4$ alkyl; and (xxii) —$OR^{10b}$;

(C) unsubstituted $C_3$-$C_8$ cycloalkyl;

(D) substituted $C_3$-$C_8$ cycloalkyl having one, two, three, or four substituents independently selected from the group consisting of (i)unsubstituted 4- to 10-membered heterocyclo; (ii) substituted 4- to 10-membered heterocyclo having one or two substituents, independently selected from the group consisting of amino and $C_1$-$C_4$ alkyl; (iii) unsubstituted 5- or 6-membered heteroaryl; (iv) substituted 5- or 6-membered heteroaryl having one, two, or three substituents independently selected from the group consisting of halo, $C_1$-$C_4$ alkyl, (3- to 8-membered heterocyclo)alkyl, hydroxy, and amino; (v) —$NR^{5i}R^{5j}$; (vi) cyano; (vii) —N($R^{3d}$)C(═O)$R^{4f}$; (viii) hydroxy; and (ix) $C_1$-$C_4$ alkyl;

(E) unsubstituted 5- to 10-membered heteroaryl;

(F) substituted 5- to 10-membered heteroaryl having one, two, three, or four substituents independently selected from the group consisting of (i) halo; (ii) $C_1$-$C_4$ alkyl; ($C_1$-$C_4$ alkoxy)$C_1$-$C_4$ alkyl; (hydroxy)$C_1$-$C_4$ alkyl; $C_3$-$C_6$ cycloalkyl; (amino)$C_1$-$C_4$ alkyl; unsubstituted $C_3$-$C_6$ cycloalkyl; substituted $C_3$-$C_6$ cycloalkyl having one, two, three, or four substituents independently selected from the group consisting of —$NR^{5g}R^{5h}$; unsubstituted 4- to 14-membered heterocyclo; substituted 4- to 14-membered heterocyclo having one or two substituents independently selected from the group consisting of hydroxy, amino, and $C_1$-$C_4$ alkyl; —$NR^{5q}R^{5r}$; and (ix) (3- to 8-membered heterocyclo)$C_1$-$C_4$ alkyl;

(G) unsubstituted $C_6$-$C_{10}$ aryl;

(H) substituted $C_6$-$C_{10}$ aryl, having one, two, three, or four substituents independently selected from the group consisting of (i) halo; (ii) $C_1$-$C_4$ alkyl; (iii) —CH—$_2$N(H)S(═O)$_2R^8$; (iv) (5- to 9-membered heteroaryl)$C_1$-$C_4$ alkyl; (v) —$OR^{10a}$; (vi) —N($R^{3b}$)C(═O)$R^{4b}$; (vii) (amino)$C_1$-$C_4$ alkyl; and (viii) (hydroxy)$C_1$-$C_4$ alkyl;

(I) (carboxamido)$C_1$-$C_4$ alkyl;

(J) —$OR^{10c}$;

(K) —$NR^{5o}R^{5p}$;

(L) (3- to 8-membered heterocyclo)$C_1$-$C_4$ alkyl;

(M) (amino)$C_1$-$C_4$ alkyl;

(N) (hydroxy)$C_1$-$C_4$ alkyl;

(O) —C(═O)$NR^{5s}R^{5t}$;

(P) (5- to 9-membered heteroaryl)$C_1$-$C_4$ alkyl; and (Q) —S(═O)$_2R^{9b}$;

$R^{2c}$ is selected from the group consisting of hydrogen, $C_1$-$C_4$ alkyl, halogen, and $C_1$-$C_4$ haloalkyl;

$R^{2d}$ is selected from the group consisting of hydrogen, $C_1$-$C_4$ alkyl, halogen, cyano, and $C_1$-$C_4$ haloalkyl;

$R^{2e}$is selected from the group consisting of hydrogen, $C_1$-$C_4$ alkyl, halogen, and $C_1$-$C_4$ haloalkyl;

$R^{3a}$, $R^{3b}$, $R^{3c}$, and $R^{3d}$ are each independently selected from the group consisting of hydrogen, $C_1$-$C_4$ alkyl, optionally substituted $C_3$-$C_6$ cycloalkyl, and optionally substituted 4- to 14-membered heterocyclo;

$R^{4a}$, $R^{4b}$, $R^{4c}$, $R^{4d}$, $R^{4e}$, and $R^{4f}$ are each independently selected from the group consisting of $C_1$-$C_6$ alkyl; $C_1$-$C_6$ haloalkyl; $C_3$-$C_6$ cycloalkyl; $C_1$-$C_6$ alkoxy; ($C_1$-$C_4$ alkoxy)$C_1$-$C_4$ alkyl; ($C_{6-10}$ aryl)$C_1$-$C_4$ alkyl; (5- to 9-membered heteroaryl)$C_1$-$C_4$ alkyl; (amino)$C_1$-$C_4$ alkyl; (hydroxy)$C_1$-$C_4$ alkyl; (cyano)$C_1$-$C_4$ alkyl; unsubstituted 4- to 14-membered heterocyclo; substituted 4- to 14-membered heterocyclo having one or two substituents independently selected from the group consisting of halo and $C_1$-$C_4$ alkyl; unsubstituted $C_6$-$C_{10}$ aryl; substituted $C_6$-$C_{10}$ aryl, having one, two, three, or four substituents independently selected from the group consisting of halo and $C_1$-$C_4$ alkyl; unsubstituted 5- or 6-membered heteroaryl; and substituted 5- or 6-membered heteroaryl having one, two, three, or four substituents independently selected from the group consisting of halo and $C_1$-$C_4$ alkyl;

$R^{5a}$ and $R^{5b}$ are independently selected from the group consisting of hydrogen; $C_1$-$C_4$ alkyl; $C_1$-$C_4$ haloalkyl; (hydroxy)$C_1$-$C_4$ alkyl; (amino)$C_1$-$C_4$ alkyl; ($C_1$-$C_4$ alkoxy)$C_1$-$C_4$ alkyl; (5- to 9-membered heteroaryl)$C_1$-$C_4$ alkyl; unsubstituted 5- or 6-membered heteroaryl; substituted 5- or 6-membered heteroaryl having one or two substituents independently selected from the group consisting of halo and $C_1$-$C_4$ alkyl; unsubstituted 4- to 14-membered heterocyclo; and substituted 4- to 14-membered heterocyclo having one or two substituents independently selected from the group consisting of hydroxy, amino, and $C_1$-$C_4$ alkyl;

$R^{5c}$ and $R^{5d}$ are independently selected from the group consisting of hydrogen; $C_1$-$C_4$ alkyl; $C_1$-$C_4$ haloalkyl; (hydroxy)$C_1$-$C_4$ alkyl; (amino)$C_1$-$C_4$ alkyl; ($C_1$-$C_4$ alkoxy)$C_1$-$C_4$ alkyl; (5- to 9-membered heteroaryl)$C_1$-$C_4$ alkyl; unsubstituted 5- or 6-membered heteroaryl; substituted 5- or 6-membered heteroaryl having one or two substituents independently selected from the group consisting of halo and $C_1$-$C_4$ alkyl; unsubstituted 4- to 14-membered heterocyclo; and substituted 4- to 14-membered heterocyclo having one or two substituents independently selected from the group consisting of hydroxy, amino, and $C_1$-$C_4$ alkyl; or $R^{5c}$ and $R^{5d}$ taken together with the nitrogen atom to which they are attached form an optionally substituted 4- to 14-membered heterocyclo;

$R^{5e}$ and $R^{5f}$ are independently selected from the group consisting of hydrogen; $C_1$-$C_4$ alkyl; $C_1$-$C_4$ haloalkyl; (hydroxy)$C_1$-$C_4$ alkyl; (amino)$C_1$-$C_4$ alkyl; ($C_1$-$C_4$ alkoxy)$C_1$-$C_4$ alkyl; (5- to 9-membered heteroaryl)$C_1$-$C_4$ alkyl; unsubstituted 5- or 6-membered heteroaryl; substituted 5- or 6-membered heteroaryl having one or two substituents independently selected from the group consisting of halo and $C_1$-$C_4$ alkyl; unsubstituted 4- to 14-membered heterocyclo; and substituted 4- to 14-membered heterocyclo having one or two substituents independently selected from the group consisting of hydroxy, amino, and $C_1$-$C_4$ alkyl; or $R^{5e}$ and $R^{5f}$ taken together with the nitrogen atom to which they are attached form an optionally substituted 4- to 14-membered heterocyclo;

$R^{5g}$ and $R^{5h}$ are independently selected from the group consisting of hydrogen; $C_1$-$C_4$ alkyl; $C_1$-$C_4$ haloalkyl; (hydroxy)$C_1$-$C_4$ alkyl; (amino)$C_1$-$C_4$ alkyl; ($C_1$-$C_4$ alkoxy)$C_1$-$C_4$ alkyl; (5- to 9-membered heteroaryl)$C_1$-$C_4$ alkyl; unsubstituted 5- or 6-membered heteroaryl; substituted 5- or 6-membered heteroaryl having one or two substituents independently selected from the group consisting of halo and $C_1$-$C_4$ alkyl; unsubstituted 4- to 14-membered heterocyclo; and substituted 4- to 14-membered heterocyclo having one or two substituents independently selected from the group consisting of hydroxy, amino, and $C_1$-$C_4$ alkyl; or $R^{5g}$ and $R^{5h}$ taken together with the nitrogen atom to which they are attached form an optionally substituted 4- to 14-membered heterocyclo;

$R^{5i}$ and $R^{5j}$ are independently selected from the group consisting of hydrogen; $C_1$-$C_4$ alkyl; $C_1$-$C_4$ haloalkyl; (hydroxy)$C_1$-$C_4$ alkyl; (amino)$C_1$-$C_4$ alkyl; ($C_1$-$C_4$ alkoxy)$C_1$-$C_4$ alkyl; (5- to 9-membered heteroaryl)$C_1$-$C_4$ alkyl; unsubstituted 5- or 6-membered heteroaryl; substituted 5- or 6-membered heteroaryl having one or two substituents independently selected from the group consisting of halo and $C_1$-$C_4$ alkyl; unsubstituted 4- to 14-membered heterocyclo; and substituted 4- to 14-membered heterocyclo having one or two substituents independently selected from the group consisting of hydroxy, amino, and $C_1$-$C_4$ alkyl; or $R^{5i}$ and $R^{5j}$ taken together with the nitrogen atom to which they are attached form an optionally substituted 4- to 14-membered heterocyclo;

$R^{5k}$ and $R^{5l}$ are independently selected from the group consisting of hydrogen; $C_1$-$C_4$ alkyl; $C_1$-$C_4$ haloalkyl; (hydroxy)$C_1$-$C_4$ alkyl; (amino)$C_1$-$C_4$ alkyl; ($C_1$-$C_4$ alkoxy)$C_1$-$C_4$ alkyl; (5- to 9-membered heteroaryl)$C_1$-$C_4$ alkyl; unsubstituted 5- or 6-membered heteroaryl; substituted 5- or 6-membered heteroaryl having one or two substituents independently selected from the group consisting of halo and $C_1$-$C_4$ alkyl; unsubstituted 4- to 14-membered heterocyclo; and substituted 4- to 14-membered heterocyclo having one or two substituents independently selected from the group consisting of hydroxy, amino, and $C_1$-$C_4$ alkyl; or $R^{5k}$ and $R^{5l}$ taken together with the nitrogen atom to which they are attached form an optionally substituted 4- to 14-membered heterocyclo;

$R^{5m}$ and $R^{5n}$ are independently selected from the group consisting of hydrogen; $C_1$-$C_4$ alkyl; $C_1$-$C_4$ haloalkyl; (hydroxy)$C_1$-$C_4$ alkyl; (amino)$C_1$-$C_4$ alkyl; ($C_1$-$C_4$ alkoxy)$C_1$-$C_4$ alkyl; (5- to 9-membered heteroaryl)$C_1$-$C_4$ alkyl; unsubstituted 5- or 6-membered heteroaryl; substituted 5- or 6-membered heteroaryl having one or two substituents independently selected from the group consisting of halo and $C_1$-$C_4$ alkyl; unsubstituted 4- to 14-membered heterocyclo; and substituted 4- to 14-membered heterocyclo having one or two substituents independently selected from the group consisting of hydroxy, amino, and $C_1$-$C_4$ alkyl; or $R^{5m}$ and $R^{5n}$ taken together with the nitrogen atom to which they are attached form an optionally substituted 4- to 14-membered heterocyclo;

$R^{5o}$ and $R^{5p}$ are independently selected from the group consisting of hydrogen; $C_1$-$C_4$ alkyl; $C_1$-$C_4$ haloalkyl; (hydroxy)$C_1$-$C_4$ alkyl; (amino)$C_1$-$C_4$ alkyl; ($C_1$-$C_4$ alkoxy)$C_1$-$C_4$ alkyl; (5- to 9-membered heteroaryl)$C_1$-$C_4$ alkyl; unsubstituted 5- or 6-membered heteroaryl; substituted 5- or 6-membered heteroaryl having one or two substituents independently selected from the group consisting of halo and $C_1$-$C_4$ alkyl; unsubstituted 4- to 14-membered heterocyclo; and substituted 4- to 14-membered heterocyclo having one or two substituents independently selected from the group consisting of hydroxy, amino, and $C_1$-$C_4$ alkyl; or $R^{5o}$ and $R^{5p}$ taken together with the nitrogen atom to which they are attached form an optionally substituted 4- to 14-membered heterocyclo;

$R^{5q}$ and $R^{5r}$ are independently selected from the group consisting of hydrogen; $C_1$-$C_4$ alkyl; $C_1$-$C_4$ haloalkyl; (hydroxy)$C_1$-$C_4$ alkyl; (amino)$C_1$-$C_4$ alkyl; ($C_1$-$C_4$ alkoxy)$C_1$-$C_4$ alkyl; (5- to 9-membered heteroaryl)$C_1$-$C_4$ alkyl; unsubstituted 5- or 6-membered heteroaryl; substituted 5- or 6-membered heteroaryl having one or two substituents independently selected from the group consisting of halo and $C_1$-$C_4$ alkyl; unsubstituted 4- to 14-membered heterocyclo; and substituted 4- to 14-membered heterocyclo having one or two substituents independently selected from the group consisting of hydroxy, amino, and $C_1$-$C_4$ alkyl;

$R^{5s}$ and $R^{5t}$ are independently selected from the group consisting of hydrogen; $C_1$-$C_4$ alkyl; $C_1$-$C_4$ haloalkyl; (hydroxy)$C_1$-$C_4$ alkyl; (amino)$C_1$-$C_4$ alkyl; ($C_1$-$C_4$ alkoxy)$C_1$-$C_4$ alkyl; (5- to 9-membered heteroaryl)$C_1$-$C_4$ alkyl; unsubstituted 5- or 6-membered heteroaryl; substituted 5- or 6-membered heteroaryl having one or two substituents independently selected from the group consisting of halo and $C_1$-$C_4$ alkyl; unsubstituted 4- to 14-membered heterocyclo; and substituted 4- to 14-membered heterocyclo having one or two substituents independently selected from the group consisting of hydroxy, amino, and $C_1$-$C_4$ alkyl;

$R^{6a}$, $R^{6b}$, $R^{6c}$, and $R^{6d}$ are each independently selected from the group consisting of hydrogen and $C_1$-$C_4$ alkyl;

$R^8$ is $C_1$-$C_6$ alkyl;

$R^{9a}$ is selected from the group consisting of $C_1$-$C_6$ alkyl; unsubstituted $C_3$-$C_8$ cycloalkyl; and substituted $C_3$-$C_8$ cycloalkyl having one or two substituents independently selected from the group consisting of halo, $C_1$-$C_4$ alkyl, amino, and (amino)$C_1$-$C_4$ alkyl;

$R^{9b}$ is selected from the group consisting of $C_1$-$C_6$ alkyl and amino;

$R^{10a}$ is selected from the group consisting of alkyl, (hydroxy)$C_1$-$C_4$ alkyl, and (amino)$C_1$-$C_4$ alkyl;

$R^{10b}$ is (amino)$C_1$-$C_4$ alkyl; and $R^{10c}$ is (amino)$C_1$-$C_4$ alkyl, or a pharmaceutically acceptable salt or solvate thereof.

In another embodiment, Compounds of the Disclosure are compounds having Formula III or Formula III-A, wherein $R^{2b}$ is an optionally substituted 3- to 10-membered heterocycle linked to the rest of the molecule through a nitrogen atom, e.g., $R^{2b}$ is:

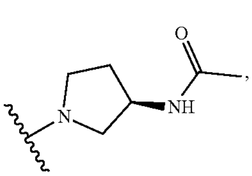,
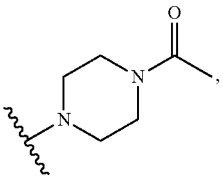,
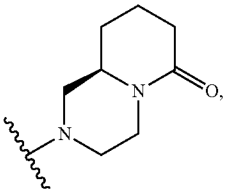,
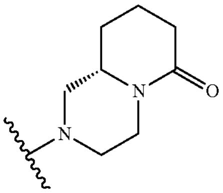

and the like.

In another embodiment, Compounds of the Disclosure are compounds having Formula III or Formula III-A, wherein:

$R^{2b}$ is selected from the group consisting of:

$R^{2b}$-1

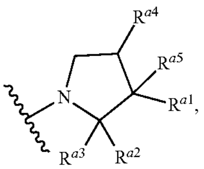

$R^{2b}$-2

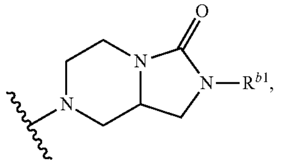

$R^{2b}$-3

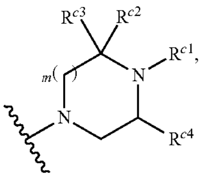

-continued $R^{2b}$-4

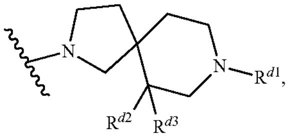

$R^{2b}$-5

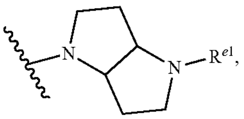

$R^{2b}$-6

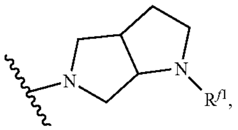

$R^{2b}$-7

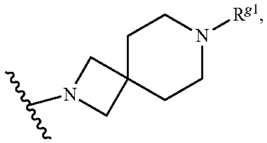

$R^{2b}$-8

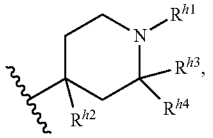

$R^{2b}$-9

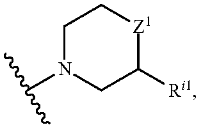

$R^{2b}$-10

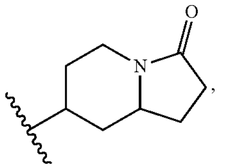

$R^{2b}$-11

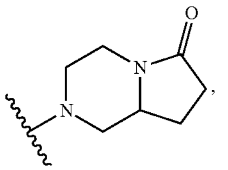

$R^{2b}$-12

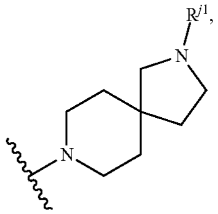

-continued

R$^{2b}$-13

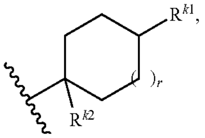

R$^{2b}$-14

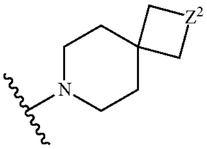

R$^{2b}$-15

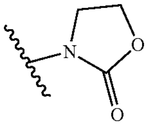

R$^{2b}$-16

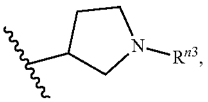

R$^{2b}$-17

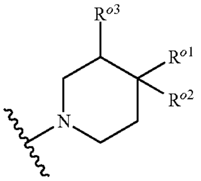

R$^{2b}$-18

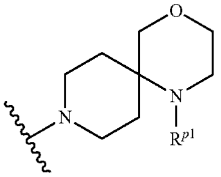

R$^{2b}$-19

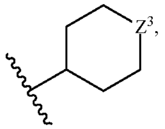

R$^{2b}$-20

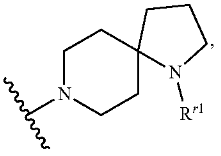

R$^{2b}$-21

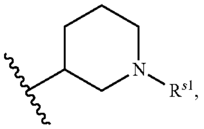

R$^{2b}$-22

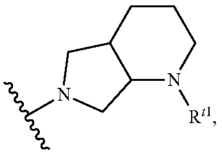

-continued

R$^{2b}$-23

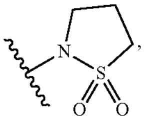

R$^{2b}$-24

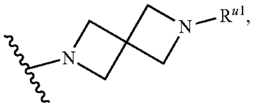

R$^{2b}$-25

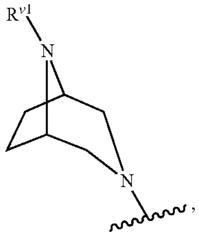

R$^{2b}$-26

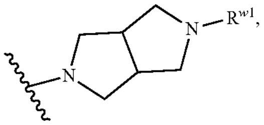

R$^{2b}$-27

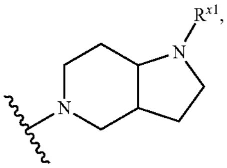

R$^{2b}$-28

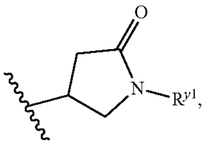

R$^{2b}$-29

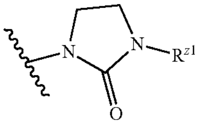

and

R$^{2b}$-30

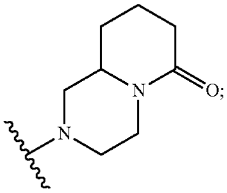

$R^{a1}$ is selected from the group consisting of —$N(R^{3a})C(=O)R^{4a}$; —$NR^{5a}R^{5b}$; unsubstituted 4- to 10-membered heterocyclo; substituted 4- to 10-membered heterocyclo having one, two, or three substituents independently selected from the group consisting of hydroxy, —$NR^{5}cR^{5d}$, $C_1$-$C_4$ alkyl, $C_1$-$C_6$ alkoxy, —$C(R^{6a})(R^{6b})C(=O)NR^{5e}R^{5f}$, —$C(=O)R^{4b}$, (hydroxy)$C_1$-$C_4$ alkyl, and halo;

$R^{a2}$ and $R^{a3}$ are each hydrogen; or $R^{a2}$ and $R^{a3}$ taken together with the carbon atom to which they are attached form a C(=O) group;

$R^{a4}$ is selected from the group consisting of hydrogen, halo, and hydroxy;

$R^{a5}$ is selected from the group consisting of hydrogen, $C_1$-$C_4$ alkyl, and $C_3$-$C_6$ cycloalkyl;

$R^{b1}$ is selected from the group consisting of hydrogen, $C_1$-$C_4$ alkyl, and $C_3$-$C_6$ cycloalkyl;

$R^{c1}$ is selected from the group consisting of hydrogen, $C_1$-$C_4$ alkyl, $C_3$-$C_6$ cycloalkyl, and —C(═O)$R^{4c}$;

$R^{c2}$ and $R^{c3}$ are each independently selected from the group consisting of hydrogen, $C_1$-$C_4$ alkyl, and $C_1$-$C_4$ haloalkyl; or $R^{c2}$ and $R^{c3}$ taken together with the carbon atom to which they are attached form a C(═O) group;

$R^{c4}$ is selected from the group consisting of hydrogen and $C_1$-$C_4$ alkyl;

m is 1 or 2;

$R^{d1}$ is selected from the group consisting of hydrogen, $C_1$-$C_4$ alkyl, and —C(═O)$R^{4c}$, $R^{d2}$ and $R^{d3}$ are each independently selected from the group consisting of hydrogen and fluoro;

$R^{e1}$ is selected from the group consisting of hydrogen, $C_1$-$C_4$ alkyl, $C_3$-$C_6$ cycloalkyl, and —C(═O)$R^{4c}$;

$R^{f1}$ is selected from the group consisting of hydrogen, $C_1$-$C_4$ alkyl, $C_3$-$C_6$ cycloalkyl, and —C(═O)$R^{4c}$, $R^{g1}$ is selected from the group consisting of hydrogen, $C_1$-$C_4$ alkyl, —C(═O)$R^{4c}$, $C_1$-$C_4$ haloalkyl, ($C_1$-$C_4$ alkoxy) $C_1$-$C_4$ alkyl $R^{h1}$ is selected from the group consisting of hydrogen, $C_1$-$C_4$ alkyl, $C_3$-$C_6$ cycloalkyl, and —C(═O)$R^{4c}$;

$R^{h2}$ is selected from the group consisting of hydrogen and $C_1$-$C_4$ alkyl;

$R^{h3}$ and $R^{h4}$ are each independently selected from the group consisting of hydrogen and $C_1$-$C_4$ alkyl; or $R^{h3}$ and $R^{h4}$ taken together with the carbon atom to which they are attached form a C(═O) group;

$R^{i1}$ is selected from the group consisting of hydrogen, $C_1$-$C_4$ alkyl, $C_3$-$C_6$ cycloalkyl, (hydroxy)$C_1$-$C_4$ alkyl, —N($R^{3a}$)C(═O)$R^{4a}$, and (amino)$C_1$-$C_4$ alkyl;

$Z^1$ is selected from the group consisting of —$CH_2$— and —O—;

$R^{j1}$ is selected from the group consisting of hydrogen, $C_1$-$C_4$ alkyl, $C_3$-$C_6$ cycloalkyl, and —C(═O)$R^{4c}$;

$R^{k1}$ is selected from the group consisting of $C_1$-$C_4$ alkyl, unsubstituted 4- to 14-membered heterocyclo and —$NR^{5a}R^{5b}$;

$R^{k2}$ is selected from the group consisting of hydrogen, hydroxy, and $C_1$-$C_4$ alkyl;

r is 0, 1, or 2;

$Z^2$ is selected from the group consisting of —O— and —N($R^{m3}$)—;

$R^{m3}$ is selected from the group consisting of hydrogen, $C_1$-$C_4$ alkyl, and $C_1$-$C_4$ haloalkyl;

$R^{n3}$ is selected from the group consisting of hydrogen, $C_1$-$C_4$ alkyl, and —C(═O)$R^{4c}$;

$R^{o1}$ is selected from the group consisting of hydroxy, (hydroxy)$C_1$-$C_4$ alkyl, (amino)$C_1$-$C_4$ alkyl, ($C_1$-$C_4$ alkoxy) $C_1$-$C_4$ alkyl, $C_1$-$C_4$ alkoxy, —$NR^{5a}R^{5b}$, unsubstituted 4- to 14-membered heterocyclo, substituted 4- to 14-membered heterocyclo having one, two, or three substituents independently selected from the group consisting of halo, $C_1$-$C_4$ alkyl and $C_1$-$C_4$ alkoxy;

$R^{o2}$ is selected from the group consisting of hydrogen, $C_1$-$C_4$ alkyl, and ($C_1$-$C_4$ alkoxy)$C_1$-$C_4$ alkyl $R^{o3}$ is selected from the group consisting of hydrogen, fluoro, and $C_1$-$C_4$ alkyl;

$R^{p1}$ is selected from the group consisting of hydrogen, $C_1$-$C_4$ alkyl, and —C(═O)$R^{4c}$;

$Z^3$ is selected from the group consisting of —O— and —N($R^{q1}$)—;

$R^{q1}$ is selected from the group consisting of hydrogen and $C_1$-$C_4$ alkyl;

$R^{r1}$ is selected from the group consisting of hydrogen, $C_1$-$C_4$ alkyl, and —C(═O)$R^{4c}$;

$R^{s1}$ is selected from the group consisting of hydrogen, $C_1$-$C_4$ alkyl, and —C(═O)$R^{4c}$;

$R^{t1}$ is selected from the group consisting of hydrogen, $C_1$-$C_4$ alkyl, and —C(═O)$R^{4c}$;

$R^{u1}$ is selected from the group consisting of hydrogen, $C_1$-$C_4$ alkyl, and —C(═O)$R^{4c}$;

$R^{v1}$ is selected from the group consisting of hydrogen, $C_1$-$C_4$ alkyl, and —C(═O)$R^{4c}$;

$R^{s1}$ is selected from the group consisting of hydrogen, $C_1$-$C_4$ alkyl, and —C(═O)$R^{4c}$;

$R^{x1}$ is selected from the group consisting of hydrogen, $C_1$-$C_4$ alkyl, and —C(═O)$R^{4c}$;

$R^{y1}$ is selected from the group consisting of hydrogen and $C_1$-$C_4$ alkyl; and $R^{z1}$ is selected from the group consisting of hydrogen and $C_1$-$C_4$ alkyl, or a pharmaceutically acceptable salt or solvate thereof.

In another embodiment, Compounds of the Disclosure are compounds having Formula III or Formula III-A, wherein:

$R^{2b}$ is selected from the group consisting of:

$R^{2b}$-1A

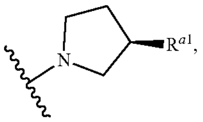

$R^{2b}$-1B

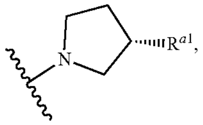

$R^{2b}$-1C

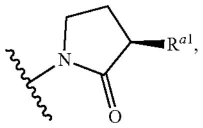

$R^{2b}$-1D

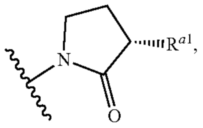

$R^{2b}$-2A

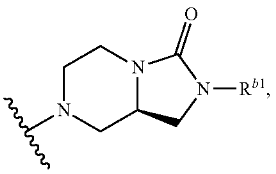

$R^{2b}$-2B

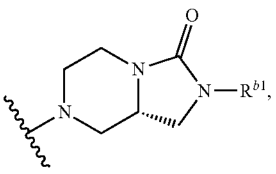

-continued
$R^{2b}$-3A
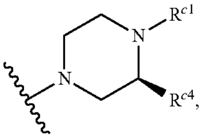
$R^{2b}$-3B
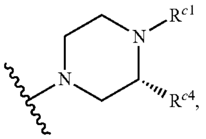
$R^{2b}$-5A
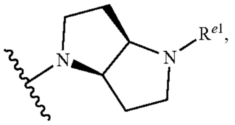
$R^{2b}$-5B
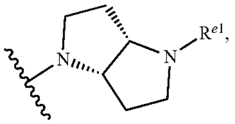
$R^{2b}$-6A
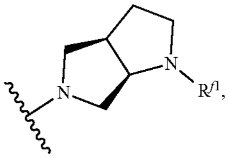
$R^{2b}$-6B
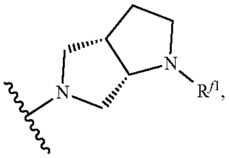
$R^{2b}$-8A
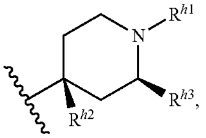
$R^{2b}$-8B
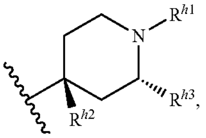
$R^{2b}$-8C
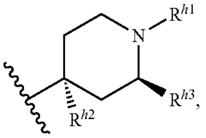
$R^{2b}$-8D
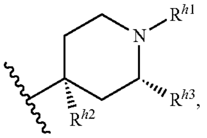
-continued
$R^{2b}$-10A
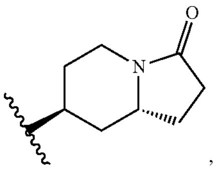
,
$R^{2b}$-10B
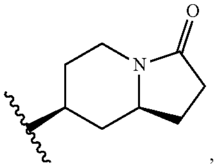
,
$R^{2b}$-10C
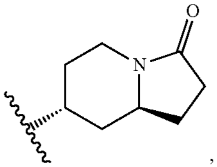
,
$R^{2b}$-10D
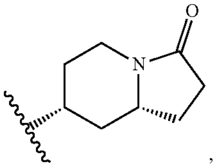
,
$R^{2b}$-11A
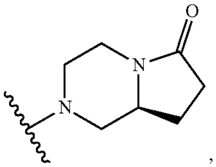
,
$R^{2b}$-11B
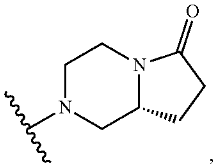
,
$R^{2b}$-13A
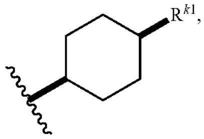
$R^{2b}$-13B
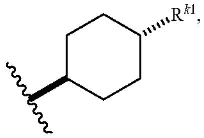
$R^{2b}$-13C
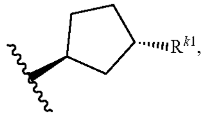

-continued $R^{2b}$-13D

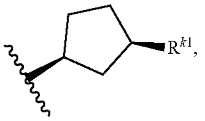

$R^{2b}$-13E

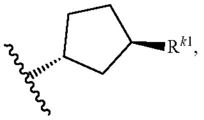

$R^{2b}$-13F

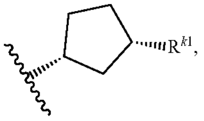

$R^{2b}$-16A

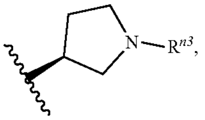

$R^{2b}$-16B

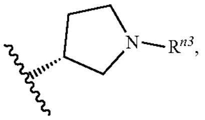

$R^{2b}$-21A

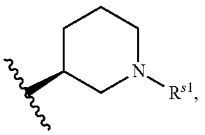

$R^{2b}$-21B

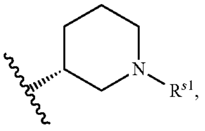

$R^{2b}$-22A

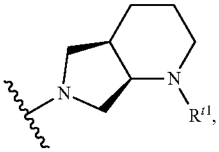

$R^{2b}$-22B

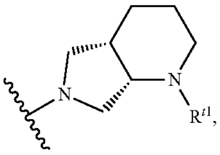

$R^{2b}$-26A

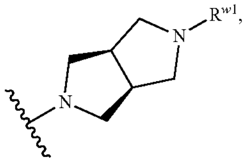

-continued $R^{2b}$-26B

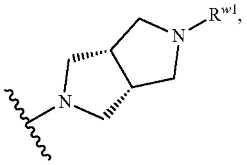

$R^{2b}$-27A

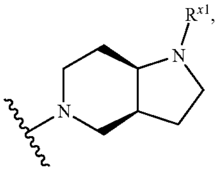

$R^{2b}$-27B

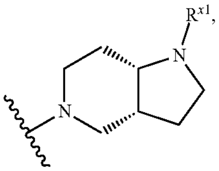

$R^{2b}$-28A

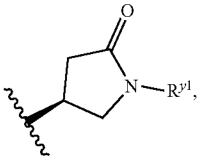

$R^{2b}$-28B

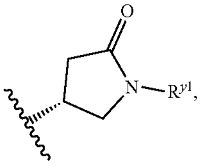

$R^{2b}$-30A

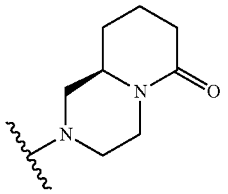

and $R^{2b}$-30B

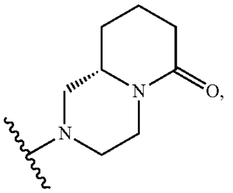

or a pharmaceutically acceptable salt or solvate thereof.

In another embodiment, Compounds of the Disclosure are compounds having Formula III or Formula III-A, wherein $R^{2b}$ is $R^{2b}$-1, $R^{2b}$-1A, $R^{2b}$-1B, $R^{2b}$-1C, or $R^{2b}$-1D, or a pharmaceutically acceptable salt or solvate thereof. In another embodiment, $R^{a1}$ is —N($R^{3a}$)C(═O)$R^{4a}$. In another embodiment, $R^{a1}$ is —$NR^{5a}R^{5b}$. In another embodiment, $R^{a1}$ is —$NR^{5a}R^{5b}$ and $R^{5a}$ and $R^{5b}$ are independently selected from the group consisting of hydrogen and $C_1$-$C_4$ alkyl. In another embodiment, $R^{a1}$ is optionally substituted 4- to 10-membered heterocyclo.

In another embodiment, Compounds of the Disclosure are compounds having Formula III or Formula III-A, wherein $R^{2b}$ is $R^{2b}$-2, $R^{2b}$-2A, or $R^{2b}$-2b, or a pharmaceutically acceptable salt or solvate thereof. In another embodiment, $R^{b1}$ is $C_1$-$C_4$ alkyl.

In another embodiment, Compounds of the Disclosure are compounds having Formula III or Formula III-A, wherein $R^{2b}$ is $R^{2b}$-3, $R^{2b}$-3A, or $R^{2b}$-3B, or a pharmaceutically acceptable salt or solvate thereof. In another embodiment, $R^{c1}$ is selected from the group consisting of $C_1$-$C_4$ alkyl, $C_3$-$C_6$ cycloalkyl, and —C(═O)$R^{4c}$. In another embodiment, $R^{c2}$ and $R^{c3}$ are each hydrogen. In another embodiment, $R^{c2}$ and $R^{c3}$ taken together with the carbon atom to which they are attached form a C(═O) group. In another embodiment, $R^{c4}$ is hydrogen. In another embodiment, m is 1.

In another embodiment, Compounds of the Disclosure are compounds having Formula III or Formula III-A, wherein $R^{2b}$ is $R^{2b}$-4, or a pharmaceutically acceptable salt or solvate thereof. In another embodiment, $R^{d1}$ is C(═O)$R^{4c}$. In another embodiment, $R^{d2}$ and $R^{d3}$ are each hydrogen or fluoro.

In another embodiment, Compounds of the Disclosure are compounds having Formula III or Formula III-A, wherein $R^{2b}$ is $R^{2b}$-5, $R^{2b}$-5A, or $R^{2b}$-5B, or a pharmaceutically acceptable salt or solvate thereof. In another embodiment, $R^{e1}$ is —C(═O)$R^{4c}$.

In another embodiment, Compounds of the Disclosure are compounds having Formula III or Formula III-A, wherein $R^{2b}$ is $R^{2b}$-6, $R^{2b}$-6A, or $R^{2b}$-6B, or a pharmaceutically acceptable salt or solvate thereof. In another embodiment, $R^{f1}$ is C(═O)$R^{4c}$.

In another embodiment, Compounds of the Disclosure are compounds having Formula III or Formula III-A, wherein $R^{2b}$ is $R^{2b}$-7, or a pharmaceutically acceptable salt or solvate thereof. In another embodiment, $R^{g1}$ is C(═O)$R^{4c}$.

In another embodiment, Compounds of the Disclosure are compounds having Formula III or Formula III-A, wherein $R^{2b}$ is $R^{2b}$-8, $R^{2b}$-8A, $R^{2b}$-8B, $R^{2b}$-8C, or $R^{2b}$-8D, or a pharmaceutically acceptable salt or solvate thereof. In another embodiment, $R^{h1}$ is —C(═O)$R^{4c}$. In another embodiment, $R^{h2}$ is selected from the group consisting of hydrogen and $C_1$-$C_3$ alkyl. In another embodiment, $R^{h3}$ is hydrogen.

In another embodiment, Compounds of the Disclosure are compounds having Formula III or Formula III-A, wherein $R^{2b}$ is $R^{2b}$-9, or a pharmaceutically acceptable salt or solvate thereof.

In another embodiment, Compounds of the Disclosure are compounds having Formula III or Formula III-A, wherein $R^{2b}$ is selected from the group consisting of $R^{2b}$-10, $R^{2b}$-10A, $R^{2b}$-10B, $R^{2b}$-10C, and $R^{2b}$-10d, or a pharmaceutically acceptable salt or solvate thereof.

In another embodiment, Compounds of the Disclosure are compounds having Formula III or Formula III-A, wherein $R^{2b}$ is selected from the group consisting of $R^{2b}$-11, $R^{2b}$-11A and $R^{2b}$-11B, or a pharmaceutically acceptable salt or solvate thereof.

In another embodiment, Compounds of the Disclosure are compounds having Formula III or Formula III-A, wherein $R^{2b}$ is $R^{2b}$-12, or a pharmaceutically acceptable salt or solvate thereof. In another embodiment, $R^{j1}$ is —C(═O)$R^{4c}$.

In another embodiment, Compounds of the Disclosure are compounds having Formula III or Formula III-A, wherein $R^{2b}$ is selected from the group consisting of $R^{2b}$-13, $R^{2b}$-13A, $R^{2b}$-13B, $R^{2b}$-13C, $R^{2b}$-13D, $R^{2b}$-13E, and $R^{2b}$-13F, or a pharmaceutically acceptable salt or solvate thereof.

In another embodiment, Compounds of the Disclosure are compounds having Formula III or Formula III-A, wherein $R^{2b}$ is $R^{2b}$-14, or a pharmaceutically acceptable salt or solvate thereof.

In another embodiment, Compounds of the Disclosure are compounds having Formula III or Formula III-A, wherein $R^{2b}$ is $R^{2b}$-15, or a pharmaceutically acceptable salt or solvate thereof.

In another embodiment, Compounds of the Disclosure are compounds having Formula III or Formula III-A, wherein $R^{2b}$ is selected from the group consisting of $R^{2b}$-16, $R^{2b}$-16A and $R^{2b}$-16B, or a pharmaceutically acceptable salt or solvate thereof. In another embodiment, $R^{n3}$ is —C(═O)$R^{4c}$.

In another embodiment, Compounds of the Disclosure are compounds having Formula III or Formula III-A, wherein $R^{2b}$ is $R^{2b}$-17, or a pharmaceutically acceptable salt or solvate thereof.

In another embodiment, Compounds of the Disclosure are compounds having Formula III or Formula III-A, wherein $R^{2b}$ is $R^{2b}$-18, or a pharmaceutically acceptable salt or solvate thereof.

In another embodiment, Compounds of the Disclosure are compounds having Formula III or Formula III-A, wherein $R^{2b}$ is $R^{2b}$-19, or a pharmaceutically acceptable salt or solvate thereof.

In another embodiment, Compounds of the Disclosure are compounds having Formula III or Formula III-A, wherein $R^{2b}$ is $R^{2b}$-20, or a pharmaceutically acceptable salt or solvate thereof.

In another embodiment, Compounds of the Disclosure are compounds having Formula III or Formula III-A, wherein $R^{2b}$ is selected from the group consisting of $R^{2b}$-21, $R^{2b}$-21A and $R^{2b}$-21B, or a pharmaceutically acceptable salt or solvate thereof.

In another embodiment, Compounds of the Disclosure are compounds having Formula III, wherein $R^{2b}$ is selected from the group consisting of $R^{2b}$-22, $R^{2b}$-22A and $R^{2b}$-22B, or a pharmaceutically acceptable salt or solvate thereof.

In another embodiment, Compounds of the Disclosure are compounds having Formula III or Formula III-A, wherein $R^{2b}$ is $R^{2b}$-23, or a pharmaceutically acceptable salt or solvate thereof.

In another embodiment, Compounds of the Disclosure are compounds having Formula III or Formula III-A, wherein $R^{2b}$ is $R^{2b}$-24, or a pharmaceutically acceptable salt or solvate thereof.

In another embodiment, Compounds of the Disclosure are compounds having Formula III or Formula III-A, wherein $R^{2b}$ is $R^{2b}$-25, or a pharmaceutically acceptable salt or solvate thereof.

In another embodiment, Compounds of the Disclosure are compounds having Formula III or Formula III-A, wherein $R^{2b}$ is selected from the group consisting of $R^{2b}$-26, $R^{2b}$-26A and $R^{2b}$-26B, or a pharmaceutically acceptable salt or solvate thereof.

In another embodiment, Compounds of the Disclosure are compounds having Formula III or Formula III-A, wherein $R^{2b}$ is selected from the group consisting of $R^{2b}$-27, $R^{2b}$-27A and $R^{2b}$-27B, or a pharmaceutically acceptable salt or solvate thereof.

In another embodiment, Compounds of the Disclosure are compounds having Formula III or Formula III-A, wherein $R^{2b}$ is selected from the group consisting of $R^{2b}$-28, $R^{2b}$-28A and $R^{2b}$-28B, or a pharmaceutically acceptable salt or solvate thereof.

In another embodiment, Compounds of the Disclosure are compounds having Formula III or Formula III-A, wherein $R^{2b}$ is $R^{2b}$-29, or a pharmaceutically acceptable salt or solvate thereof.

In another embodiment, Compounds of the Disclosure are compounds having Formula III or Formula III-A, wherein $R^{2b}$ is $R^{2b}$-30, $R^{2b}$-30A, or $R^{2b}$-30B, or a pharmaceutically acceptable salt or solvate thereof.

In another embodiment, Compounds of the Disclosure are compounds having Formula III or Formula III-A, wherein $R^{2b}$ is any one or more of the $R^{11a}$ groups provided in connection with Formula IV, see below, or a pharmaceutically acceptable salt or solvate thereof.

In another embodiment, Compounds of the Disclosure are compounds having Formula III or Formula III-A, wherein $R^{4c}$ is $C_1$-$C_4$ alkyl, or a pharmaceutically acceptable salt or solvate thereof.

In another embodiment, Compounds of the Disclosure are compounds having Formula III or Formula III-A, wherein $R^{2d}$ is selected from the group consisting of hydrogen, fluoro, and chloro, or a pharmaceutically acceptable salt or solvate thereof.

In another embodiment, Compounds of the Disclosure are compounds having Formula III or Formula III-A, wherein $R^{2d}$ is hydrogen, or a pharmaceutically acceptable salt or solvate thereof.

In another embodiment, Compounds of the Disclosure are compounds having Formula III in any of the above described embodiments, wherein $A^1$ and $A^2$ are —C(H)═; $R^{2e}$ is hydrogen; and $R^{2d}$ is selected from the group consisting of hydrogen and halogen, or a pharmaceutically acceptable salt or solvate thereof.

In another embodiment, Compounds of the Disclosure are compounds having Formula III or Formula III-A, wherein $R^{2d}$ is fluoro, or a pharmaceutically acceptable salt or solvate thereof.

In another embodiment, Compounds of the Disclosure are compounds having Formula IV:

IV

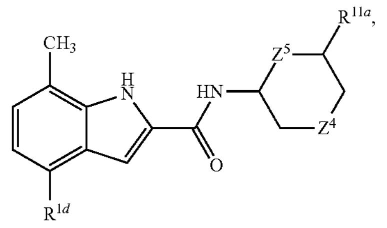

wherein:

$Z^4$ is selected from the group consisting of —O—, —$C(R^{28a})(R^{28b})$—, and —$N(R^{23})$—; or $Z^4$ is absent;

$Z^5$ is selected from the group consisting of —$CH_2$— and —$CH_2CH_2$—;

$R^{11a}$ is selected from the group consisting of optionally substituted alkyl, optionally substituted heterocyclo, optionally substituted heteroaryl, and —$N(R^{12b})C(═O)R^{13c}$;

$R^{12b}$ is selected from the group consisting of hydrogen, alkyl, cycloalkyl, and heterocyclo;

$R^{13c}$ is selected from the group consisting of alkyl, haloalkyl, alkoxy, (alkoxy)alkyl, (hydroxy)alkyl, (cyano)alkyl, optionally substituted aryl, optionally substituted heteroaryl, optionally substituted cycloalkyl, and optionally substituted heterocycle, amino, (amino)alkyl, ($C_3$-$C_6$ cycloalkyl)oxy, and (4- to 8-membered heterocyclo)oxy;

$R^{23}$ is selected from the group consisting of hydrogen and $C_1$-$C_4$ alkyl;

$R^{28a}$ and $R^{28b}$ are independently selected from the group consisting of hydrogen, alkyl, and halo; and $R^{1d}$ is as defined in connection with Formula I, or a pharmaceutically acceptable salt or solvate thereof.

In another embodiment, Compounds of the Disclosure are compounds having Formula IV, wherein $Z^4$ is selected from the group consisting of —O— and —$CH_2$—; or $Z^4$ is absent, or a pharmaceutically acceptable salt or solvate thereof.

In another embodiment, Compounds of the Disclosure are compounds having Formula IV, wherein:

$Z^4$ is selected from the group consisting of —O— and —$CH_2$—; or $Z^4$ is absent;

$Z^5$ is selected from the group consisting of —$CH_2$— and —$CH_2CH_2$—;

$R^{13c}$ is selected from the group consisting of alkyl, haloalkyl, alkoxy, (alkoxy)alkyl, (hydroxy)alkyl, (cyano)alkyl, optionally substituted aryl, optionally substituted heteroaryl, optionally substituted cycloalkyl, and optionally substituted heterocycle, and $R^{1d}$ is as defined in connection with Formula I, or a pharmaceutically acceptable salt or solvate thereof.

In another embodiment, Compounds of the Disclosure are compounds having Formula IV-A:

IV-A

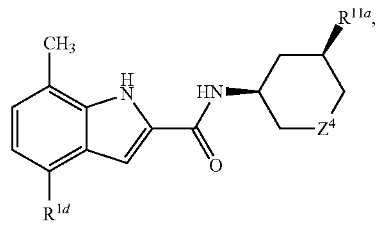

or a pharmaceutically acceptable salt or solvate thereof, wherein $R^{1d}$, $R^{11a}$ and $Z^4$ are as defined in connection with Formula IV.

In another embodiment, Compounds of the Disclosure are compounds having Formula IV-B:

IV-B

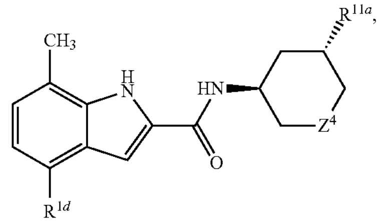

or a pharmaceutically acceptable salt or solvate thereof, wherein $R^{1d}$, $R^{11a}$ and $Z^4$ are as defined in connection with Formula IV.

In another embodiment, Compounds of the Disclosure are compounds having Formula IV-C:

IV-C

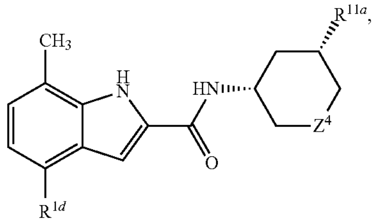

or a pharmaceutically acceptable salt or solvate thereof, wherein $R^{1d}$, $R^{11a}$ and $Z^4$ are as defined in connection with Formula IV.

In another embodiment, Compounds of the Disclosure are compounds having Formula IV-D:

IV-D

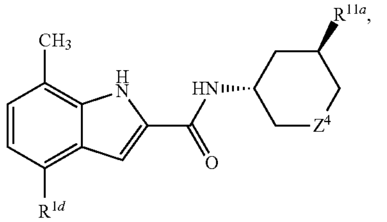

or a pharmaceutically acceptable salt or solvate thereof, wherein $R^{1d}$, $R^{11a}$ and $Z^4$ are as defined in connection with Formula IV.

In another embodiment, Compounds of the Disclosure are compounds having any one of Formulae IV, IV-A, IV-B, IV-C, or IV-D, wherein:

$R^{11a}$ is selected from the group consisting of: (A) unsubstituted 4- to 14-membered heterocyclo; (B) substituted 4- to 14-membered heterocyclo having one, two or three substituents independently selected from the group consisting of —$N(R^{12a})C(=O)R^{13a}$; —$C(=O)R^{13b}$; $C_1$-$C_4$ alkyl; ($C_1$-$C_4$ alkoxy)$C_1$-$C_4$ alkyl; (hydroxy)$C_1$-$C_4$ alkyl; $C_1$-$C_4$ haloalkyl; amino; hydroxy; —$N(R^{12a})S(=O)_2R^{24}$; —$S(=O)_2R^{24}$; unsubstituted $C_3$-$C_6$ cycloalkyl; substituted $C_3$-$C_6$ cycloalkyl having one or two substituents independently selected from the group consisting of halo, hydroxy, $C_1$-$C_4$ alkyl, amino, and (amino)$C_1$-$C_4$ alkyl; unsubstituted 4- to 14-membered heterocyclo; and substituted 4- to 14-membered heterocyclo having one or two substituents independently selected from the group consisting of amino, hydroxy, and $C_1$-$C_4$ alkyl; (C) unsubstituted 5- to 10-membered heteroaryl; (D) substituted 5- or 6-membered heteroaryl having one, two, three, or four substituents independently selected from the group consisting of halo, $C_1$-$C_4$ alkyl, and (amino)alkyl; (E) $C_1$-$C_6$ alkyl; and (F) —$N(R^{12b})C(=O)R^{13c}$;

$R^{12a}$ and $R^{12b}$ are each independently selected from the group consisting of hydrogen, $C_1$-$C_4$ alkyl, ($C_1$-$C_4$ alkoxy) $C_1$-$C_4$ alkyl, and (hydroxy)$C_1$-$C_4$ alkyl;

$R^{13a}$, $R^{13b}$, and $R^{13c}$ are each independently selected from the group consisting of $C_1$-$C_6$ alkyl; $C_1$-$C_6$ haloalkyl; unsubstituted $C_3$-$C_6$ cycloalkyl; $C_1$-$C_6$ alkoxy; ($C_1$-$C_4$ alkoxy)$C_1$-$C_4$ alkyl; (hydroxy)$C_1$-$C_4$ alkyl; (cyano)alkyl; unsubstituted $C_6$-$C_{10}$ aryl; substituted $C_6$-$C_{10}$ aryl, having one, two, three, or four substituents independently selected from the group consisting of halo, amino, hydroxy, and $C_1$-$C_4$ alkyl; unsubstituted 5- or 6-membered heteroaryl; substituted 5- or 6-membered heteroaryl having one, two, three, or four substituents independently selected from the group consisting of halo, amino, hydroxy, and $C_1$-$C_4$ alkyl; unsubstituted 4- to 14-membered heterocyclo; substituted 4- to 14-membered heterocyclo having one or two substituents independently selected from the group consisting of amino, hydroxy, and $C_1$-$C_4$ alkyl; amino; (amino)alkyl; ($C_3$-$C_6$ cycloalkyl)oxy; and (4- to 8-membered heterocyclo)oxy; and $R^{24}$ is selected from the group consisting of $C_1$-$C_4$ alkyl and (hydroxy)$C_1$-$C_4$ alkyl.

In another embodiment, Compounds of the Disclosure are compounds having Formula IV, IV-A, IV-B, IV-C, or IV-D, wherein $Z^4$ is —$C(R^{28a})(R^{28b})$—; and $R^{28a}$ and $R^{28b}$ are independently selected from the group consisting of hydrogen, $C_1$-$C_4$ alkyl, and fluoro, or a pharmaceutically acceptable salt or solvate thereof.

In another embodiment, Compounds of the Disclosure are compounds having Formula IV, IV-A, IV-B, IV-C, or IV-D, wherein $Z^4$ is —$C(R^{28a})(R^{28b})$—; $R^{28a}$ is hydrogen; and $R^{28b}$ is selected from the group consisting of $C_1$-$C_4$ alkyl and fluoro, or a pharmaceutically acceptable salt or solvate thereof.

In another embodiment, Compounds of the Disclosure are compounds having Formula IV, IV-A, IV-B, IV-C, or IV-D, wherein $Z^4$ is —$C(R^{28a})(R^{28b})$—; and $R^{28a}$ and $R^{28b}$ are independently $C_1$-$C_4$ alkyl, or a pharmaceutically acceptable salt or solvate thereof.

In another embodiment, Compounds of the Disclosure are compounds having Formula IV, IV-A, IV-B, IV-C, or IV-D, wherein $Z^4$ is selected from the group consisting of —O—, —$CH_2$—, and —$N(R^{23})$, or $Z^4$ is absent, or a pharmaceutically acceptable salt or solvate thereof.

In another embodiment, Compounds of the Disclosure are compounds having any one of Formulae IV, IV-A, IV-B, IV-C, or IV-D, wherein $Z^4$ is —$CH_2$—, or a pharmaceutically acceptable salt or solvate thereof.

In another embodiment, Compounds of the Disclosure are compounds having any one of Formulae IV, IV-A, IV-B, IV-C, or IV-D, wherein $R^{11a}$ is an optionally substituted 3- to 10-membered heterocycle linked to the rest of the molecule through a nitrogen atom, e.g., $R^{11a}$ is

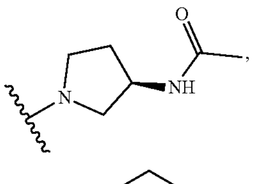

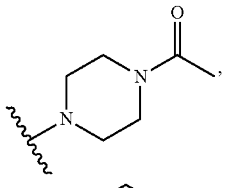

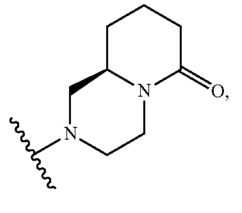

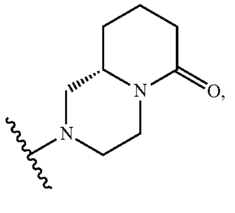

and the like.

In another embodiment, Compounds of the Disclosure are compounds having any one of Formulae IV, IV-A, IV-B, IV-C, or IV-D, wherein $R^{11a}$ is a substituted 4- to 14-membered heterocyclo selected from the group consisting of:

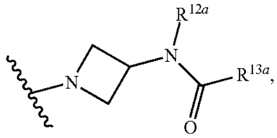
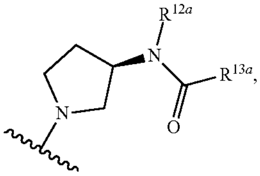
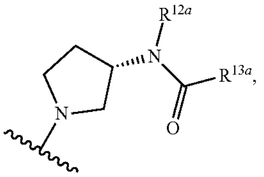
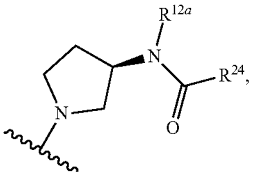
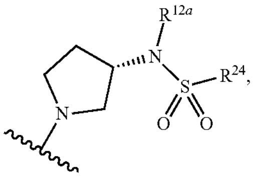
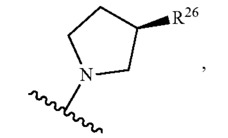
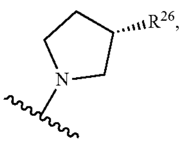
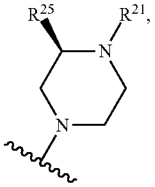
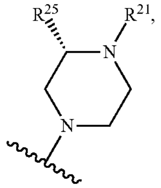
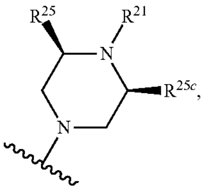
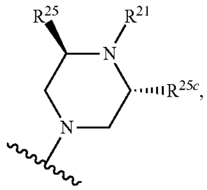
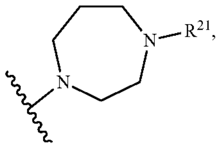
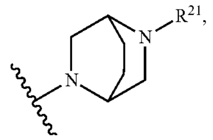
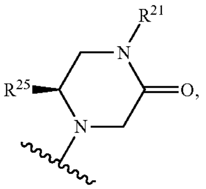
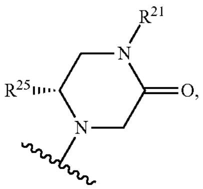
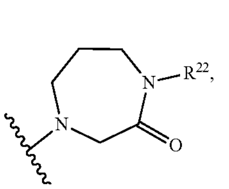
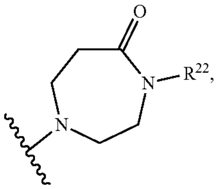
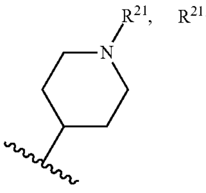
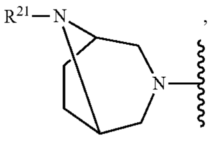

-continued

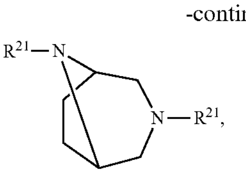
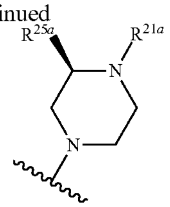

and

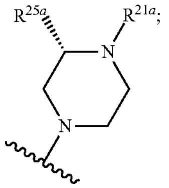

$R^{12a}$ is selected from the group consisting of hydrogen, $C_1$-$C_3$ alkyl, ($C_1$-$C_4$ alkoxy)$C_1$-$C_4$ alkyl; and (hydroxy)$C_1$-$C_4$ alkyl;

$R^{13a}$ is selected from the group consisting of $C_1$-$C_4$ alkyl; amino; unsubstituted $C_3$-$C_6$ cycloalkyl; substituted $C_3$-$C_6$ cycloalkyl having one or two substituents independently selected from the group consisting of halo, hydroxy, $C_1$-$C_4$ alkyl, amino, and (amino)$C_1$-$C_4$ alkyl; ($C_1$-$C_4$ alkoxy)$C_1$-$C_4$ alkyl; (hydroxy)$C_1$-$C_4$ alkyl; unsubstituted 4- to 14-membered heterocyclo; and substituted 4- to 14-membered heterocyclo having one or two substituents independently selected from the group consisting of amino, hydroxy, and $C_1$-$C_4$ alkyl;

$R^{13b}$ is selected from the group consisting of $C_1$-$C_4$ alkyl; amino; $C_1$-$C_4$ haloalkyl; $C_1$-$C_4$ alkoxy; (hydroxy)$C_1$-$C_4$ alkyl; ($C_1$-$C_4$ alkoxy)$C_1$-$C_4$ alkyl; (amino)alkyl; unsubstituted $C_3$-$C_6$ cycloalkyl; substituted $C_3$-$C_6$ cycloalkyl having one or two substituents independently selected from the group consisting of halo, hydroxy, $C_1$-$C_4$ alkyl, amino, and (amino)$C_1$-$C_4$ alkyl; unsubstituted 4- to 14-membered heterocyclo; and substituted 4- to 14-membered heterocyclo having one or two substituents independently selected from the group consisting of amino, hydroxy, and $C_1$-$C_4$ alkyl; ($C_3$-$C_6$ cycloalkyl)oxy; and (4- to 8-membered heterocyclo)oxy;

$R^{21}$ is selected from the group consisting of hydrogen, —C(=O)$R^{13b}$, $C_1$-$C_4$ alkyl, $C_1$-$C_4$ haloalkyl, unsubstituted 4- to 14-membered heterocyclo, and —S(=O)$_2$$R^{24}$;

$R^{22}$ is $C_1$-$C_4$ alkyl; unsubstituted $C_3$-$C_6$ cycloalkyl; substituted $C_3$-$C_6$ cycloalkyl having one or two substituents independently selected from the group consisting of halo, hydroxy, $C_1$-$C_4$ alkyl, amino, and (amino)$C_1$-$C_4$ alkyl; unsubstituted 4- to 14-membered heterocyclo; and substituted 4- to 14-membered heterocyclo having one or two substituents independently selected from the group consisting of amino, hydroxy, and $C_1$-$C_4$ alkyl;

$R^{24}$ is selected from the group consisting of $C_1$-$C_4$ alkyl and (hydroxy)$C_1$-$C_4$ alkyl;

$R^{25}$ is selected from the group consisting of hydrogen, $C_1$-$C_4$ alkyl, and $C_1$-$C_4$ haloalkyl;

$R^{25b}$ and $R^{25c}$ are independently selected from the group consisting of $C_1$-$C_4$ alkyl and $C_1$-$C_4$ haloalkyl;

$R^{26}$ is selected from the group consisting of unsubstituted 4- to 14-membered heterocyclo; and substituted 4- to 14-membered heterocyclo having one or two substituents independently selected from the group consisting of amino, hydroxy, and $C_1$-$C_4$ alkyl; and $R^{21a}$ and $R^{25a}$ taken together with the atoms to which they are attached form an optionally substituted 4- to 8-membered heterocyclo, or a pharmaceutically acceptable salt or solvate thereof.

In another embodiment, Compounds of the Disclosure are compounds having any one of Formulae IV, IV-A, IV-B, IV-C, or IV-D, wherein $R^{11a}$ is selected from the group consisting of:
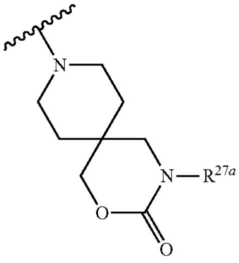
,
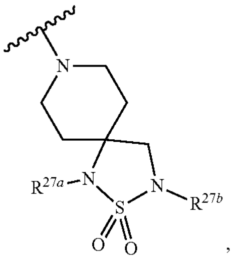
,
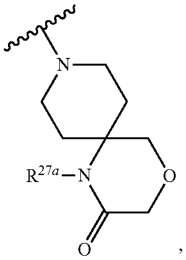
,
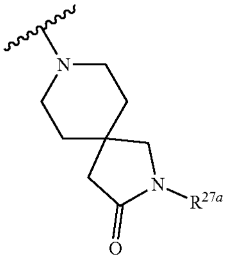
,
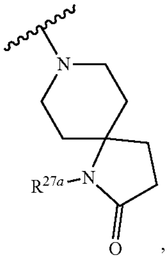
,
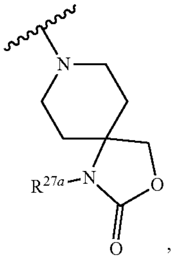
,
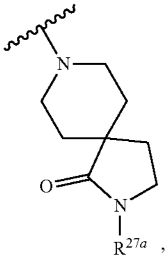
,
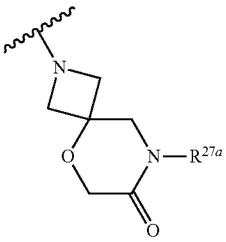
,
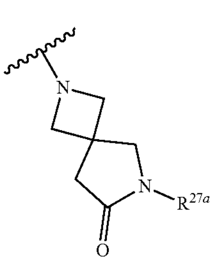
,
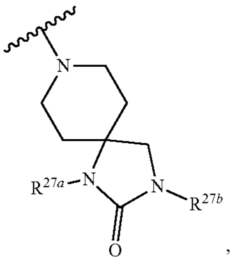
,
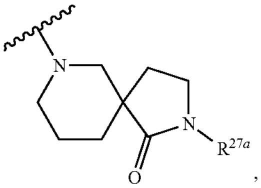
,
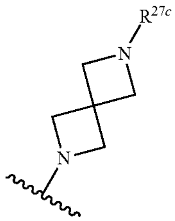
,
-continued
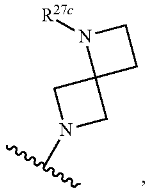
,
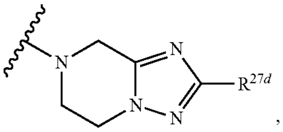
,
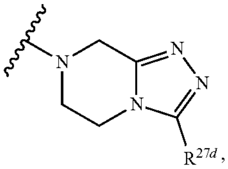
,
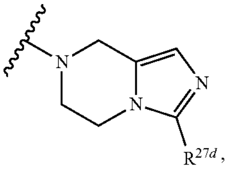
,
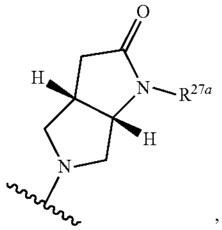
,
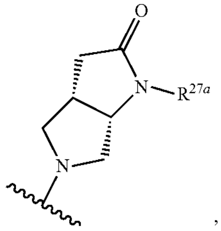
,
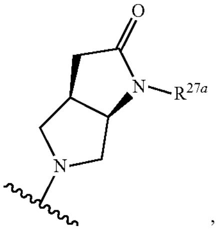
,
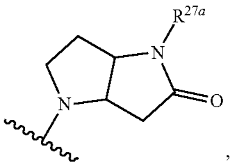
,
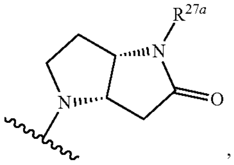
,
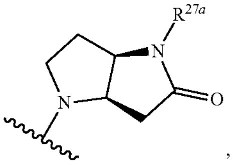
,
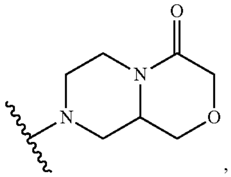
,
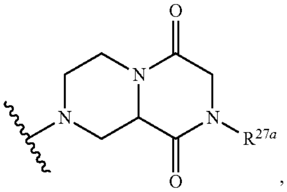
,
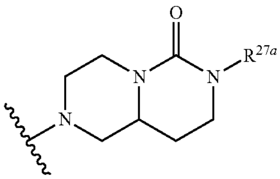
,
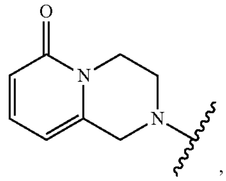
,
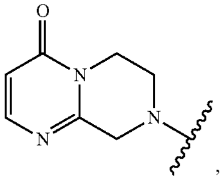
,
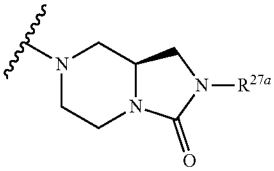
,
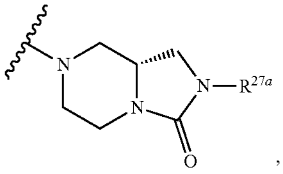
,
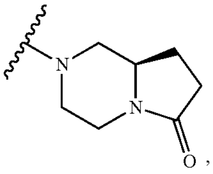
, -continued

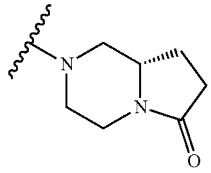,
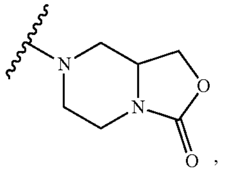,
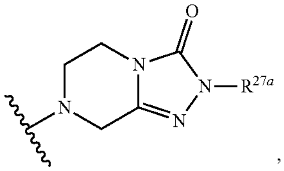,
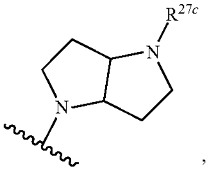,
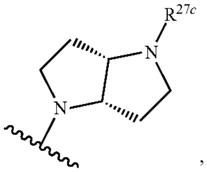,
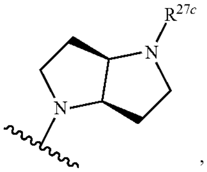,
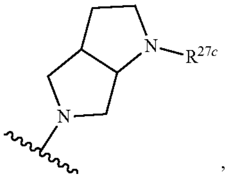,
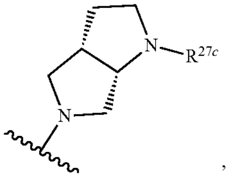,
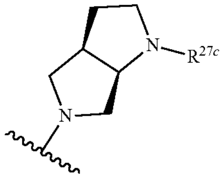
and
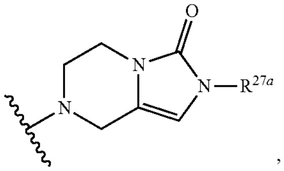, wherein:

$R^{27a}$ and $R^{27b}$ are each independently selected from the group consisting of hydrogen, $C_1$-$C_4$ alkyl, $C_1$-$C_4$ haloalkyl, ($C_1$-$C_4$ alkoxy)$C_1$-$C_4$ alkyl; and (hydroxy)$C_1$-$C_4$ alkyl;

$R^{27c}$ is selected from the group consisting of hydrogen; —C(═O)$R^{13b}$; $C_1$-$C_4$ alkyl; $C_1$-$C_4$ haloalkyl; unsubstituted 4- to 14-membered heterocyclo; and substituted 4- to 14-membered heterocyclo having one or two substituents independently selected from the group consisting of amino, hydroxy, and $C_1$-$C_4$ alkyl; and —S(═O)$_2R^{24}$;

$R^{27d}$ is selected from the group consisting of hydrogen; $C_1$-$C_4$ alkyl; and $C_1$-$C_4$ haloalkyl;

$R^{13b}$ is selected from the group consisting of $C_1$-$C_4$ alkyl; amino$C_1$-$C_4$ haloalkyl; $C_1$-$C_4$ alkoxy; (hydroxy)$C_1$-$C_4$ alkyl; ($C_1$-$C_4$ alkoxy)$C_1$-$C_4$ alkyl; (amino)alkyl; unsubstituted $C_3$-$C_6$ cycloalkyl; substituted $C_3$-$C_6$ cycloalkyl having one or two substituents independently selected from the group consisting of halo, hydroxy, $C_1$-$C_4$ alkyl, amino, and (amino) $C_1$-$C_4$ alkyl; unsubstituted 4- to 14-membered heterocyclo; substituted 4- to 14-membered heterocyclo having one or two substituents independently selected from the group consisting of amino, hydroxy, and $C_1$-$C_4$ alkyl; ($C_3$-$C_6$ cycloalkyl)oxy; and (4- to 8-membered heterocyclo)oxy; and $R^{24}$ is selected from the group consisting of $C_1$-$C_4$ alkyl and (hydroxy)$C_1$-$C_4$ alkyl, or a pharmaceutically acceptable salt or solvate thereof.

In another embodiment, Compounds of the Disclosure are compounds having any one of Formulae IV, IV-A, IV-B, IV-C, or IV-D, wherein $R^{11a}$ is selected from the group consisting of

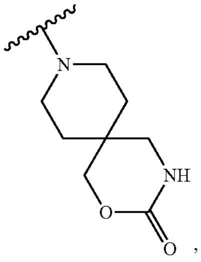,
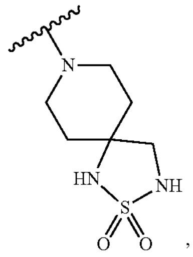,
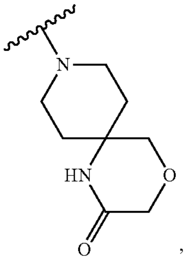,
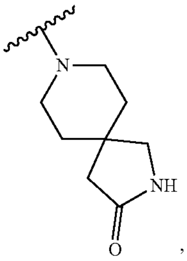,
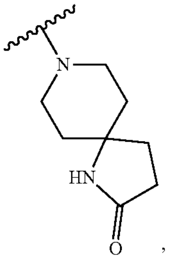,
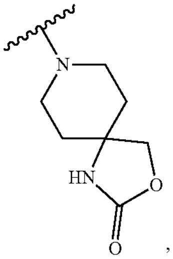,
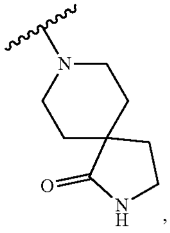,
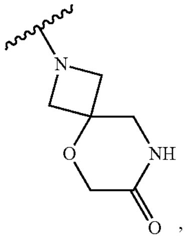,
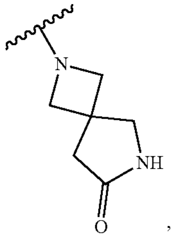,
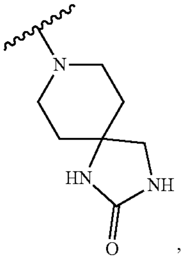,
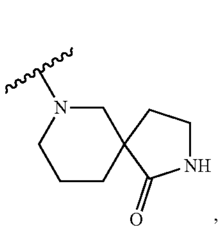,
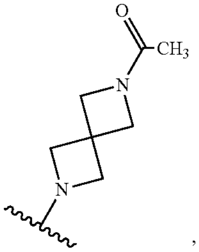, -continued
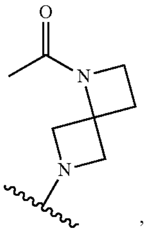
,
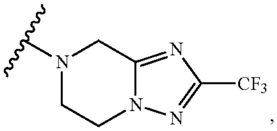
,
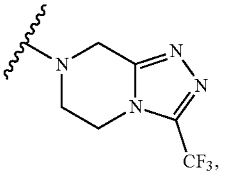
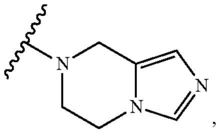
,
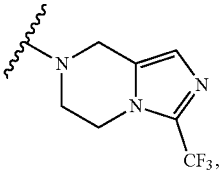
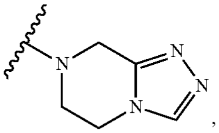
,
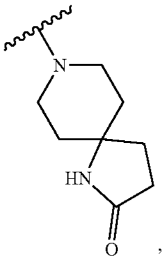
,
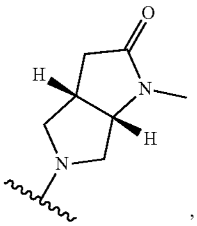
,
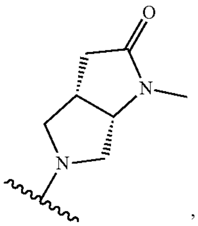
,
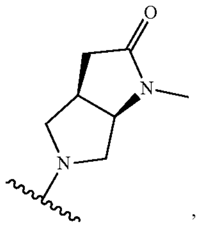
,
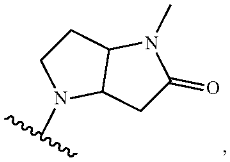
,
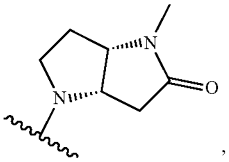
,
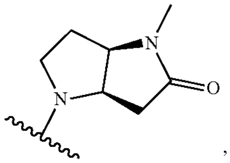
,
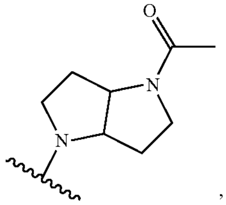
,
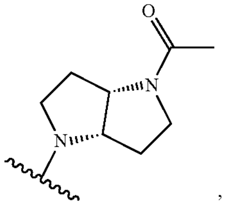
,
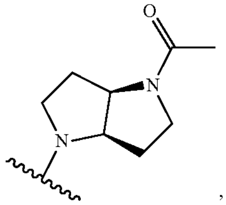
,
-continued
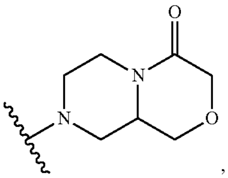
,
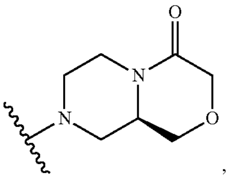
,
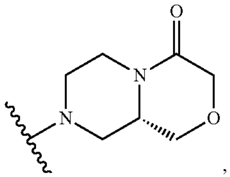
,
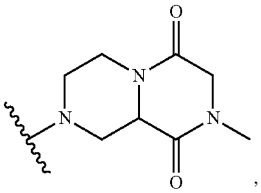
,
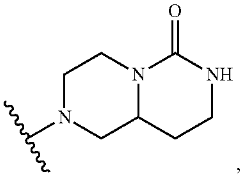
,
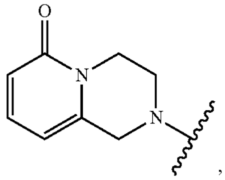
,
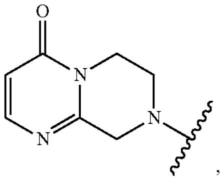
,
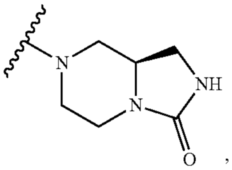
,
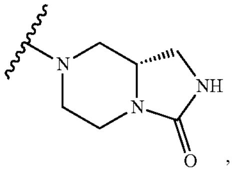
,
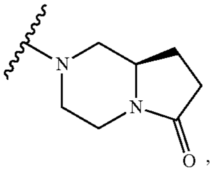
,
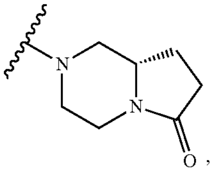
,
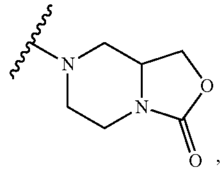
,
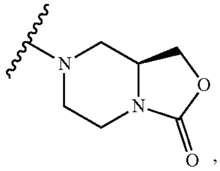
,
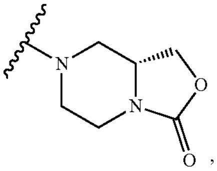
,
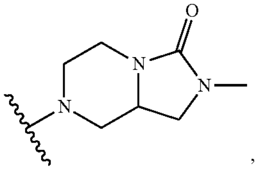
,
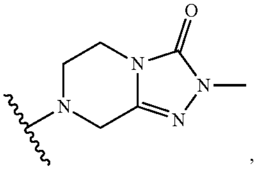
,
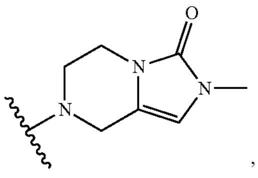
,
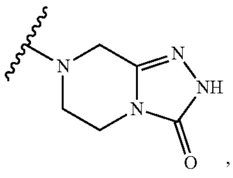
, -continued

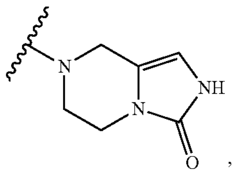
,
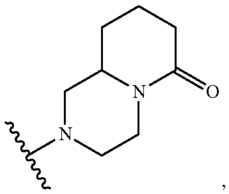
,
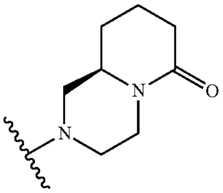
and
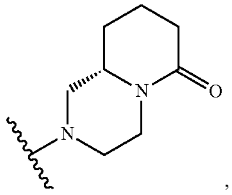
, or a pharmaceutically acceptable salt or solvate thereof In another embodiment, Compounds of the Disclosure are compounds having any one of Formulae IV, IV-A, IV-B, IV-C, or IV-D, wherein $R^{11a}$ is selected from the group consisting of unsubstituted 4- to 14-membered heterocyclo; substituted 4- to 14-membered heterocyclo having one or two substituents independently selected from the group consisting of $—N(R^{12a})C(=O)R^{13a}$, $—C(=O)R^{13b}$, and $C_1$-$C_4$ alkyl; unsubstituted 5- to 10-membered heteroaryl; and substituted 5- or 6-membered heteroaryl having one or two substituents independently selected from the group consisting of halo and $C_1$-$C_4$ alkyl, or a pharmaceutically acceptable salt or solvate thereof.

In another embodiment, Compounds of the Disclosure are compounds having any one of Formulae IV, IV-A, IV-B, IV-C, or IV-D, wherein $R^{11a}$ is a substituted 4- to 14-membered heterocyclo is selected from the group consisting of:

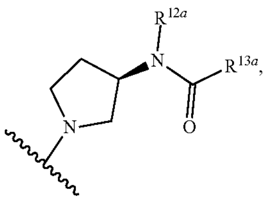
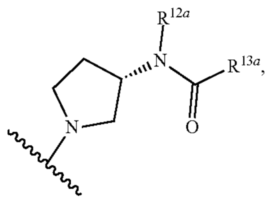
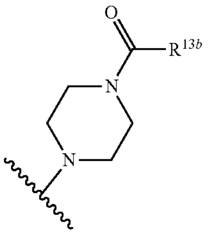
and
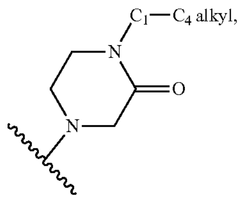

or a pharmaceutically acceptable salt or solvate thereof. In another embodiment, $R^{12}$a is selected from the group consisting of hydrogen and $C_1$-$C_3$ alkyl; $R^{13a}$ is $C_1$-$C_4$ alkyl; and $R^{13b}$ is $C_1$-$C_4$ alkyl, or a pharmaceutically acceptable salt or solvate thereof. In another embodiment, $R^{12a}$ is selected from the group consisting of hydrogen and methyl; $R^{13a}$ is methyl; and $R^{13b}$ is methyl, or a pharmaceutically acceptable salt or solvate thereof.

In another embodiment, Compounds of the Disclosure are compounds having any one of Formulae IV, IV-A, IV-B, IV-C, or IV-D, wherein $R^{11a}$ is any one or more of the $R^{2b}$ groups provided in connection with Formula III, see above, or a pharmaceutically acceptable salt or solvate thereof.

In another embodiment, Compounds of the Disclosure are compounds having any one of Formulae IV, IV-A, IV-B, IV-C, or IV-D, wherein:

$R^{11a}$ is selected from the group consisting of:

$R^{11a}$-1

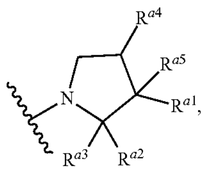

$R^{11a}$-2

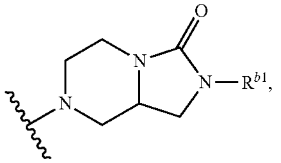

$R^{11a}$-3

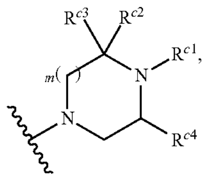

$R^{11a}$-4

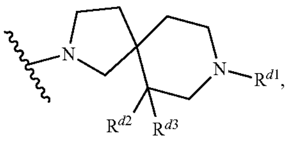

$R^{11a}$-5

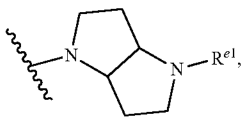

$R^{11a}$-6

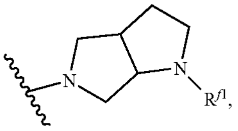

$R^{11a}$-7

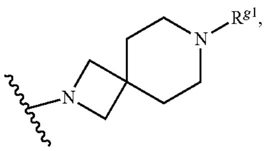

$R^{11a}$-8

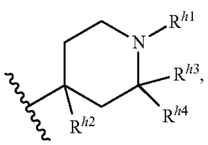

$R^{11a}$-9

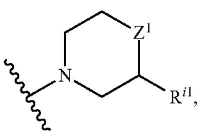

-continued
R$^{11a}$-10
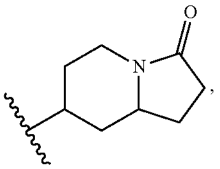
R$^{11a}$-11
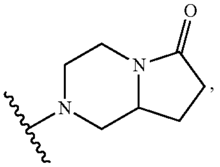
R$^{11a}$-12
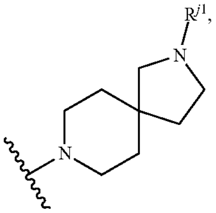
R$^{11a}$-13
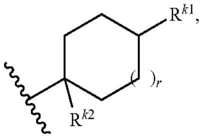
R$^{11a}$-14
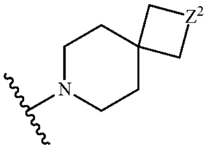
R$^{11a}$-15
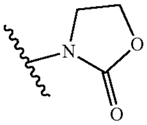
R$^{11a}$-16
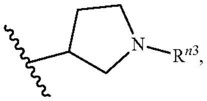
R$^{11a}$-17
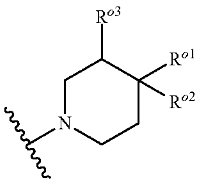
R$^{11a}$-18
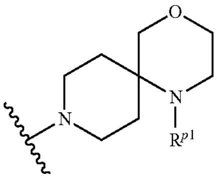
-continued
R$^{11a}$-19
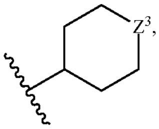
R$^{11a}$-20
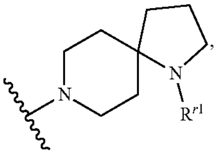
R$^{11a}$-21
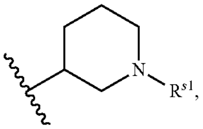
R$^{11a}$-22
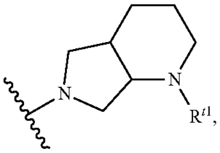
R$^{11a}$-23
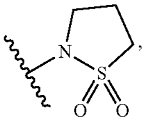
R$^{11a}$-24
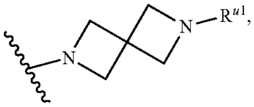
R$^{11a}$-25
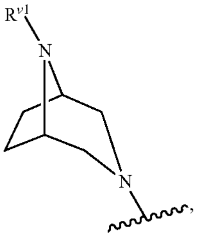
R$^{11a}$-26
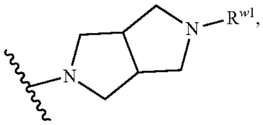
R$^{11a}$-27
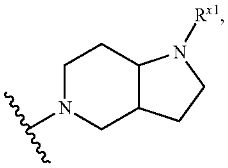

-continued $R^{11a}$-28

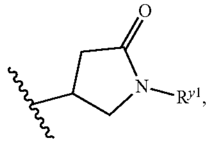

$R^{11a}$-29

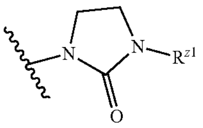

and $R^{11a}$-30

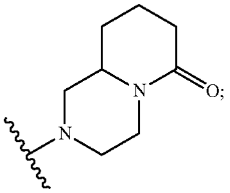

and $R^{a1}$, $R^{a2}$, $R^{a3}$, $R^{a4}$, $R^{a5}$, $R^{b1}$, $R^{c1}$, $R^{c2}$, $R^{c3}$, $R^{c4}$, m, $R^{d1}$, $R^{d2}$, $R^{d3}$, $R^{e1}$, $R^{f1}$, $R^{g1}$, $R^{h1}$, $R^{h2}$, $R^{h3}$, $R^{h4}$, $R^{i1}$, $Z^1$, $R^{j1}$, $R^{k1}$, $R^{k2}$, r, $Z^2$, $R^{n3}$, $R^{o1}$, $R^{o2}$, $R^{o3}$, $R^{p1}$, $Z^3$, $R^{r1}$, $R^{s1}$, $R^{t1}$, $R^{u1}$, $R^{v1}$, $R^{w1}$, $R^{x1}$, $R^{y1}$, and $R^{z1}$ are as defined in connection with Formula III; or a pharmaceutically acceptable salt or solvate thereof.

In another embodiment, Compounds of the Disclosure are compounds having any one of Formulae IV, IV-A, IV-B, IV-C, or IV-D, wherein:

$R^{11a}$ is selected from the group consisting of:

$R^{11a}$-1A

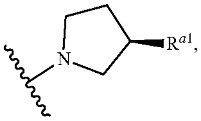

$R^{11a}$-1B

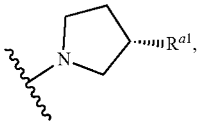

$R^{11a}$-1C

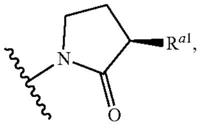

$R^{11a}$-1D

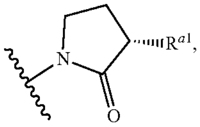

$R^{11a}$-2A

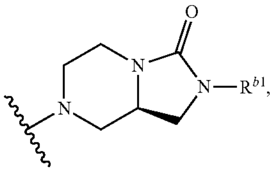

-continued $R^{11a}$-2B

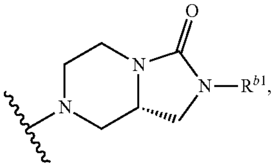

$R^{11a}$-3A

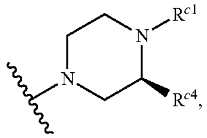

$R^{11a}$-3B

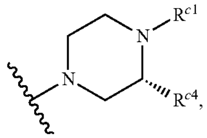

$R^{11a}$-5A

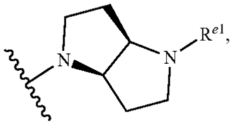

$R^{11a}$-5B

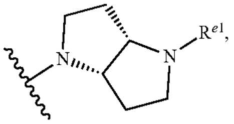

$R^{11a}$-6A

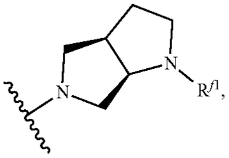

$R^{11a}$-6B

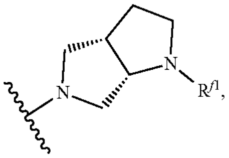

$R^{11a}$-8A

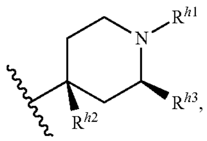

$R^{11a}$-8B

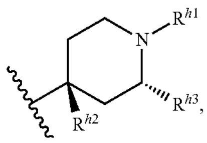

$R^{11a}$-8C

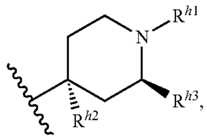

-continued
$R^{11a}$-8D
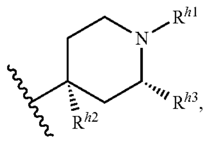
$R^{11a}$-10A
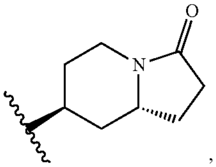
,
$R^{11a}$-10B
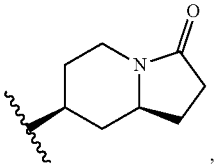
,
$R^{11a}$-10C
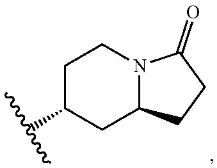
,
$R^{11a}$-10D
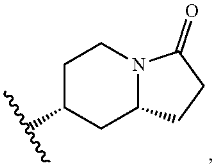
,
$R^{11a}$-11A
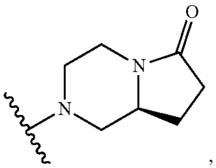
,
$R^{11a}$-11B
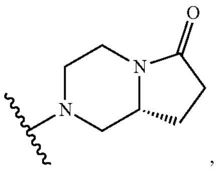
,
$R^{11a}$-13A
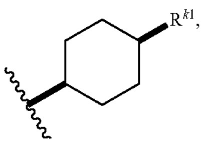
$R^{11a}$-13B
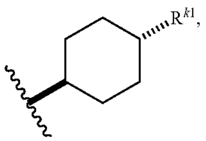
-continued
$R^{11a}$-13C
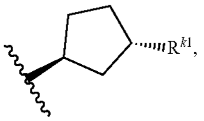
$R^{11a}$-13D
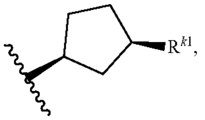
$R^{11a}$-13E
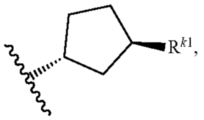
$R^{11a}$-13F
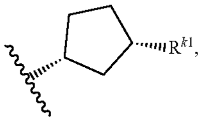
$R^{11a}$-16A
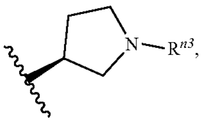
$R^{11a}$-16B
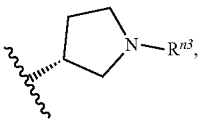
$R^{11a}$-21A
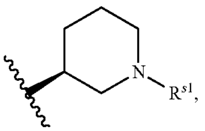
$R^{11a}$-21B
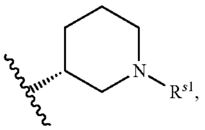
$R^{11a}$-22A
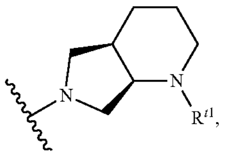
$R^{11a}$-22B
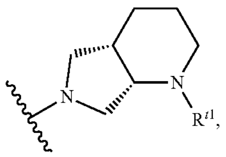

-continued $R^{11a}$-26A

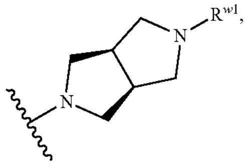

$R^{11a}$-26B

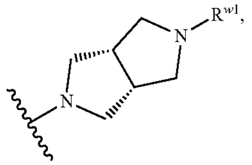

$R^{11a}$-27A

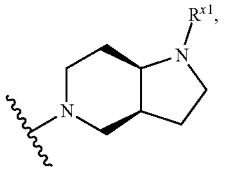

$R^{11a}$-27B

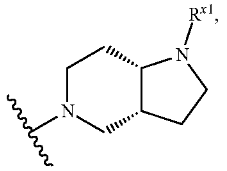

$R^{11a}$-28A

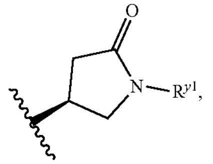

$R^{11a}$-28B

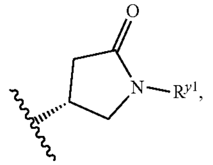

$R^{11a}$-30A

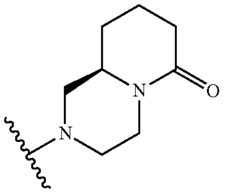

and $R^{11a}$-30B

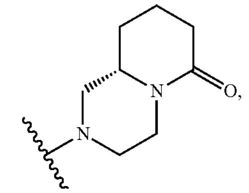

and $R^{a1}$, $R^{a5}$, $R^{b1}$, $R^{c1}$, $R^{f1}$, $R^{h1}$, $R^{h2}$, $R^{h3}$, $R^{k1}$, $R^{n3}$, $R^{s1}$, $R^{t1}$, $R^{w1}$, $R^{x1}$, and $R^{y1}$ are as defined in connection with Formula III; or a pharmaceutically acceptable salt or solvate thereof.

In another embodiment, Compounds of the Disclosure are compounds having any one of Formulae IV, IV-A, IV-B, IV-C, or IV-D, wherein $R^{11a}$ is $R^{11a}$-1, $R^{11a}$-1A, $R^{11a}$-1B, $R^{11a}$-1C, or $R^{11a}$-1D, or a pharmaceutically acceptable salt or solvate thereof. In another embodiment, $R^{a1}$ is —N($R^{3a}$)C(═O)$R^{4a}$. In another embodiment, $R^{a1}$ is —$NR^{5a}R^{5b}$. In another embodiment, $R^{a1}$ is —$NR^{5a}R^{5b}$ and $R^{5a}$ and $R^{5b}$ are independently selected from the group consisting of hydrogen and $C_1$-$C_4$ alkyl. In another embodiment, $R^{a1}$ is optionally substituted 4- to 10-membered heterocyclo.

In another embodiment, Compounds of the Disclosure are compounds having any one of Formulae IV, IV-A, IV-B, IV-C, or IV-D, wherein $R^{11a}$ is $R^{11a}$-2, $R^{11a}$-2A or $R^{11a}$-2b, or a pharmaceutically acceptable salt or solvate thereof. In another embodiment, $R^{b1}$ is $C_1$-$C_4$ alkyl.

In another embodiment, Compounds of the Disclosure are compounds having any one of Formulae IV, IV-A, IV-B, IV-C, or IV-D, wherein $R^{11a}$ is $R^{11a}$-3, $R^{11a}$-3A, or $R^{11a}$-3B, or a pharmaceutically acceptable salt or solvate thereof. In another embodiment, $R^{c1}$ is selected from the group consisting of $C_1$-$C_4$ alkyl, $C_3$-$C_6$ cycloalkyl, and —C(═O)$R^{4c}$. In another embodiment, $R^{c2}$ and $R^{c3}$ are each hydrogen. In another embodiment, $R^{c2}$ and $R^{c3}$ taken together with the carbon atom to which they are attached form a C(═O) group. In another embodiment, $R^{c4}$ is hydrogen. In another embodiment, m is 1.

In another embodiment, Compounds of the Disclosure are compounds having any one of Formulae IV, IV-A, IV-B, IV-C, or IV-D, wherein $R^{11a}$ is $R^{11a}$-4, or a pharmaceutically acceptable salt or solvate thereof. In another embodiment, $R^{d1}$ is C(═O)$R^{4c}$. In another embodiment, $R^{d2}$ and $R^{d3}$ are each hydrogen or fluoro.

In another embodiment, Compounds of the Disclosure are compounds having any one of Formulae IV, IV-A, IV-B, IV-C, or IV-D, wherein $R^{11a}$ is $R^{11a}$-5, $R^{11a}$-5A, or $R^{11a}$-5B, or a pharmaceutically acceptable salt or solvate thereof. In another embodiment, $R^{e1}$ is —C(═O)$R^{4c}$.

In another embodiment, Compounds of the Disclosure are compounds having any one of Formulae IV, IV-A, IV-B, IV-C, or IV-D, wherein $R^{11a}$ is $R^{11a}$-6, $R^{11a}$-6A, or $R^{11a}$-6B, or a pharmaceutically acceptable salt or solvate thereof. In another embodiment, $R^{f1}$ is C(═O)$R^{4c}$.

In another embodiment, Compounds of the Disclosure are compounds having any one of Formulae IV, IV-A, IV-B, IV-C, or IV-D, wherein $R^{11a}$ is $R^{11a}$-7, or a pharmaceutically acceptable salt or solvate thereof. In another embodiment, $R^{g1}$ is C(═O)$R^{4c}$.

In another embodiment, Compounds of the Disclosure are compounds having any one of Formulae IV, IV-A, IV-B, IV-C, or IV-D, wherein $R^{11a}$ is $R^{11a}$-8, $R^{11a}$-8A, $R^{11a}$-8B, $R^{11a}$-8C or $R^{11a}$-8D, or a pharmaceutically acceptable salt or solvate thereof. In another embodiment, $R^{h1}$ is —C(═O)$R^{4c}$. In another embodiment, $R^{h2}$ is selected from the group consisting of hydrogen and $C_1$-$C_3$ alkyl. In another embodiment, $R^{h3}$ is hydrogen.

In another embodiment, Compounds of the Disclosure are compounds any one of Formulae IV, IV-A, IV-B, IV-C, or IV-D, wherein $R^{11a}$ is $R^{11a}$-9, or a pharmaceutically acceptable salt or solvate thereof.

In another embodiment, Compounds of the Disclosure are compounds having any one of Formulae IV, IV-A, IV-B, IV-C, or IV-D, wherein $R^{11a}$ is selected from the group consisting of $R^{11a}$-10, $R^{11a}$-10A, $R^{11a}$-10B, $R^{11a}$-10C, and $R^{11a}$-10d, or a pharmaceutically acceptable salt or solvate thereof.

In another embodiment, Compounds of the Disclosure are compounds having any one of Formulae IV, IV-A, IV-B, IV-C, or IV-D, wherein $R^{11a}$ is selected from the group consisting of $R^{11a}$-11, $R^{11a}$-11A and $R^{11a}$-11B, or a pharmaceutically acceptable salt or solvate thereof.

In another embodiment, Compounds of the Disclosure are compounds having any one of Formulae IV, IV-A, IV-B, IV-C, or IV-D, wherein $R^{11a}$ is $R^{11a}$-12, or a pharmaceutically acceptable salt or solvate thereof. In another embodiment, $R^{j1}$ is —C(═O)$R^{4c}$.

In another embodiment, Compounds of the Disclosure are compounds having any one of Formulae IV, IV-A, IV-B, IV-C, or IV-D, wherein $R^{11a}$ is selected from the group consisting of $R^{11a}$-13, $R^{11a}$-13A, $R^{11a}$-13B, $R^{11a}$-13C, $R^{11a}$-13D, $R^{11a}$-13E, and $R^{11a}$-13F, or a pharmaceutically acceptable salt or solvate thereof.

In another embodiment, Compounds of the Disclosure are compounds having any one of Formulae IV, IV-A, IV-B, IV-C, or IV-D, wherein $R^{11a}$ is $R^{11a}$-14, or a pharmaceutically acceptable salt or solvate thereof.

In another embodiment, Compounds of the Disclosure are compounds having any one of Formulae IV, IV-A, IV-B, IV-C, or IV-D, wherein $R^{11a}$ is $R^{11a}$-15, or a pharmaceutically acceptable salt or solvate thereof.

In another embodiment, Compounds of the Disclosure are compounds having any one of Formulae IV, IV-A, IV-B, IV-C, or IV-D, wherein $R^{11a}$ is selected from the group consisting of $R^{11a}$-16, $R^{11a}$-16A and $R^{11a}$-16B, or a pharmaceutically acceptable salt or solvate thereof. In another embodiment, $R^{n3}$ is —C(═O)$R^{4c}$.

In another embodiment, Compounds of the Disclosure are compounds having any one of Formulae IV, IV-A, IV-B, IV-C, or IV-D, wherein $R^{11a}$ is $R^{11a}$-17, or a pharmaceutically acceptable salt or solvate thereof.

In another embodiment, Compounds of the Disclosure are compounds having any one of Formulae IV, IV-A, IV-B, IV-C, or IV-D, wherein $R^{11a}$ is $R^{11a}$-18, or a pharmaceutically acceptable salt or solvate thereof.

In another embodiment, Compounds of the Disclosure are compounds having any one of Formulae IV, IV-A, IV-B, IV-C, or IV-D, wherein $R^{11a}$ is $R^{11a}$-19, or a pharmaceutically acceptable salt or solvate thereof.

In another embodiment, Compounds of the Disclosure are compounds having any one of Formulae IV, IV-A, IV-B, IV-C, or IV-D, wherein $R^{11a}$ is $R^{11a}$-20, or a pharmaceutically acceptable salt or solvate thereof.

In another embodiment, Compounds of the Disclosure are compounds having any one of Formulae IV, IV-A, IV-B, IV-C, or IV-D, wherein $R^{11a}$ is selected from the group consisting of $R^{11a}$-21, $R^{11a}$-21A and $R^{11a}$-21B, or a pharmaceutically acceptable salt or solvate thereof.

In another embodiment, Compounds of the Disclosure are compounds having any one of Formulae IV, IV-A, IV-B, IV-C, or IV-D, wherein $R^{11a}$ is selected from the group consisting of $R^{11a}$-22, $R^{11a}$-22A and $R^{11a}$-22B, or a pharmaceutically acceptable salt or solvate thereof.

In another embodiment, Compounds of the Disclosure are compounds having any one of Formulae IV, IV-A, IV-B, IV-C, or IV-D, wherein $R^{11a}$ is $R^{11a}$-23, or a pharmaceutically acceptable salt or solvate thereof.

In another embodiment, Compounds of the Disclosure are compounds having any one of Formulae IV, IV-A, IV-B, IV-C, or IV-D, wherein $R^{11a}$ is $R^{11a}$-24, or a pharmaceutically acceptable salt or solvate thereof.

In another embodiment, Compounds of the Disclosure are compounds having any one of Formulae IV, IV-A, IV-B, IV-C, or IV-D, wherein $R^{11a}$ is $R^{11a}$-25, or a pharmaceutically acceptable salt or solvate thereof.

In another embodiment, Compounds of the Disclosure are compounds having any one of Formulae IV, IV-A, IV-B, IV-C, or IV-D, wherein $R^{11a}$ is selected from the group consisting of $R^{11a}$-26, $R^{11a}$-26A and $R^{11a}$-26B, or a pharmaceutically acceptable salt or solvate thereof.

In another embodiment, Compounds of the Disclosure are compounds having any one of Formulae IV, IV-A, IV-B, IV-C, or IV-D, wherein $R^{11a}$ is selected from the group consisting of $R^{11a}$-27, $R^{11a}$-27A and $R^{11a}$-27B, or a pharmaceutically acceptable salt or solvate thereof.

In another embodiment, Compounds of the Disclosure are compounds having any one of Formulae IV, IV-A, IV-B, IV-C, or IV-D, wherein $R^{11a}$ is selected from the group consisting of $R^{11a}$-28, $R^{11a}$-28A and $R^{11a}$-28B, or a pharmaceutically acceptable salt or solvate thereof.

In another embodiment, Compounds of the Disclosure are compounds having any one of Formulae IV, IV-A, IV-B, IV-C, or IV-D, wherein $R^{11a}$ is $R^{11a}$-29, or a pharmaceutically acceptable salt or solvate thereof.

In another embodiment, Compounds of the Disclosure are compounds having any one of Formulae IV, IV-A, IV-B, IV-C, or IV-D, wherein $R^{11a}$ is $R^{11a}$-30, $R^{11a}$-30A, or $R^{11a}$-30B, or a pharmaceutically acceptable salt or solvate thereof.

In another embodiment, Compounds of the Disclosure are compounds having any one of Formulae IV-A, IV-B, IV-C, or IV-D, wherein:

$Z^4$ is —$CH_2$—;

$R^{11a}$ is selected from the group consisting of:

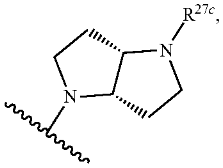,
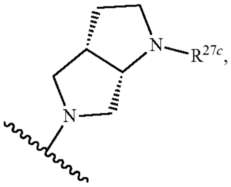,
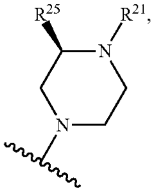,
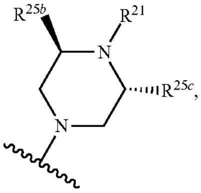,
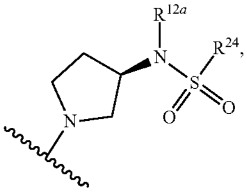,
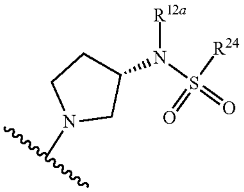 and
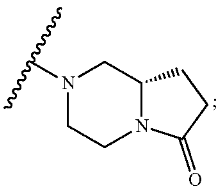;

$R^{12a}$ is selected from the group consisting of hydrogen and $C_1$-$C_3$ alkyl;

$R^{21}$ is —C(═O)$R^{13b}$;

$R^{27c}$ is —C(═O)$R^{13b}$;

$R^{13b}$ is selected from the group consisting of $C_1$-$C_4$ alkyl and (hydroxy)$C_1$-$C_4$ alkyl;

$R^{24}$ is $C_1$-$C_4$ alkyl;

$R^{25}$ is selected from the group consisting of hydrogen, $C_1$-$C_4$ alkyl, and $C_1$-$C_4$ haloalkyl; and $R^{25b}$ and $R^{25c}$ are independently selected from the group consisting of $C_1$-$C_4$ alkyl and $C_1$-$C_4$ haloalkyl, or a pharmaceutically acceptable salt or solvate thereof.

In another embodiment, Compounds of the Disclosure are compounds having any one of Formulae IV-A, IV-B, IV-C, or IV-D, wherein:

$Z^4$ is —$CH_2$—; and $R^{11a}$ is selected from the group consisting of:

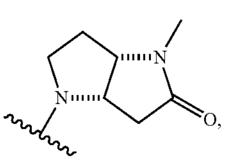

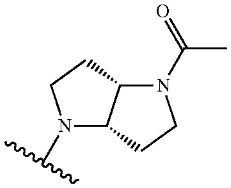

,

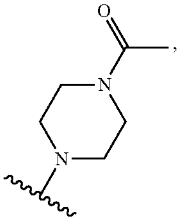

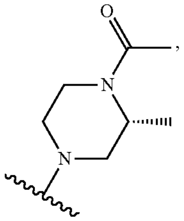

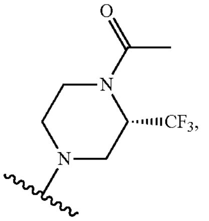

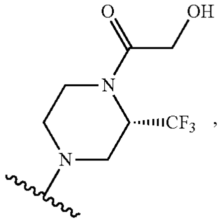

,

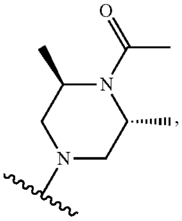

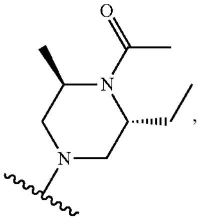

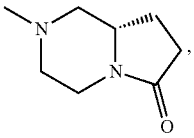

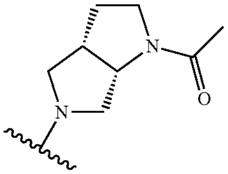

and

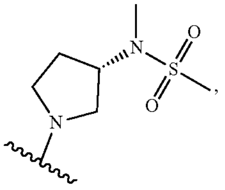

or a pharmaceutically acceptable salt or solvate thereof.

In another embodiment, Compounds of the Disclosure are compounds having any one of Formulae IV-A, IV-B, IV-C, or IV-D, wherein:

$Z^4$ is —$CH_2$—; and $R^{11a}$ is selected from the group consisting of:

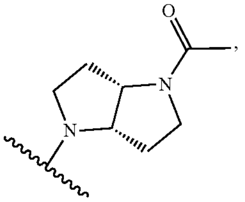

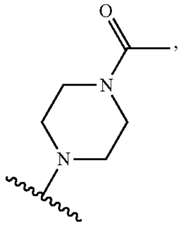

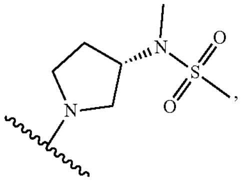

and

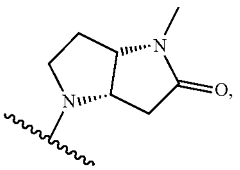

or a pharmaceutically acceptable salt or solvate thereof.

In another embodiment, Compounds of the Disclosure are compounds having any one of Formulae IV-A, IV-B, IV-C, or IV-D, wherein:

$Z^4$ is —$CH_2$—;

$R^{11a}$ is:

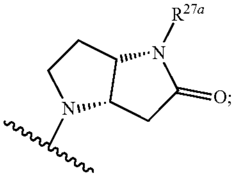

and $R^{27a}$ is selected from the group consisting of hydrogen, $C_1$-$C_4$ alkyl, $C_1$-$C_4$ haloalkyl, ($C_1$-$C_4$ alkoxy)$C_1$-$C_4$ alkyl, and (hydroxy)$C_1$-$C_4$ alkyl, or a pharmaceutically acceptable salt or solvate thereof. In another embodiment, $R^{27a}$ is methyl.

In another embodiment, Compounds of the Disclosure are compounds Formula V:

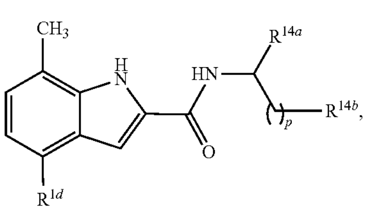

V wherein:

$R^{14a}$ is selected from the group consisting of optionally substituted alkyl and optionally substituted heteroaryl;

$R^{14b}$ is selected from the group consisting of optionally substituted alkyl, optionally substituted heteroaryl, optionally substituted aryl, optionally substituted heterocyclo, optionally substituted cycloalkyl, and carboxamido; and p is 0, 1, 2, or 3; or a pharmaceutically acceptable salt or solvate thereof.

In another embodiment, Compounds of the Disclosure are compounds having Formula V-A:

V-A

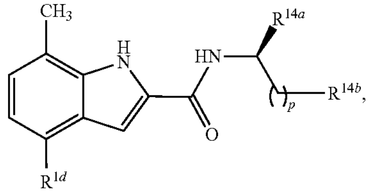

wherein $R^{1d}$, $R^{14a}$, $R^{14d}$, and p are as defined in connection with Formula V, or a pharmaceutically acceptable salt or solvate thereof.

In another embodiment, Compounds of the Disclosure are compounds having Formula V-B:

V-B

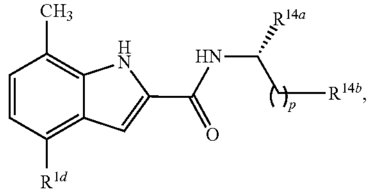

wherein $R^{1d}$, $R^{14a}$, $R^{14d}$, and p are as defined in connection with Formula V, or a pharmaceutically acceptable salt or solvate thereof.

In another embodiment, Compounds of the Disclosure are compounds having any one of Formulae V, V-A, or V-B, wherein:

$R^{14a}$ is selected from the group consisting of (A) unsubstituted 5- to 10-membered heteroaryl; (B) substituted 5- or 10-membered heteroaryl having one, two, three, or four substituents independently selected from the group consisting of (i) halo; (ii) $C_1$-$C_4$ alkyl; (iii) $C_1$-$C_4$ alkoxy; (iv) (3- to 8-membered heterocyclo)$C_1$-$C_4$ alkyl; (v) (5- to 9-membered heteroaryl)$C_1$-$C_4$ alkyl; (vi) —C(═O)$NR^{15a}R^{15b}$; (vii) unsubstituted 5- to 10-membered heteroaryl; (viii) substituted 5- or 10-membered heteroaryl having one, two, or three substituents independently selected from the group consisting of halo, $C_1$-$C_4$ alkyl, (3- to 8-membered heterocyclo)$C_1$-$C_4$ alkyl, 5- to 9-membered heteroaryl, and —$NR^{15e}R^{15f}$; (ix) —$OR^{16}$ (x) unsubstituted $C_3$-$C_6$ cycloalkyl; (xi) substituted $C_3$-$C_6$ cycloalkyl having one, two, three, or four substituents independently selected from the group consisting of $C_1$-$C_4$ alkyl and —$N(R^{17a})C(═O)R^{18a}$; (xii) cyano; (xiii) unsubstituted 4- to 14-membered heterocyclo; (xiv) substituted 4- to 14-membered heterocyclo having one or two substituents independently selected from the group consisting of $C_1$-$C_4$ alkyl, (5- to 9-membered heteroaryl)$C_1$-$C_4$ alkyl; (xv) (carboxy)$C_1$-$C_4$ alkyl; (xvi) (carboxamido)$C_1$-$C_4$ alkyl; and (xvii) carboxy; and (C) $C_1$-$C_6$ alkyl;

$R^{14b}$ is selected from the group consisting of: (A) unsubstituted 5- to 10-membered heteroaryl; (B) substituted 5- or 10-membered heteroaryl having one, two, three, or four substituents independently selected from the group consisting of halo, $C_1$-$C_4$ alkyl, and ($C_3$-$C_6$ cycloalkyl)$C_1$-$C_4$ alkyl; (C) unsubstituted $C_6$-$C_{10}$ aryl; (D) substituted $C_6$-$C_{10}$ aryl, having one, two, three, or four substituents independently selected from the group consisting of halo, $C_1$-$C_4$ alkyl, and (3- to 8-membered heterocyclo)$C_1$-$C_4$ alkyl; (E) unsubstituted 4- to 14-membered heterocyclo; (F) substituted 4- to 14-membered heterocyclo having one, two, three, or four substituents independently selected from the group consisting of hydroxy, amino, and $C_1$-$C_4$ alkyl; (G) —C(═O)$NR^{15c}R^{15d}$; (H) unsubstituted $C_3$-$C_6$ cycloalkyl; and (I) $C_1$-$C_6$ alkyl;

p is 0, 1, 2, or 3;

$R^{15a}$ and $R^{15b}$ are independently selected from the group consisting of: (A) hydrogen; (B) $C_1$-$C_6$ alkyl; (C) $C_1$-$C_6$ haloalkyl; (D) ($C_1$-$C_4$ alkoxy)$C_1$-$C_4$ alkyl; (E) (hydroxy)$C_1$-$C_4$ alkyl; (F) (cyano)alkyl; (G) unsubstituted $C_6$-$C_{10}$ aryl; (H) substituted $C_6$-$C_{10}$ aryl, having one, two, three, or four substituents independently selected from the group consisting of halo, amino, hydroxy, and $C_1$-$C_4$ alkyl; (I) unsubstituted 5- or 6-membered heteroaryl; (J) substituted 5- or 6-membered heteroaryl having one, two, three, or four substituents independently selected from the group consisting of halo, amino, hydroxy, and $C_1$-$C_4$ alkyl; (K) unsubstituted 4- to 14-membered heterocyclo; (L) substituted 4- to 14-membered heterocyclo having one or two substituents independently selected from the group consisting of amino, hydroxy, and $C_1$-$C_4$ alkyl; (M) unsubstituted $C_3$-$C_8$ cycloalkyl; and (N) substituted $C_3$-$C_8$ cycloalkyl having one, two, three, or four substituents independently selected from the group consisting of $C_1$-$C_6$ alkyl and —$NR^{15g}R^{15h}$; or $R^{15a}$ and $R^{15b}$ taken together with the nitrogen atom to which they are attached form an optionally substituted 4- to 14-membered heterocyclo;

$R^{15c}$ and $R^{15d}$ are independently selected from the group consisting of: (A) hydrogen; (B) $C_1$-$C_6$ alkyl; (C) $C_1$-$C_6$ haloalkyl; (D) ($C_1$-$C_4$ alkoxy)$C_1$-$C_4$ alkyl; (E) (hydroxy)$C_1$-$C_4$ alkyl; (F) (cyano)alkyl; (G) unsubstituted $C_6$-$C_{10}$ aryl; (H) substituted $C_6$-$C_{10}$ aryl, having one, two, three, or four substituents independently selected from the group consisting of halo, amino, hydroxy, and $C_1$-$C_4$ alkyl; (I) unsubstituted 5- or 6-membered heteroaryl; (J) substituted 5- or 6-membered heteroaryl having one, two, three, or four substituents independently selected from the group consisting of halo, amino, hydroxy, and $C_1$-$C_4$ alkyl; (K) unsubstituted 4- to 14-membered heterocyclo; (L) substituted 4- to 14-membered heterocyclo having one or two substituents independently selected from the group consisting of amino, hydroxy, and $C_1$-$C_4$ alkyl; (M) unsubstituted $C_3$-$C_8$ cycloalkyl; and (N) substituted $C_3$-$C_8$ cycloalkyl having one, two, three, or four substituents independently selected from the group consisting of $C_1$-$C_6$ alkyl and —$NR^{15g}R^{15h}$; or $R^{15c}$ and $R^{15d}$ taken together with the nitrogen atom to which they are attached form an optionally substituted 4- to 14-membered heterocyclo;

$R^{15e}$ and $R^{15f}$ are independently selected from the group consisting of: (A) hydrogen; (B) $C_1$-$C_6$ alkyl; (C) $C_1$-$C_6$ haloalkyl; (D) ($C_1$-$C_4$ alkoxy)$C_1$-$C_4$ alkyl; (E) (hydroxy)$C_1$-$C_4$ alkyl; (F) (cyano)alkyl; (G) unsubstituted $C_6$-$C_{10}$ aryl; (H) substituted $C_6$-$C_{10}$ aryl, having one, two, three, or four substituents independently selected from the group consisting of halo, amino, hydroxy, and $C_1$-$C_4$ alkyl; (I) unsubstituted 5- or 6-membered heteroaryl; (J) substituted 5- or 6-membered heteroaryl having one, two, three, or four substituents independently selected from the group consisting of halo, amino, hydroxy, and $C_1$-$C_4$ alkyl; (K) unsubstituted 4- to 14-membered heterocyclo; (L) substituted 4- to 14-membered heterocyclo having one or two substituents independently selected from the group consisting of amino, hydroxy, and $C_1$-$C_4$ alkyl; (M) unsubstituted $C_3$-$C_8$ cycloalkyl; and (N) substituted $C_3$-$C_8$ cycloalkyl having one, two, three, or four substituents independently selected from the group consisting of $C_1$-$C_6$ alkyl and —$NR^{15g}R^{15h}$; or $R^{15e}$ and $R^{15f}$ taken together with the nitrogen atom to which they are attached form an optionally substituted 4- to 14-membered heterocyclo;

$R^{15g}$ and $R^{15h}$ are independently selected from the group consisting of: (A) hydrogen; (B) $C_1$-$C_6$ alkyl; (C) $C_1$-$C_6$ haloalkyl; (D) $C_1$-$C_6$ alkoxy; (E) ($C_1$-$C_4$ alkoxy)$C_1$-$C_4$ alkyl; (F) (hydroxy)$C_1$-$C_4$ alkyl; (G) (cyano)alkyl; (H) unsubstituted $C_6$-$C_{10}$ aryl; (I) substituted $C_6$-$C_{10}$ aryl, having one, two, three, or four substituents independently selected from the group consisting of halo, amino, hydroxy, and $C_1$-$C_4$ alkyl; (J) unsubstituted 5- or 6-membered heteroaryl; (K) substituted 5- or 6-membered heteroaryl having one, two, three, or four substituents independently selected from the group consisting of halo, amino, hydroxy, and $C_1$-$C_4$ alkyl; (L) unsubstituted 4- to 14-membered heterocyclo; (M) substituted 4- to 14-membered heterocyclo having one or two substituents independently selected from the group consisting of amino, hydroxy, and $C_1$-$C_4$ alkyl; (N) unsubstituted $C_3$-$C_8$ cycloalkyl; and (O) substituted $C_3$-$C_8$ cycloalkyl having one, two, three, or four substituents independently selected from the group consisting of $C_1$-$C_6$ alkyl and —$NR^{15g}R^{15h}$; or $R^{15g}$ and $R^{15g}$ taken together with the nitrogen atom to which they are attached form an optionally substituted 4- to 14-membered heterocyclo;

$R^{16}$ is (amino)(hydroxy)$C_1$-$C_4$ alkyl;

$R^{17}$ is selected from the group consisting of hydrogen and $C_1$-$C_4$ alkyl;

$R^{18a}$ is selected from the group consisting of: (A) $C_1$-$C_6$ alkyl; (B) $C_1$-$C_6$ haloalkyl; (C) $C_1$-$C_6$ alkoxy; (D) ($C_1$-$C_4$ alkoxy)$C_1$-$C_4$ alkyl; (E) (hydroxy)$C_1$-$C_4$ alkyl; (F) (cyano) alkyl; (G) unsubstituted $C_6$-$C_{10}$ aryl; (H) substituted $C_6$-$C_{10}$ aryl, having one, two, three, or four substituents independently selected from the group consisting of halo, amino, hydroxy, and $C_1$-$C_4$ alkyl; (I) unsubstituted 5- or 6-membered heteroaryl; (J) substituted 5- or 6-membered heteroaryl having one, two, three, or four substituents independently selected from the group consisting of halo, amino, hydroxy, and $C_1$-$C_4$ alkyl; (K) unsubstituted 4- to 14-membered heterocyclo; (L) substituted 4- to 14-membered heterocyclo having one or two substituents independently selected from the group consisting of amino, hydroxy, and $C_1$-$C_4$ alkyl; (M) unsubstituted $C_3$-$C_8$ cycloalkyl; and (N) substituted $C_3$-$C_8$ cycloalkyl having one, two, three, or four substituents independently selected from the group consisting of amino, hydroxy, and $C_1$-$C_4$ alkyl, or a pharmaceutically acceptable salt or solvate thereof.

In another embodiment, Compounds of the Disclosure are compounds having any one of Formulae V, V-A, or V-B, wherein $R^{14a}$ is selected from the group consisting of unsubstituted 5- to 10-membered heteroaryl; and substituted 5- or 10-membered heteroaryl having one, two, or three substituents independently selected from the group consisting of $C_1$-$C_4$ alkyl; $C_1$-$C_4$ alkoxy; (3- to 8-membered heterocyclo) $C_1$-$C_4$ alkyl; (5- to 9-membered heteroaryl)$C_1$-$C_4$ alkyl; —C(═O)$NR^{15a}R^{15b}$; unsubstituted 5- to 10-membered heteroaryl; substituted 5- or 10-membered heteroaryl having one, two, or three substituents independently selected from the group consisting of halo, $C_1$-$C_4$ alkyl, (3- to 8-membered heterocyclo)$C_1$-$C_4$ alkyl, 5- to 9-membered heteroaryl, and —$NR^{15e}R^{15f}$; unsubstituted $C_3$-$C_6$ cycloalkyl; and substituted $C_3$-$C_6$ cycloalkyl having one, two, or three substituents independently selected from the group consisting of $C_1$-$C_4$ alkyl and —$N(R^{17a})C(═O)R^{18a}$, or a pharmaceutically acceptable salt or solvate thereof.

In another embodiment, Compounds of the Disclosure are compounds having any one of Formulae V, V-A, or V-B, wherein $R^{14a}$ is a substituted pyridyl having one, two, or three substituents independently selected from the group consisting of $C_1$-$C_4$ alkyl; $C_1$-$C_4$ alkoxy; (3- to 8-membered heterocyclo)$C_1$-$C_4$ alkyl; (5- to 9-membered heteroaryl)$C_1$-$C_4$ alkyl; —C(═O)$NR^{15a}R^{15b}$; unsubstituted 5- to 10-membered heteroaryl; substituted 5- to 10-membered heteroaryl having one, two, or three substituents independently selected from the group consisting of halo, $C_1$-$C_4$ alkyl, (3- to 8-membered heterocyclo)$C_1$-$C_4$ alkyl, 5- to 9-membered heteroaryl, and —$NR^{15e}R^{15f}$; unsubstituted $C_3$-$C_6$ cycloalkyl; and substituted $C_3$-$C_6$ cycloalkyl having one, two, or three substituents independently selected from the group consisting of $C_1$-$C_4$ alkyl and —$N(R^{17a})C(═O)R^{18a}$, or a pharmaceutically acceptable salt or solvate thereof.

In another embodiment, Compounds of the Disclosure are compounds having any one of Formulae V, V-A, or V-B, wherein $R^{14b}$ is selected from the group consisting of unsubstituted 5- to 10-membered heteroaryl; substituted 5- to 10-membered heteroaryl having one or two substituents independently selected from the group consisting of $C_1$-$C_4$ alkyl and ($C_3$-$C_6$ cycloalkyl)$C_1$-$C_4$ alkyl; unsubstituted $C_6$-$C_{10}$ aryl; substituted $C_6$-$C_{10}$ aryl, having one or two substituents independently selected from the group consisting of $C_1$-$C_4$ alkyl and (3- to 8-membered heterocyclo)$C_1$-$C_4$ alkyl; unsubstituted 4- to 14-membered heterocyclo; substituted 4- to 14-membered heterocyclo having one or two substituents independently selected from the group consisting of hydroxy, amino, and $C_1$-$C_4$ alkyl; and unsubstituted $C_3$-$C_6$ cycloalkyl, or a pharmaceutically acceptable salt or solvate thereof.

In another embodiment, Compounds of the Disclosure are compounds having any one of Formulae V, V-A, or V-B, wherein $R^{14b}$ is selected from the group consisting of unsubstituted 5- or 6-membered heteroaryl; substituted 5- or 6-membered heteroaryl having one or two substituents independently selected from the group consisting of $C_1$-$C_4$ alkyl and ($C_3$-$C_6$ cycloalkyl)$C_1$-$C_4$ alkyl; unsubstituted phenyl; substituted phenyl, having one or two substituents independently selected from the group consisting of $C_1$-$C_4$ alkyl and (3- to 8-membered heterocyclo)$C_1$-$C_4$ alkyl; and unsubstituted $C_3$-$C_6$ cycloalkyl, or a pharmaceutically acceptable salt or solvate thereof.

In another embodiment, Compounds of the Disclosure are compounds having any one of Formulae V, V-A, or V-B, wherein p is 0, or a pharmaceutically acceptable salt or solvate thereof.

In another embodiment, Compounds of the Disclosure are compounds having any one of Formulae V, V-A, or V-B, wherein p is 1, or a pharmaceutically acceptable salt or solvate thereof.

In another embodiment, Compounds of the Disclosure are compounds having Formula VI:

VI

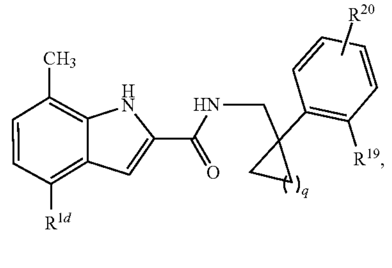

wherein:

$R^{19}$ is selected from the group consisting of unsubstituted 4- to 14-membered heterocyclo; and substituted 4- to 14-membered heterocyclo having one or two substituents independently selected from the group consisting of amino, hydroxy, and $C_1$-$C_4$ alkyl;

$R^{20}$ is selected from the group consisting of hydrogen, halo, and $C_1$-$C_4$ alkyl; and q is 1, 2, or 3, or a pharmaceutically acceptable salt or solvate thereof.

In another embodiment, Compounds of the Disclosure are compounds having Formula VI, wherein q is 1.

In another embodiment, Compounds of the Disclosure are compounds having Formula VII:

VII

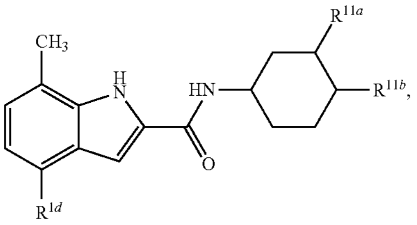

wherein:

$R^{11b}$ is selected from the group consisting of $C_1$-$C_4$ alkyl, halo, and $C_1$-$C_4$ haloalkyl; and $R^{1d}$ and $R^{11a}$ are as defined in connection with Formula IV, or a pharmaceutically acceptable salt or solvate thereof.

In another embodiment, Compounds of the Disclosure are compounds having Formula VII-A:

VII-A

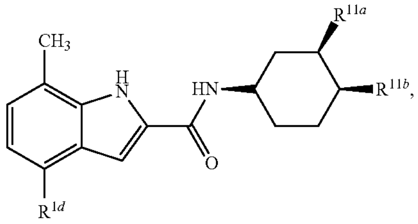

wherein $R^{1d}$, $R^{11a}$, and $R^{11b}$ are as defined in connection with Formula VII, or a pharmaceutically acceptable salt or solvate thereof.

In another embodiment, Compounds of the Disclosure are compounds having Formula VII-B:

VII-B

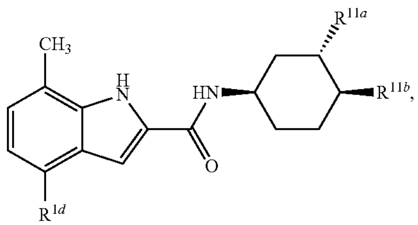

wherein $R^{1d}$, $R^{11a}$, and $R^{11b}$ are as defined in connection with Formula VII, or a pharmaceutically acceptable salt or solvate thereof.

In another embodiment, Compounds of the Disclosure are compounds having Formula VII-C:

VII-C

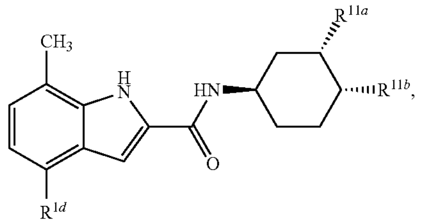

wherein $R^{1d}$, $R^{11a}$, and $R^{11b}$ are as defined in connection with Formula VII, or a pharmaceutically acceptable salt or solvate thereof.

In another embodiment, Compounds of the Disclosure are compounds having Formula VII-D:

VII-D

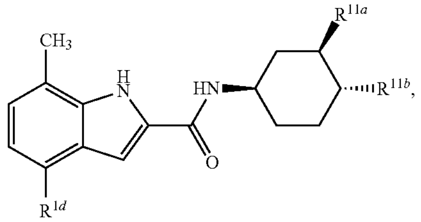

wherein $R^{1d}$, $R^{11a}$, and $R^{11b}$ are as defined in connection with Formula VII, or a pharmaceutically acceptable salt or solvate thereof.

In another embodiment, Compounds of the Disclosure are compounds having Formula VII-E:

VII-E

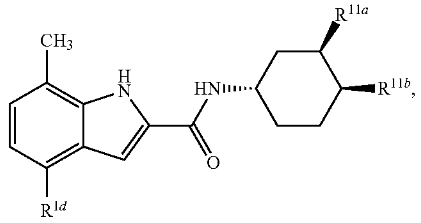

wherein $R^{1d}$, $R^{11a}$, and $R^{11b}$ are as defined in connection with Formula VII, or a pharmaceutically acceptable salt or solvate thereof.

In another embodiment, Compounds of the Disclosure are compounds having Formula VII-F:

VII-F

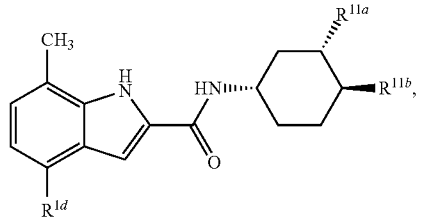

wherein $R^{1d}$, $R^{11a}$, and $R^{11b}$ are as defined in connection with Formula VII, or a pharmaceutically acceptable salt or solvate thereof.

In another embodiment, Compounds of the Disclosure are compounds having Formula VII-G:

VII-G

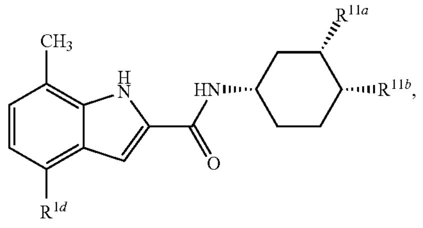

wherein $R^{1d}$, $R^{11a}$, and $R^{11b}$ are as defined in connection with Formula VII, or a pharmaceutically acceptable salt or solvate thereof.

In another embodiment, Compounds of the Disclosure are compounds having Formula VII-H:

VII-H

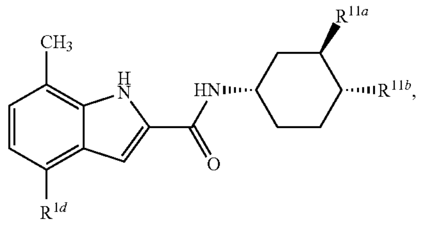

wherein $R^{1d}$, $R^{11a}$, and $R^{11b}$ are as defined in connection with Formula VII, or a pharmaceutically acceptable salt or solvate thereof.

In another embodiment, Compounds of the Disclosure are compounds having Formula VIII:

VIII

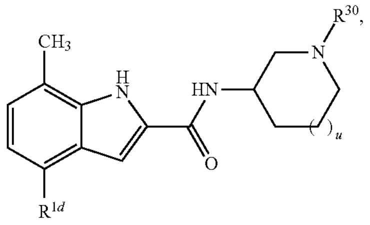

wherein:

$R^{30}$ is selected from the group consisting of hydrogen; $C_1$-$C_6$ alkyl; unsubstituted $C_3$-$C_6$ cycloalkyl; substituted $C_3$-$C_6$ cycloalkyl having one or two substituents independently selected from the group consisting of halo, hydroxy, $C_1$-$C_4$ alkyl, amino, and (amino)$C_1$-$C_4$ alkyl; unsubstituted 4- to 14-membered heterocyclo; and substituted 4- to 14-membered heterocyclo having one or two substituents independently selected from the group consisting of amino, hydroxy, and $C_1$-$C_4$ alkyl; —C(═O)$R^{13b}$, and —S(═O)$_2$ $R^{24}$;

$R^{13b}$ is selected from the group consisting of $C_1$-$C_4$ alkyl; amino; $C_1$-$C_4$ haloalkyl; $C_1$-$C_4$ alkoxy; (hydroxy)$C_1$-$C_4$ alkyl; ($C_1$-$C_4$ alkoxy)$C_1$-$C_4$ alkyl; (amino)alkyl; unsubstituted $C_3$-$C_6$ cycloalkyl; substituted $C_3$-$C_6$ cycloalkyl having one or two substituents independently selected from the group consisting of halo, hydroxy, $C_1$-$C_4$ alkyl, amino, and (amino)$C_1$-$C_4$ alkyl; unsubstituted 4- to 14-membered heterocyclo; substituted 4- to 14-membered heterocyclo having one or two substituents independently selected from the group consisting of amino, hydroxy, and $C_1$-$C_4$ alkyl; ($C_3$-$C_6$ cycloalkyl)oxy; and (4- to 8-membered heterocyclo)oxy;

$R^{24}$ is selected from the group consisting of $C_1$-$C_4$ alkyl and (hydroxy)$C_1$-$C_4$ alkyl;

u is 0, 1, 2, or 3; and $R^{1d}$ is as defined in connection with Formula I, or a pharmaceutically acceptable salt or solvate thereof.

In another embodiment, Compounds of the Disclosure are compounds having Formula VIII-A:

VIII-A

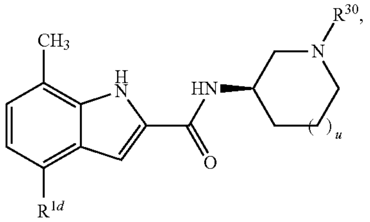

wherein $R^{1d}$, $R^{30}$, and u are as defined in connection with Formula VIII, or a pharmaceutically acceptable salt or solvate thereof.

In another embodiment, Compounds of the Disclosure are compounds having Formula VIII-B:

VIII-B

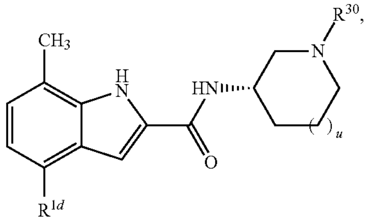

wherein $R^{1d}$, $R^{30}$, and u are as defined in connection with Formula VIII, or a pharmaceutically acceptable salt or solvate thereof.

In another embodiment, Compounds of the Disclosure are compounds of Table 1, and the pharmaceutically acceptable salts or solvates thereof. The chemical names of the compounds of Table 1 were generated by Chemdraw® Professional version 17.0.0.206. Mass spectroscopy and biological data of representative Compounds of the Disclosure are provided in Table 1B and/or PCT/US2019/046569. In another embodiment, Compounds of the Disclosure are compounds of Table 1B, and the pharmaceutically acceptable salts or solvates thereof. The biological data in Table 1B were generated following the protocols described in EXAMPLES 11 and 12 of PCT/US2019/046569.

In another embodiment, Compounds of the Disclosure are selected from the group consisting of Cpd. Nos. 1, 2, 3, 4, 5, 6, 7, 8, 9, 10, 11, 12, 13, 14, 15, 16, 17, 18, 824, 828, 839, 870, 922, 930, 942, 995, 1007, 1025, 1043, 1044, 1045, 1048, 1051, 1055, 1070, 1078, 1083, 1097, 1117, 1138, 1180, 1184, and 1192, and the pharmaceutically acceptable salts or solvates thereof. In another embodiment, Compounds of the Disclosure are selected from the group consisting of Cpd. Nos. 15, 922, 930, 942, 1055, 1070, 1117, 1180, 1184, and 1192, and the pharmaceutically acceptable salts or solvates thereof. In another embodiment, Compounds of the Disclosure are selected from the group consisting of Cpd. Nos. 1228, 1229, 1230, 1231, 1232, 1233, 1234 and 1235, and the pharmaceutically acceptable salts or solvates thereof.

In another embodiment, Compounds of the Disclosure are selected from the group consisting of Cpd. Nos. 15, 942, 1184, and 1232, and the pharmaceutically acceptable salts or solvates thereof.

In a non-limiting embodiment, the Compound of the Disclosure is Cpd. No. 15.

In a non-limiting embodiment, the Compound of the Disclosure is Cpd. No. 1228. In a non-limiting embodiment, the Compound of the Disclosure is Cpd. No. 1229. In a non-limiting embodiment, the Compound of the Disclosure is Cpd. No. 1230. In a non-limiting embodiment, the Compound of the Disclosure is Cpd. No. 1231. In a non-limiting embodiment, the Compound of the Disclosure is Cpd. No. 1232. In a non-limiting embodiment, the Compound of the Disclosure is Cpd. No. 1233. In a non-limiting embodiment, the Compound of the Disclosure is Cpd. No. 1234. In a non-limiting embodiment, the Compound of the Disclosure is Cpd. No. 1235. In a non-limiting embodiment, the Compound of the Disclosure is a pharmaceutically acceptable salt or solvate of Cpd. No. 15. In a non-limiting embodiment, the Compound of the Disclosure is a pharmaceutically acceptable salt or solvate of Cpd. No. 1228. In a non-limiting embodiment, the Compound of the Disclosure is a pharmaceutically acceptable salt or solvate of Cpd. No. 1229. In a non-limiting embodiment, the Compound of the Disclosure is a pharmaceutically acceptable salt or solvate of Cpd. No. 1230. In a non-limiting embodiment, the Compound of the Disclosure is a pharmaceutically acceptable salt or solvate of Cpd. No. 1231. In a non-limiting embodiment, the Compound of the Disclosure is a pharmaceutically acceptable salt or solvate of Cpd. No. 1232. In a non-limiting embodiment, the Compound of the Disclosure is a pharmaceutically acceptable salt or solvate of Cpd. No. 1233. In a non-limiting embodiment, the Compound of the Disclosure is a pharmaceutically acceptable salt or solvate of Cpd. No. 1234. In a non-limiting embodiment, the Compound of the Disclosure is a pharmaceutically acceptable salt or solvate of Cpd. No. 1235

TABLE 1

| Cpd. No. | Chemical Name |
|---|---|
| 1 | 4-fluoro-N-(3-fluoro-5-(3-(N-methylacetamido)pyrrolidin-1-yl)phenyl)-7-methyl-1H-indole-2-carboxamide |
| 2 | 4-fluoro-N-(3-fluoro-5-(3-(2-methyl-3-oxohexahydroimidazo[1,5-a]pyrazin-7(1H)-yl)pyrrolidin-1-yl)phenyl)-7-methyl-1H-indole-2-carboxamide |
| 3 | N-(3-(3-(dimethylamino)-2-oxopyrrolidin-1-yl)-5-fluorophenyl)-4-fluoro-7-methyl-1H-indole-2-carboxamide |
| 4 | N-(3-(3-(4-(2-(dimethylamino)-2-oxoethyl)piperazin-1-yl)pyrrolidin-1-yl)-5-fluorophenyl)-4-fluoro-7-methyl-1H-indole-2-carboxamide |
| 5 | N-(3-(8-acetyl-2,8-diazaspiro[4.5]decan-2-yl)-5-fluorophenyl)-4-fluoro-7-methyl-1H-indole-2-carboxamide |
| 6 | N-(3-(3-(4-(2-amino-2-oxoethyl)piperazin-1-yl)pyrrolidin-1-yl)-5-fluorophenyl)-4-fluoro-7-methyl-1H-indole-2-carboxamide |
| 7 | N-(3-(4-acetylpiperazin-1-yl)-5-fluorophenyl)-4-fluoro-7-methyl-1H-indole-2-carboxamide |
| 8 | N-(3-(3-(1,1-dioxidothiomorpholino)pyrrolidin-1-yl)-5-fluorophenyl)-4-fluoro-7-methyl-1H-indole-2-carboxamide |
| 9 | N-(3-(3-(4-acetylpiperazin-1-yl)pyrrolidin-1-yl)-5-fluorophenyl)-4-fluoro-7-methyl-1H-indole-2-carboxamide |
| 10 | N-(3-(4-cyclopropyl-3-oxopiperazin-1-yl)-5-fluorophenyl)-4-fluoro-7-methyl-1H-indole-2-carboxamide |
| 11 | 4-fluoro-N-(3-fluoro-5-(3-morpholinopyrrolidin-1-yl)phenyl)-7-methyl-1H-indole-2-carboxamide |
| 12 | 4-fluoro-N-(3-fluoro-5-(4-(2-methoxyacetyl)piperazin-1-yl)phenyl)-7-methyl-1H-indole-2-carboxamide |
| 13 | N-(3-(4-acetylhexahydropyrrolo[3,2-b]pyrrol-1(2H)-yl)-5-fluorophenyl)-4-fluoro-7-methyl-1H-indole-2-carboxamide |
| 14 | N-(3-(1-acetylhexahydropyrrolo[3,4-b]pyrrol-5(1H)-yl)-5-fluorophenyl)-4-fluoro-7-methyl-1H-indole-2-carboxamide |
| 15 | N-((1R,3S)-3-(4-acetylpiperazin-1-yl)cyclohexyl)-4-fluoro-7-methyl-1H-indole-2-carboxamide |
| 16 | 4-fluoro-N-(3-fluoro-5-(3-(2-(hydroxymethyl)morpholino)pyrrolidin-1-yl)phenyl)-7-methyl-1H-indole-2-carboxamide |
| 17 | 4-fluoro-N-(3-fluoro-5-(3-(4-methyl-3-oxopiperazin-1-yl)pyrrolidin-1-yl)phenyl)-7-methyl-1H-indole-2-carboxamide |
| 18 | 4-fluoro-N-(3-fluoro-5-(2-oxo-[1,3'-bipyrrolidin]-1'-yl)phenyl)-7-methyl-1H-indole-2-carboxamide |
| 19 | N-(3-(7-acetyl-2,7-diazaspiro[3.5]nonan-2-yl)-5-fluorophenyl)-4-fluoro-7-methyl-1H-indole-2-carboxamide |
| 20 | 4-fluoro-N-(3-fluoro-5-(4-methyl-3-oxopiperazin-1-yl)phenyl)-7-methyl-1H-indole-2-carboxamide |
| 21 | 4-fluoro-N-(3-fluoro-5-(4-methyl-5-oxo-1,4-diazepan-1-yl)phenyl)-7-methyl-1H-indole-2-carboxamide |
| 22 | N-(3-chloro-5-(3-morpholinopyrrolidin-1-yl)phenyl)-4-fluoro-7-methyl-1H-indole-2-carboxamide |
| 23 | N-(3-(1-acetyl-4-methylpiperidin-4-yl)-5-fluorophenyl)-4-fluoro-7-methyl-1H-indole-2-carboxamide |

TABLE 1-continued

| Cpd. No. | Chemical Name |
|---|---|
| 24 | 4-fluoro-N-(3-fluoro-5-(2-(2-hydroxyethyl)morpholino)phenyl)-7-methyl-1H-indole-2-carboxamide |
| 25 | N-(3-(4-(dimethylcarbamoyl)piperazin-1-yl)-5-fluorophenyl)-4-fluoro-7-methyl-1H-indole-2-carboxamide |
| 26 | 4-fluoro-N-(3-fluoro-5-((7S,8aS)-3-oxooctahydroindolizin-7-yl)phenyl)-7-methyl-1H-indole-2-carboxamide |
| 27 | 4-fluoro-7-methyl-N-(3-(6-oxohexahydropyrrolo[1,2-a]pyrazin-2(1H)-yl)phenyl)-1H-indole-2-carboxamide |
| 28 | N-(3-(6,6-difluoro-2,8-diazaspiro[4.5]decan-2-yl)-5-fluorophenyl)-4-fluoro-7-methyl-1H-indole-2-carboxamide |
| 29 | N-(3-(3-(5,6-dihydroimidazo[1,2-a]pyrazin-7(8H)-yl)pyrrolidin-1-yl)-5-fluorophenyl)-4-fluoro-7-methyl-1H-indole-2-carboxamide |
| 30 | N-(3-(2-acetyl-2,8-diazaspiro[4.5]decan-8-yl)-5-fluorophenyl)-4-fluoro-7-methyl-1H-indole-2-carboxamide |
| 31 | N-(3-(4-acetylpiperazin-1-yl)-5-chlorophenyl)-4-fluoro-7-methyl-1H-indole-2-carboxamide |
| 32 | N-(3-(4-acetyl-3-methylpiperazin-1-yl)phenyl)-4-fluoro-7-methyl-1H-indole-2-carboxamide |
| 34 | N-(3-(4-acetylpiperazin-1-yl)phenyl)-4-fluoro-7-methyl-1H-indole-2-carboxamide |
| 35 | 4-fluoro-N-(3-fluoro-5-((1s,4s)-4-morpholinocyclohexyl)phenyl)-7-methyl-1H-indole-2-carboxamide |
| 36 | 4-fluoro-7-methyl-N-(3-(4-propionylpiperazin-1-yl)phenyl)-1H-indole-2-carboxamide |
| 37 | 4-fluoro-7-methyl-N-(3-(3-oxooctahydroindolizin-7-yl)phenyl)-1H-indole-2-carboxamide |
| 38 | 4-fluoro-7-methyl-N-(3-(3-(N-methylacetamido)pyrrolidin-1-yl)phenyl)-1H-indole-2-carboxamide |
| 39 | N-(3-(3-(4-(dimethylglycyl)piperazin-1-yl)pyrrolidin-1-yl)-5-fluorophenyl)-4-fluoro-7-methyl-1H-indole-2-carboxamide |
| 40 | N-(3-(7-(2,2-difluoroethyl)-2,7-diazaspiro[3.5]nonan-2-yl)-5-fluorophenyl)-4-fluoro-7-methyl-1H-indole-2-carboxamide |
| 41 | N-(3-(7-(2,2-difluoroethyl)-2,7-diazaspiro[3.5]nonan-2-yl)phenyl)-4-fluoro-7-methyl-1H-indole-2-carboxamide |
| 42 | 4-fluoro-7-methyl-N-(3-(3-(N-methylacetamido)piperidin-1-yl)phenyl)-1H-indole-2-carboxamide |
| 43 | N-(3-(4-(dimethylalanyl)piperazin-1-yl)-5-fluorophenyl)-4-fluoro-7-methyl-1H-indole-2-carboxamide |
| 44 | 4-fluoro-N-(3-(4-(2-methoxyacetyl)piperazin-1-yl)phenyl)-7-methyl-1H-indole-2-carboxamide |
| 45 | N-(3-(1-acetylpiperidin-4-yl)phenyl)-4-fluoro-7-methyl-1H-indole-2-carboxamide |
| 46 | 4-fluoro-7-methyl-N-((1R,3S)-3-(3-(N-methylacetamido)pyrrolidin-1-yl)cyclohexyl)-1H-indole-2-carboxamide |
| 47 | 4-fluoro-N-(3-fluoro-5-(3-((2-fluoroethyl)(methyl)amino)pyrrolidin-1-yl)phenyl)-7-methyl-1H-indole-2-carboxamide |
| 48 | 4-fluoro-N-(3-fluoro-5-(2-(hydroxymethyl)morpholino)phenyl)-7-methyl-1H-indole-2-carboxamide |
| 49 | 4-fluoro-7-methyl-N-(3-(4-nicotinoylpiperazin-1-yl)phenyl)-1H-indole-2-carboxamide |
| 50 | 4-fluoro-N-(3-(2-(2-hydroxyethyl)morpholino)phenyl)-7-methyl-1H-indole-2-carboxamide |
| 51 | 4-fluoro-7-methyl-N-(3-((7R,8aR)-3-oxooctahydroindolizin-7-yl)phenyl)-1H-indole-2-carboxamide |
| 52 | N-(3-(4-acetylpiperazin-1-yl)-2-fluorophenyl)-4-fluoro-7-methyl-1H-indole-2-carboxamide |
| 53 | N-(3-(3-(dimethylamino)pyrrolidin-1-yl)-5-fluorophenyl)-4-fluoro-7-methyl-1H-indole-2-carboxamide |
| 54 | 4-fluoro-7-methyl-N-(3-(2-methyl-3-oxohexahydroimidazo[1,5-a]pyrazin-7(1H)-yl)phenyl)-1H-indole-2-carboxamide |
| 55 | N-(3-(4-(dimethylcarbamoyl)piperazin-1-yl)phenyl)-4-fluoro-7-methyl-1H-indole-2-carboxamide |
| 56 | N-(3-(1-acetylpyrrolidin-3-yl)-5-fluorophenyl)-4-fluoro-7-methyl-1H-indole-2-carboxamide |
| 57 | N-(3-(2-oxa-7-azaspiro[3.5]nonan-7-yl)phenyl)-4-fluoro-7-methyl-1H-indole-2-carboxamide |
| 58 | 4-fluoro-7-methyl-N-(3-(4-methyl-3-oxopiperazin-1-yl)phenyl)-1H-indole-2-carboxamide |
| 59 | N-(3-(3-(dimethylamino)pyrrolidin-1-yl)phenyl)-4-fluoro-7-methyl-1H-indole-2-carboxamide |
| 60 | N-(3-(1,3,4-oxadiazol-2-yl)phenyl)-4-fluoro-7-methyl-1H-indole-2-carboxamide |
| 61 | N-(3-((3S,4S)-3-(dimethylamino)-4-hydroxypyrrolidin-1-yl)phenyl)-4-fluoro-7-methyl-1H-indole-2-carboxamide |
| 62 | N-(3-(4-(dimethylglycyl)piperazin-1-yl)-5-fluorophenyl)-4-fluoro-7-methyl-1H-indole-2-carboxamide |
| 63 | N-(3-(3-(dimethylamino)-4-fluoropyrrolidin-1-yl)phenyl)-4-fluoro-7-methyl-1H-indole-2-carboxamide |

TABLE 1-continued

| Cpd. No. | Chemical Name |
|---|---|
| 64 | 4-fluoro-7-methyl-N-(3-(pyrimidin-5-yl)phenyl)-1H-indole-2-carboxamide |
| 65 | 4-fluoro-7-methyl-N-(3-(5-methyl-1,3,4-thiadiazol-2-yl)phenyl)-1H-indole-2-carboxamide |
| 66 | 4-fluoro-7-methyl-N-(3-(2-oxooxazolidin-3-yl)phenyl)-1H-indole-2-carboxamide |
| 68 | N-(3-((1r,4r)-4-(dimethylamino)cyclohexyl)phenyl)-4-fluoro-7-methyl-1H-indole-2-carboxamide |
| 69 | N-(3-((1s,4s)-4-(dimethylamino)cyclohexyl)-5-fluorophenyl)-4-fluoro-7-methyl-1H-indole-2-carboxamide |
| 70 | N-(3-(4-(dimethylglycyl)-3-methylpiperazin-1-yl)-5-fluorophenyl)-4-fluoro-7-methyl-1H-indole-2-carboxamide |
| 71 | N-(3-(4-acetyl-3-ethylpiperazin-1-yl)phenyl)-4-fluoro-7-methyl-1H-indole-2-carboxamide |
| 72 | 4-fluoro-N-(3-(4-(2-hydroxyacetyl)piperazin-1-yl)phenyl)-7-methyl-1H-indole-2-carboxamide |
| 73 | N-(3-(1-acetylpyrrolidin-3-yl)phenyl)-4-fluoro-7-methyl-1H-indole-2-carboxamide |
| 74 | 4-fluoro-7-methyl-N-(3-(3-morpholinopyrrolidin-1-yl)phenyl)-1H-indole-2-carboxamide |
| 75 | 4-fluoro-N-(3-(4-(3-methoxypropanoyl)piperazin-1-yl)phenyl)-7-methyl-1H-indole-2-carboxamide |
| 76 | 4-fluoro-7-methyl-N-(3-(4-morpholinopiperidin-1-yl)phenyl)-1H-indole-2-carboxamide |
| 77 | N-(3-(4-acetyl-3-(trifluoromethyl)piperazin-1-yl)phenyl)-4-fluoro-7-methyl-1H-indole-2-carboxamide |
| 78 | 4-fluoro-7-methyl-N-(3-(4-(N-methylacetamido)piperidin-1-yl)phenyl)-1H-indole-2-carboxamide |
| 79 | N-(3-(4-acetylpiperazin-1-yl)-4-fluorophenyl)-4-fluoro-7-methyl-1H-indole-2-carboxamide |
| 80 | N-(3-(4-(dimethylamino)piperidin-1-yl)-5-fluorophenyl)-4-fluoro-7-methyl-1H-indole-2-carboxamide |
| 81 | 4-fluoro-N-(3-(5-(methoxymethyl)-1,3,4-thiadiazol-2-yl)phenyl)-7-methyl-1H-indole-2-carboxamide |
| 82 | 4-fluoro-N-(7-fluoroisoquinolin-5-yl)-7-methyl-1H-indole-2-carboxamide |
| 83 | methyl 2-(3-(4-fluoro-7-methyl-1H-indole-2-carboxamido)phenyl)-2,8-diazaspiro[4.5]decane-8-carboxylate |
| 84 | N-(3-(4-acetylpiperazin-1-yl)phenyl)-7-bromo-4-fluoro-1H-indole-2-carboxamide |
| 85 | 4-fluoro-7-methyl-N-(2-(1-methyl-1H-pyrazol-4-yl)-1-(3-methylpyridin-2-yl)ethyl)-1H-indole-2-carboxamide |
| 86 | N-(3-(1,8-diazaspiro[4.5]decan-8-yl)phenyl)-4-fluoro-7-methyl-1H-indole-2-carboxamide |
| 87 | 4-fluoro-N-(3-(4-hydroxy-4-methylpiperidin-1-yl)phenyl)-7-methyl-1H-indole-2-carboxamide |
| 88 | N-(3-(4-ethyl-3-oxopiperazin-1-yl)phenyl)-4-fluoro-7-methyl-1H-indole-2-carboxamide |
| 89 | 4-fluoro-N-(3-fluoro-5-(1'-methyl-5'-oxo-[1,3'-bipyrrolidin]-3-yl)phenyl)-7-methyl-1H-indole-2-carboxamide |
| 90 | 4-fluoro-7-methyl-N-(3-((7S,8aS)-3-oxooctahydroindolizin-7-yl)phenyl)-1H-indole-2-carboxamide |
| 91 | N-(3-chloro-5-(4-methylpiperazin-1-yl)phenyl)-4-fluoro-7-methyl-1H-indole-2-carboxamide |
| 92 | 4-fluoro-N-(3-(4-(2-fluoroacetyl)piperazin-1-yl)phenyl)-7-methyl-1H-indole-2-carboxamide |
| 93 | N-(3-(4-(cyclopropanecarbonyl)piperazin-1-yl)phenyl)-4-fluoro-7-methyl-1H-indole-2-carboxamide |
| 94 | (R)-N-(3-(3-(dimethylamino)pyrrolidin-1-yl)phenyl)-4-fluoro-7-methyl-1H-indole-2-carboxamide |
| 95 | N-(3-(4-oxa-1,9-diazaspiro[5.5]undecan-9-yl)phenyl)-4-fluoro-7-methyl-1H-indole-2-carboxamide |
| 96 | 4-fluoro-N-(3-fluoro-5-((7R,8aS)-3-oxooctahydroindolizin-7-yl)phenyl)-7-methyl-1H-indole-2-carboxamide |
| 97 | N-(3-((3R,5S)-4-acetyl-3,5-dimethylpiperazin-1-yl)phenyl)-4-fluoro-7-methyl-1H-indole-2-carboxamide |
| 98 | 4-fluoro-7-methyl-N-(3-(2-methyl-2,7-diazaspiro[3.5]nonan-7-yl)phenyl)-1H-indole-2-carboxamide |
| 99 | N-(3-(4-(dimethylamino)-3-methylpiperidin-1-yl)phenyl)-4-fluoro-7-methyl-1H-indole-2-carboxamide |
| 100 | N-(3-(4-cyclopropyl-3-oxopiperazin-1-yl)phenyl)-4-fluoro-7-methyl-1H-indole-2-carboxamide |
| 101 | 4-fluoro-7-methyl-N-(3-(tetrahydro-2H-pyran-4-yl)phenyl)-1H-indole-2-carboxamide |
| 102 | (S)-N-(3-(3-(dimethylamino)pyrrolidin-1-yl)phenyl)-4-fluoro-7-methyl-1H-indole-2-carboxamide |
| 103 | N-(3-(4,4-bis(hydroxymethyl)piperidin-1-yl)phenyl)-4-fluoro-7-methyl-1H-indole-2-carboxamide |
| 104 | N-(3-(1-acetyl-1,8-diazaspiro[4.5]decan-8-yl)-5-fluorophenyl)-4-fluoro-7-methyl-1H-indole-2-carboxamide |

TABLE 1-continued

| Cpd. No. | Chemical Name |
|---|---|
| 105 | 4-fluoro-N-(3-fluoro-5-((3aS,6aS)-1-methylhexahydropyrrolo[3,4-b]pyrrol-5(1H)-yl)phenyl)-7-methyl-1H-indole-2-carboxamide |
| 106 | N-(3-chloro-5-((1s,4s)-4-(dimethylamino)cyclohexyl)phenyl)-4-fluoro-7-methyl-1H-indole-2-carboxamide |
| 107 | 4-fluoro-N-(3-(5-(hydroxymethyl)-1,3,4-thiadiazol-2-yl)phenyl)-7-methyl-1H-indole-2-carboxamide |
| 108 | 4-fluoro-7-methyl-N-(3-(oxazol-5-yl)phenyl)-1H-indole-2-carboxamide |
| 109 | 4-fluoro-N-(3-(7-(2-methoxyethyl)-2,7-diazaspiro[3.5]nonan-2-yl)phenyl)-7-methyl-1H-indole-2-carboxamide |
| 110 | 4-fluoro-7-methyl-N-(3-(2-(2,2,2-trifluoroethyl)-2,7-diazaspiro[3.5]nonan-7-yl)phenyl)-1H-indole-2-carboxamide |
| 111 | N-(3-((3R,4S)-4-(dimethylamino)-3-methylpiperidin-1-yl)phenyl)-4-fluoro-7-methyl-1H-indole-2-carboxamide |
| 112 | methyl 2-(3-(4-fluoro-7-methyl-1H-indole-2-carboxamido)phenyl)-2,7-diazaspiro[3.5]nonane-7-carboxylate |
| 113 | N-(3-(4-(dimethylamino)piperidin-1-yl)phenyl)-4-fluoro-7-methyl-1H-indole-2-carboxamide |
| 114 | 4-fluoro-N-(3-fluoro-5-((8aR)-3-oxooctahydroindolizin-7-yl)phenyl)-7-methyl-1H-indole-2-carboxamide |
| 115 | 4-fluoro-N-(3-(2-(hydroxymethyl)morpholino)phenyl)-7-methyl-1H-indole-2-carboxamide |
| 116 | 4-fluoro-7-methyl-N-(3-(pyridin-4-yl)phenyl)-1H-indole-2-carboxamide |
| 117 | N-(3-(4-((dimethylamino)methyl)piperidin-1-yl)phenyl)-4-fluoro-7-methyl-1H-indole-2-carboxamide |
| 118 | 4-fluoro-7-methyl-N-(3-(2-oxopyrrolidin-1-yl)phenyl)-1H-indole-2-carboxamide |
| 119 | N-(3-(5-cyclopropyl-1,3,4-oxadiazol-2-yl)phenyl)-4-fluoro-7-methyl-1H-indole-2-carboxamide |
| 120 | N-(3-chloro-5-(3-(dimethylamino)pyrrolidin-1-yl)phenyl)-4-fluoro-7-methyl-1H-indole-2-carboxamide |
| 121 | methyl 4-(3-(4-fluoro-7-methyl-1H-indole-2-carboxamido)phenyl)piperazine-1-carboxylate |
| 122 | 4-fluoro-N-(3-fluoro-5-((3aR,6aR)-1-methylhexahydropyrrolo[3,4-b]pyrrol-5(1H)-yl)phenyl)-7-methyl-1H-indole-2-carboxamide |
| 123 | N-(3-(1-acetylpiperidin-3-yl)phenyl)-4-fluoro-7-methyl-1H-indole-2-carboxamide |
| 124 | 4-fluoro-7-methyl-N-(3-(octahydro-6H-pyrrolo[3,4-b]pyridin-6-yl)phenyl)-1H-indole-2-carboxamide |
| 125 | N-(3-(1,1-dioxidoisothiazolidin-2-yl)phenyl)-4-fluoro-7-methyl-1H-indole-2-carboxamide |
| 126 | 4-fluoro-N-(3-(4-hydroxypiperidin-1-yl)phenyl)-7-methyl-1H-indole-2-carboxamide |
| 127 | methyl 8-(3-(4-fluoro-7-methyl-1H-indole-2-carboxamido)phenyl)-2,8-diazaspiro[4.5]decane-2-carboxylate |
| 128 | 4-fluoro-7-methyl-N-(3-(3-(methylamino)pyrrolidin-1-yl)phenyl)-1H-indole-2-carboxamide |
| 129 | 4-fluoro-7-methyl-N-(3-(2-methylmorpholino)phenyl)-1H-indole-2-carboxamide |
| 130 | 4-fluoro-N-(3-(3-((2-fluoroethyl)(methyl)amino)pyrrolidin-1-yl)phenyl)-7-methyl-1H-indole-2-carboxamide |
| 131 | 4-fluoro-7-methyl-N-((1S,3R)-3-(pyrimidin-5-yl)cyclohexyl)-1H-indole-2-carboxamide |
| 132 | N-(3-(5-((dimethylamino)methyl)-1,3,4-thiadiazol-2-yl)phenyl)-4-fluoro-7-methyl-1H-indole-2-carboxamide |
| 133 | 4-fluoro-N-(3-(2-(methoxymethyl)morpholino)phenyl)-7-methyl-1H-indole-2-carboxamide |
| 134 | 4-fluoro-N-(isoquinolin-5-yl)-7-methyl-1H-indole-2-carboxamide |
| 135 | 4-fluoro-7-methyl-N-(3-(6-methyl-2,6-diazaspiro[3.3]heptan-2-yl)phenyl)-1H-indole-2-carboxamide |
| 136 | 4-fluoro-7-methyl-N-(4'-(methylsulfonamidomethyl)-[1,1'-biphenyl]-3-yl)-1H-indole-2-carboxamide |
| 137 | 4-fluoro-7-methyl-N-(3-(pyridin-3-yl)phenyl)-1H-indole-2-carboxamide |
| 138 | 4-fluoro-7-methyl-N-(3-(4-(1-methylpiperidine-3-carbonyl)piperazin-1-yl)phenyl)-1H-indole-2-carboxamide |
| 139 | 4-fluoro-7-methyl-N-(3-(4-(methylcarbamoyl)piperazin-1-yl)phenyl)-1H-indole-2-carboxamide |
| 140 | N-(3-(1-(dimethylglycyl)pyrrolidin-3-yl)-5-fluorophenyl)-4-fluoro-7-methyl-1H-indole-2-carboxamide |
| 141 | N-(2-(1-(cyclopropylmethyl)-1H-pyrazol-4-yl)-1-(3-methylpyridin-2-yl)ethyl)-4-fluoro-7-methyl-1H-indole-2-carboxamide |
| 142 | N-(3-(1-(2,2-difluoroethyl)-1,8-diazaspiro[4.5]decan-8-yl)phenyl)-4-fluoro-7-methyl-1H-indole-2-carboxamide |
| 143 | N-(3-(2-cyclopropylmorpholino)phenyl)-4-fluoro-7-methyl-1H-indole-2-carboxamide |
| 144 | 4-fluoro-7-methyl-N-(3-(4-(methylamino)piperidin-1-yl)phenyl)-1H-indole-2-carboxamide |
| 145 | N-(3-chloro-5-(pyrimidin-5-yl)phenyl)-4-fluoro-7-methyl-1H-indole-2-carboxamide |

TABLE 1-continued

| Cpd. No. | Chemical Name |
|---|---|
| 146 | 4-fluoro-7-methyl-N-(3-(4-(tetrahydrofuran-3-yl)piperazin-1-yl)phenyl)-1H-indole-2-carboxamide |
| 147 | 4-fluoro-7-methyl-N-(3-(3-oxopiperazin-1-yl)phenyl)-1H-indole-2-carboxamide |
| 148 | 4-fluoro-N-(3-(3-((2-hydroxyethyl)(methyl)amino)pyrrolidin-1-yl)phenyl)-7-methyl-1H-indole-2-carboxamide |
| 149 | 4-fluoro-N-(3-(4-(3-hydroxypropanoyl)piperazin-1-yl)phenyl)-7-methyl-1H-indole-2-carboxamide |
| 150 | N-(3-(4-(3-aminopropyl)piperidin-1-yl)phenyl)-4-fluoro-7-methyl-1H-indole-2-carboxamide |
| 151 | 4-fluoro-7-methyl-N-(3-(1-methyl-1H-pyrazol-4-yl)phenyl)-1H-indole-2-carboxamide |
| 152 | 4-fluoro-7-methyl-N-(3-(4-(4-methylpiperazin-1-yl)piperidin-1-yl)phenyl)-1H-indole-2-carboxamide |
| 153 | N-(3-(3-(4,4-difluoropiperidin-1-yl)pyrrolidin-1-yl)phenyl)-4-fluoro-7-methyl-1H-indole-2-carboxamide |
| 154 | N-(3-((3R,4R)-3-(dimethylamino)-4-hydroxypyrrolidin-1-yl)phenyl)-4-fluoro-7-methyl-1H-indole-2-carboxamide |
| 155 | 4-fluoro-N-(3-(4-(3-methoxyazetidin-1-yl)piperidin-1-yl)phenyl)-7-methyl-1H-indole-2-carboxamide |
| 156 | 4-fluoro-N-(3-(3-((2-methoxyethyl)(methyl)amino)pyrrolidin-1-yl)phenyl)-7-methyl-1H-indole-2-carboxamide |
| 157 | 4-fluoro-7-methyl-N-(3-(4-(pyridin-3-ylamino)piperidin-1-yl)phenyl)-1H-indole-2-carboxamide |
| 159 | 4-fluoro-N-(3-fluoro-5-(3-methyl-3-morpholinopyrrolidin-1-yl)phenyl)-7-methyl-1H-indole-2-carboxamide |
| 160 | 4-fluoro-7-methyl-N-(3-(1-methyl-2-oxopiperidin-4-yl)phenyl)-1H-indole-2-carboxamide |
| 161 | N-((5-((1H-imidazol-1-yl)methyl)-3-methylpyridin-2-yl)(cyclopropyl)methyl)-4-fluoro-7-methyl-1H-indole-2-carboxamide |
| 162 | N-(3-(1H-1,2,4-triazol-1-yl)phenyl)-4-fluoro-7-methyl-1H-indole-2-carboxamide |
| 163 | N-(3-(8-acetyl-3,8-diazabicyclo[3.2.1]octan-3-yl)phenyl)-4-fluoro-7-methyl-1H-indole-2-carboxamide |
| 164 | 4-fluoro-7-methyl-N-(3-(1-(2-morpholinoethyl)-1H-pyrazol-4-yl)phenyl)-1H-indole-2-carboxamide |
| 165 | 4-fluoro-7-methyl-N-(3-(5-methylhexahydropyrrolo[3,4-c]pyrrol-2(1H)-yl)phenyl)-1H-indole-2-carboxamide |
| 166 | 4-fluoro-7-methyl-N-(3-((7S,8aR)-3-oxooctahydroindolizin-7-yl)phenyl)-1H-indole-2-carboxamide |
| 167 | N-(3-(2-((dimethylamino)methyl)morpholino)phenyl)-4-fluoro-7-methyl-1H-indole-2-carboxamide |
| 168 | 4-fluoro-7-methyl-N-(3-(1-methylpiperidin-4-yl)phenyl)-1H-indole-2-carboxamide |
| 169 | 4-fluoro-7-methyl-N-((1R,3S)-3-(4-methyl-3-oxopiperazin-1-yl)cyclohexyl)-1H-indole-2-carboxamide |
| 170 | N-(3-(4-(2-cyanoacetyl)piperazin-1-yl)phenyl)-4-fluoro-7-methyl-1H-indole-2-carboxamide |
| 171 | 4-fluoro-7-methyl-N-(3-(1-methyl-1H-imidazol-2-yl)phenyl)-1H-indole-2-carboxamide |
| 172 | 4-fluoro-7-methyl-N-(3-(1-methyloctahydro-5H-pyrrolo[3,2-c]pyridin-5-yl)phenyl)-1H-indole-2-carboxamide |
| 173 | N-(3-(4,4-bis(methoxymethyl)piperidin-1-yl)phenyl)-4-fluoro-7-methyl-1H-indole-2-carboxamide |
| 174 | 4-fluoro-N-(3-(3-(3-hydroxyazetidin-1-yl)pyrrolidin-1-yl)phenyl)-7-methyl-1H-indole-2-carboxamide |
| 175 | N-(2-(1-(cyclopropylmethyl)-1H-pyrazol-4-yl)-1-(3-methylpyridin-2-yl)ethyl)-7-methyl-1H-indole-2-carboxamide |
| 176 | 4-fluoro-7-methyl-N-(3-(4-(methylsulfonyl)piperazin-1-yl)phenyl)-1H-indole-2-carboxamide |
| 177 | 4-fluoro-7-methyl-N-(3-(5-oxopyrrolidin-3-yl)phenyl)-1H-indole-2-carboxamide |
| 178 | N-(3-(3-(azetidin-1-yl)pyrrolidin-1-yl)phenyl)-4-fluoro-7-methyl-1H-indole-2-carboxamide |
| 179 | N-(3-(2,7-diazaspiro[3.5]nonan-7-yl)phenyl)-4-fluoro-7-methyl-1H-indole-2-carboxamide |
| 180 | 4-fluoro-7-methyl-N-(3-(4-(pyrrolidin-1-yl)piperidin-1-yl)phenyl)-1H-indole-2-carboxamide |
| 181 | 4-fluoro-7-methyl-N-(3-(3-oxohexahydroimidazo[1,5-a]pyrazin-7(1H)-yl)phenyl)-1H-indole-2-carboxamide |
| 182 | 4-fluoro-7-methyl-N-(3-(1-methyloctahydro-6H-pyrrolo[3,4-b]pyridin-6-yl)phenyl)-1H-indole-2-carboxamide |
| 183 | 4-fluoro-N-(3-fluoro-5-(4-methyl-3-oxo-1,4-diazepan-1-yl)phenyl)-7-methyl-1H-indole-2-carboxamide |
| 184 | N-(3-(2,7-diazaspiro[3.5]nonan-2-yl)phenyl)-4-fluoro-7-methyl-1H-indole-2-carboxamide |
| 185 | N-(5-(4-acetylpiperazin-1-yl)-2-fluorophenyl)-4-fluoro-7-methyl-1H-indole-2-carboxamide |
| 186 | N-(3-((3R,4S)-4-(dimethylamino)-3-fluoropiperidin-1-yl)phenyl)-4-fluoro-7-methyl-1H-indole-2-carboxamide |

TABLE 1-continued

| Cpd. No. | Chemical Name |
|---|---|
| 187 | N-(3-(4-(dimethylamino)piperidin-1-yl)-5-methylphenyl)-4-fluoro-7-methyl-1H-indole-2-carboxamide |
| 188 | N-(3-chloro-5-(4-(3-morpholinopropyl)piperidin-1-yl)phenyl)-4-fluoro-7-methyl-1H-indole-2-carboxamide |
| 189 | N-(3-(2,8-diazaspiro[4.5]decan-2-yl)phenyl)-4-fluoro-7-methyl-1H-indole-2-carboxamide |
| 190 | N-(3-chloro-5-(4-(dimethylamino)piperidin-1-yl)phenyl)-4-fluoro-7-methyl-1H-indole-2-carboxamide |
| 191 | 4-fluoro-7-methyl-N-(3-(3-methyl-2-oxoimidazolidin-1-yl)phenyl)-1H-indole-2-carboxamide |
| 192 | N-(3-(4-aminopiperidin-1-yl)phenyl)-4-fluoro-7-methyl-1H-indole-2-carboxamide |
| 193 | N-(3-(4-acetyl-3-isobutylpiperazin-1-yl)phenyl)-4-fluoro-7-methyl-1H-indole-2-carboxamide |
| 194 | 4-fluoro-7-methyl-N-(3-morpholinophenyl)-1H-indole-2-carboxamide |
| 195 | N-(3-(4-(dimethylamino)-1-hydroxycyclohexyl)phenyl)-4-fluoro-7-methyl-1H-indole-2-carboxamide |
| 196 | 4-fluoro-N-(3-(isoxazol-5-yl)phenyl)-7-methyl-1H-indole-2-carboxamide |
| 197 | 4-fluoro-7-methyl-N-(3-(1-methyl-1H-imidazol-5-yl)phenyl)-1H-indole-2-carboxamide |
| 198 | 4-fluoro-N-(3-(4-methoxypiperidin-1-yl)phenyl)-7-methyl-1H-indole-2-carboxamide |
| 199 | N-(3-(4-(cyclopropylmethyl)piperazin-1-yl)phenyl)-4-fluoro-7-methyl-1H-indole-2-carboxamide |
| 200 | 4-fluoro-7-methyl-N-(3-(5-oxo-1,4-diazepan-1-yl)phenyl)-1H-indole-2-carboxamide |
| 201 | 4-fluoro-N-(3-(4-isopropyl-3-oxopiperazin-1-yl)phenyl)-7-methyl-1H-indole-2-carboxamide |
| 202 | N-(3-((3S,4R)-4-(dimethylamino)-3-methylpiperidin-1-yl)phenyl)-4-fluoro-7-methyl-1H-indole-2-carboxamide |
| 203 | N-(3-(2-((ethylamino)methyl)morpholino)phenyl)-4-fluoro-7-methyl-1H-indole-2-carboxamide |
| 204 | 4-fluoro-N-(3-(4-(2-hydroxyethyl)piperazin-1-yl)phenyl)-7-methyl-1H-indole-2-carboxamide |
| 205 | 4-fluoro-N-(3-(4-isopropyl-3-methylpiperazin-1-yl)phenyl)-7-methyl-1H-indole-2-carboxamide |
| 206 | N-(3-(2-(2,2-difluoroethyl)-2,8-diazaspiro[4.5]decan-8-yl)phenyl)-4-fluoro-7-methyl-1H-indole-2-carboxamide |
| 207 | 4-fluoro-7-methyl-N-(3-(4-(tetrahydro-2H-pyran-4-yl)piperazin-1-yl)phenyl)-1H-indole-2-carboxamide |
| 208 | N-(3-(4-(dimethylglycyl)piperazin-1-yl)phenyl)-4-fluoro-7-methyl-1H-indole-2-carboxamide |
| 209 | 4-fluoro-7-methyl-N-(3-(3-oxomorpholino)phenyl)-1H-indole-2-carboxamide |
| 210 | 4-fluoro-N-(3-(4-((2-hydroxyethyl)amino)piperidin-1-yl)phenyl)-7-methyl-1H-indole-2-carboxamide |
| 211 | 4-fluoro-7-methyl-N-((1R,3S)-3-morpholinocyclohexyl)-1H-indole-2-carboxamide |
| 212 | 4-fluoro-7-methyl-N-(3-(1-methyl-1,8-diazaspiro[4.5]decan-8-yl)phenyl)-1H-indole-2-carboxamide |
| 213 | N-(1-((1r,4r)-4-(dimethylamino)cyclohexyl)-1H-indazol-4-yl)-4-fluoro-7-methyl-1H-indole-2-carboxamide |
| 214 | N-(3-((3R,5R)-4-acetyl-3,5-dimethylpiperazin-1-yl)phenyl)-4-fluoro-7-methyl-1H-indole-2-carboxamide |
| 215 | 4-fluoro-7-methyl-N-(3-(pyrrolo[1,2-a]pyrazin-7-yl)phenyl)-1H-indole-2-carboxamide |
| 216 | 4-fluoro-7-methyl-N-(3-(3-methylmorpholino)phenyl)-1H-indole-2-carboxamide |
| 217 | N-(3-((1R,3R)-3-(dimethylamino)cyclopentyl)phenyl)-4-fluoro-7-methyl-1H-indole-2-carboxamide |
| 218 | N-(3-(6-oxa-3-azabicyclo[3.1.1]heptan-3-yl)phenyl)-4-fluoro-7-methyl-1H-indole-2-carboxamide |
| 219 | 4-fluoro-N-(3-(1-(2-hydroxyethyl)-1H-pyrazol-4-yl)phenyl)-7-methyl-1H-indole-2-carboxamide |
| 220 | 4-fluoro-N-(3-(hexahydropyrrolo[1,2-a]pyrazin-2(1H)-yl)phenyl)-7-methyl-1H-indole-2-carboxamide |
| 221 | N-(3-(1H-imidazol-1-yl)phenyl)-4-fluoro-7-methyl-1H-indole-2-carboxamide |
| 222 | N-(3-(4-(dimethylamino)-4-methylpiperidin-1-yl)phenyl)-4-fluoro-7-methyl-1H-indole-2-carboxamide |
| 223 | 4-fluoro-N-(3-(4-(2-methoxyethyl)piperazin-1-yl)phenyl)-7-methyl-1H-indole-2-carboxamide |
| 224 | 4-fluoro-7-methyl-N-(3-(oxetan-3-yl)phenyl)-1H-indole-2-carboxamide |
| 225 | 4-fluoro-7-methyl-N-(3-(4-(propylamino)piperidin-1-yl)phenyl)-1H-indole-2-carboxamide |
| 226 | N-(3-(1-(dimethylglycyl)pyrrolidin-3-yl)phenyl)-4-fluoro-7-methyl-1H-indole-2-carboxamide |
| 227 | N-(3-(4-(bis(2-hydroxyethyl)amino)piperidin-1-yl)phenyl)-4-fluoro-7-methyl-1H-indole-2-carboxamide |

TABLE 1-continued

| Cpd. No. | Chemical Name |
|---|---|
| 228 | N-(4'-((1H-imidazol-1-yl)methyl)-[1,1'-biphenyl]-3-yl)-4-fluoro-7-methyl-1H-indole-2-carboxamide |
| 229 | 4-fluoro-7-methyl-N-(3-(4-methyl-3-(trifluoromethyl)piperazin-1-yl)phenyl)-1H-indole-2-carboxamide |
| 230 | 4-fluoro-N-(3-fluoro-5-(1'-methyl-2'-oxo-[1,3'-bipyrrolidin]-3-yl)phenyl)-7-methyl-1H-indole-2-carboxamide |
| 231 | 4-fluoro-N-(4'-(2-hydroxyethoxy)-[1,1'-biphenyl]-3-yl)-7-methyl-1H-indole-2-carboxamide |
| 232 | 4-fluoro-7-methyl-N-(5-(4-methylpiperazin-1-yl)imidazo[1,5-a]pyridin-7-yl)-1H-indole-2-carboxamide |
| 233 | N-(3-(5,6-dihydroimidazo[1,2-a]pyrazin-7(8H)-yl)phenyl)-4-fluoro-7-methyl-1H-indole-2-carboxamide |
| 234 | 4-fluoro-7-methyl-N-(3-(4-methylpiperazin-1-yl)phenyl)-1H-indole-2-carboxamide |
| 235 | 4-fluoro-7-methyl-N-(3-(pyrazolo[1,5-a]pyridin-4-yl)phenyl)-1H-indole-2-carboxamide |
| 236 | N-(3-(4-cyclopropylpiperazin-1-yl)phenyl)-4-fluoro-7-methyl-1H-indole-2-carboxamide |
| 237 | 4-fluoro-7-methyl-N-(3-(4-methyl-4H-1,2,4-triazol-3-yl)phenyl)-1H-indole-2-carboxamide |
| 238 | 4-fluoro-7-methyl-N-(quinolin-5-yl)-1H-indole-2-carboxamide |
| 239 | 4-fluoro-7-methyl-N-(3-(1-methyl-1H-pyrazol-5-yl)phenyl)-1H-indole-2-carboxamide |
| 240 | N-(3-(4-(2-aminoethoxy)piperidin-1-yl)phenyl)-4-fluoro-7-methyl-1H-indole-2-carboxamide |
| 241 | N-(3-(2,8-diazaspiro[4.5]decan-8-yl)phenyl)-4-fluoro-7-methyl-1H-indole-2-carboxamide |
| 242 | N-(3-(4-acetylpiperazin-1-yl)-5-(trifluoromethyl)phenyl)-4-fluoro-7-methyl-1H-indole-2-carboxamide |
| 243 | 4-fluoro-N-(3-(4-isopropylpiperazin-1-yl)phenyl)-7-methyl-1H-indole-2-carboxamide |
| 244 | 4-fluoro-7-methyl-N-(3-(2-(4-methylpiperazin-1-yl)ethyl)phenyl)-1H-indole-2-carboxamide |
| 245 | 4-fluoro-7-methyl-N-(3-(1-methylhexahydropyrrolo[3,4-b]pyrrol-5(1H)-yl)phenyl)-1H-indole-2-carboxamide |
| 246 | N-(3-(4-(3-aminopropyl)piperidin-1-yl)-5-chlorophenyl)-4-fluoro-7-methyl-1H-indole-2-carboxamide |
| 247 | 4-fluoro-7-methyl-N-(1-(1-methylpiperidin-4-yl)-1H-indazol-4-yl)-1H-indole-2-carboxamide |
| 248 | N-(3-(4-acetyl-1,4-diazepan-1-yl)phenyl)-4-fluoro-7-methyl-1H-indole-2-carboxamide |
| 249 | N-(3-(1,2,4-oxadiazol-3-yl)phenyl)-4-fluoro-7-methyl-1H-indole-2-carboxamide |
| 250 | N-(3-(8-oxa-3-azabicyclo[3.2.1]octan-3-yl)phenyl)-4-fluoro-7-methyl-1H-indole-2-carboxamide |
| 251 | N-(3-(4-(dimethylamino)bicyclo[4.1.0]heptan-1-yl)phenyl)-4-fluoro-7-methyl-1H-indole-2-carboxamide |
| 252 | N-(3-(1H-pyrazol-4-yl)phenyl)-4-fluoro-7-methyl-1H-indole-2-carboxamide |
| 253 | N-(3-(4-(dimethylamino)-4-(methoxymethyl)piperidin-1-yl)phenyl)-4-fluoro-7-methyl-1H-indole-2-carboxamide |
| 254 | N-(3-(4-((dimethylamino)methyl)-4-hydroxypiperidin-1-yl)phenyl)-4-fluoro-7-methyl-1H-indole-2-carboxamide |
| 255 | N-(3-(1-cyano-4-(dimethylamino)cyclohexyl)phenyl)-4-fluoro-7-methyl-1H-indole-2-carboxamide |
| 256 | N-(3-(2-(dimethylamino)-2-oxoethyl)phenyl)-4-fluoro-7-methyl-1H-indole-2-carboxamide |
| 257 | N-(3-(6-acetyl-3,6-diazabicyclo[3.1.1]heptan-3-yl)phenyl)-4-fluoro-7-methyl-1H-indole-2-carboxamide |
| 258 | 4-fluoro-7-methyl-N-(1-(3-methyl-5-(2-(4-methylpiperazin-1-yl)ethyl)pyridin-2-yl)-2-phenylethyl)-1H-indole-2-carboxamide |
| 259 | N-(3-(8-(2,2-difluoroethyl)-2,8-diazaspiro[4.5]decan-2-yl)phenyl)-4-fluoro-7-methyl-1H-indole-2-carboxamide |
| 260 | tert-butyl 4-(3-(4-fluoro-7-methyl-1H-indole-2-carboxamido)phenyl)piperazine-1-carboxylate |
| 261 | 4-fluoro-7-methyl-N-(3-(oxazol-2-yl)phenyl)-1H-indole-2-carboxamide |
| 262 | 4-fluoro-N-(3-(4-methoxy-4-methylpiperidin-1-yl)phenyl)-7-methyl-1H-indole-2-carboxamide |
| 263 | N-(3'-acetamido-[1,1'-biphenyl]-3-yl)-4-fluoro-7-methyl-1H-indole-2-carboxamide |
| 264 | N-(3-((1S,3S)-3-(dimethylamino)cyclopentyl)phenyl)-4-fluoro-7-methyl-1H-indole-2-carboxamide |
| 265 | 4-fluoro-N-(3-(3-(hydroxymethyl)morpholino)phenyl)-7-methyl-1H-indole-2-carboxamide |
| 266 | N-(3'-((dimethylamino)methyl)-[1,1'-biphenyl]-3-yl)-4-fluoro-7-methyl-1H-indole-2-carboxamide |
| 267 | N-(3-(1-acetyl-4-carbamoylpiperidin-4-yl)-5-fluorophenyl)-4-fluoro-7-methyl-1H-indole-2-carboxamide |

TABLE 1-continued

| Cpd. No. | Chemical Name |
|---|---|
| 268 | 4-fluoro-N-(3-(4-hydroxy-1'-methyl-[4,4'-bipiperidin]-1-yl)phenyl)-7-methyl-1H-indole-2-carboxamide |
| 269 | N-(cyclopropyl(4-methoxy-3-methylpyridin-2-yl)methyl)-4-fluoro-7-methyl-1H-indole-2-carboxamide |
| 270 | 4-fluoro-7-methyl-N-(4-methyl-3-(4-methylpiperazin-1-yl)phenyl)-1H-indole-2-carboxamide |
| 271 | N-(3-(4-acetylpiperazin-1-yl)-5-fluorophenyl)-4-fluoro-1H-indole-2-carboxamide |
| 272 | 4-fluoro-N-(3-(imidazo[1,2-a]pyridin-5-yl)phenyl)-7-methyl-1H-indole-2-carboxamide |
| 273 | N-(cyclopropyl(3-methyl-5-((2-oxo-2,3-dihydro-1H-imidazol-1-yl)methyl)pyridin-2-yl)methyl)-4-fluoro-7-methyl-1H-indole-2-carboxamide |
| 274 | N-(3-(4-(dimethylamino)piperidin-1-yl)-5-(fluoromethyl)phenyl)-4-fluoro-7-methyl-1H-indole-2-carboxamide |
| 275 | N-(3-chloro-5-(4-(3-morpholinopropyl)piperidin-1-yl)phenyl)-4-fluoro-7-methyl-1H-indole-2-carboxamide |
| 276 | N-(3-(3-((dimethylamino)methyl)-1H-1,2,4-triazol-1-yl)phenyl)-4-fluoro-7-methyl-1H-indole-2-carboxamide |
| 277 | 4-fluoro-N-(3-(2-(hydroxymethyl)-4-methylpiperazin-1-yl)phenyl)-7-methyl-1H-indole-2-carboxamide |
| 278 | 4-fluoro-N-(3-(imidazo[1,5-a]pyridin-6-yl)phenyl)-7-methyl-1H-indole-2-carboxamide |
| 279 | 4-fluoro-7-methyl-N-(3-(4-methyl-1,4-diazepan-1-yl)phenyl)-1H-indole-2-carboxamide |
| 280 | 4-fluoro-N-(3-(4-isopropyl-2-methylpiperazin-1-yl)phenyl)-7-methyl-1H-indole-2-carboxamide |
| 281 | N-(3-(4H-1,2,4-triazol-4-yl)phenyl)-4-fluoro-7-methyl-1H-indole-2-carboxamide |
| 282 | N-(3-(3-(dimethylamino)cyclopentyl)phenyl)-4-fluoro-7-methyl-1H-indole-2-carboxamide |
| 283 | 4-fluoro-7-methyl-N-(3-(pyrrolidin-3-yl)phenyl)-1H-indole-2-carboxamide |
| 284 | N-(3-(2-oxa-5-azabicyclo[2.2.1]heptan-5-yl)phenyl)-4-fluoro-7-methyl-1H-indole-2-carboxamide |
| 285 | 4-fluoro-7-methyl-N-(3-(pyridin-2-yl)phenyl)-1H-indole-2-carboxamide |
| 286 | 4-fluoro-N-(3-(imidazo[1,2-a]pyridin-2-yl)phenyl)-7-methyl-1H-indole-2-carboxamide |
| 287 | N-(3-(4-oxa-7-azaspiro[2.5]octan-7-yl)phenyl)-4-fluoro-7-methyl-1H-indole-2-carboxamide |
| 288 | 4-fluoro-7-methyl-N-(3-(4-(methylamino)-4-oxobutyl)phenyl)-1H-indole-2-carboxamide |
| 289 | N-(3-(2,5-dimethylmorpholino)phenyl)-4-fluoro-7-methyl-1H-indole-2-carboxamide |
| 290 | 4-fluoro-7-methyl-N-(3-(pyrazolo[1,5-a]pyridin-3-yl)phenyl)-1H-indole-2-carboxamide |
| 291 | N-(3-(3-oxa-8-azabicyclo[3.2.1]octan-8-yl)phenyl)-4-fluoro-7-methyl-1H-indole-2-carboxamide |
| 292 | N-(3-(5-acetyl-2,5-diazabicyclo[2.2.1]heptan-2-yl)phenyl)-4-fluoro-7-methyl-1H-indole-2-carboxamide |
| 293 | 4-fluoro-7-methyl-N-(3-(3-(methylamino)-3-oxopropyl)phenyl)-1H-indole-2-carboxamide |
| 294 | 4-fluoro-7-methyl-N-(3-(1-methyloctahydro-1H-indol-5-yl)phenyl)-1H-indole-2-carboxamide |
| 295 | N-(2-(4-acetylpiperazin-1-yl)pyrimidin-4-yl)-4-fluoro-7-methyl-1H-indole-2-carboxamide |
| 296 | N-(3-(1,2,4-oxadiazol-5-yl)phenyl)-4-fluoro-7-methyl-1H-indole-2-carboxamide |
| 297 | 4-fluoro-7-methyl-N-(3-(piperidin-1-yl)phenyl)-1H-indole-2-carboxamide |
| 298 | N-(3-((3S,5S)-4-acetyl-3,5-dimethylpiperazin-1-yl)phenyl)-4-fluoro-7-methyl-1H-indole-2-carboxamide |
| 299 | 4-fluoro-N-(3-(imidazo[1,5-a]pyridin-1-yl)phenyl)-7-methyl-1H-indole-2-carboxamide |
| 300 | N-(3-(2-amino-2-oxoethyl)phenyl)-4-fluoro-7-methyl-1H-indole-2-carboxamide |
| 301 | N-(3-((3S,4R)-4-(dimethylamino)-3-fluoropiperidin-1-yl)phenyl)-4-fluoro-7-methyl-1H-indole-2-carboxamide |
| 302 | N-(3-((1R,3S)-3-(dimethylamino)cyclopentyl)phenyl)-4-fluoro-7-methyl-1H-indole-2-carboxamide |
| 303 | N-(3-((2S,4R)-4-(dimethylamino)-2-methylpiperidin-1-yl)phenyl)-4-fluoro-7-methyl-1H-indole-2-carboxamide |
| 304 | N-(3-(4H-1,2,4-triazol-3-yl)phenyl)-4-fluoro-7-methyl-1H-indole-2-carboxamide |
| 305 | 4-fluoro-7-methyl-N-(5-(3-(N-methylacetamido)piperidin-1-yl)tetrahydro-2H-pyran-3-yl)-1H-indole-2-carboxamide |
| 306 | N-(3-(3-cyclopropylmorpholino)phenyl)-4-fluoro-7-methyl-1H-indole-2-carboxamide |
| 307 | 4-fluoro-7-methyl-N-(3-(morpholin-3-yl)phenyl)-1H-indole-2-carboxamide |
| 308 | N-(3-((2R,4R)-4-(dimethylamino)-2-methylpiperidin-1-yl)phenyl)-4-fluoro-7-methyl-1H-indole-2-carboxamide |
| 309 | N-((5-((1H-imidazol-1-yl)methyl)-3-methylpyridin-2-yl)(cyclopropyl)methyl)-7-methyl-1H-indole-2-carboxamide |
| 310 | N-(3-(3-aminopiperidin-1-yl)phenyl)-4-fluoro-7-methyl-1H-indole-2-carboxamide |

TABLE 1-continued

| Cpd. No. | Chemical Name |
|---|---|
| 311 | N-(3-(difluoromethyl)-5-(4-(dimethylamino)piperidin-1-yl)phenyl)-4-fluoro-7-methyl-1H-indole-2-carboxamide |
| 312 | 4-fluoro-7-methyl-N-(3-(4-phenylpiperazin-1-yl)phenyl)-1H-indole-2-carboxamide |
| 313 | N-(3-((1r,4r)-4-(dimethylamino)cyclohexyl)-5-fluorophenyl)-4-fluoro-7-methyl-1H-indole-2-carboxamide |
| 314 | 4-fluoro-7-methyl-N-(3-(pyrrolidine-2-carboxamido)phenyl)-1H-indole-2-carboxamide |
| 315 | """4-fluoro-N-(3-(2-hydroxypropan-2-yl)phenyl)-7-methyl-1H-indole-2-carboxamide |
| 316 | 4-fluoro-7-methyl-N-(3-(pyrimidin-2-yl)phenyl)-1H-indole-2-carboxamide |
| 317 | N-(cyclopropyl(5-((2,4-dimethyl-1H-imidazol-1-yl)methyl)-3-methylpyridin-2-yl)methyl)-4-fluoro-7-methyl-1H-indole-2-carboxamide |
| 318 | N-(3-(2,4-dimethylpiperazin-1-yl)phenyl)-4-fluoro-7-methyl-1H-indole-2-carboxamide |
| 319 | N-(3-(5-amino-1,3,4-oxadiazol-2-yl)phenyl)-4-fluoro-7-methyl-1H-indole-2-carboxamide |
| 320 | 4-fluoro-7-methyl-N-(2-methyl-3-(4-methylpiperazin-1-yl)phenyl)-1H-indole-2-carboxamide |
| 321 | 4-fluoro-7-methyl-N-(3-(2-oxopiperazin-1-yl)phenyl)-1H-indole-2-carboxamide |
| 322 | N-(3-(1H-pyrazol-5-yl)phenyl)-4-fluoro-7-methyl-1H-indole-2-carboxamide |
| 323 | N-(3-(2-(dimethylamino)ethoxy)phenyl)-4-fluoro-7-methyl-1H-indole-2-carboxamide |
| 324 | N-(3-((1S,3R)-3-(dimethylamino)cyclopentyl)phenyl)-4-fluoro-7-methyl-1H-indole-2-carboxamide |
| 325 | 4-fluoro-7-methyl-N-(3-(methyl(piperidin-4-yl)amino)phenyl)-1H-indole-2-carboxamide |
| 326 | 4-fluoro-7-methyl-N-(3-(6-(methylamino)pyridin-2-yl)phenyl)-1H-indole-2-carboxamide |
| 327 | 4-fluoro-7-methyl-N-(2-oxo-2,3,4,5-tetrahydro-1H-benzo[d]azepin-1-yl)-1H-indole-2-carboxamide |
| 328 | N-(3-(5,6-dihydro-[1,2,4]triazolo[4,3-a]pyrazin-7(8H)-yl)phenyl)-4-fluoro-7-methyl-1H-indole-2-carboxamide |
| 329 | N-(3-(dimethylcarbamoyl)phenyl)-4-fluoro-7-methyl-1H-indole-2-carboxamide |
| 330 | 4-fluoro-7-methyl-N-(3-((1-methylpyrrolidin-3-yl)amino)phenyl)-1H-indole-2-carboxamide |
| 331 | 4-fluoro-N-(3-(3-(2-hydroxyethyl)morpholino)phenyl)-7-methyl-1H-indole-2-carboxamide |
| 332 | 4-fluoro-7-methyl-N-(3-(pyrrolidin-1-yl)phenyl)-1H-indole-2-carboxamide |
| 333 | N-(3-chloro-5-(morpholinomethyl)phenyl)-4-fluoro-7-methyl-1H-indole-2-carboxamide |
| 334 | 4-fluoro-7-methyl-N-(1-(3-methylpyridin-2-yl)-4-morpholino-4-oxobutyl)-1H-indole-2-carboxamide |
| 335 | N-(3-(3-(dimethylamino)piperidin-1-yl)phenyl)-4-fluoro-7-methyl-1H-indole-2-carboxamide |
| 336 | 4-fluoro-N-(3-(4-isopropylpiperidin-1-yl)phenyl)-7-methyl-1H-indole-2-carboxamide |
| 337 | N-(3-(1H-imidazol-4-yl)phenyl)-4-fluoro-7-methyl-1H-indole-2-carboxamide |
| 338 | 4-fluoro-7-methyl-N-(8-(4-methylpiperazin-1-yl)imidazo[1,2-a]pyridin-6-yl)-1H-indole-2-carboxamide |
| 339 | N-(3-chloro-5-((1r,4r)-4-(dimethylamino)cyclohexyl)phenyl)-4-fluoro-7-methyl-1H-indole-2-carboxamide |
| 340 | 4-fluoro-7-methyl-N-(2-(4-methylpiperazin-1-yl)pyridin-4-yl)-1H-indole-2-carboxamide |
| 341 | 4-fluoro-N-(3-(2-hydroxyethyl)phenyl)-7-methyl-1H-indole-2-carboxamide |
| 342 | 4-fluoro-7-methyl-N-(3-(methyl(1-methylpyrrolidin-3-yl)amino)phenyl)-1H-indole-2-carboxamide |
| 343 | N-(3-((1s,4s)-4-(dimethylamino)cyclohexyl)phenyl)-4-fluoro-7-methyl-1H-indole-2-carboxamide |
| 344 | 4-fluoro-7-methyl-N-(6-(4-methylpiperazin-1-yl)pyridin-2-yl)-1H-indole-2-carboxamide |
| 345 | N-(3-cyano-5-(4-(dimethylamino)piperidin-1-yl)phenyl)-4-fluoro-7-methyl-1H-indole-2-carboxamide |
| 346 | 4-fluoro-N-(4'-(hydroxymethyl)-[1,1'-biphenyl]-3-yl)-7-methyl-1H-indole-2-carboxamide |
| 347 | N-(3-(3-(4-aminopiperidin-1-yl)pyrrolidin-1-yl)phenyl)-4-fluoro-7-methyl-1H-indole-2-carboxamide |
| 348 | 4-fluoro-7-methyl-N-(3-(5-methyl-2,5-diazabicyclo[2.2.1]heptan-2-yl)phenyl)-1H-indole-2-carboxamide |
| 349 | 4-fluoro-7-methyl-N-(3-(3-methyl-3,8-diazabicyclo[3.2.1]octan-8-yl)phenyl)-1H-indole-2-carboxamide |
| 350 | 4-fluoro-7-methyl-N-(8-(4-methylpiperazin-1-yl)quinolin-6-yl)-1H-indole-2-carboxamide |
| 351 | 4-fluoro-7-methyl-N-(3-(methyl(1-methylpiperidin-4-yl)amino)phenyl)-1H-indole-2-carboxamide |
| 352 | 4-fluoro-7-methyl-N-(3-((1-methylpiperidin-3-yl)methyl)phenyl)-1H-indole-2-carboxamide |

TABLE 1-continued

| Cpd. No. | Chemical Name |
|---|---|
| 353 | 4-fluoro-N-(3-fluoro-5-((1r,4r)-4-morpholinocyclohexyl)phenyl)-7-methyl-1H-indole-2-carboxamide |
| 354 | 4-fluoro-7-methyl-N-(3-(pyrazolo[1,5-a]pyridin-2-yl)phenyl)-1H-indole-2-carboxamide |
| 355 | 4-fluoro-7-methyl-N-(5-(4-methylpiperazin-1-yl)imidazo[1,2-a]pyridin-7-yl)-1H-indole-2-carboxamide |
| 356 | N-(2-(1-(cyclopropylmethyl)-1H-imidazol-4-yl)-1-(3-methylpyridin-2-yl)ethyl)-4-fluoro-7-methyl-1H-indole-2-carboxamide |
| 357 | N-(3-((1H-imidazol-2-yl)methyl)phenyl)-4-fluoro-7-methyl-1H-indole-2-carboxamide |
| 358 | 4-fluoro-7-methyl-N-(1-(3-methylpyridin-2-yl)-2-(4-(morpholinomethyl)phenyl)ethyl)-1H-indole-2-carboxamide |
| 359 | N-((1S,3S)-3-(4-acetylpiperazin-1-yl)cyclohexyl)-4-fluoro-7-methyl-1H-indole-2-carboxamide |
| 360 | N-(5-(4-acetylpiperazin-1-yl)-1-methylpiperidin-3-yl)-4-fluoro-7-methyl-1H-indole-2-carboxamide |
| 361 | 4-fluoro-7-methyl-N-(8-oxo-6,7,8,9-tetrahydro-5H-pyrido[2,3-d]azepin-9-yl)-1H-indole-2-carboxamide |
| 362 | N-((1S,3S)-3-(1,4-oxazepan-4-yl)cyclohexyl)-4-fluoro-7-methyl-1H-indole-2-carboxamide |
| 363 | N-(5-(4-acetylpiperazin-1-yl)tetrahydro-2H-pyran-3-yl)-4-fluoro-7-methyl-1H-indole-2-carboxamide |
| 364 | 4-fluoro-7-methyl-N-(2,3,4,5-tetrahydro-1H-benzo[d]azepin-1-yl)-1H-indole-2-carboxamide |
| 365 | N-(3-(3-acetyl-3,6-diazabicyclo[3.1.1]heptan-6-yl)phenyl)-4-fluoro-7-methyl-1H-indole-2-carboxamide |
| 366 | N-(1'-acetyl-[1,4'-bipiperidin]-3-yl)-4-fluoro-7-methyl-1H-indole-2-carboxamide |
| 367 | 4-fluoro-7-methyl-N-(1'-methyl-2'-oxo-[1,4'-bipiperidin]-3-yl)-1H-indole-2-carboxamide |
| 368 | 4-fluoro-7-methyl-N-(5-(pyrimidin-5-yl)tetrahydro-2H-pyran-3-yl)-1H-indole-2-carboxamide |
| 369 | 4-fluoro-7-methyl-N-((1S,3S)-3-(pyrimidin-5-yl)cyclohexyl)-1H-indole-2-carboxamide |
| 370 | 4-fluoro-7-methyl-N-((1S,3S)-3-(4-methyl-3-oxo-1,4-diazepan-1-yl)cyclohexyl)-1H-indole-2-carboxamide |
| 371 | 4-fluoro-7-methyl-N-(5-(1-methylpiperidin-4-yl)-1H-imidazol-2-yl)-1H-indole-2-carboxamide |
| 372 | N-((1R,3R)-3-(4-acetylpiperazin-1-yl)cyclohexyl)-4-fluoro-7-methyl-1H-indole-2-carboxamide |
| 373 | N-((1S,3R)-3-(4-acetylpiperazin-1-yl)cyclohexyl)-4-fluoro-7-methyl-1H-indole-2-carboxamide |
| 374 | 4-fluoro-7-methyl-N-(3-morpholinocyclohexyl)-1H-indole-2-carboxamide |
| 375 | N-(3-(4-(dimethylamino)-4-(trifluoromethyl)piperidin-1-yl)phenyl)-4-fluoro-7-methyl-1H-indole-2-carboxamide |
| 376 | N-(3-(4-acetylpiperazin-1-yl)cyclopentyl)-4-fluoro-7-methyl-1H-indole-2-carboxamide |
| 377 | N-(1-(2-(dimethylamino)-2-oxoethyl)piperidin-3-yl)-4-fluoro-7-methyl-1H-indole-2-carboxamide |
| 378 | N-(1-(3-(dimethylamino)-3-oxopropyl)piperidin-3-yl)-4-fluoro-7-methyl-1H-indole-2-carboxamide |
| 379 | 4-fluoro-7-methyl-N-((1R,3R)-3-(pyrimidin-5-yl)cyclohexyl)-1H-indole-2-carboxamide |
| 380 | 4-fluoro-7-methyl-N-((1R,3S)-3-(pyrimidin-5-yl)cyclohexyl)-1H-indole-2-carboxamide |
| 381 | 4-fluoro-7-methyl-N-((1R,3R)-3-morpholinocyclohexyl)-1H-indole-2-carboxamide |
| 382 | 4-fluoro-7-methyl-N-((1R,3R)-3-(4-methyl-3-oxopiperazin-1-yl)cyclohexyl)-1H-indole-2-carboxamide |
| 383 | N-(4-(4-acetylpiperazin-1-yl)cyclohexyl)-4-fluoro-7-methyl-1H-indole-2-carboxamide |
| 384 | 4-fluoro-7-methyl-N-(1-(2-(methylamino)-2-oxoethyl)piperidin-3-yl)-1H-indole-2-carboxamide |
| 385 | 4-fluoro-7-methyl-N-((1R,3R)-3-(3-(N-methylacetamido)pyrrolidin-1-yl)cyclohexyl)-1H-indole-2-carboxamide |
| 386 | 4-fluoro-7-methyl-N-(1-(3-(methylamino)-3-oxopropyl)piperidin-3-yl)-1H-indole-2-carboxamide |
| 387 | 4-fluoro-7-methyl-N-((1R,3R)-3-(4-methyl-3-oxo-1,4-diazepan-1-yl)cyclohexyl)-1H-indole-2-carboxamide |
| 388 | N-((1R,3R)-3-(1,4-oxazepan-4-yl)cyclohexyl)-4-fluoro-7-methyl-1H-indole-2-carboxamide |
| 389 | 4-fluoro-7-methyl-N-(1-(3-(N-methylacetamido)propyl)piperidin-3-yl)-1H-indole-2-carboxamide |
| 390 | 4-fluoro-7-methyl-N-(3-methyl-2-oxo-2,3,4,5-tetrahydro-1H-benzo[d]azepin-1-yl)-1H-indole-2-carboxamide |
| 391 | 4-fluoro-7-methyl-N-(3-(4-methylpiperazin-1-yl)-2H-indazol-7-yl)-1H-indole-2-carboxamide |

TABLE 1-continued

| Cpd. No. | Chemical Name |
|---|---|
| 392 | 4-fluoro-7-methyl-N-((1-(2-(4-methylpiperazin-1-yl)phenyl)cyclopropyl)methyl)-1H-indole-2-carboxamide |
| 393 | 7-methyl-N-(3-morpholinophenyl)-1H-indole-2-carboxamide |
| 394 | 4-fluoro-7-methyl-N-(3-(1-methyl-1H-pyrazol-3-yl)phenyl)-1H-indole-2-carboxamide |
| 395 | N-(3-(1-aminocyclopropyl)phenyl)-4-fluoro-7-methyl-1H-indole-2-carboxamide |
| 396 | N-(3-(4-glycylpiperazin-1-yl)phenyl)-7-methyl-1H-indole-2-carboxamide |
| 397 | N-(3-(5-amino-1H-pyrazol-4-yl)phenyl)-4-fluoro-7-methyl-1H-indole-2-carboxamide |
| 398 | N-(3-(4-(dimethylamino)piperidin-1-yl)-5-ethylphenyl)-4-fluoro-7-methyl-1H-indole-2-carboxamide |
| 399 | 4-fluoro-7-methyl-N-(3-(methylsulfonyl)phenyl)-1H-indole-2-carboxamide |
| 400 | N-(cyclopropyl(3-methylimidazo[1,2-a]pyridin-2-yl)methyl)-4-fluoro-7-methyl-1H-indole-2-carboxamide |
| 401 | 4-fluoro-7-methyl-N-(8-(4-methylpiperazin-1-yl)isoquinolin-6-yl)-1H-indole-2-carboxamide |
| 402 | N-(cyclopropyl(5-methyl-6'-(morpholinomethyl)-[3,3'-bipyridin]-6-yl)methyl)-7-methyl-1H-indole-2-carboxamide |
| 403 | 4-fluoro-7-methyl-N-(5,6,7,8-tetrahydroisoquinolin-5-yl)-1H-indole-2-carboxamide |
| 404 | N-(cyclopropyl(3-methyl-5-(pyrimidin-2-yl)pyridin-2-yl)methyl)-7-methyl-1H-indole-2-carboxamide |
| 405 | N-(3-(4-((2-(diethylamino)ethyl)sulfonyl)piperazin-1-yl)phenyl)-7-methyl-1H-indole-2-carboxamide |
| 406 | N-(cyclopropyl(5-methyl-[3,3'-bipyridin]-6-yl)methyl)-7-methyl-1H-indole-2-carboxamide |
| 407 | 4-fluoro-7-methyl-N-(2-methyl-5-(4-methylpiperazin-1-yl)phenyl)-1H-indole-2-carboxamide |
| 408 | 7-methyl-N-(1-(3-methylpyridin-2-yl)-2-phenylethyl)-1H-indole-2-carboxamide |
| 409 | 4-fluoro-7-methyl-N-(3-((4-methylpiperazin-1-yl)methyl)isoquinolin-6-yl)-1H-indole-2-carboxamide |
| 410 | 4-fluoro-7-methyl-N-(5-(4-methylpiperazin-1-yl)pyridin-3-yl)-1H-indole-2-carboxamide |
| 411 | 4-fluoro-7-methyl-N-(3-(3-methyl-2-oxo-3,8-diazabicyclo[3.2.1]octan-8-yl)phenyl)-1H-indole-2-carboxamide |
| 412 | N-(cyclopropyl(3-methyl-5-((1-methylpiperidin-4-yl)carbamoyl)pyridin-2-yl)methyl)-4-fluoro-7-methyl-1H-indole-2-carboxamide |
| 413 | N-(3-(4-((2-aminoethyl)amino)piperidin-1-yl)phenyl)-4-fluoro-7-methyl-1H-indole-2-carboxamide |
| 414 | 4-fluoro-7-methyl-N-(1-(3-methyl-5-(2-(4-methylpiperazin-1-yl)ethyl)pyridin-2-yl)-3-phenylpropyl)-1H-indole-2-carboxamide |
| 415 | N-(3-(4-(dimethylamino)piperidin-1-yl)-2H-indazol-7-yl)-4-fluoro-7-methyl-1H-indole-2-carboxamide |
| 416 | 4-fluoro-7-methyl-N-(2-(piperidin-4-ylamino)quinazolin-6-yl)-1H-indole-2-carboxamide |
| 417 | 4-fluoro-7-methyl-N-(3-(4-(1-phenylethyl)piperazin-1-yl)phenyl)-1H-indole-2-carboxamide |
| 418 | N-(3-(2-aminoethyl)phenyl)-4-fluoro-7-methyl-1H-indole-2-carboxamide |
| 419 | N-((3-chloropyridin-2-yl)(cyclopropyl)methyl)-7-methyl-1H-indole-2-carboxamide |
| 420 | 7-methyl-N-(1-(3-methylpyridin-2-yl)-4-morpholino-4-oxobutyl)-1H-indole-2-carboxamide |
| 421 | 4-fluoro-7-methyl-N-(3-((4-methylpiperazin-1-yl)methyl)phenyl)-1H-indole-2-carboxamide |
| 422 | N-(3-(3-oxa-6-azabicyclo[3.1.1]heptan-6-yl)phenyl)-4-fluoro-7-methyl-1H-indole-2-carboxamide |
| 423 | N-(cyclopropyl(3-methyl-5-(4-(2-(pyridin-3-yl)acetamido)cyclohexyl)pyridin-2-yl)methyl)-7-methyl-1H-indole-2-carboxamide |
| 424 | N-(cyclopropyl(3-methylpyrazolo[1,5-a]pyridin-2-yl)methyl)-4-fluoro-7-methyl-1H-indole-2-carboxamide |
| 425 | 4-fluoro-7-methyl-N-(3-(pyrrolidin-2-yl)phenyl)-1H-indole-2-carboxamide |
| 426 | N-((6'-amino-5-methyl-[3,3'-bipyridin]-6-yl)(cyclopropyl)methyl)-7-methyl-1H-indole-2-carboxamide |
| 427 | N-(3-((dimethylamino)methyl)imidazo[1,2-a]pyridin-6-yl)-7-methyl-1H-indole-2-carboxamide |
| 428 | N-(3-(1H-imidazol-2-yl)phenyl)-4-fluoro-7-methyl-1H-indole-2-carboxamide |
| 429 | N-(3-(4-((4-aminocyclohexyl)sulfonyl)piperazin-1-yl)phenyl)-7-methyl-1H-indole-2-carboxamide |
| 430 | N-(cyclopropyl(5-(2-hydroxy-3-((pyridin-3-ylmethyl)amino)propoxy)-3-methylpyridin-2-yl)methyl)-7-methyl-1H-indole-2-carboxamide |
| 431 | 7-methyl-N-(1-(3-methylpyridin-2-yl)-4-morpholino-4-oxobutyl)-4-vinyl-1H-indole-2-carboxamide |
| 432 | N-((4-cyano-3-methylpyridin-2-yl)(cyclopropyl)methyl)-4-fluoro-7-methyl-1H-indole-2-carboxamide |
| 433 | N-(3-(4-(((1H-imidazol-5-yl)methyl)amino)piperidin-1-yl)phenyl)-4-fluoro-7-methyl-1H-indole-2-carboxamide |

TABLE 1-continued

| Cpd. No. | Chemical Name |
|---|---|
| 434 | N-(4-(4-hydroxypiperidin-1-yl)-1-(3-methylpyridin-2-yl)-4-oxobutyl)-7-methyl-1H-indole-2-carboxamide |
| 435 | N-(cyclopropyl(3-methyl-5-(2-(4-methylpiperazin-1-yl)ethyl)pyridin-2-yl)methyl)-7-methyl-1H-indole-2-carboxamide |
| 436 | N-(3-(8-(dimethylamino)-3-azabicyclo[3.2.1]octan-3-yl)phenyl)-4-fluoro-7-methyl-1H-indole-2-carboxamide |
| 437 | N-(isoquinolin-6-yl)-7-methyl-1H-indole-2-carboxamide |
| 438 | 4-fluoro-7-methyl-N-(3-(piperidin-2-yl)phenyl)-1H-indole-2-carboxamide |
| 439 | N-(3-(4-(2-aminoacetamido)piperidin-1-yl)phenyl)-7-methyl-1H-indole-2-carboxamide |
| 440 | N-(cyclopropyl(3-methyl-5-(4-(3-(pyridin-3-yl)propyl)piperazin-1-yl)pyridin-2-yl)methyl)-7-methyl-1H-indole-2-carboxamide |
| 441 | N-(cyclopropyl(3-methyl-5-(2-(4-methylpiperazin-1-yl)-2-oxoethyl)pyridin-2-yl)methyl)-7-methyl-1H-indole-2-carboxamide |
| 442 | 7-methyl-N-(2-methyl-5-(morpholinomethyl)phenyl)-1H-indole-2-carboxamide |
| 443 | N-(6-(4-((2-aminoethyl)sulfonyl)piperazin-1-yl)pyridin-2-yl)-7-methyl-1H-indole-2-carboxamide |
| 444 | N-(3-(5-amino-1H-pyrazol-3-yl)phenyl)-4-fluoro-7-methyl-1H-indole-2-carboxamide |
| 445 | N-((5-(1H-imidazol-2-yl)-3-methylpyridin-2-yl)(cyclopropyl)methyl)-7-methyl-1H-indole-2-carboxamide |
| 446 | N-(4-(dimethylamino)-1-(3-methylpyridin-2-yl)-4-oxobutyl)-7-methyl-1H-indole-2-carboxamide |
| 447 | N-(cyclopropyl(3-methyl-5-(2-(2-(pyridin-3-yl)acetamido)ethyl)pyridin-2-yl)methyl)-7-methyl-1H-indole-2-carboxamide |
| 448 | 7-methyl-N-(7-(4-methylpiperazine-1-carbonyl)naphthalen-2-yl)-1H-indole-2-carboxamide |
| 449 | N-(3-(4-((2-aminoethyl)sulfonyl)piperazin-1-yl)phenyl)-7-methyl-1H-indole-2-carboxamide |
| 450 | N-(cyclopropyl(4-methylpyridazin-3-yl)methyl)-4-fluoro-7-methyl-1H-indole-2-carboxamide |
| 451 | N-((5-(((1S,2R)-2-aminocyclobutyl)carbamoyl)-3-methylpyridin-2-yl)(cyclopropyl)methyl)-7-methyl-1H-indole-2-carboxamide |
| 452 | N-(3-(4-((2-aminoethyl)amino)piperidin-1-yl)phenyl)-7-methyl-1H-indole-2-carboxamide |
| 453 | 7-methyl-N-(7-((4-methylpiperazin-1-yl)methyl)naphthalen-2-yl)-1H-indole-2-carboxamide |
| 454 | 4-fluoro-7-methyl-N-(3-sulfamoylphenyl)-1H-indole-2-carboxamide |
| 455 | N-((5-(((1R,2R)-2-aminocyclobutyl)carbamoyl)-3-methylpyridin-2-yl)(cyclopropyl)methyl)-7-methyl-1H-indole-2-carboxamide |
| 456 | 7-methyl-N-(4-methyl-3-(morpholinomethyl)phenyl)-1H-indole-2-carboxamide |
| 457 | 7-methyl-N-((1-(2-morpholinophenyl)cyclopropyl)methyl)-1H-indole-2-carboxamide |
| 458 | 4-fluoro-7-methyl-N-(3-oxo-1,2,3,4-tetrahydroisoquinolin-4-yl)-1H-indole-2-carboxamide |
| 459 | N-(imidazo[1,2-a]pyridin-6-yl)-7-methyl-1H-indole-2-carboxamide |
| 460 | N-(4-(5,6-dihydroimidazo[1,5-a]pyrazin-7(8H)-yl)-1-(3-methylpyridin-2-yl)-4-oxobutyl)-7-methyl-1H-indole-2-carboxamide |
| 461 | N-(cyclopropyl(5-(2-hydroxy-3-((3-methoxybenzyl)amino)propoxy)-3-methylpyridin-2-yl)methyl)-7-methyl-1H-indole-2-carboxamide |
| 462 | N-(cyclopropyl(3-methylpyridin-2-yl)methyl)-4-fluoro-7-methyl-1H-indole-2-carboxamide |
| 463 | (R)-N-(cyclopropyl(3-methylpyridin-2-yl)methyl)-7-methyl-1H-indole-2-carboxamide |
| 464 | 7-ethyl-N-(1-(3-methylpyridin-2-yl)-4-morpholino-4-oxobutyl)-1H-indole-2-carboxamide |
| 465 | 7-methyl-N-(3-((4-methylpiperazin-1-yl)methyl)isoquinolin-6-yl)-1H-indole-2-carboxamide |
| 466 | 7-methyl-N-(quinazolin-7-yl)-1H-indole-2-carboxamide |
| 467 | N-(3-(4-(2-aminoethyl)piperazin-1-yl)phenyl)-7-methyl-1H-indole-2-carboxamide |
| 468 | N-(3-(3-((dimethylamino)methyl)morpholino)phenyl)-4-fluoro-7-methyl-1H-indole-2-carboxamide |
| 469 | 7-methyl-N-(2-methyl-5-(4-methylpiperazin-1-yl)phenyl)-1H-indole-2-carboxamide |
| 470 | N-(cyclopropyl(3-methyl-5-((1-methylpiperidin-4-yl)carbamoyl)pyridin-2-yl)methyl)-7-methyl-1H-indole-2-carboxamide |
| 471 | 7-methyl-N-(1-(3-methylpyridin-2-yl)propyl)-1H-indole-2-carboxamide |
| 472 | N-(cyclopropyl(3-methylquinolin-2-yl)methyl)-7-methyl-1H-indole-2-carboxamide |
| 473 | 7-methyl-N-(2-(piperidin-4-ylamino)quinazolin-6-yl)-1H-indole-2-carboxamide |
| 474 | 7-methyl-N-(2-methyl-1-(3-methylpyridin-2-yl)propyl)-1H-indole-2-carboxamide |
| 475 | N-(cyclopropyl(3-methylpyridin-2-yl)methyl)-7-methyl-1H-indole-2-carboxamide |
| 476 | N-(5-(4-((2-aminoethyl)sulfonyl)piperazin-1-yl)-2-methylphenyl)-7-methyl-1H-indole-2-carboxamide |

TABLE 1-continued

| Cpd. No. | Chemical Name |
|---|---|
| 477 | N-(cyclopropyl(3-methyl-5-((4-methylpiperazin-1-yl)methyl)pyridin-2-yl)methyl)-7-methyl-1H-indole-2-carboxamide |
| 478 | 7-methyl-N-(3-(morpholinomethyl)phenyl)-1H-indole-2-carboxamide |
| 479 | 7-methyl-N-phenyl-1H-indole-2-carboxamide |
| 480 | 7-methyl-N-(1-(3-methylpyridin-2-yl)ethyl)-1H-indole-2-carboxamide |
| 481 | N-(cyclopropyl(7-methylimidazo[1,2-b]pyridazin-6-yl)methyl)-4-fluoro-7-methyl-1H-indole-2-carboxamide |
| 482 | 7-methyl-N-(2-oxo-2,3,4,5-tetrahydro-1H-benzo[d]azepin-1-yl)-1H-indole-2-carboxamide |
| 483 | 7-methyl-N-(2-(2-morpholinophenyl)propyl)-1H-indole-2-carboxamide |
| 484 | N-(imidazo[1,2-a]pyrimidin-6-yl)-7-methyl-1H-indole-2-carboxamide |
| 485 | 4-ethyl-7-methyl-N-(1-(3-methylpyridin-2-yl)-4-morpholino-4-oxobutyl)-1H-indole-2-carboxamide |
| 486 | N-(3-((diethylamino)methyl)phenyl)-7-methyl-1H-indole-2-carboxamide |
| 487 | 7-methyl-N-(7-(morpholinomethyl)naphthalen-2-yl)-1H-indole-2-carboxamide |
| 488 | 7-methyl-N-(3-((4-methylpiperazin-1-yl)methyl)phenyl)-1H-indole-2-carboxamide |
| 489 | 7-methyl-N-(1-(3-methylpyridin-2-yl)-2-morpholinoethyl)-1H-indole-2-carboxamide |
| 490 | 7-methyl-N-(2-methyl-5-morpholinophenyl)-1H-indole-2-carboxamide |
| 491 | N-(2-(dimethylamino)-2-oxo-1-(pyridin-2-yl)ethyl)-4-fluoro-7-methyl-1H-indole-2-carboxamide |
| 492 | N-(cyclopropyl(2-hydroxy-6-methylphenyl)methyl)-7-methyl-1H-indole-2-carboxamide |
| 493 | N-(cyclopropyl(5-methylpyrimidin-4-yl)methyl)-7-methyl-1H-indole-2-carboxamide |
| 494 | 7-methyl-N-(1-(3-methylpyridin-2-yl)-5-morpholino-5-oxopentyl)-1H-indole-2-carboxamide |
| 495 | N-(3-((dimethylamino)methyl)-5-methylimidazo[1,2-a]pyridin-6-yl)-7-methyl-1H-indole-2-carboxamide |
| 496 | N-((5-(((1r,4r)-4-aminocyclohexyl)carbamoyl)-3-methylpyridin-2-yl)(cyclopropyl)methyl)-7-methyl-1H-indole-2-carboxamide |
| 497 | N-(cyclopropyl(3-methylpyridin-2-yl)methyl)-5-fluoro-7-methyl-1H-indole-2-carboxamide |
| 498 | 4-fluoro-7-methyl-N-(5,6,7,8-tetrahydroquinolin-8-yl)-1H-indole-2-carboxamide |
| 499 | N-(2-(4-acetylpiperazin-1-yl)benzyl)-7-methyl-1H-indole-2-carboxamide |
| 500 | N-(2-cyclopropyl-1-(3-methylpyridin-2-yl)ethyl)-7-methyl-1H-indole-2-carboxamide |
| 501 | N-(3-(2-amino-1H-imidazol-4-yl)phenyl)-4-fluoro-7-methyl-1H-indole-2-carboxamide |
| 502 | N-(3-(5-aminoisoxazol-3-yl)phenyl)-4-fluoro-7-methyl-1H-indole-2-carboxamide |
| 503 | N-(2-amino-2-oxo-1-(pyridin-2-yl)ethyl)-4-fluoro-7-methyl-1H-indole-2-carboxamide |
| 504 | 7-methyl-N-((1r,4r)-4-methylcyclohexyl)-1H-indole-2-carboxamide |
| 505 | 7-methyl-N-(tetrahydro-2H-pyran-4-yl)-1H-indole-2-carboxamide |
| 506 | N-(cyclopropyl(3-methyl-6-oxo-1,6-dihydropyridin-2-yl)methyl)-7-methyl-1H-indole-2-carboxamide |
| 507 | N-(cyclopropyl(isoquinolin-1-yl)methyl)-4-fluoro-7-methyl-1H-indole-2-carboxamide |
| 508 | 7-methyl-N-((2-morpholinocyclohexyl)methyl)-1H-indole-2-carboxamide |
| 509 | N-(3-(4-acetylpiperazin-1-yl)phenyl)-7-cyclopropyl-1H-indole-2-carboxamide |
| 510 | N-(cyclopropyl(3-methyl-5-(pyrrolidin-3-ylcarbamoyl)pyridin-2-yl)methyl)-7-methyl-1H-indole-2-carboxamide |
| 511 | 7-methyl-N-(2-morpholinophenethyl)-1H-indole-2-carboxamide |
| 512 | N-((1r,4r)-4-acetamidocyclohexyl)-4-fluoro-7-methyl-1H-indole-2-carboxamide |
| 513 | N-(cyclobutyl(3-methylpyridin-2-yl)methyl)-7-methyl-1H-indole-2-carboxamide |
| 514 | 4-methoxy-7-methyl-N-(1-(3-methylpyridin-2-yl)-4-morpholino-4-oxobutyl)-1H-indole-2-carboxamide |
| 515 | 7-methoxy-N-(1-(3-methylpyridin-2-yl)-4-morpholino-4-oxobutyl)-1H-indole-2-carboxamide |
| 516 | N-((5-(((1R,3R)-3-aminocyclopentyl)carbamoyl)-3-methylpyridin-2-yl)(cyclopropyl)methyl)-7-methyl-1H-indole-2-carboxamide |
| 517 | 4-fluoro-7-methyl-N-(2-oxo-2-(phenylamino)-1-(pyridin-2-yl)ethyl)-1H-indole-2-carboxamide |
| 518 | N-(cyclopropyl(3-methylpyrazin-2-yl)methyl)-7-methyl-1H-indole-2-carboxamide |
| 519 | 4-fluoro-7-methyl-N-(5-(1-methylpiperidin-4-yl)-1,3,4-thiadiazol-2-yl)-1H-indole-2-carboxamide |
| 520 | 7-methyl-N-(2-oxo-2,3,4,5-tetrahydro-1H-benzo[b]azepin-4-yl)-1H-indole-2-carboxamide |
| 521 | N-(cyclopropyl(3-ethylpyridin-2-yl)methyl)-7-methyl-1H-indole-2-carboxamide |
| 522 | N-cyclohexyl-7-methyl-1H-indole-2-carboxamide |
| 523 | 7-methyl-N-(1-(3-methylpyridin-2-yl)-4-oxo-4-(pyridin-3-ylamino)butyl)-1H-indole-2-carboxamide |
| 524 | N-(3-(5-amino-1H-1,2,4-triazol-3-yl)phenyl)-4-fluoro-7-methyl-1H-indole-2-carboxamide |

TABLE 1-continued

| Cpd. No. | Chemical Name |
|---|---|
| 525 | methyl (R)-3-(4-bromophenyl)-3-(7-methyl-1H-indole-2-carboxamido)propanoate |
| 526 | 7-methyl-N-(naphthalen-2-yl)-1H-indole-2-carboxamide |
| 527 | methyl (R)-3-(4-cyanophenyl)-3-(7-methyl-1H-indole-2-carboxamido)propanoate |
| 528 | 7-methyl-N-(2-(pyrrolidin-1-yl)benzyl)-1H-indole-2-carboxamide |
| 529 | N-(cyclopropyl(3,6-dimethyl-5-((1-methylpiperidin-4-yl)carbamoyl)pyridin-2-yl)methyl)-7-methyl-1H-indole-2-carboxamide |
| 530 | N-(3-(4-amino-[1,4'-bipiperidin]-1'-yl)phenyl)-4-fluoro-7-methyl-1H-indole-2-carboxamide |
| 531 | N-(6-(4-((2-aminoethyl)amino)piperidin-1-yl)pyridin-2-yl)-7-methyl-1H-indole-2-carboxamide |
| 532 | 4-fluoro-7-methyl-N-(3-(5-oxo-4,5-dihydro-1H-1,2,4-triazol-3-yl)phenyl)-1H-indole-2-carboxamide |
| 533 | 7-methyl-N-(quinazolin-6-yl)-1H-indole-2-carboxamide |
| 534 | 4-fluoro-7-methyl-N-(quinazolin-8-yl)-1H-indole-2-carboxamide |
| 535 | N-((5-(azetidin-3-ylcarbamoyl)-3-methylpyridin-2-yl)(cyclopropyl)methyl)-7-methyl-1H-indole-2-carboxamide |
| 536 | N-(3-((dimethylamino)methyl)imidazo[1,2-a]pyridin-6-yl)-4-fluoro-7-methyl-1H-indole-2-carboxamide |
| 537 | N-(6-(diethylamino)-5,6,7,8-tetrahydronaphthalen-2-yl)-7-methyl-1H-indole-2-carboxamide |
| 538 | 7-methyl-N-(4-oxo-3,4-dihydroquinazolin-6-yl)-1H-indole-2-carboxamide |
| 539 | 4-fluoro-7-methyl-N-(3-(4-methyl-2-phenylpiperazin-1-yl)phenyl)-1H-indole-2-carboxamide |
| 540 | 4-fluoro-7-methyl-N-(2-(4-methylpiperazin-1-yl)phenethyl)-1H-indole-2-carboxamide |
| 541 | 7-methyl-N-(2-(piperazin-1-ylmethyl)quinazolin-6-yl)-1H-indole-2-carboxamide |
| 542 | 2-(6-(cyclopropyl(4-fluoro-7-methyl-1H-indole-2-carboxamido)methyl)-5-methylpyridin-3-yl)acetic acid |
| 543 | N-((3R,4S)-1-(4-aminobutanoyl)-3-methylpiperidin-4-yl)-7-methyl-1H-indole-2-carboxamide |
| 544 | 6-(cyclopropyl(4-fluoro-7-methyl-1H-indole-2-carboxamido)methyl)-5-methylnicotinic acid |
| 545 | 4-fluoro-7-methyl-N-(3-(5-oxo-4,5-dihydro-1,2,4-oxadiazol-3-yl)phenyl)-1H-indole-2-carboxamide |
| 546 | N-(2-((dimethylamino)methyl)imidazo[1,2-a]pyridin-6-yl)-7-methyl-1H-indole-2-carboxamide |
| 547 | N-(3-(2,3-dihydro-4H-benzo[b][1,4]oxazin-4-yl)phenyl)-4-fluoro-7-methyl-1H-indole-2-carboxamide |
| 548 | 4-fluoro-7-methyl-N-(1-(1-methylpiperidin-4-yl)-1H-pyrazol-3-yl)-1H-indole-2-carboxamide |
| 549 | N-(2-(4-(2-(dimethylamino)ethyl)piperidin-1-yl)phenethyl)-7-methyl-1H-indole-2-carboxamide |
| 550 | N-(2-(benzylamino)-2-oxo-1-(pyridin-2-yl)ethyl)-4-fluoro-7-methyl-1H-indole-2-carboxamide |
| 551 | N-(3-((dimethylamino)methyl)-7-methylimidazo[1,2-a]pyridin-6-yl)-7-methyl-1H-indole-2-carboxamide |
| 552 | N-((1R,3s,5S)-8-(4-aminobutanoyl)-8-azabicyclo[3.2.1]octan-3-yl)-7-methyl-1H-indole-2-carboxamide |
| 553 | N-((1r,4r)-4-(3-aminopropanamido)cyclohexyl)-7-bromo-1H-indole-2-carboxamide |
| 554 | 7-methyl-N-(2-(4-methylpiperazin-1-yl)benzyl)-1H-indole-2-carboxamide |
| 555 | N-(3-(4-cyclopropyl-3,4-dihydroquinoxalin-1(2H)-yl)phenyl)-4-fluoro-7-methyl-1H-indole-2-carboxamide |
| 556 | methyl 3-(2-fluorophenyl)-3-(7-methyl-1H-indole-2-carboxamido)propanoate |
| 557 | 4-fluoro-7-methyl-N-(5-(1-methylpiperidin-4-yl)-1,3,4-oxadiazol-2-yl)-1H-indole-2-carboxamide |
| 558 | 4-fluoro-7-methyl-N-(5-(1-methylpiperidin-4-yl)-1H-pyrazol-3-yl)-1H-indole-2-carboxamide |
| 559 | 4-fluoro-7-methyl-N-(5-(1-methylpiperidin-4-yl)-4H-1,2,4-triazol-3-yl)-1H-indole-2-carboxamide |
| 560 | 4-fluoro-7-methyl-N-(2-morpholino-2-oxo-1-(pyridin-2-yl)ethyl)-1H-indole-2-carboxamide |
| 561 | 4-fluoro-7-methyl-N-(1-(1-methylpiperidin-4-yl)-1H-imidazol-4-yl)-1H-indole-2-carboxamide |
| 562 | 4-fluoro-7-methyl-N-(2-(1-methylpiperidin-4-yl)-1H-imidazol-5-yl)-1H-indole-2-carboxamide |
| 563 | N-(cyclopentyl(3-methylpyridin-2-yl)methyl)-7-methyl-1H-indole-2-carboxamide |
| 564 | N-(cyclopropyl(2-oxoindolin-7-yl)methyl)-7-methyl-1H-indole-2-carboxamide |
| 565 | N-(1-(4-(dimethylamino)cyclohexyl)-1H-pyrazol-4-yl)-4-fluoro-7-methyl-1H-indole-2-carboxamide |
| 566 | N-(2-(2-((dimethylamino)methyl)morpholino)phenethyl)-7-methyl-1H-indole-2-carboxamide |
| 567 | 7-methyl-N-(1-(3-methylpyridin-2-yl)-4-(piperazin-1-yl)butyl)-1H-indole-2-carboxamide |
| 568 | N-(2,2-dimethyl-1-(3-methylpyridin-2-yl)propyl)-7-methyl-1H-indole-2-carboxamide |

TABLE 1-continued

| Cpd. No. | Chemical Name |
|---|---|
| 569 | 4-fluoro-7-methyl-N-(1-(1-methylpiperidin-4-yl)-1H-pyrazol-4-yl)-1H-indole-2-carboxamide |
| 570 | 7-methyl-N-(pyrazolo[1,5-a]pyridin-7-ylmethyl)-1H-indole-2-carboxamide |
| 571 | 7-methyl-N-(1-(3-methylpyridin-2-yl)-4-oxo-4-((tetrahydrofuran-3-yl)amino)butyl)-1H-indole-2-carboxamide |
| 572 | 7-methyl-N-(1-(3-methylpyridin-2-yl)-4-oxo-4-(piperazin-1-yl)butyl)-1H-indole-2-carboxamide |
| 573 | N-((5-(((1S,2S)-2-aminocyclobutyl)carbamoyl)-3-methylpyridin-2-yl)(cyclopropyl)methyl)-7-methyl-1H-indole-2-carboxamide |
| 574 | N-(cyclopropyl(3-methylpyridin-2-yl)methyl)-7-(hydroxymethyl)-1H-indole-2-carboxamide |
| 575 | 7-methyl-N-(2-morpholinobenzyl)-1H-indole-2-carboxamide |
| 576 | 2-(cyclopropyl(7-methyl-1H-indole-2-carboxamido)methyl)-3-methylpyridine 1-oxide |
| 577 | N-(cyclopropyl(2-methyl-4-(piperazine-1-carbonyl)phenyl)methyl)-7-methyl-1H-indole-2-carboxamide |
| 578 | N-(imidazo[1,2-a]pyridin-7-yl)-7-methyl-1H-indole-2-carboxamide |
| 579 | N-(4-((4-aminocyclohexyl)amino)-1-(3-methylpyridin-2-yl)-4-oxobutyl)-7-methyl-1H-indole-2-carboxamide |
| 580 | N-(2-(1H-imidazol-1-yl)phenethyl)-7-methyl-1H-indole-2-carboxamide |
| 581 | N-((1r,4r)-4-((3-aminopropyl)sulfonamido)cyclohexyl)-7-methyl-1H-indole-2-carboxamide |
| 582 | N-(4-(diethylamino)-1-(3-methylpyridin-2-yl)butyl)-7-methyl-1H-indole-2-carboxamide |
| 583 | N-(cyclopropyl(2-methyl-5-(piperazine-1-carbonyl)phenyl)methyl)-7-methyl-1H-indole-2-carboxamide |
| 584 | N-((5-(((1R,2S)-2-aminocyclobutyl)carbamoyl)-3-methylpyridin-2-yl)(cyclopropyl)methyl)-7-methyl-1H-indole-2-carboxamide |
| 585 | 4-fluoro-7-methyl-N-(2-(methylamino)-2-oxo-1-(pyridin-2-yl)ethyl)-1H-indole-2-carboxamide |
| 586 | ethyl 3-(7-methyl-1H-indole-2-carboxamido)-3-phenylpropanoate |
| 587 | 7-methyl-N-((1r,4r)-4-(3-(piperidin-1-yl)propanamido)cyclohexyl)-1H-indole-2-carboxamide |
| 588 | N-((3S,4R)-1-(4-aminobutanoyl)-3-methylpiperidin-4-yl)-7-methyl-1H-indole-2-carboxamide |
| 589 | N-((1r,4r)-4-(3-(diethylamino)propanamido)cyclohexyl)-7-methyl-1H-indole-2-carboxamide |
| 590 | N-((3R,4R)-1-(4-aminobutanoyl)-3-methylpiperidin-4-yl)-7-methyl-1H-indole-2-carboxamide |
| 591 | 7-methyl-N-(3-(3-methylpyridin-2-yl)azetidin-3-yl)-1H-indole-2-carboxamide |
| 592 | N-((1s,4s)-4-(3-aminopropanamido)cyclohexyl)-7-methyl-1H-indole-2-carboxamide |
| 593 | N-(1-(4-aminobutanoyl)pyrrolidin-3-yl)-7-methyl-1H-indole-2-carboxamide |
| 594 | N-(1-(4-aminobutanoyl)azetidin-3-yl)-7-methyl-1H-indole-2-carboxamide |
| 595 | 7-methyl-N-(2-(3-methylpyridin-2-yl)propan-2-yl)-1H-indole-2-carboxamide |
| 596 | N-((1s,3s)-3-(3-aminopropanamido)cyclobutyl)-7-methyl-1H-indole-2-carboxamide |
| 597 | N-((1r,3r)-3-(3-aminopropanamido)cyclobutyl)-7-methyl-1H-indole-2-carboxamide |
| 598 | N-(cyclopropyl(3-methylpyridin-2-yl)methyl)-7-methyl-1H-pyrrolo[2,3-c]pyridine-2-carboxamide |
| 599 | N-(cyclopropyl(3-methylpyridin-2-yl)methyl)-7-methyl-1H-pyrrolo[3,2-b]pyridine-2-carboxamide |
| 600 | N-(3-(3-aminopropanamido)cyclopentyl)-7-methyl-1H-indole-2-carboxamide |
| 601 | N,7-dimethyl-N-(1-(3-methylpyridin-2-yl)-2-morpholinoethyl)-1H-indole-2-carboxamide |
| 602 | N-((5-(aminomethyl)-3-methylisoxazol-4-yl)(cyclopropyl)methyl)-7-methyl-1H-indole-2-carboxamide |
| 603 | N-(2-(dimethylamino)-1-(pyridin-3-yl)ethyl)-7-methyl-1H-indole-2-carboxamide |
| 604 | N-(cyclopropyl(3-methylpyridin-2-yl)methyl)pyrazolo[1,5-a]pyrimidine-2-carboxamide |
| 605 | 7-methyl-N-((1r,4r)-4-(2-(pyridin-3-yl)acetamido)cyclohexyl)-1H-indole-2-carboxamide |
| 606 | N-(cyclopropyl(3-methylpyridin-2-yl)methyl)-4-(hydroxymethyl)-7-methyl-1H-indole-2-carboxamide |
| 607 | N-(cyclopropyl(3-methylpyridin-2-yl)methyl)-7-methylindoline-2-carboxamide |
| 608 | N-(cyclopropyl(3-methylpyridin-2-yl)methyl)-7-methyl-1H-pyrrolo[3,2-c]pyridine-2-carboxamide |
| 609 | 4-fluoro-7-methyl-N-(quinolin-8-yl)-1H-indole-2-carboxamide |
| 612 | 4-fluoro-7-methyl-N-(4-(4-methylpiperazin-1-yl)pyridin-2-yl)-1H-indole-2-carboxamide |
| 613 | (S)-N-(cyclopropyl(3-methylpyridin-2-yl)methyl)-7-methyl-1H-indole-2-carboxamide |
| 614 | N-((3S,4S)-1-(4-aminobutanoyl)-3-methylpiperidin-4-yl)-7-methyl-1H-indole-2-carboxamide |
| 615 | N-(cyclopropyl(6-((dimethylamino)methyl)pyridin-2-yl)methyl)-7-methyl-1H-indole-2-carboxamide |

TABLE 1-continued

| Cpd. No. | Chemical Name |
|---|---|
| 616 | (R)-N-(2-hydroxy-1-phenylethyl)-7-methyl-1H-indole-2-carboxamide |
| 617 | 7-methyl-N-(2-oxo-6-phenylazepan-4-yl)-1H-indole-2-carboxamide |
| 618 | 7-((1H-pyrazol-5-yl)methyl)-N-(cyclopropyl(3-methylpyridin-2-yl)methyl)-1H-indole-2-carboxamide |
| 619 | (2,3-dihydrospiro[indene-1,2'-pyrrolidin]-1'-yl)(7-methyl-1H-indol-2-yl)methanone |
| 620 | 7-methyl-N-(1-oxo-2,3,4,5-tetrahydro-1H-benzo[c]azepin-5-yl)-1H-indole-2-carboxamide |
| 622 | N-(5-chloro-2-morpholinophenethyl)-7-methyl-1H-indole-2-carboxamide |
| 623 | N-(imidazo[1,2-a]pyrazin-6-yl)-7-methyl-1H-indole-2-carboxamide |
| 624 | 7-methyl-N-(2-methyl-3-(morpholinomethyl)phenyl)-1H-indole-2-carboxamide |
| 625 | N-((1S,4S,5S)-2-(4-aminobutanoyl)-2-azabicyclo[2.2.2]octan-5-yl)-7-methyl-1H-indole-2-carboxamide |
| 626 | 7-methyl-N-(1-(pyrimidin-2-yl)piperidin-3-yl)-1H-indole-2-carboxamide |
| 627 | N-(2-(dimethylamino)-1-(3-methylpyridin-2-yl)ethyl)-7-methyl-1H-indole-2-carboxamide |
| 628 | ethyl 4-(7-methyl-1H-indole-2-carboxamido)piperidine-1-carboxylate |
| 629 | N-((1r,4r)-4-(3-aminopropanamido)-4-methylcyclohexyl)-7-methyl-1H-indole-2-carboxamide |
| 630 | ethyl 3-cyclobutyl-2-(7-methyl-1H-indole-2-carboxamido)propanoate |
| 631 | N-((1R,4R,5S)-2-(3-aminopropanoyl)-2-azabicyclo[2.2.2]octan-5-yl)-7-methyl-1H-indole-2-carboxamide |
| 632 | 7-methyl-N-(pyridin-4-yl)-1H-indole-2-carboxamide |
| 633 | 7-methyl-N-(6-(morpholinomethyl)pyridin-2-yl)-1H-indole-2-carboxamide |
| 634 | methyl (R)-3-(3-chlorophenyl)-3-(7-methyl-1H-indole-2-carboxamido)propanoate |
| 635 | N-(2-(2'-(aminomethyl)-[1,1'-biphenyl]-2-yl)ethyl)-7-methyl-1H-indole-2-carboxamide |
| 636 | 7-methyl-N-(2-(piperazin-1-yl)benzyl)-1H-indole-2-carboxamide |
| 637 | N-(di(pyridin-2-yl)methyl)-7-methyl-1H-indole-2-carboxamide |
| 638 | N-(2-(dimethylamino)benzyl)-7-methyl-1H-indole-2-carboxamide |
| 639 | N-(1-(4-aminobutanoyl)piperidin-4-yl)-7-methyl-1H-indole-2-carboxamide |
| 640 | N-(8-(3-aminopropanamido)bicyclo[3.2.1]octan-3-yl)-7-methyl-1H-indole-2-carboxamide |
| 641 | N-((1s,4s)-4-(3-aminopropanamido)-4-methylcyclohexyl)-7-methyl-1H-indole-2-carboxamide |
| 642 | 7-methyl-N-(2,2,2-trifluoro-1-(3-fluorophenyl)ethyl)-1H-indole-2-carboxamide |
| 643 | 7-methyl-N-(1-(pyridin-3-yl)cyclopropyl)-1H-indole-2-carboxamide |
| 644 | N-((1r,4r)-4-(3-aminopropanamido)cyclohexyl)-4,7-dimethyl-1H-indole-2-carboxamide |
| 645 | N-((1r,4r)-4-(3-aminopropanamido)cyclohexyl)-N,7-dimethyl-1H-indole-2-carboxamide |
| 646 | N-(1-((3-aminopropyl)sulfonyl)piperidin-3-yl)-7-methyl-1H-indole-2-carboxamide |
| 648 | methyl 3-(furan-2-yl)-3-(7-methyl-1H-indole-2-carboxamido)propanoate |
| 649 | methyl 3-(7-methyl-1H-indole-2-carboxamido)-3-(thiophen-3-yl)propanoate |
| 650 | methyl 3-(7-methyl-1H-indole-2-carboxamido)-3-(thiophen-2-yl)propanoate |
| 652 | N-(1-(4-(1H-pyrazol-1-yl)phenyl)ethyl)-7-methyl-1H-indole-2-carboxamide |
| 653 | N-(4-chloro-2-morpholinophenethyl)-7-methyl-1H-indole-2-carboxamide |
| 654 | N-((1S,4R)-bicyclo[2.2.1]heptan-2-yl)-7-methyl-1H-indole-2-carboxamide |
| 655 | N-((1r,4r)-4-(3-aminopropanamido)cyclohexyl)-3,7-dimethyl-1H-indole-2-carboxamide |
| 656 | N-((1R,3r,5S)-8-(4-aminobutanoyl)-8-azabicyclo[3.2.1]octan-3-yl)-7-methyl-3a,7a-dihydro-1H-indole-2-carboxamide |
| 657 | N-((1S,4S,5R)-2-(4-aminobutanoyl)-2-azabicyclo[2.2.2]octan-5-yl)-7-methyl-1H-indole-2-carboxamide |
| 658 | methyl (R)-3-(7-methyl-1H-indole-2-carboxamido)-3-(pyridin-3-yl)propanoate |
| 659 | methyl 3-(3-methoxyphenyl)-3-(7-methyl-1H-indole-2-carboxamido)propanoate |
| 660 | N-(cyclopropyl(pyridin-2-yl)methyl)-7-methyl-1H-indole-2-carboxamide |
| 661 | N-((1r,4r)-4-((2-aminoethyl)sulfonamido)cyclohexyl)-7-methyl-1H-indole-2-carboxamide |
| 662 | N-((1s,4s)-4-(hydroxymethyl)cyclohexyl)-7-methyl-1H-indole-2-carboxamide |
| 663 | N-(1-((3-aminopropyl)sulfonyl)piperidin-4-yl)-7-methyl-1H-indole-2-carboxamide |
| 664 | N-(1-(4-aminobutanoyl)piperidin-3-yl)-7-methyl-1H-indole-2-carboxamide |
| 665 | 7-methyl-N-(pyrimidin-5-yl)-1H-indole-2-carboxamide |
| 666 | methyl (R)-3-(7-methyl-1H-indole-2-carboxamido)-3-phenylpropanoate |
| 667 | N-((6-(2-amino-2-oxoethyl)pyridin-2-yl)(cyclopropyl)methyl)-7-methyl-1H-indole-2-carboxamide |
| 668 | 7-methyl-N-(1-(3-methyl-1,2,4-oxadiazol-5-yl)propyl)-1H-indole-2-carboxamide |
| 669 | methyl 3-(3-bromophenyl)-3-(7-methyl-1H-indole-2-carboxamido)propanoate |
| 670 | N-(1-acetylpiperidin-4-yl)-7-methyl-1H-indole-2-carboxamide |
| 671 | methyl 3-(7-methyl-1H-indole-2-carboxamido)-3-(pyridin-3-yl)propanoate |
| 672 | N-((1R,4R,5R)-2-(3-aminopropanoyl)-2-azabicyclo[2.2.2]octan-5-yl)-7-methyl-1H-indole-2-carboxamide |
| 673 | 7-methyl-N-(pyridin-2-yl)-1H-indole-2-carboxamide |
| 674 | 7-methyl-N-(3-(pyrrolidin-1-ylmethyl)benzyl)-1H-indole-2-carboxamide |
| 675 | ethyl 3,3,3-trifluoro-2-(7-methyl-1H-indole-2-carboxamido)propanoate |

TABLE 1-continued

| Cpd. No. | Chemical Name |
|---|---|
| 676 | methyl (S)-3-(7-methyl-1H-indole-2-carboxamido)-3-(pyridin-3-yl)propanoate |
| 677 | methyl (S)-3-(7-methyl-1H-indole-2-carboxamido)-3-(o-tolyl)propanoate |
| 678 | 7-methyl-N-(3,3,3-trifluoro-2-hydroxypropyl)-1H-indole-2-carboxamide |
| 679 | 7-methyl-N-(2-(5-oxopyrrolidin-2-yl)phenyl)-1H-indole-2-carboxamide |
| 680 | N-(cyclopropyl(pyrimidin-2-yl)methyl)-7-methyl-1H-indole-2-carboxamide |
| 681 | N-(2-(3,5-dimethoxyphenyl)-2-hydroxyethyl)-7-methyl-1H-indole-2-carboxamide |
| 682 | 7-methyl-N-(3-(methylamino)-1-(3-methylpyridin-2-yl)-3-oxopropyl)-1H-indole-2-carboxamide |
| 683 | methyl (S)-3-(4-chlorophenyl)-3-(7-methyl-1H-indole-2-carboxamido)propanoate |
| 684 | (3,4-dihydroisoquinolin-2(1H)-yl)(7-methyl-1H-indol-2-yl)methanone |
| 685 | N-(3-(3-aminopropanamido)bicyclo[3.2.1]octan-8-yl)-7-methyl-1H-indole-2-carboxamide |
| 686 | N-(2-hydroxy-2-(o-tolyl)ethyl)-7-methyl-1H-indole-2-carboxamide |
| 687 | (S)-7-methyl-N-(2,2,2-trifluoro-1-phenylethyl)-1H-indole-2-carboxamide |
| 688 | 7-methyl-N-(1-(4-methylthiazol-2-yl)ethyl)-1H-indole-2-carboxamide |
| 689 | N-(cyclopropyl(pyridin-3-yl)methyl)-7-methyl-1H-indole-2-carboxamide |
| 690 | methyl (S)-3-(7-methyl-1H-indole-2-carboxamido)-3-phenylpropanoate |
| 691 | 7-methyl-N-(4-(morpholinomethyl)phenyl)-1H-indole-2-carboxamide |
| 692 | (R)-N-(1-hydroxy-3-phenylpropan-2-yl)-7-methyl-1H-indole-2-carboxamide |
| 693 | 7-methyl-N-((1-methyl-1H-pyrazol-5-yl)methyl)-1H-indole-2-carboxamide |
| 694 | dimethyl (7-methyl-1H-indole-2-carbonyl)-D-aspartate |
| 695 | N-(2-hydroxy-2-(3-methoxyphenyl)ethyl)-7-methyl-1H-indole-2-carboxamide |
| 697 | N-((1r,4r)-4-(3-aminopropanamido)cyclohexyl)-7-chloro-1H-indole-2-carboxamide |
| 698 | N-((1r,4r)-4-acetamidocyclohexyl)-7-methyl-1H-indole-2-carboxamide |
| 699 | 7-methyl-N-(2-oxo-1,2,3,4-tetrahydroquinolin-3-yl)-1H-indole-2-carboxamide |
| 700 | ethyl 3-(7-methyl-1H-indole-2-carboxamido)-3-(pyridin-4-yl)propanoate |
| 701 | methyl 2-(7-methyl-1H-indole-2-carboxamido)-2-phenylacetate |
| 702 | 7-methyl-N-((5-methylisoxazol-4-yl)methyl)-1H-indole-2-carboxamide |
| 703 | (S)-N-(2-hydroxy-1-phenylethyl)-7-methyl-1H-indole-2-carboxamide |
| 704 | 7-methyl-N-(2-oxo-2,3,4,5-tetrahydro-1H-benzo[b]azepin-5-yl)-1H-indole-2-carboxamide |
| 705 | N-(2-hydroxy-1-phenylethyl)-7-methyl-1H-indole-2-carboxamide |
| 706 | N-((1r,4r)-4-aminocyclohexyl)-7-bromo-1H-indole-2-carboxamide |
| 707 | methyl 3-(3-fluorophenyl)-3-(7-methyl-1H-indole-2-carboxamido)propanoate |
| 708 | dimethyl (7-methyl-1H-indole-2-carbonyl)-L-aspartate |
| 709 | 7-methyl-N-(3-(morpholinomethyl)benzyl)-1H-indole-2-carboxamide |
| 710 | N-(imidazo[1,2-alpyrazin-6-ylmethyl)-7-methyl-1H-indole-2-carboxamide |
| 711 | N-((1r,4r)-4-(3-aminopropanamido)cyclohexyl)-3-ethyl-7-methyl-1H-indole-2-carboxamide |
| 712 | 7-methyl-N-(1-(1-methyl-1H-pyrazol-3-yl)ethyl)-1H-indole-2-carboxamide |
| 713 | (R)-7-methyl-N-(1-(m-tolyl)ethyl)-1H-indole-2-carboxamide |
| 714 | 7-methyl-N-(1-(naphthalen-1-yl)ethyl)-1H-indole-2-carboxamide |
| 715 | 7-methyl-N-(piperidin-4-yl)-1H-indole-2-carboxamide |
| 716 | 7-methyl-N-(2-(piperidin-1-yl)benzyl)-1H-indole-2-carboxamide |
| 717 | N-(cyclopropyl(3-methylpyridin-2-yl)methyl)-7-(trifluoromethyl)-1H-indole-2-carboxamide |
| 718 | (7-methyl-1H-indol-2-yl)(1,3,4,5-tetrahydro-2H-benzo[c]azepin-2-yl)methanone |
| 719 | 7-methyl-N-((5-methylisoxazol-3-yl)methyl)-1H-indole-2-carboxamide |
| 720 | N-(2-(2,6-difluorophenyl)-2-hydroxyethyl)-7-methyl-1H-indole-2-carboxamide |
| 721 | N-((2,5-dimethyloxazol-4-yl)methyl)-7-methyl-1H-indole-2-carboxamide |
| 722 | 7-methyl-N-((3-methylpyridin-2-yl)(pyrrolidin-3-yl)methyl)-1H-indole-2-carboxamide |
| 723 | 7-methyl-N-((5-methylpyrazin-2-yl)methyl)-1H-indole-2-carboxamide |
| 724 | 7-methyl-N-(4-(morpholinomethyl)pyridin-2-yl)-1H-indole-2-carboxamide |
| 725 | N-(3-(dimethylamino)-1-(pyridin-3-yl)propyl)-7-methyl-1H-indole-2-carboxamide |
| 726 | (R)-7-methyl-N-(2,2,2-trifluoro-1-phenylethyl)-1H-indole-2-carboxamide |
| 727 | N-(cyclopropyl(5-((dimethylamino)methyl)pyridin-3-yl)methyl)-7-methyl-1H-indole-2-carboxamide |
| 728 | N-(3-(dimethylamino)-1-(3-methylpyridin-2-yl)propyl)-7-methyl-1H-indole-2-carboxamide |
| 729 | N-((1H-imidazol-5-yl)methyl)-7-methyl-1H-indole-2-carboxamide |
| 730 | N-((1r,4r)-4-aminocyclohexyl)-4,7-dimethyl-1H-indole-2-carboxamide |
| 731 | N-(2-cyclopropyl-2-hydroxyethyl)-7-methyl-1H-indole-2-carboxamide |
| 732 | 7-methyl-N-((4-methyl-1,2,5-oxadiazol-3-yl)methyl)-1H-indole-2-carboxamide |
| 733 | 7-methyl-N-(oxazol-4-ylmethyl)-1H-indole-2-carboxamide |
| 735 | 7-methyl-N-(1-(3-methyl-1,2,4-oxadiazol-5-yl)ethyl)-1H-indole-2-carboxamide |
| 736 | N-((1r,4r)-4-aminocyclohexyl)-3,7-dimethyl-1H-indole-2-carboxamide |
| 738 | N-((1r,4r)-4-(3-aminopropanamido)cyclohexyl)-5,7-dimethyl-1H-indole-2-carboxamide |
| 746 | 7-methyl-N-(2-morpholinoethyl)-1H-indole-2-carboxamide |
| 747 | 7-methyl-N-((tetrahydrofuran-2-yl)methyl)-1H-indole-2-carboxamide |
| 748 | N-(2,3-dihydro-1H-inden-1-yl)-7-methyl-1H-indole-2-carboxamide |
| 749 | 7-methyl-N-(1-phenylethyl)-1H-indole-2-carboxamide |
| 750 | 7-methyl-N-(3-(piperidin-1-yl)benzyl)-1H-indole-2-carboxamide |
| 751 | 7-methyl-N-(3-(piperidin-1-ylsulfonyl)benzyl)-1H-indole-2-carboxamide |

TABLE 1-continued

| Cpd. No. | Chemical Name |
|---|---|
| 752 | N-(1-benzylpiperidin-4-yl)-7-methyl-1H-indole-2-carboxamide |
| 753 | 7-methyl-N-(1,2,3,4-tetrahydronaphthalen-1-yl)-1H-indole-2-carboxamide |
| 754 | N-(2-hydroxy-2-(4-methoxyphenyl)ethyl)-7-methyl-1H-indole-2-carboxamide |
| 755 | 7-methyl-N-(4-(morpholinomethyl)benzyl)-1H-indole-2-carboxamide |
| 756 | N-((1r,4r)-4-aminocyclohexyl)-5,7-dimethyl-1H-indole-2-carboxamide |
| 757 | 2-(4-(7-methyl-1H-indole-2-carbonyl)piperazin-1-yl)nicotinamide |
| 758 | 7-methyl-N-(4-(piperidin-1-ylsulfonyl)benzyl)-1H-indole-2-carboxamide |
| 759 | N-((1s,3s)-3-(hydroxymethyl)cyclobutyl)-7-methyl-1H-indole-2-carboxamide |
| 761 | N-((1r,4r)-4-aminocyclohexyl)-N,7-dimethyl-1H-indole-2-carboxamide |
| 763 | (S)-N-(1-hydroxy-3-methylbutan-2-yl)-7-methyl-1H-indole-2-carboxamide |
| 764 | methyl 3-(4-chlorophenyl)-3-(7-methyl-1H-indole-2-carboxamido)propanoate |
| 765 | (S)-N-(1-hydroxy-3-phenylpropan-2-yl)-7-methyl-1H-indole-2-carboxamide |
| 766 | tert-butyl (2-(7-methyl-1H-indole-2-carboxamido)propyl)carbamate |
| 767 | N-(2-(cyclopropylmethoxy)benzyl)-7-methyl-1H-indole-2-carboxamide |
| 768 | 7-methyl-N-((1-methyl-1H-1,2,4-triazol-5-yl)methyl)-1H-indole-2-carboxamide |
| 769 | N-(1-cyclopropyl-2,2,2-trifluoroethyl)-7-methyl-1H-indole-2-carboxamide |
| 771 | 1-(7-methyl-1H-indole-2-carbonyl)piperidine-4-carboxamide |
| 773 | methyl 3-(4-isopropylphenyl)-3-(7-methyl-1H-indole-2-carboxamido)propanoate |
| 774 | methyl 3-(2-bromophenyl)-3-(7-methyl-1H-indole-2-carboxamido)propanoate |
| 775 | methyl 3-(7-methyl-1H-indole-2-carboxamido)-3-phenylpropanoate |
| 776 | methyl 3-(4-fluorophenyl)-3-(7-methyl-1H-indole-2-carboxamido)propanoate |
| 777 | methyl 3-(4-methoxyphenyl)-3-(7-methyl-1H-indole-2-carboxamido)propanoate |
| 778 | methyl 3-(4-bromophenyl)-3-(7-methyl-1H-indole-2-carboxamido)propanoate |
| 779 | N-(benzo[d]oxazol-2-ylmethyl)-7-methyl-1H-indole-2-carboxamide |
| 780 | 7-methyl-N-((1r,4r)-4-(trifluoromethyl)cyclohexyl)-1H-indole-2-carboxamide |
| 781 | 2-(4-(7-methyl-1H-indole-2-carbonyl)piperazin-1-yl)acetamide |
| 782 | 7-methyl-N-(2-(5-methyl-1,2,4-oxadiazol-3-yl)ethyl)-1H-indole-2-carboxamide |
| 783 | methyl 3-(7-methyl-1H-indole-2-carboxamido)-3-(p-tolyl)propanoate |
| 784 | N-(3,3-difluoro-2-hydroxypropyl)-7-methyl-1H-indole-2-carboxamide |
| 785 | 7-methyl-N-(1-(5-methyl-1,2,4-oxadiazol-3-yl)ethyl)-1H-indole-2-carboxamide |
| 786 | 1-(7-methyl-1H-indole-2-carbonyl)pyrrolidine-2-carboxamide |
| 787 | 4-(7-methyl-1H-indole-2-carbonyl)piperazine-1-carboxamide |
| 788 | 7-methyl-N-(1-(2-(trifluoromethyl)phenyl)ethyl)-1H-indole-2-carboxamide |
| 790 | 7-methyl-N-(1-(3-(trifluoromethyl)phenyl)ethyl)-1H-indole-2-carboxamide |
| 791 | 7-methyl-N-((1r,4r)-4-(2,2,2-trifluoroacetamido)cyclohexyl)-1H-indole-2-carboxamide |
| 793 | 7-methyl-N-(2-morpholinophenyl)-1H-indole-2-carboxamide |
| 794 | (3-aminopiperidin-1-yl)(7-methyl-1H-indol-2-yl)methanone |
| 795 | 7-methyl-N-(pyridin-3-yl)-1H-indole-2-carboxamide |
| 796 | N-(imidazo[1,2-a]pyridin-2-yl)-7-methyl-1H-indole-2-carboxamide |
| 797 | ethyl (1R,2R)-2-(7-methyl-1H-indole-2-carboxamido)cyclohexane-1-carboxylate |
| 798 | 3-amino-N-(1-(7-methyl-1H-indole-2-carbonyl)piperidin-3-yl)propanamide |
| 799 | (3-(dimethylamino)piperidin-1-yl)(7-methyl-1H-indol-2-yl)methanone |
| 800 | (7-methyl-1H-indol-2-yl)(3-(methylamino)piperidin-1-yl)methanone |
| 801 | N-(cyclopropyl(o-tolyl)methyl)-7-methyl-1H-indole-2-carboxamide |
| 802 | N-(cyclopropyl(3-methylpyridin-2-yl)methyl)-7-isopropyl-1H-indole-2-carboxamide |
| 803 | N-(cyclopropyl(pyridin-2-yl)methyl)-7-ethyl-1H-indole-2-carboxamide |
| 804 | 7-methyl-N-(quinazolin-2-yl)-1H-indole-2-carboxamide |
| 805 | 7-cyclopropyl-N-(cyclopropyl(3-methylpyridin-2-yl)methyl)-1H-indole-2-carboxamide |
| 808 | N-(cyclopropyl(3-methylpyridin-2-yl)methyl)-6-fluoro-7-methyl-1H-indole-2-carboxamide |
| 809 | 7-methyl-N-(3-(methylamino)-3-oxo-1-(pyridin-3-yl)propyl)-1H-indole-2-carboxamide |
| 810 | (5,6-dihydroimidazo[1,5-a]pyrazin-7(8H)-yl)(7-methyl-1H-indol-2-yl)methanone |
| 811 | (5,6-dihydro-[1,2,4]triazolo[4,3-a]pyrazin-7(8H)-yl)(7-methyl-1H-indol-2-yl)methanone |
| 812 | (5,6-dihydro-[1,2,4]triazolo[1,5-a]pyrazin-7(8H)-yl)(7-methyl-1H-indol-2-yl)methanone |
| 814 | 2-(7-methyl-1H-indole-2-carbonyl)-1,2,3,4-tetrahydro-5H-benzo[c]azepin-5-one |
| 815 | N-(3-(dimethylamino)-2-phenylpropyl)-7-methyl-1H-indole-2-carboxamide |
| 816 | 7-methyl-N-(2-oxo-7-phenylazepan-4-yl)-1H-indole-2-carboxamide |
| 817 | N-((3-benzylpyridin-2-yl)(cyclopropyl)methyl)-7-methyl-1H-indole-2-carboxamide |
| 818 | N-(2-([1,1'-biphenyl]-2-yl)ethyl)-7-methyl-1H-indole-2-carboxamide |
| 819 | N-(cyclopropyl(3-methylpyridin-2-yl)methyl)-7-propyl-1H-indole-2-carboxamide |
| 820 | (2,3-dihydrospiro[indene-1,3'-pyrrolidin]-1'-yl)(7-methyl-1H-indol-2-yl)methanone |
| 821 | 7-(cyclobutylmethyl)-N-(cyclopropyl(3-methylpyridin-2-yl)methyl)-1H-indole-2-carboxamide |
| 822 | 4-fluoro-7-methyl-N-((1R,3R)-3-(3-oxo-1,4-diazepan-1-yl)cyclohexyl)-1H-indole-2-carboxamide |
| 823 | 4-fluoro-7-methyl-N-((1R,3S)-3-(3-oxo-1,4-diazepan-1-yl)cyclohexyl)-1H-indole-2-carboxamide |
| 824 | ethyl 4-((1S,3R)-3-(4-fluoro-7-methyl-1H-indole-2-carboxamido)cyclohexyl)piperazine-1-carboxylate |

TABLE 1-continued

| Cpd. No. | Chemical Name |
|---|---|
| 825 | ethyl 4-((1R,3R)-3-(4-fluoro-7-methyl-1H-indole-2-carboxamido)cyclohexyl)piperazine-1-carboxylate |
| 826 | 4-fluoro-7-methyl-N-((1R,3S)-3-(4-(2,2,2-trifluoroethyl)piperazin-1-yl)cyclohexyl)-1H-indole-2-carboxamide |
| 827 | 4-fluoro-7-methyl-N-((1R,3R)-3-(4-(2,2,2-trifluoroethyl)piperazin-1-yl)cyclohexyl)-1H-indole-2-carboxamide |
| 828 | 4-fluoro-7-methyl-N-((1R,3S)-3-(4-(morpholine-4-carbonyl)piperazin-1-yl)cyclohexyl)-1H-indole-2-carboxamide |
| 829 | 4-fluoro-7-methyl-N-((1R,3R)-3-(4-(morpholine-4-carbonyl)piperazin-1-yl)cyclohexyl)-1H-indole-2-carboxamide |
| 830 | N-((1R,3S)-3-(4-(cyclopropanecarbonyl)piperazin-1-yl)cyclohexyl)-4-fluoro-7-methyl-1H-indole-2-carboxamide |
| 831 | N-((1R,3R)-3-(4-(cyclopropanecarbonyl)piperazin-1-yl)cyclohexyl)-4-fluoro-7-methyl-1H-indole-2-carboxamide |
| 832 | 4-fluoro-7-methyl-N-((1R)-3-(4-methyl-5-oxo-1,4-diazepan-1-yl)cyclohexyl)-1H-indole-2-carboxamide |
| 833 | N-((1R,3S)-3-(3-acetamidopyrrolidin-1-yl)cyclohexyl)-4-fluoro-7-methyl-1H-indole-2-carboxamide |
| 834 | N-((1R,3R)-3-(3-acetamidopyrrolidin-1-yl)cyclohexyl)-4-fluoro-7-methyl-1H-indole-2-carboxamide |
| 835 | N-((1R,3S)-3-(4-ethyl-3-oxopiperazin-1-yl)cyclohexyl)-4-fluoro-7-methyl-1H-indole-2-carboxamide |
| 836 | N-((1R,3R)-3-(4-ethyl-3-oxopiperazin-1-yl)cyclohexyl)-4-fluoro-7-methyl-1H-indole-2-carboxamide |
| 837 | 4-fluoro-N-((1R,3S)-3-(4-isobutyrylpiperazin-1-yl)cyclohexyl)-7-methyl-1H-indole-2-carboxamide |
| 838 | 4-fluoro-N-((1R,3R)-3-(4-isobutyrylpiperazin-1-yl)cyclohexyl)-7-methyl-1H-indole-2-carboxamide |
| 839 | 4-fluoro-7-methyl-N-((1R,3S)-3-(4-propionylpiperazin-1-yl)cyclohexyl)-1H-indole-2-carboxamide |
| 840 | 4-fluoro-7-methyl-N-((1R,3R)-3-(4-propionylpiperazin-1-yl)cyclohexyl)-1H-indole-2-carboxamide |
| 841 | 4-fluoro-7-methyl-N-((1R,3S)-3-((S)-3-(N-methylacetamido)pyrrolidin-1-yl)cyclohexyl)-1H-indole-2-carboxamide |
| 842 | 4-fluoro-7-methyl-N-((1R,3R)-3-((S)-3-(N-methylacetamido)pyrrolidin-1-yl)cyclohexyl)-1H-indole-2-carboxamide |
| 843 | 4-fluoro-N-((1R,3S)-3-(3-(N-(2-methoxyethyl)acetamido)pyrrolidin-1-yl)cyclohexyl)-7-methyl-1H-indole-2-carboxamide |
| 844 | 4-fluoro-N-((1R,3R)-3-(3-(N-(2-methoxyethyl)acetamido)pyrrolidin-1-yl)cyclohexyl)-7-methyl-1H-indole-2-carboxamide |
| 845 | 4-fluoro-N-((1R,3R)-3-(3-(N-(2-methoxyethyl)acetamido)pyrrolidin-1-yl)cyclohexyl)-7-methyl-1H-indole-2-carboxamide |
| 846 | 4-fluoro-N-((1R,3S)-3-(4-(2-methoxyacetyl)piperazin-1-yl)cyclohexyl)-7-methyl-1H-indole-2-carboxamide |
| 847 | 4-fluoro-N-((1R,3R)-3-(4-(2-methoxyacetyl)piperazin-1-yl)cyclohexyl)-7-methyl-1H-indole-2-carboxamide |
| 848 | 4-fluoro-7-methyl-N-((1R,3S)-3-((R)-3-(N-methylacetamido)pyrrolidin-1-yl)cyclohexyl)-1H-indole-2-carboxamide |
| 849 | 4-fluoro-7-methyl-N-((1R,3R)-3-((R)-3-(N-methylacetamido)pyrrolidin-1-yl)cyclohexyl)-1H-indole-2-carboxamide |
| 850 | 4-fluoro-7-methyl-N-((1R,3S)-3-(4-(methylsulfonyl)piperazin-1-yl)cyclohexyl)-1H-indole-2-carboxamide |
| 851 | 4-fluoro-7-methyl-N-((1R,3R)-3-(4-(methylsulfonyl)piperazin-1-yl)cyclohexyl)-1H-indole-2-carboxamide |
| 852 | N-((1R,3S)-3-(5,6-dihydroimidazo[1,2-a]pyrazin-7(8H)-yl)cyclohexyl)-4-fluoro-7-methyl-1H-indole-2-carboxamide |
| 853 | N-((1R,3R)-3-(5,6-dihydroimidazo[1,2-a]pyrazin-7(8H)-yl)cyclohexyl)-4-fluoro-7-methyl-1H-indole-2-carboxamide |
| 854 | N-((1R,3S)-3-(4-(dimethylglycyl)piperazin-1-yl)cyclohexyl)-4-fluoro-7-methyl-1H-indole-2-carboxamide |
| 855 | N-((1R,3R)-3-(4-(dimethylglycyl)piperazin-1-yl)cyclohexyl)-4-fluoro-7-methyl-1H-indole-2-carboxamide |
| 856 | N-((1R,3S)-3-(4-acetylpiperazin-1-yl)cyclohexyl)-7-methyl-1H-indole-2-carboxamide |
| 857 | N-((1R,3R)-3-(4-acetylpiperazin-1-yl)cyclohexyl)-7-methyl-1H-indole-2-carboxamide |
| 858 | 4-fluoro-7-methyl-N-((1R)-3-(4-(2-(methylamino)-2-oxoethyl)piperazin-1-yl)cyclohexyl)-1H-indole-2-carboxamide |
| 859 | N-((1R)-3-(4-(2-(dimethylamino)-2-oxoethyl)piperazin-1-yl)cyclohexyl)-4-fluoro-7-methyl-1H-indole-2-carboxamide |
| 860 | N-((1R,3S)-3-(5,6-dihydro-[1,2,4]triazolo[4,3-a]pyrazin-7(8H)-yl)cyclohexyl)-4-fluoro-7-methyl-1H-indole-2-carboxamide |
| 861 | N-((1R,3R)-3-(5,6-dihydro-[1,2,4]triazolo[4,3-a]pyrazin-7(8H)-yl)cyclohexyl)-4-fluoro-7-methyl-1H-indole-2-carboxamide |
| 862 | 4-fluoro-N-((1R)-3-(3-(N-isopropylacetamido)pyrrolidin-1-yl)cyclohexyl)-7-methyl-1H-indole-2-carboxamide |

TABLE 1-continued

| Cpd. No. | Chemical Name |
|---|---|
| 863 | 4-fluoro-7-methyl-N-((1R,3S)-3-(6-oxohexahydropyrrolo[1,2-a]pyrazin-2(1H)-yl)cyclohexyl)-1H-indole-2-carboxamide |
| 864 | 4-fluoro-7-methyl-N-((1R,3R)-3-(6-oxohexahydropyrrolo[1,2-a]pyrazin-2(1H)-yl)cyclohexyl)-1H-indole-2-carboxamide |
| 865 | 4-fluoro-7-methyl-N-((1R,3S)-3-(3-oxotetrahydro-3H-oxazolo[3,4-a]pyrazin-7(1H)-yl)cyclohexyl)-1H-indole-2-carboxamide |
| 866 | 4-fluoro-7-methyl-N-((1R,3R)-3-(3-oxotetrahydro-3H-oxazolo[3,4-a]pyrazin-7(1H)-yl)cyclohexyl)-1H-indole-2-carboxamide |
| 867 | N-(1-(1-acetylpiperidin-4-yl)azepan-3-yl)-4-fluoro-7-methyl-1H-indole-2-carboxamide |
| 868 | N-((1R,3S)-3-(5,6-dihydro-[1,2,4]triazolo[1,5-a]pyrazin-7(8H)-yl)cyclohexyl)-4-fluoro-7-methyl-1H-indole-2-carboxamide |
| 869 | N-((1R,3R)-3-(5,6-dihydro-[1,2,4]triazolo[1,5-a]pyrazin-7(8H)-yl)cyclohexyl)-4-fluoro-7-methyl-1H-indole-2-carboxamide |
| 870 | 4-fluoro-N-((1R,3S)-3-(4-(2-hydroxyacetyl)piperazin-1-yl)cyclohexyl)-7-methyl-1H-indole-2-carboxamide |
| 871 | 4-fluoro-N-((1R,3R)-3-(4-(2-hydroxyacetyl)piperazin-1-yl)cyclohexyl)-7-methyl-1H-indole-2-carboxamide |
| 872 | 4-fluoro-N-((1R,3S)-3-(3-(N-(2-hydroxyethyl)acetamido)pyrrolidin-1-yl)cyclohexyl)-7-methyl-1H-indole-2-carboxamide |
| 873 | 4-fluoro-N-((1R,3R)-3-(3-(N-(2-hydroxyethyl)acetamido)pyrrolidin-1-yl)cyclohexyl)-7-methyl-1H-indole-2-carboxamide |
| 874 | 4-fluoro-7-methyl-N-((1R)-3-(1-oxo-2,8-diazaspiro[4.5]decan-8-yl)cyclohexyl)-1H-indole-2-carboxamide |
| 875 | ethyl (R)-3-(4-fluoro-7-methyl-1H-indole-2-carboxamido)-[1,4'-bipiperidine]-1'-carboxylate |
| 876 | ethyl (S)-3-(4-fluoro-7-methyl-1H-indole-2-carboxamido)-[1,4'-bipiperidine]-1'-carboxylate |
| 877 | 1-(4-((1-(4-fluoro-7-methyl-1H-indole-2-carbonyl)piperidin-3-yl)methyl)piperazin-1-yl)ethan-1-one |
| 878 | N-((1R,3S)-3-(4-(2,2-difluoroacetyl)piperazin-1-yl)cyclohexyl)-4-fluoro-7-methyl-1H-indole-2-carboxamide |
| 879 | N-((1R,3R)-3-(4-(2,2-difluoroacetyl)piperazin-1-yl)cyclohexyl)-4-fluoro-7-methyl-1H-indole-2-carboxamide |
| 880 | 4-fluoro-N-((1R,3S)-3-(3-(2-methoxy-N-methylacetamido)pyrrolidin-1-yl)cyclohexyl)-7-methyl-1H-indole-2-carboxamide |
| 881 | 4-fluoro-N-((1R,3R)-3-(3-(2-methoxy-N-methylacetamido)pyrrolidin-1-yl)cyclohexyl)-7-methyl-1H-indole-2-carboxamide |
| 882 | 4-fluoro-7-methyl-N-((1R,3S)-3-(1-oxo-2,7-diazaspiro[4.5]decan-7-yl)cyclohexyl)-1H-indole-2-carboxamide |
| 883 | 4-fluoro-7-methyl-N-((1R,3R)-3-(1-oxo-2,7-diazaspiro[4.5]decan-7-yl)cyclohexyl)-1H-indole-2-carboxamide |
| 884 | N-((1R,3S)-3-(2,4-dimethyl-3-oxopiperazin-1-yl)cyclohexyl)-4-fluoro-7-methyl-1H-indole-2-carboxamide |
| 885 | N-((1R,3R)-3-(2,4-dimethyl-3-oxopiperazin-1-yl)cyclohexyl)-4-fluoro-7-methyl-1H-indole-2-carboxamide |
| 886 | 1-(4-(1-(4-fluoro-7-methyl-1H-indole-2-carbonyl)piperidine-3-carbonyl)piperazin-1-yl)ethan-1-one |
| 887 | 4-fluoro-7-methyl-N-((1R,3S)-3-(4-methyl-3-oxo-1,4-diazepan-1-yl)cyclohexyl)-1H-indole-2-carboxamide |
| 888 | N-((1R,3S)-3-(6-acetyl-2,6-diazaspiro[3.3]heptan-2-yl)cyclohexyl)-4-fluoro-7-methyl-1H-indole-2-carboxamide |
| 889 | N-((1R,3R)-3-(6-acetyl-2,6-diazaspiro[3.3]heptan-2-yl)cyclohexyl)-4-fluoro-7-methyl-1H-indole-2-carboxamide |
| 890 | 4-fluoro-7-methyl-N-((1R)-3-(2-oxo-1,3,8-triazaspiro[4.5]decan-8-yl)cyclohexyl)-1H-indole-2-carboxamide |
| 891 | (R)-N-(1'-(dimethylglycyl)-[1,4'-bipiperidin]-3-yl)-4-fluoro-7-methyl-1H-indole-2-carboxamide |
| 892 | (S)-N-(1'-(dimethylglycyl)-[1,4'-bipiperidin]-3-yl)-4-fluoro-7-methyl-1H-indole-2-carboxamide |
| 893 | 4-fluoro-7-methyl-N-((1R)-3-(5-oxo-1,4-diazepan-1-yl)cyclohexyl)-1H-indole-2-carboxamide |
| 894 | 4-fluoro-7-methyl-N-((1R)-3-(2-oxo-1,8-diazaspiro[4.5]decan-8-yl)cyclohexyl)-1H-indole-2-carboxamide |
| 895 | 4-fluoro-7-methyl-N-(3-(2-oxo-3-oxa-1,8-diazaspiro[4.5]decan-8-yl)cyclohexyl)-1H-indole-2-carboxamide |
| 896 | 4-fluoro-7-methyl-N-((1R)-3-(3-oxo-2,8-diazaspiro[4.5]decan-8-yl)cyclohexyl)-1H-indole-2-carboxamide |
| 897 | 4-fluoro-7-methyl-N-((1R,3S)-3-(7-oxo-2,6-diazaspiro[3.4]octan-2-yl)cyclohexyl)-1H-indole-2-carboxamide |
| 898 | 4-fluoro-7-methyl-N-((1R,3R)-3-(7-oxo-2,6-diazaspiro[3.4]octan-2-yl)cyclohexyl)-1H-indole-2-carboxamide |
| 899 | 4-fluoro-7-methyl-N-((1R,3S)-3-(3-(N-methylmethylsulfonamido)pyrrolidin-1-yl)cyclohexyl)-1H-indole-2-carboxamide |
| 900 | 4-fluoro-7-methyl-N-((1R,3R)-3-((R)-3-(N-methylmethylsulfonamido)pyrrolidin-1-yl)cyclohexyl)-1H-indole-2-carboxamide |

TABLE 1-continued

| Cpd. No. | Chemical Name |
|---|---|
| 901 | 4-fluoro-7-methyl-N-((1R,3R)-3-((S)-3-(N-methylmethylsulfonamido)pyrrolidin-1-yl)cyclohexyl)-1H-indole-2-carboxamide |
| 902 | 4-fluoro-7-methyl-N-((1R,3R)-3-(pyridin-3-yl)cyclohexyl)-1H-indole-2-carboxamide |
| 903 | 4-fluoro-7-methyl-N-((1R,3S)-3-(pyridin-3-yl)cyclohexyl)-1H-indole-2-carboxamide |
| 904 | 4-fluoro-7-methyl-N-((1S,3S)-3-(pyridin-3-yl)cyclohexyl)-1H-indole-2-carboxamide |
| 905 | 4-fluoro-7-methyl-N-((1S,3R)-3-(pyridin-3-yl)cyclohexyl)-1H-indole-2-carboxamide |
| 906 | N-((1R,3S)-3-(4-acetyl-3-methylpiperazin-1-yl)cyclohexyl)-4-fluoro-7-methyl-1H-indole-2-carboxamide |
| 907 | N-((1R,3R)-3-(4-acetyl-3-methylpiperazin-1-yl)cyclohexyl)-4-fluoro-7-methyl-1H-indole-2-carboxamide |
| 908 | N-((1R,3S)-3-(3-(2-(dimethylamino)-N-methylacetamido)pyrrolidin-1-yl)cyclohexyl)-4-fluoro-7-methyl-1H-indole-2-carboxamide |
| 909 | N-((1R,3R)-3-(3-(2-(dimethylamino)-N-methylacetamido)pyrrolidin-1-yl)cyclohexyl)-4-fluoro-7-methyl-1H-indole-2-carboxamide |
| 910 | 4-fluoro-7-methyl-N-((1R,3S)-3-(2-oxo-[1,3'-bipyrrolidin]-1'-yl)cyclohexyl)-1H-indole-2-carboxamide |
| 911 | 4-fluoro-7-methyl-N-((1R,3R)-3-(2-oxo-[1,3'-bipyrrolidin]-1'-yl)cyclohexyl)-1H-indole-2-carboxamide |
| 912 | 4-fluoro-7-methyl-N-((1R,3R)-3-(pyridin-4-yl)cyclohexyl)-1H-indole-2-carboxamide |
| 913 | 4-fluoro-7-methyl-N-((1R,3S)-3-(pyridin-4-yl)cyclohexyl)-1H-indole-2-carboxamide |
| 914 | 4-fluoro-7-methyl-N-((1S,3R)-3-(pyridin-4-yl)cyclohexyl)-1H-indole-2-carboxamide |
| 915 | 4-fluoro-7-methyl-N-((1S,3S)-3-(pyridin-4-yl)cyclohexyl)-1H-indole-2-carboxamide |
| 916 | 4-fluoro-7-methyl-N-((1R,3S)-3-(4-methyl-2-oxopiperazin-1-yl)cyclohexyl)-1H-indole-2-carboxamide |
| 917 | 4-fluoro-7-methyl-N-((1R,3R)-3-(4-methyl-2-oxopiperazin-1-yl)cyclohexyl)-1H-indole-2-carboxamide |
| 918 | 4-fluoro-7-methyl-N-((1R,3S)-3-(4-(oxetane-3-carbonyl)piperazin-1-yl)cyclohexyl)-1H-indole-2-carboxamide |
| 919 | 4-fluoro-7-methyl-N-((1R,3R)-3-(4-(oxetane-3-carbonyl)piperazin-1-yl)cyclohexyl)-1H-indole-2-carboxamide |
| 920 | 4-fluoro-7-methyl-N-((1R,3S)-3-((R)-6-oxohexahydropyrrolo[1,2-a]pyrazin-2(1H)-yl)cyclohexyl)-1H-indole-2-carboxamide |
| 921 | 4-fluoro-7-methyl-N-((1R,3R)-3-((R)-6-oxohexahydropyrrolo[1,2-a]pyrazin-2(1H)-yl)cyclohexyl)-1H-indole-2-carboxamide |
| 922 | 4-fluoro-7-methyl-N-((1R,3S)-3-((S)-6-oxohexahydropyrrolo[1,2-a]pyrazin-2(1H)-yl)cyclohexyl)-1H-indole-2-carboxamide |
| 923 | 4-fluoro-7-methyl-N-((1R,3R)-3-((S)-6-oxohexahydropyrrolo[1,2-a]pyrazin-2(1H)-yl)cyclohexyl)-1H-indole-2-carboxamide |
| 924 | 4-fluoro-7-methyl-N-((1R,3S)-3-(4-(tetrahydrofuran-3-yl)piperazin-1-yl)cyclohexyl)-1H-indole-2-carboxamide |
| 925 | 4-fluoro-7-methyl-N-((1R,3R)-3-(4-(tetrahydrofuran-3-yl)piperazin-1-yl)cyclohexyl)-1H-indole-2-carboxamide |
| 926 | N-((1R,3S)-3-(8-acetyl-3,8-diazabicyclo[3.2.1]octan-3-yl)cyclohexyl)-4-fluoro-7-methyl-1H-indole-2-carboxamide |
| 927 | N-((1R,3R)-3-(8-acetyl-3,8-diazabicyclo[3.2.1]octan-3-yl)cyclohexyl)-4-fluoro-7-methyl-1H-indole-2-carboxamide |
| 928 | 4-fluoro-7-methyl-N-((1R,3S)-3-(3-oxo-2,8-diazaspiro[4.5]decan-8-yl)cyclohexyl)-1H-indole-2-carboxamide |
| 929 | 4-fluoro-7-methyl-N-((1R,3R)-3-(3-oxo-2,8-diazaspiro[4.5]decan-8-yl)cyclohexyl)-1H-indole-2-carboxamide |
| 930 | N-((1R,3S)-3-((R)-4-acetyl-3-methylpiperazin-1-yl)cyclohexyl)-4-fluoro-7-methyl-1H-indole-2-carboxamide |
| 931 | N-((1R,3R)-3-((R)-4-acetyl-3-methylpiperazin-1-yl)cyclohexyl)-4-fluoro-7-methyl-1H-indole-2-carboxamide |
| 932 | 4-fluoro-7-methyl-N-((1R,3S)-3-(5-oxo-1,4-diazepan-1-yl)cyclohexyl)-1H-indole-2-carboxamide |
| 933 | 4-fluoro-7-methyl-N-((1R,3R)-3-(5-oxo-1,4-diazepan-1-yl)cyclohexyl)-1H-indole-2-carboxamide |
| 934 | 4-fluoro-N-((1R,3S)-3-(3-(2-hydroxy-N-methylacetamido)pyrrolidin-1-yl)cyclohexyl)-7-methyl-1H-indole-2-carboxamide |
| 935 | 4-fluoro-N-((1R,3R)-3-(3-(2-hydroxy-N-methylacetamido)pyrrolidin-1-yl)cyclohexyl)-7-methyl-1H-indole-2-carboxamide |
| 936 | N-((1R,3S)-3-(5-acetyl-2,5-diazabicyclo[2.2.1]heptan-2-yl)cyclohexyl)-4-fluoro-7-methyl-1H-indole-2-carboxamide |
| 937 | N-((1R,3R)-3-(5-acetyl-2,5-diazabicyclo[2.2.1]heptan-2-yl)cyclohexyl)-4-fluoro-7-methyl-1H-indole-2-carboxamide |
| 938 | 4-fluoro-7-methyl-N-((1R,3S)-3-(2-oxo-1,8-diazaspiro[4.5]decan-8-yl)cyclohexyl)-1H-indole-2-carboxamide |

TABLE 1-continued

| Cpd. No. | Chemical Name |
|---|---|
| 939 | 4-fluoro-7-methyl-N-((1R,3R)-3-(2-oxo-1,8-diazaspiro[4.5]decan-8-yl)cyclohexyl)-1H-indole-2-carboxamide |
| 940 | 4-fluoro-7-methyl-N-((1R,3S)-3-(2-oxo-1,3,8-triazaspiro[4.5]decan-8-yl)cyclohexyl)-1H-indole-2-carboxamide |
| 941 | 4-fluoro-7-methyl-N-((1R,3R)-3-(2-oxo-1,3,8-triazaspiro[4.5]decan-8-yl)cyclohexyl)-1H-indole-2-carboxamide |
| 942 | 4-fluoro-7-methyl-N-((1R,3S)-3-((S)-3-(N-methylmethylsulfonamido)pyrrolidin-1-yl)cyclohexyl)-1H-indole-2-carboxamide |
| 943 | 4-fluoro-7-methyl-N-((1R,3S)-3-((R)-3-(N-methylmethylsulfonamido)pyrrolidin-1-yl)cyclohexyl)-1H-indole-2-carboxamide |
| 944 | 4-fluoro-7-methyl-N-((1R,3S)-3-(4-methyl-5-oxo-1,4-diazepan-1-yl)cyclohexyl)-1H-indole-2-carboxamide |
| 945 | 4-fluoro-7-methyl-N-((1R,3R)-3-(4-methyl-5-oxo-1,4-diazepan-1-yl)cyclohexyl)-1H-indole-2-carboxamide |
| 946 | 4-fluoro-7-methyl-N-((1R,3S)-3-(3-(N-methyloxetane-3-carboxamido)pyrrolidin-1-yl)cyclohexyl)-1H-indole-2-carboxamide |
| 947 | 4-fluoro-7-methyl-N-((1R,3R)-3-(3-(N-methyloxetane-3-carboxamido)pyrrolidin-1-yl)cyclohexyl)-1H-indole-2-carboxamide |
| 948 | N-((1R,3S)-3-(4-(ethylcarbamoyl)piperazin-1-yl)cyclohexyl)-4-fluoro-7-methyl-1H-indole-2-carboxamide |
| 949 | N-((1R,3R)-3-(4-(ethylcarbamoyl)piperazin-1-yl)cyclohexyl)-4-fluoro-7-methyl-1H-indole-2-carboxamide |
| 950 | N-((1R,3S)-3-(1-acetyl-1,6-diazaspiro[3.3]heptan-6-yl)cyclohexyl)-4-fluoro-7-methyl-1H-indole-2-carboxamide |
| 951 | N-((1R,3R)-3-(1-acetyl-1,6-diazaspiro[3.3]heptan-6-yl)cyclohexyl)-4-fluoro-7-methyl-1H-indole-2-carboxamide |
| 952 | N-((1R,3S)-3-(3-acetyl-3,8-diazabicyclo[3.2.1]octan-8-yl)cyclohexyl)-4-fluoro-7-methyl-1H-indole-2-carboxamide |
| 953 | N-((1R,3R)-3-(3-acetyl-3,8-diazabicyclo[3.2.1]octan-8-yl)cyclohexyl)-4-fluoro-7-methyl-1H-indole-2-carboxamide |
| 954 | N-((1R,3S)-3-(5-((dimethylamino)methyl)-1,3,4-oxadiazol-2-yl)cyclohexyl)-4-fluoro-7-methyl-1H-indole-2-carboxamide |
| 955 | N-((1S,3R)-3-(5-((dimethylamino)methyl)-1,3,4-oxadiazol-2-yl)cyclohexyl)-4-fluoro-7-methyl-1H-indole-2-carboxamide |
| 956 | 4-fluoro-7-methyl-N-((1R,3R)-3-(piperazin-1-yl)cyclohexyl)-1H-indole-2-carboxamide |
| 957 | 4-fluoro-7-methyl-N-((1R,3R)-3-(piperazin-1-yl)cyclohexyl)-1H-indole-2-carboxamide |
| 958 | 4-fluoro-7-methyl-N-((1R,3S)-3-(3-(2-oxooxazolidin-3-yl)pyrrolidin-1-yl)cyclohexyl)-1H-indole-2-carboxamide |
| 959 | 4-fluoro-7-methyl-N-((1R,3R)-3-(3-(2-oxooxazolidin-3-yl)pyrrolidin-1-yl)cyclohexyl)-1H-indole-2-carboxamide |
| 960 | 4-fluoro-7-methyl-N-((1R,3S)-3-(3-(N-methylacetamido)azetidin-1-yl)cyclohexyl)-1H-indole-2-carboxamide |
| 961 | N-((1R,3S)-3-(5-acetyl-2,5-diazabicyclo[2.2.2]octan-2-yl)cyclohexyl)-4-fluoro-7-methyl-1H-indole-2-carboxamide |
| 962 | N-((1R,3R)-3-(5-acetyl-2,5-diazabicyclo[2.2.2]octan-2-yl)cyclohexyl)-4-fluoro-7-methyl-1H-indole-2-carboxamide |
| 963 | 4-fluoro-7-methyl-N-((1R,3S)-3-(2-oxo-3-oxa-1,8-diazaspiro[4.5]decan-8-yl)cyclohexyl)-1H-indole-2-carboxamide |
| 964 | 4-fluoro-7-methyl-N-((1R,3R)-3-(2-oxo-3-oxa-1,8-diazaspiro[4.5]decan-8-yl)cyclohexyl)-1H-indole-2-carboxamide |
| 965 | 4-fluoro-7-methyl-N-((1R,3S)-3-(2-oxo-1-(2,2,2-trifluoroethyl)-1,8-diazaspiro[4.5]decan-8-yl)cyclohexyl)-1H-indole-2-carboxamide |
| 966 | 4-fluoro-7-methyl-N-((1R,3R)-3-(2-oxo-1-(2,2,2-trifluoroethyl)-1,8-diazaspiro[4.5]decan-8-yl)cyclohexyl)-1H-indole-2-carboxamide |
| 967 | N-((1R,3S)-3-((S)-4-acetyl-3-methylpiperazin-1-yl)cyclohexyl)-4-fluoro-7-methyl-1H-indole-2-carboxamide |
| 968 | N-((1R,3R)-3-((S)-4-acetyl-3-methylpiperazin-1-yl)cyclohexyl)-4-fluoro-7-methyl-1H-indole-2-carboxamide |
| 969 | 4-fluoro-7-methyl-N-((1R,3S)-3-(3-(N-methylisobutyramido)pyrrolidin-1-yl)cyclohexyl)-1H-indole-2-carboxamide |
| 970 | 4-fluoro-7-methyl-N-((1R,3R)-3-(3-(N-methylisobutyramido)pyrrolidin-1-yl)cyclohexyl)-1H-indole-2-carboxamide |
| 971 | 4-fluoro-7-methyl-N-((1R,3S)-3-(3-(N-methylcyclopropanecarboxamido)pyrrolidin-1-yl)cyclohexyl)-1H-indole-2-carboxamide |
| 972 | 4-fluoro-7-methyl-N-((1R,3R)-3-(3-(N-methylcyclopropanecarboxamido)pyrrolidin-1-yl)cyclohexyl)-1H-indole-2-carboxamide |
| 973 | 4-fluoro-7-methyl-N-((1R,3S)-3-(3-oxo-4-(tetrahydrofuran-3-yl)piperazin-1-yl)cyclohexyl)-1H-indole-2-carboxamide |
| 974 | 4-fluoro-7-methyl-N-((1R,3R)-3-(3-oxo-4-(tetrahydrofuran-3-yl)piperazin-1-yl)cyclohexyl)-1H-indole-2-carboxamide |
| 975 | 4-fluoro-7-methyl-N-((1R,3S)-3-(5-methyl-1,3,4-oxadiazol-2-yl)cyclohexyl)-1H-indole-2-carboxamide |

TABLE 1-continued

| Cpd. No. | Chemical Name |
|---|---|
| 976 | 4-fluoro-7-methyl-N-((1S,3R)-3-(5-methyl-1,3,4-oxadiazol-2-yl)cyclohexyl)-1H-indole-2-carboxamide |
| 977 | N-((1R,3S)-3-(4-cyclopropyl-3-oxopiperazin-1-yl)cyclohexyl)-4-fluoro-7-methyl-1H-indole-2-carboxamide |
| 978 | N-((1R,3R)-3-(4-cyclopropyl-3-oxopiperazin-1-yl)cyclohexyl)-4-fluoro-7-methyl-1H-indole-2-carboxamide |
| 979 | N-((1R,3S)-3-(4-acetyl-1,4-diazepan-1-yl)cyclohexyl)-4-fluoro-7-methyl-1H-indole-2-carboxamide |
| 980 | N-((1R,3R)-3-(4-acetyl-1,4-diazepan-1-yl)cyclohexyl)-4-fluoro-7-methyl-1H-indole-2-carboxamide |
| 981 | 4-fluoro-7-methyl-N-((1R,3S)-3-(4-(methylsulfonyl)-1,4-diazepan-1-yl)cyclohexyl)-1H-indole-2-carboxamide |
| 982 | 4-fluoro-7-methyl-N-((1R,3R)-3-(4-(methylsulfonyl)-1,4-diazepan-1-yl)cyclohexyl)-1H-indole-2-carboxamide |
| 983 | 4-fluoro-N-((1R,3S)-3-((R)-3-(2-hydroxy-N-methylacetamido)pyrrolidin-1-yl)cyclohexyl)-7-methyl-1H-indole-2-carboxamide |
| 984 | 4-fluoro-N-((1R,3R)-3-((R)-3-(2-hydroxy-N-methylacetamido)pyrrolidin-1-yl)cyclohexyl)-7-methyl-1H-indole-2-carboxamide |
| 985 | N-((3S,5S)-5-(4-acetylpiperazin-1-yl)tetrahydro-2H-pyran-3-yl)-4-fluoro-7-methyl-1H-indole-2-carboxamide |
| 986 | N-((3S,5R)-5-(4-acetylpiperazin-1-yl)tetrahydro-2H-pyran-3-yl)-4-fluoro-7-methyl-1H-indole-2-carboxamide |
| 987 | N-((3R,5R)-5-(4-acetylpiperazin-1-yl)tetrahydro-2H-pyran-3-yl)-4-fluoro-7-methyl-1H-indole-2-carboxamide |
| 988 | N-((3R,5S)-5-(4-acetylpiperazin-1-yl)tetrahydro-2H-pyran-3-yl)-4-fluoro-7-methyl-1H-indole-2-carboxamide |
| 989 | 4-fluoro-7-methyl-N-((1R,3S)-3-(3-(trifluoromethyl)-5,6-dihydro-[1,2,4]triazolo[4,3-a]pyrazin-7(8H)-yl)cyclohexyl)-1H-indole-2-carboxamide |
| 990 | 4-fluoro-7-methyl-N-((1R,3R)-3-(3-(trifluoromethyl)-5,6-dihydro-[1,2,4]triazolo[4,3-a]pyrazin-7(8H)-yl)cyclohexyl)-1H-indole-2-carboxamide |
| 991 | N-((1R,3S)-3-(5,6-dihydroimidazo[1,5-a]pyrazin-7(8H)-yl)cyclohexyl)-4-fluoro-7-methyl-1H-indole-2-carboxamide |
| 992 | N-((1R,3R)-3-(5,6-dihydroimidazo[1,5-a]pyrazin-7(8H)-yl)cyclohexyl)-4-fluoro-7-methyl-1H-indole-2-carboxamide |
| 993 | 4-fluoro-7-methyl-N-((1R,3S)-3-(3-(trifluoromethyl)-5,6-dihydroimidazo[1,5-a]pyrazin-7(8H)-yl)cyclohexyl)-1H-indole-2-carboxamide |
| 994 | 4-fluoro-7-methyl-N-((1R,3R)-3-(3-(trifluoromethyl)-5,6-dihydroimidazo[1,5-a]pyrazin-7(8H)-yl)cyclohexyl)-1H-indole-2-carboxamide |
| 995 | 4-fluoro-N-((1R,3S)-3-((S)-3-(2-hydroxy-N-methylacetamido)pyrrolidin-1-yl)cyclohexyl)-7-methyl-1H-indole-2-carboxamide |
| 996 | 4-fluoro-N-((1R,3R)-3-((S)-3-(2-hydroxy-N-methylacetamido)pyrrolidin-1-yl)cyclohexyl)-7-methyl-1H-indole-2-carboxamide |
| 997 | isopropyl 4-((1S,3R)-3-(4-fluoro-7-methyl-1H-indole-2-carboxamido)cyclohexyl)piperazine-1-carboxylate |
| 998 | isopropyl 4-((1R,3R)-3-(4-fluoro-7-methyl-1H-indole-2-carboxamido)cyclohexyl)piperazine-1-carboxylate |
| 999 | tetrahydro-2H-pyran-4-yl 4-((1S,3R)-3-(4-fluoro-7-methyl-1H-indole-2-carboxamido)cyclohexyl)piperazine-1-carboxylate |
| 1000 | tetrahydro-2H-pyran-4-yl 4-((1R,3R)-3-(4-fluoro-7-methyl-1H-indole-2-carboxamido)cyclohexyl)piperazine-1-carboxylate |
| 1001 | 4-fluoro-7-methyl-N-((1R,3S)-3-(3-(trifluoromethyl)-5,6-dihydroimidazo[1,5-a]pyrazin-7(8H)-yl)cyclohexyl)-1H-indole-2-carboxamide |
| 1002 | N-((1R,3S)-3-(3-(dimethylamino)-2-oxopyrrolidin-1-yl)cyclohexyl)-4-fluoro-7-methyl-1H-indole-2-carboxamide |
| 1003 | 4-fluoro-7-methyl-N-((1R,3S)-3-(pyrimidin-4-yl)cyclohexyl)-1H-indole-2-carboxamide |
| 1004 | 4-fluoro-7-methyl-N-((1R,3S)-3-(2-oxo-4-(tetrahydrofuran-3-yl)piperazin-1-yl)cyclohexyl)-1H-indole-2-carboxamide |
| 1005 | N-((1R,3S)-3-(4-ethyl-2-oxopiperazin-1-yl)cyclohexyl)-4-fluoro-7-methyl-1H-indole-2-carboxamide |
| 1006 | N-((3S,5R)-5-(4-acetylpiperazin-1-yl)-1-methylpiperidin-3-yl)-4-fluoro-7-methyl-1H-indole-2-carboxamide |
| 1007 | N-((1R,3S)-3-(1-acetylpiperidin-4-yl)cyclohexyl)-4-fluoro-7-methyl-1H-indole-2-carboxamide |
| 1008 | 4-fluoro-7-methyl-N-((1R,3S)-3-(3-oxo-2-oxa-4,9-diazaspiro[5.5]undecan-9-yl)cyclohexyl)-1H-indole-2-carboxamide |
| 1009 | N-((1R,3S)-3-(2,2-dioxido-2-thia-1,3,8-triazaspiro[4.5]decan-8-yl)cyclohexyl)-4-fluoro-7-methyl-1H-indole-2-carboxamide |
| 1010 | 4-fluoro-7-methyl-N-((1R,3S)-3-(2-oxo-4-oxa-1,9-diazaspiro[5.5]undecan-9-yl)cyclohexyl)-1H-indole-2-carboxamide |
| 1011 | 4-fluoro-7-methyl-N-((1R,3S)-3-(5-methyl-1,2,4-oxadiazol-3-yl)cyclohexyl)-1H-indole-2-carboxamide |
| 1012 | 4-fluoro-7-methyl-N-((1R,3S)-3-(6-oxo-1,6-dihydro-1,2,4-triazin-3-yl)cyclohexyl)-1H-indole-2-carboxamide |
| 1013 | 4-fluoro-7-methyl-N-((1R,3S)-3-(6-oxo-1,6-dihydropyrimidin-2-yl)cyclohexyl)-1H-indole-2-carboxamide |

TABLE 1-continued

| Cpd. No. | Chemical Name |
|---|---|
| 1014 | N-((1R,3S)-3-(5-((dimethylamino)methyl)-1,2,4-oxadiazol-3-yl)cyclohexyl)-4-fluoro-7-methyl-1H-indole-2-carboxamide |
| 1015 | N-((1R,3R)-3-(4-acetylpiperazin-1-yl)-4-fluorocyclohexyl)-4-fluoro-7-methyl-1H-indole-2-carboxamide |
| 1016 | N-((1R,3R)-3-(4-acetylpiperazin-1-yl)-4-(trifluoromethyl)cyclohexyl)-4-fluoro-7-methyl-1H-indole-2-carboxamide |
| 1017 | N-((1R,3S)-3-(4-acetyl-2-(trifluoromethyl)piperazin-1-yl)cyclohexyl)-4-fluoro-7-methyl-1H-indole-2-carboxamide |
| 1018 | N-((1R,3S)-3-(4-acetyl-3-(trifluoromethyl)piperazin-1-yl)cyclohexyl)-4-fluoro-7-methyl-1H-indole-2-carboxamide |
| 1019 | 4-fluoro-7-methyl-N-((1R,3S)-3-(3-oxo-2,8-diazaspiro[4.5]decan-8-yl)cyclohexyl)-1H-indole-2-carboxamide |
| 1020 | 4-fluoro-7-methyl-N-((1R,3S)-3-(7-oxo-5-oxa-2,8-diazaspiro[3.5]nonan-2-yl)cyclohexyl)-1H-indole-2-carboxamide |
| 1021 | N-((1R,3S)-3-(4-acetyl-2-methylpiperazin-1-yl)cyclohexyl)-4-fluoro-7-methyl-1H-indole-2-carboxamide |
| 1022 | N-((1R,3S)-3-(4-acetyl-3-(hydroxymethyl)piperazin-1-yl)cyclohexyl)-4-fluoro-7-methyl-1H-indole-2-carboxamide |
| 1023 | N-((1R,3S)-3-(4-acetyl-2-(hydroxymethyl)piperazin-1-yl)cyclohexyl)-4-fluoro-7-methyl-1H-indole-2-carboxamide |
| 1024 | N-((1R,3S)-3-(7-acetyl-4,7-diazaspiro[2.5]octan-4-yl)cyclohexyl)-4-fluoro-7-methyl-1H-indole-2-carboxamide |
| 1025 | N-((1R,3S)-3-(4-acetyl-4,7-diazaspiro[2.5]octan-7-yl)cyclohexyl)-4-fluoro-7-methyl-1H-indole-2-carboxamide |
| 1026 | N-((1R,3S)-3-(3,4-dimethyl-2-oxopiperazin-1-yl)cyclohexyl)-4-fluoro-7-methyl-1H-indole-2-carboxamide |
| 1027 | 4-fluoro-7-methyl-N-(1-(pyridin-4-yl)piperidin-3-yl)-1H-indole-2-carboxamide |
| 1028 | 4-fluoro-7-methyl-N-(1'-methyl-2'-oxo-[1,4'-bipiperidin]-3-yl)-1H-indole-2-carboxamide |
| 1029 | isopropyl 4-((1S,3R)-3-(4-fluoro-7-methyl-1H-indole-2-carboxamido)cyclohexyl)piperazine-1-carboxylate |
| 1030 | tetrahydro-2H-pyran-4-yl 4-((1S,3R)-3-(4-fluoro-7-methyl-1H-indole-2-carboxamido)cyclohexyl)piperazine-1-carboxylate |
| 1031 | 4-fluoro-7-methyl-N-((1R,3S)-3-(2-(trifluoromethyl)-5,6-dihydro-[1,2,4]triazolo[1,5-a]pyrazin-7(8H)-yl)cyclohexyl)-1H-indole-2-carboxamide |
| 1032 | N-((1R,3S)-3-((4-acetylpiperazin-1-yl)methyl)cyclohexyl)-4-fluoro-7-methyl-1H-indole-2-carboxamide |
| 1033 | N-((1R,3S)-3-(5,6-dihydroimidazo[1,5-a]pyrazin-7(8H)-yl)cyclohexyl)-4-fluoro-7-methyl-1H-indole-2-carboxamide |
| 1034 | 4-fluoro-7-methyl-N-((1R,3S)-3-(3-(trifluoromethyl)-5,6-dihydroimidazo[1,5-a]pyrazin-7(8H)-yl)cyclohexyl)-1H-indole-2-carboxamide |
| 1035 | 4-fluoro-N-((1R,3R,4R)-4-fluoro-3-(2-oxo-1,8-diazaspiro[4.5]decan-8-yl)cyclohexyl)-7-methyl-1H-indole-2-carboxamide |
| 1036 | 4-fluoro-N-((1R,3R,4R)-4-fluoro-3-((S)-3-(N-methylacetamido)pyrrolidin-1-yl)cyclohexyl)-7-methyl-1H-indole-2-carboxamide |
| 1037 | 4-fluoro-7-methyl-N-((1R,3S)-3-(4-((tetrahydro-2H-pyran-4-yl)carbamoyl)piperazin-1-yl)cyclohexyl)-1H-indole-2-carboxamide |
| 1038 | 4-fluoro-7-methyl-N-((1R,3S)-3-((3aS,6aS)-1-methyl-2-oxohexahydropyrrolo[3,4-b]pyrrol-5(1H)-yl)cyclohexyl)-1H-indole-2-carboxamide |
| 1039 | 4-fluoro-7-methyl-N-((1R,3S)-3-((3aR,6aR)-1-methyl-2-oxohexahydropyrrolo[3,4-b]pyrrol-5(1H)-yl)cyclohexyl)-1H-indole-2-carboxamide |
| 1040 | 4-fluoro-7-methyl-N-((1R,3S)-3-(4-methyl-5-oxohexahydropyrrolo[3,2-b]pyrrol-1(2H)-yl)cyclohexyl)-1H-indole-2-carboxamide |
| 1041 | 4-fluoro-N-((1R,3S)-3-((S)-3-(2-hydroxy-N-methylacetamido)pyrrolidin-1-yl)cyclohexyl)-7-methyl-1H-indole-2-carboxamide |
| 1042 | 4-fluoro-N-((1R,3S)-3-((R)-3-(2-methoxy-N-methylacetamido)pyrrolidin-1-yl)cyclohexyl)-7-methyl-1H-indole-2-carboxamide |
| 1043 | 4-fluoro-N-((1R,3S)-3-((S)-3-(2-methoxy-N-methylacetamido)pyrrolidin-1-yl)cyclohexyl)-7-methyl-1H-indole-2-carboxamide |
| 1044 | 4-fluoro-7-methyl-N-((1R,3S)-3-(6-oxooctahydro-2H-pyrido[1,2-a]pyrazin-2-yl)cyclohexyl)-1H-indole-2-carboxamide |
| 1045 | 4-fluoro-7-methyl-N-((1R,3S)-3-(4-oxohexahydropyrazino[2,1-c][1,4]oxazin-8(1H)-yl)cyclohexyl)-1H-indole-2-carboxamide |
| 1046 | 4-fluoro-7-methyl-N-((1R,3S)-3-(8-methyl-6,9-dioxooctahydro-2H-pyrazino[1,2-a]pyrazin-2-yl)cyclohexyl)-1H-indole-2-carboxamide |
| 1047 | 4-fluoro-7-methyl-N-((1R,3S)-3-(6-oxooctahydro-2H-pyrazino[1,2-c]pyrimidin-2-yl)cyclohexyl)-1H-indole-2-carboxamide |
| 1048 | 4-fluoro-7-methyl-N-((1R,3S)-3-(6-oxo-1,3,4,6-tetrahydro-2H-pyrido[1,2-a]pyrazin-2-yl)cyclohexyl)-1H-indole-2-carboxamide |
| 1049 | 4-fluoro-7-methyl-N-((1R,3S)-3-(4-oxo-4,6,7,9-tetrahydro-8H-pyrazino[1,2-a]pyrimidin-8-yl)cyclohexyl)-1H-indole-2-carboxamide |
| 1050 | 4-fluoro-7-methyl-N-((1R,3S)-3-(3-oxohexahydroimidazo[1,5-a]pyrazin-7(1H)-yl)cyclohexyl)-1H-indole-2-carboxamide |
| 1051 | 4-fluoro-7-methyl-N-((1R,3S)-3-(2-methyl-3-oxohexahydroimidazo[1,5-a]pyrazin-7(1H)-yl)cyclohexyl)-1H-indole-2-carboxamide |

TABLE 1-continued

| Cpd. No. | Chemical Name |
|---|---|
| 1052 | 4-fluoro-N-((1R,3S)-3-(3-(2-hydroxy-N,2-dimethylpropanamido)pyrrolidin-1-yl)cyclohexyl)-7-methyl-1H-indole-2-carboxamide |
| 1053 | N-((1R,3S)-3-(3-(N-ethyl-2-hydroxyacetamido)pyrrolidin-1-yl)cyclohexyl)-4-fluoro-7-methyl-1H-indole-2-carboxamide |
| 1054 | N-((1R,3S)-3-(3-(N-ethylmethylsulfonamido)pyrrolidin-1-yl)cyclohexyl)-4-fluoro-7-methyl-1H-indole-2-carboxamide |
| 1055 | N-((1R,3S)-3-(4-acetyl-3-ethylpiperazin-1-yl)cyclohexyl)-4-fluoro-7-methyl-1H-indole-2-carboxamide |
| 1056 | 4-fluoro-7-methyl-N-((1R,3S)-3-(2-methyl-3-oxo-2,5,6,8-tetrahydro-[1,2,4]triazolo[4,3-a]pyrazin-7(3H)-yl)cyclohexyl)-1H-indole-2-carboxamide |
| 1057 | 4-fluoro-7-methyl-N-((1R,3S)-3-(2-methyl-3-oxo-2,5,6,8-tetrahydroimidazo[1,5-a]pyrazin-7(3H)-yl)cyclohexyl)-1H-indole-2-carboxamide |
| 1058 | 4-fluoro-7-methyl-N-((1R,3S)-3-(3-oxo-2,5,6,8-tetrahydro-[1,2,4]triazolo[4,3-a]pyrazin-7(3H)-yl)cyclohexyl)-1H-indole-2-carboxamide |
| 1059 | 4-fluoro-7-methyl-N-((1R,3S)-3-(3-oxo-2,5,6,8-tetrahydroimidazo[1,5-a]pyrazin-7(3H)-yl)cyclohexyl)-1H-indole-2-carboxamide |
| 1060 | 4-fluoro-N-((1R,3S)-3-((S)-3-((1-hydroxy-N-methylmethyl)sulfonamido)pyrrolidin-1-yl)cyclohexyl)-7-methyl-1H-indole-2-carboxamide |
| 1061 | 4-fluoro-N-((1R,3S)-3-((S)-3-(N-(2-hydroxyethyl)methylsulfonamido)pyrrolidin-1-yl)cyclohexyl)-7-methyl-1H-indole-2-carboxamide |
| 1062 | N-((1R,3S)-3-((3R,5R)-4-acetyl-3,5-dimethylpiperazin-1-yl)cyclohexyl)-4-fluoro-7-methyl-1H-indole-2-carboxamide |
| 1063 | 4-fluoro-N-((1R,3R)-3-((S)-3-(2-methoxy-N-methylacetamido)pyrrolidin-1-yl)cyclohexyl)-7-methyl-1H-indole-2-carboxamide |
| 1064 | 4-fluoro-7-methyl-N-((1R,3R)-3-(pyrimidin-4-yl)cyclohexyl)-1H-indole-2-carboxamide |
| 1065 | 4-fluoro-7-methyl-N-((1S,3R)-3-(5-methyl-1,2,4-oxadiazol-3-yl)cyclohexyl)-1H-indole-2-carboxamide |
| 1066 | 4-fluoro-7-methyl-N-((1R,3R)-3-(2-(trifluoromethyl)-5,6-dihydro-[1,2,4]triazolo[1,5-a]pyrazin-7(8H)-yl)cyclohexyl)-1H-indole-2-carboxamide |
| 1067 | 4-fluoro-7-methyl-N-((1R,3R)-3-(4-oxohexahydropyrazino[2,1-c][1,4]oxazin-8(1H)-yl)cyclohexyl)-1H-indole-2-carboxamide |
| 1068 | 4-fluoro-7-methyl-N-((1R,3S)-3-(6-oxo-1,6-dihydropyrimidin-4-yl)cyclohexyl)-1H-indole-2-carboxamide |
| 1069 | N-((1R,3S)-3-((R)-4-acetyl-3-(trifluoromethyl)piperazin-1-yl)cyclohexyl)-4-fluoro-7-methyl-1H-indole-2-carboxamide |
| 1070 | N-((1R,3S)-3-((S)-4-acetyl-3-(trifluoromethyl)piperazin-1-yl)cyclohexyl)-4-fluoro-7-methyl-1H-indole-2-carboxamide |
| 1071 | N-((1R,3R)-3-((R)-4-acetyl-3-(trifluoromethyl)piperazin-1-yl)cyclohexyl)-4-fluoro-7-methyl-1H-indole-2-carboxamide |
| 1072 | N-((1R,3R)-3-((S)-4-acetyl-3-(trifluoromethyl)piperazin-1-yl)cyclohexyl)-4-fluoro-7-methyl-1H-indole-2-carboxamide |
| 1073 | N-((1R,3S)-3-((S)-4-acetyl-2-methylpiperazin-1-yl)cyclohexyl)-4-fluoro-7-methyl-1H-indole-2-carboxamide |
| 1074 | N-((1R,3R)-3-((S)-4-acetyl-2-methylpiperazin-1-yl)cyclohexyl)-4-fluoro-7-methyl-1H-indole-2-carboxamide |
| 1075 | N-((1R,3R)-3-((R)-4-acetyl-3-(hydroxymethyl)piperazin-1-yl)cyclohexyl)-4-fluoro-7-methyl-1H-indole-2-carboxamide |
| 1076 | N-((1R,3R)-3-((S)-4-acetyl-3-(hydroxymethyl)piperazin-1-yl)cyclohexyl)-4-fluoro-7-methyl-1H-indole-2-carboxamide |
| 1077 | N-((1S,3R)-3-((4-acetylpiperazin-1-yl)methyl)cyclohexyl)-4-fluoro-7-methyl-1H-indole-2-carboxamide |
| 1078 | 4-fluoro-7-methyl-N-((1R,3S)-3-((S)-6-oxooctahydro-2H-pyrido[1,2-a]pyrazin-2-yl)cyclohexyl)-1H-indole-2-carboxamide |
| 1079 | 4-fluoro-7-methyl-N-((1R,3R)-3-((R)-6-oxooctahydro-2H-pyrido[1,2-a]pyrazin-2-yl)cyclohexyl)-1H-indole-2-carboxamide |
| 1080 | 4-fluoro-7-methyl-N-((1R,3R)-3-((S)-6-oxooctahydro-2H-pyrido[1,2-a]pyrazin-2-yl)cyclohexyl)-1H-indole-2-carboxamide |
| 1081 | 4-fluoro-7-methyl-N-((1R,3R)-3-((R)-3-oxohexahydroimidazo[1,5-a]pyrazin-7(1H)-yl)cyclohexyl)-1H-indole-2-carboxamide |
| 1082 | 4-fluoro-7-methyl-N-((1R,3R)-3-((S)-3-oxohexahydroimidazo[1,5-a]pyrazin-7(1H)-yl)cyclohexyl)-1H-indole-2-carboxamide |
| 1083 | 4-fluoro-7-methyl-N-((1R,3S)-3-((R)-3-oxohexahydroimidazo[1,5-a]pyrazin-7(1H)-yl)cyclohexyl)-1H-indole-2-carboxamide |
| 1084 | 4-fluoro-7-methyl-N-((1R,3S)-3-((S)-3-oxohexahydroimidazo[1,5-a]pyrazin-7(1H)-yl)cyclohexyl)-1H-indole-2-carboxamide |
| 1085 | N-((1R,3S)-3-((S)-4-acetyl-3-ethylpiperazin-1-yl)cyclohexyl)-4-fluoro-7-methyl-1H-indole-2-carboxamide |
| 1086 | N-((1R,3R)-3-((S)-4-acetyl-3-ethylpiperazin-1-yl)cyclohexyl)-4-fluoro-7-methyl-1H-indole-2-carboxamide |
| 1087 | 4-fluoro-7-methyl-N-((1R,3S)-3-((S)-3-(methylamino)pyrrolidin-1-yl)cyclohexyl)-1H-indole-2-carboxamide |
| 1088 | 4-fluoro-7-methyl-N-((1R,3R)-3-((S)-3-(methylamino)pyrrolidin-1-yl)cyclohexyl)-1H-indole-2-carboxamide |
| 1089 | N-((1R,3S)-3-((R)-3-(dimethylamino)-2-oxopyrrolidin-1-yl)cyclohexyl)-4-fluoro-7-methyl-1H-indole-2-carboxamide |

TABLE 1-continued

| Cpd. No. | Chemical Name |
|---|---|
| 1090 | N-((1R,3S)-3-((S)-3-(dimethylamino)-2-oxopyrrolidin-1-yl)cyclohexyl)-4-fluoro-7-methyl-1H-indole-2-carboxamide |
| 1091 | N-((1R,3R)-3-((R)-4-acetyl-2-methylpiperazin-1-yl)cyclohexyl)-4-fluoro-7-methyl-1H-indole-2-carboxamide |
| 1092 | N-((1R,3S)-3-((R)-4-acetyl-2-methylpiperazin-1-yl)cyclohexyl)-4-fluoro-7-methyl-1-indole-2-carboxamide |
| 1093 | 4-fluoro-7-methyl-N-((1R,3S)-3-((R)-6-oxooctahydro-2H-pyrido[1,2-a]pyrazin-2-yl)cyclohexyl)-1H-indole-2-carboxamide |
| 1094 | N-((1R,3S)-3-((R)-4-acetyl-3-ethylpiperazin-1-yl)cyclohexyl)-4-fluoro-7-methyl-1H-indole-2-carboxamide |
| 1095 | N-((1R,3R)-3-((R)-4-acetyl-3-ethylpiperazin-1-yl)cyclohexyl)-4-fluoro-7-methyl-1H-indole-2-carboxamide |
| 1096 | N-((1R,3R)-3-((3R,5S)-4-acetyl-3,5-dimethylpiperazin-1-yl)cyclohexyl)-4-fluoro-7-methyl-1H-indole-2-carboxamide |
| 1097 | N-((1R,3S)-3-((3R,5S)-4-acetyl-3,5-dimethylpiperazin-1-yl)cyclohexyl)-4-fluoro-7-methyl-1H-indole-2-carboxamide |
| 1098 | N-((1R,3S)-3-((S)-4-acetyl-3-(hydroxymethyl)piperazin-1-yl)cyclohexyl)-4-fluoro-7-methyl-1H-indole-2-carboxamide |
| 1099 | N-((1R,3S)-3-((R)-4-acetyl-3-(hydroxymethyl)piperazin-1-yl)cyclohexyl)-4-fluoro-7-methyl-1H-indole-2-carboxamide |
| 1100 | N-((1R,3R)-3-(4-acetyl-4,7-diazaspiro[2.5]octan-7-yl)cyclohexyl)-4-fluoro-7-methyl-1H-indole-2-carboxamide |
| 1101 | 4-fluoro-7-methyl-N-((1R,3R)-3-((S)-8-methyl-6,9-dioxooctahydro-2H-pyrazino[1,2-a]pyrazin-2-yl)cyclohexyl)-1H-indole-2-carboxamide |
| 1102 | 4-fluoro-7-methyl-N-((1R,3R)-3-((R)-8-methyl-6,9-dioxooctahydro-2H-pyrazino[1,2-a]pyrazin-2-yl)cyclohexyl)-1H-indole-2-carboxamide |
| 1103 | 4-fluoro-7-methyl-N-((1R,3S)-3-((S)-8-methyl-6,9-dioxooctahydro-2H-pyrazino[1,2-a]pyrazin-2-yl)cyclohexyl)-1H-indole-2-carboxamide |
| 1104 | 4-fluoro-7-methyl-N-((1R,3S)-3-((R)-8-methyl-6,9-dioxooctahydro-2H-pyrazino[1,2-a]pyrazin-2-yl)cyclohexyl)-1H-indole-2-carboxamide |
| 1105 | 4-fluoro-7-methyl-N-((1R,3S)-3-(3-oxo-2,5,6,8-tetrahydro-[1,2,4]triazolo[4,3-a]pyrazin-7(3H)-yl)cyclohexyl)-1H-indole-2-carboxamide |
| 1106 | 4-fluoro-7-methyl-N-((1R,3R)-3-(3-oxo-2,5,6,8-tetrahydro-[1,2,4]triazolo[4,3-a]pyrazin-7(3H)-yl)cyclohexyl)-1H-indole-2-carboxamide |
| 1107 | N-((3S,5S)-5-(4-acetylpiperazin-1-yl)-1-methylpiperidin-3-yl)-4-fluoro-7-methyl-1H-indole-2-carboxamide |
| 1108 | N-((3R,5R)-5-(4-acetylpiperazin-1-yl)-1-methylpiperidin-3-yl)-4-fluoro-7-methyl-1H-indole-2-carboxamide |
| 1109 | N-((3R,5S)-5-(4-acetylpiperazin-1-yl)-1-methylpiperidin-3-yl)-4-fluoro-7-methyl-1H-indole-2-carboxamide |
| 1110 | N-((1S,3R)-3-(5-((dimethylamino)methyl)-1,2,4-oxadiazol-3-yl)cyclohexyl)-4-fluoro-7-methyl-1H-indole-2-carboxamide |
| 1111 | 4-fluoro-7-methyl-N-(3-(3-oxotetrahydro-3H-oxazolo[3,4-a]pyrazin-7(1H)-yl)cyclohexyl)-1H-indole-2-carboxamide |
| 1112 | 4-fluoro-N-((1R,3S)-3-(4-isobutyryl-3-(trifluoromethyl)piperazin-1-yl)cyclohexyl)-7-methyl-1H-indole-2-carboxamide |
| 1113 | 4-fluoro-7-methyl-N-((1R,3S)-3-(4-propionyl-3-(trifluoromethyl)piperazin-1-yl)cyclohexyl)-1H-indole-2-carboxamide |
| 1114 | N-((1R,3S)-3-(4-((E)-N'-cyano-N-methylcarbamimidoyl)piperazin-1-yl)cyclohexyl)-4-fluoro-7-methyl-1H-indole-2-carboxamide |
| 1115 | 4-fluoro-7-methyl-N-((1R,3S)-3-(4-((E)-1-(methylamino)-2-nitrovinyl)piperazin-1-yl)cyclohexyl)-1H-indole-2-carboxamide |
| 1116 | N-((1R,3S)-3-(4-((E)-1-(cyanoimino)ethyl)piperazin-1-yl)cyclohexyl)-4-fluoro-7-methyl-1H-indole-2-carboxamide |
| 1117 | 4-fluoro-N-((1R,3S)-3-(4-(2-hydroxyacetyl)-3-(trifluoromethyl)piperazin-1-yl)cyclohexyl)-7-methyl-1H-indole-2-carboxamide |
| 1118 | N-((1R,3S)-3-(1-(4-acetylpiperazin-1-yl)ethyl)cyclohexyl)-4-fluoro-7-methyl-1H-indole-2-carboxamide |
| 1119 | N-((1R,3S)-3-((R)-3-(N-ethyl-2-hydroxyacetamido)pyrrolidin-1-yl)cyclohexyl)-4-fluoro-7-methyl-1H-indole-2-carboxamide |
| 1120 | N-((1R,3R)-3-((R)-3-(N-ethyl-2-hydroxyacetamido)pyrrolidin-1-yl)cyclohexyl)-4-fluoro-7-methyl-1H-indole-2-carboxamide |
| 1121 | N-((1R,3S)-3-((R)-3-(N-ethylmethylsulfonamido)pyrrolidin-1-yl)cyclohexyl)-4-fluoro-7-methyl-1H-indole-2-carboxamide |
| 1122 | N-((1R,3R)-3-((R)-3-(N-ethylmethylsulfonamido)pyrrolidin-1-yl)cyclohexyl)-4-fluoro-7-methyl-1H-indole-2-carboxamide |
| 1123 | N-((1R,3R)-3-((3R,5R)-4-acetyl-3,5-dimethylpiperazin-1-yl)cyclohexyl)-4-fluoro-7-methyl-1H-indole-2-carboxamide |
| 1124 | N-((1R,3R)-3-(1-acetylpiperidin-4-yl)cyclohexyl)-4-fluoro-7-methyl-1H-indole-2-carboxamide |
| 1125 | 4-fluoro-7-methyl-N-((1R,3S)-3-((S)-2-methyl-3-oxohexahydroimidazo[1,5-a]pyrazin-7(1H)-yl)cyclohexyl)-1H-indole-2-carboxamide |
| 1126 | 4-fluoro-7-methyl-N-((1R,3S)-3-((R)-2-methyl-3-oxohexahydroimidazo[1,5-a]pyrazin-7(1H)-yl)cyclohexyl)-1H-indole-2-carboxamide |
| 1127 | 4-fluoro-7-methyl-N-((1R,3R)-3-((S)-2-methyl-3-oxohexahydroimidazo[1,5-a]pyrazin-7(1H)-yl)cyclohexyl)-1H-indole-2-carboxamide |

TABLE 1-continued

| Cpd. No. | Chemical Name |
|---|---|
| 1128 | 4-fluoro-7-methyl-N-((1R,3R)-3-((R)-2-methyl-3-oxohexahydroimidazo[1,5-a]pyrazin-7(1H)-yl)cyclohexyl)-1H-indole-2-carboxamide |
| 1129 | N-((1R,3S)-3-((S)-3-(N-ethyl-2-hydroxyacetamido)pyrrolidin-1-yl)cyclohexyl)-4-fluoro-7-methyl-1H-indole-2-carboxamide |
| 1130 | N-((1R,3R)-3-((S)-3-(N-ethyl-2-hydroxyacetamido)pyrrolidin-1-yl)cyclohexyl)-4-fluoro-7-methyl-1H-indole-2-carboxamide |
| 1131 | N-((1R,3S)-3-((S)-3-(N-ethylmethylsulfonamido)pyrrolidin-1-yl)cyclohexyl)-4-fluoro-7-methyl-1H-indole-2-carboxamide |
| 1132 | N-((1R,3R)-3-((S)-3-(N-ethylmethylsulfonamido)pyrrolidin-1-yl)cyclohexyl)-4-fluoro-7-methyl-1H-indole-2-carboxamide |
| 1133 | 4-fluoro-7-methyl-N-((1R,3S)-3-((R)-3-oxotetrahydro-3H-oxazolo[3,4-a]pyrazin-7(1H)-yl)cyclohexyl)-1H-indole-2-carboxamide |
| 1134 | 4-fluoro-7-methyl-N-((1R,3R)-3-((R)-3-oxotetrahydro-3H-oxazolo[3,4-a]pyrazin-7(1H)-yl)cyclohexyl)-1H-indole-2-carboxamide |
| 1135 | 4-fluoro-7-methyl-N-((1R,3R)-3-((S)-3-oxotetrahydro-3H-oxazolo[3,4-a]pyrazin-7(1H)-yl)cyclohexyl)-1H-indole-2-carboxamide |
| 1136 | 4-fluoro-7-methyl-N-((1R,3S)-3-((S)-3-oxotetrahydro-3H-oxazolo[3,4-a]pyrazin-7(1H)-yl)cyclohexyl)-1H-indole-2-carboxamide |
| 1137 | N-((1R,3R)-3-(7-acetyl-4,7-diazaspiro[2.5]octan-4-yl)cyclohexyl)-4-fluoro-7-methyl-1H-indole-2-carboxamide |
| 1138 | 4-fluoro-7-methyl-N-((1R,3S)-3-((S)-4-oxohexahydropyrazino[2,1-c][1,4]oxazin-8(1H)-yl)cyclohexyl)-1H-indole-2-carboxamide |
| 1139 | 4-fluoro-7-methyl-N-((1R,3R)-3-((S)-4-oxohexahydropyrazino[2,1-c][1,4]oxazin-8(1H)-yl)cyclohexyl)-1H-indole-2-carboxamide |
| 1140 | 4-fluoro-7-methyl-N-((1R,3S)-3-((R)-4-oxohexahydropyrazino[2,1-c][1,4]oxazin-8(1H)-yl)cyclohexyl)-1H-indole-2-carboxamide |
| 1141 | 4-fluoro-7-methyl-N-((1R,3R)-3-((R)-4-oxohexahydropyrazino[2,1-c][1,4]oxazin-8(1H)-yl)cyclohexyl)-1H-indole-2-carboxamide |
| 1142 | 4-fluoro-7-methyl-N-((1R,3R)-3-(2-methyl-3-oxo-2,5,6,8-tetrahydro-[1,2,4]triazolo[4,3-a]pyrazin-7(3H)-yl)cyclohexyl)-1H-indole-2-carboxamide |
| 1143 | 4-fluoro-7-methyl-N-((1R,3R)-3-(6-oxo-1,3,4,6-tetrahydro-2H-pyrido[1,2-a]pyrazin-2-yl)cyclohexyl)-1H-indole-2-carboxamide |
| 1144 | 4-fluoro-N-((1R,3S)-3-((S)-3-(2-hydroxy-N,2-dimethylpropanamido)pyrrolidin-1-yl)cyclohexyl)-7-methyl-1H-indole-2-carboxamide |
| 1145 | 4-fluoro-N-((1R,3R)-3-((S)-3-(2-hydroxy-N,2-dimethylpropanamido)pyrrolidin-1-yl)cyclohexyl)-7-methyl-1H-indole-2-carboxamide |
| 1146 | 4-fluoro-N-((1R,3S)-3-((R)-3-(2-hydroxy-N,2-dimethylpropanamido)pyrrolidin-1-yl)cyclohexyl)-7-methyl-1H-indole-2-carboxamide |
| 1147 | 4-fluoro-N-((1R,3R)-3-((R)-3-(2-hydroxy-N,2-dimethylpropanamido)pyrrolidin-1-yl)cyclohexyl)-7-methyl-1H-indole-2-carboxamide |
| 1148 | N-((1R,3R)-3-(4-((E)-1-(cyanoimino)ethyl)piperazin-1-yl)cyclohexyl)-4-fluoro-7-methyl-1H-indole-2-carboxamide |
| 1149 | 4-fluoro-N-((1R,3S)-3-((R)-3-(N-(2-hydroxyethyl)methylsulfonamido)pyrrolidin-1-yl)cyclohexyl)-7-methyl-1H-indole-2-carboxamide |
| 1150 | 4-fluoro-N-((1R,3R)-3-((R)-3-(N-(2-hydroxyethyl)methylsulfonamido)pyrrolidin-1-yl)cyclohexyl)-7-methyl-1H-indole-2-carboxamide |
| 1151 | 4-fluoro-N-((1R,3R)-3-((S)-3-(N-(2-hydroxyethyl)methylsulfonamido)pyrrolidin-1-yl)cyclohexyl)-7-methyl-1H-indole-2-carboxamide |
| 1152 | N-((1R,3R)-3-(4-((E)-N'-cyano-N-methylcarbamimidoyl)piperazin-1-yl)cyclohexyl)-4-fluoro-7-methyl-1H-indole-2-carboxamide |
| 1153 | N-(2-chlorobenzyl)-7-methyl-1H-indole-2-carboxamide |
| 1154 | (S)-N-(1-(2-chlorophenyl)ethyl)-7-methyl-1H-indole-2-carboxamide |
| 1155 | N-(1-(4-(1H-1,2,4-triazol-1-yl)phenyl)ethyl)-7-methyl-1H-indole-2-carboxamide |
| 1156 | N-(1-(2-chlorophenyl)ethyl)-7-methyl-1H-indole-2-carboxamide |
| 1157 | methyl 3-(2-chlorophenyl)-3-(7-methyl-1H-indole-2-carboxamido)propanoate |
| 1158 | N-(3-chloro-5-(4-(3-(pyrrolidin-1-yl)propyl)piperidin-1-yl)phenyl)-4-fluoro-7-methyl-1H-indole-2-carboxamide |
| 1159 | 4-fluoro-7-methyl-N-(1-methyl-5-(1-methylpiperidin-4-yl)-1H-imidazol-2-yl)-1H-indole-2-carboxamide |
| 1160 | 4-fluoro-N-((1R,3R)-3-((R)-3-(2-methoxy-N-methylacetamido)pyrrolidin-1-yl)cyclohexyl)-7-methyl-1H-indole-2-carboxamide |
| 1161 | 4-fluoro-N-((1R,3S)-3-((R)-3-(N-(2-hydroxyethyl)methylsulfonamido)pyrrolidin-1-yl)cyclohexyl)-7-methyl-1H-indene-2-carboxamide |
| 1162 | N-((1R,3S)-3-((3S,5S)-4-acetyl-3,5-dimethylpiperazin-1-yl)cyclohexyl)-4-fluoro-7-methyl-1H-indole-2-carboxamide |
| 1163 | N-((1R,3R)-3-((3S,5S)-4-acetyl-3,5-dimethylpiperazin-1-yl)cyclohexyl)-4-fluoro-7-methyl-1H-indole-2-carboxamide |
| 1164 | 4-fluoro-7-methyl-N-((1R,3R)-3-((R)-4-propionyl-3-(trifluoromethyl)piperazin-1-yl)cyclohexyl)-1H-indole-2-carboxamide |
| 1165 | 4-fluoro-7-methyl-N-((1R,3R)-3-(4-oxo-4,6,7,9-tetrahydro-8H-pyrazino[1,2-a]pyrimidin-8-yl)cyclohexyl)-1H-indole-2-carboxamide |
| 1166 | 4-fluoro-7-methyl-N-((1R,3R)-3-(3-oxo-2,5,6,8-tetrahydroimidazo[1,5-a]pyrazin-7(3H)-yl)cyclohexyl)-1H-indole-2-carboxamide |
| 1167 | 4-fluoro-7-methyl-N-((1R,3S)-3-((S)-4-propionyl-3-(trifluoromethyl)piperazin-1-yl)cyclohexyl)-1H-indole-2-carboxamide |
| 1168 | 4-fluoro-7-methyl-N-((1R,3R)-3-((S)-4-propionyl-3-(trifluoromethyl)piperazin-1-yl)cyclohexyl)-1H-indole-2-carboxamide |

TABLE 1-continued

| Cpd. No. | Chemical Name |
|---|---|
| 1169 | 4-fluoro-7-methyl-N-((1R,3R)-3-(4-((E)-1-(methylamino)-2-nitrovinyl)piperazin-1-yl)cyclohexyl)-1H-indole-2-carboxamide |
| 1170 | 4-fluoro-7-methyl-N-((1R,3R)-3-(4-((tetrahydro-2H-pyran-4-yl)carbamoyl)piperazin-1-yl)cyclohexyl)-1H-indole-2-carboxamide |
| 1171 | 4-fluoro-N-((1R,3S)-3-((S)-4-isobutyryl-3-(trifluoromethyl)piperazin-1-yl)cyclohexyl)-7-methyl-1H-indole-2-carboxamide |
| 1172 | 4-fluoro-N-((1R,3R)-3-((S)-4-isobutyryl-3-(trifluoromethyl)piperazin-1-yl)cyclohexyl)-7-methyl-1H-indole-2-carboxamide |
| 1173 | 4-fluoro-N-((1R,3S)-3-((S)-4-(2-hydroxyacetyl)-3-(trifluoromethyl)piperazin-1-yl)cyclohexyl)-7-methyl-1H-indole-2-carboxamide |
| 1174 | 4-fluoro-N-((1R,3R)-3-((S)-4-(2-hydroxyacetyl)-3-(trifluoromethyl)piperazin-1-yl)cyclohexyl)-7-methyl-1H-indole-2-carboxamide |
| 1175 | 4-fluoro-N-((1R,3R)-3-((R)-4-isobutyryl-3-(trifluoromethyl)piperazin-1-yl)cyclohexyl)-7-methyl-1H-indole-2-carboxamide |
| 1176 | 4-fluoro-N-((1R,3R)-3-((R)-4-(2-hydroxyacetyl)-3-(trifluoromethyl)piperazin-1-yl)cyclohexyl)-7-methyl-1H-indole-2-carboxamide |
| 1177 | N-((1R,3S)-3-((3aR,6aS)-5-acetylhexahydropyrrolo[3,4-c]pyrrol-2(1H)-yl)cyclohexyl)-4-fluoro-7-methyl-1H-indole-2-carboxamide |
| 1178 | N-((1R,3R)-3-((3aR,6aS)-5-acetylhexahydropyrrolo[3,4-c]pyrrol-2(1H)-yl)cyclohexyl)-4-fluoro-7-methyl-1H-indole-2-carboxamide |
| 1179 | 4-fluoro-7-methyl-N-((1R,3R)-3-(2-methyl-3-oxo-2,5,6,8-tetrahydroimidazo[1,5-a]pyrazin-7(3H)-yl)cyclohexyl)-1H-indole-2-carboxamide |
| 1180 | N-((1R,3S)-3-((3aS,6aS)-1-acetylhexahydropyrrolo[3,4-b]pyrrol-5(1H)-yl)cyclohexyl)-4-fluoro-7-methyl-1H-indole-2-carboxamide |
| 1181 | N-((1R,3R)-3-((3aS,6aS)-1-acetylhexahydropyrrolo[3,4-b]pyrrol-5(1H)-yl)cyclohexyl)-4-fluoro-7-methyl-1H-indole-2-carboxamide |
| 1182 | N-((1R,3S)-3-((3aR,6aR)-1-acetylhexahydropyrrolo[3,4-b]pyrrol-5(1H)-yl)cyclohexyl)-4-fluoro-7-methyl-1H-indole-2-carboxamide |
| 1183 | N-((1R,3R)-3-((3aR,6aR)-1-acetylhexahydropyrrolo[3,4-b]pyrrol-5(1H)-yl)cyclohexyl)-4-fluoro-7-methyl-1H-indole-2-carboxamide |
| 1184 | N-((1R,3S)-3-((3aS,6aS)-4-acetylhexahydropyrrolo[3,2-b]pyrrol-1(2H)-yl)cyclohexyl)-4-fluoro-7-methyl-1H-indole-2-carboxamide |
| 1185 | N-((1R,3S)-3-((3aR,6aR)-4-acetylhexahydropyrrolo[3,2-b]pyrrol-1(2H)-yl)cyclohexyl)-4-fluoro-7-methyl-1H-indole-2-carboxamide |
| 1186 | N-((1R,3R)-3-((3aS,6aS)-4-acetylhexahydropyrrolo[3,2-b]pyrrol-1(2H)-yl)cyclohexyl)-4-fluoro-7-methyl-1H-indole-2-carboxamide |
| 1187 | N-((1R,3R)-3-((3aR,6aR)-4-acetylhexahydropyrrolo[3,2-b]pyrrol-1(2H)-yl)cyclohexyl)-4-fluoro-7-methyl-1H-indole-2-carboxamide |
| 1188 | 4-fluoro-7-methyl-N-((1S,3R)-3-(6-oxo-1,4,5,6-tetrahydro-1,2,4-triazin-3-yl)cyclohexyl)-1H-indole-2-carboxamide |
| 1189 | 4-fluoro-7-methyl-N-((1R,3S)-3-(3-(N-(oxetan-3-yl)acetamido)pyrrolidin-1-yl)cyclohexyl)-1H-indole-2-carboxamide |
| 1190 | 4-fluoro-7-methyl-N-((1R,3S)-3-(3-oxo-2,8-diazaspiro[4.5]decan-8-yl)cyclohexyl)-1H-indole-2-carboxamide |
| 1191 | 4-fluoro-7-methyl-N-(1'-methyl-2'-oxo-[1,4'-bipiperidin]-3-yl)-1H-indole-2-carboxamide |
| 1192 | N-((1R,3S)-3-((3R,5R)-4-acetyl-3,5-dimethylpiperazin-1-yl)cyclohexyl)-4-fluoro-7-methyl-1H-indole-2-carboxamide |
| 1193 | N-((1R,3R)-3-((3R,5R)-4-acetyl-3,5-dimethylpiperazin-1-yl)cyclohexyl)-4-fluoro-7-methyl-1H-indole-2-carboxamide |
| 1194 | (R)-4-fluoro-N-(3-fluoro-5-(3-(N-methylacetamido)pyrrolidin-1-yl)phenyl)-7-methyl-1H-indole-2-carboxamide |
| 1195 | (S)-4-fluoro-N-(3-fluoro-5-(3-(N-methylacetamido)pyrrolidin-1-yl)phenyl)-7-methyl-1H-indole-2-carboxamide |
| 1196 | 4-fluoro-N-(3-fluoro-5-((S)-3-((R)-2-methyl-3-oxohexahydroimidazo[1,5-a]pyrazin-7(1H)-yl)pyrrolidin-1-yl)phenyl)-7-methyl-1H-indole-2-carboxamide |
| 1197 | 4-fluoro-N-(3-fluoro-5-((S)-3-((S)-2-methyl-3-oxohexahydroimidazo[1,5-a]pyrazin-7(1H)-yl)pyrrolidin-1-yl)phenyl)-7-methyl-1H-indole-2-carboxamide |
| 1198 | 4-fluoro-N-(3-fluoro-5-((R)-3-((S)-2-methyl-3-oxohexahydroimidazo[1,5-a]pyrazin-7(1H)-yl)pyrrolidin-1-yl)phenyl)-7-methyl-1H-indole-2-carboxamide |
| 1199 | 4-fluoro-N-(3-fluoro-5-((R)-3-((R)-2-methyl-3-oxohexahydroimidazo[1,5-a]pyrazin-7(1H)-yl)pyrrolidin-1-yl)phenyl)-7-methyl-1H-indole-2-carboxamide |
| 1200 | (R)-N-(3-(3-(dimethylamino)-2-oxopyrrolidin-1-yl)-5-fluorophenyl)-4-fluoro-7-methyl-1H-indole-2-carboxamide |
| 1201 | (S)-N-(3-(3-(dimethylamino)-2-oxopyrrolidin-1-yl)-5-fluorophenyl)-4-fluoro-7-methyl-1H-indole-2-carboxamide |
| 1202 | (R)-N-(3-(3-(4-(2-(dimethylamino)-2-oxoethyl)piperazin-1-yl)pyrrolidin-1-yl)-5-fluorophenyl)-4-fluoro-7-methyl-1H-indole-2-carboxamide |
| 1203 | (R)-N-(3-(3-(4-(2-(dimethylamino)-2-oxoethyl)piperazin-1-yl)pyrrolidin-1-yl)-5-fluorophenyl)-4-fluoro-7-methyl-1H-indole-2-carboxamide |
| 1204 | (S)-N-(3-(3-(4-(2-amino-2-oxoethyl)piperazin-1-yl)pyrrolidin-1-yl)-5-fluorophenyl)-4-fluoro-7-methyl-1H-indole-2-carboxamide |
| 1205 | (R)-N-(3-(3-(4-(2-amino-2-oxoethyl)piperazin-1-yl)pyrrolidin-1-yl)-5-fluorophenyl)-4-fluoro-7-methyl-1H-indole-2-carboxamide |
| 1206 | (S)-N-(3-(3-(1,1-dioxidothiomorpholino)pyrrolidin-1-yl)-5-fluorophenyl)-4-fluoro-7-methyl-1H-indole-2-carboxamide |

TABLE 1-continued

| Cpd. No. | Chemical Name |
|---|---|
| 1207 | (R)-N-(3-(3-(1,1-dioxidothiomorpholino)pyrrolidin-1-yl)-5-fluorophenyl)-4-fluoro-7-methyl-1H-indole-2-carboxamide |
| 1208 | (R)-N-(3-(3-(4-acetylpiperazin-1-yl)pyrrolidin-1-yl)-5-fluorophenyl)-4-fluoro-7-methyl-1H-indole-2-carboxamide |
| 1209 | (S)-N-(3-(3-(4-acetylpiperazin-1-yl)pyrrolidin-1-yl)-5-fluorophenyl)-4-fluoro-7-methyl-1H-indole-2-carboxamide |
| 1210 | (S)-4-fluoro-N-(3-fluoro-5-(3-morpholinopyrrolidin-1-yl)phenyl)-7-methyl-1H-indole-2-carboxamide |
| 1211 | (R)-4-fluoro-N-(3-fluoro-5-(3-morpholinopyrrolidin-1-yl)phenyl)-7-methyl-1H-indole-2-carboxamide |
| 1212 | N-(3-((3aR,6aR)-4-acetylhexahydropyrrolo[3,2-b]pyrrol-1(2H)-yl)-5-fluorophenyl)-4-fluoro-7-methyl-1H-indole-2-carboxamide |
| 1213 | N-(3-((3aR,6aS)-4-acetylhexahydropyrrolo[3,2-b]pyrrol-1(2H)-yl)-5-fluorophenyl)-4-fluoro-7-methyl-1H-indole-2-carboxamide |
| 1214 | N-(3-((3aS,6aS)-4-acetylhexahydropyrrolo[3,2-b]pyrrol-1(2H)-yl)-5-fluorophenyl)-4-fluoro-7-methyl-1H-indole-2-carboxamide |
| 1215 | N-(3-((3aS,6aR)-4-acetylhexahydropyrrolo[3,2-b]pyrrol-1(2H)-yl)-5-fluorophenyl)-4-fluoro-7-methyl-1H-indole-2-carboxamide |
| 1216 | N-(3-((3aR,6aR)-1-acetylhexahydropyrrolo[3,4-b]pyrrol-5(1H)-yl)-5-fluorophenyl)-4-fluoro-7-methyl-1H-indole-2-carboxamide |
| 1217 | N-(3-((3aS,6aR)-1-acetylhexahydropyrrolo[3,4-b]pyrrol-5(1H)-yl)-5-fluorophenyl)-4-fluoro-7-methyl-1H-indole-2-carboxamide |
| 1218 | N-(3-((3aS,6aS)-1-acetylhexahydropyrrolo[3,4-b]pyrrol-5(1H)-yl)-5-fluorophenyl)-4-fluoro-7-methyl-1H-indole-2-carboxamide |
| 1219 | N-(3-((3aR,6aS)-1-acetylhexahydropyrrolo[3,4-b]pyrrol-5(1H)-yl)-5-fluorophenyl)-4-fluoro-7-methyl-1H-indole-2-carboxamide |
| 1220 | 4-fluoro-N-(3-fluoro-5-((S)-3-((S)-2-(hydroxymethyl)morpholino)pyrrolidin-1-yl)phenyl)-7-methyl-1H-indole-2-carboxamide |
| 1221 | 4-fluoro-N-(3-fluoro-5-((S)-3-((R)-2-(hydroxymethyl)morpholino)pyrrolidin-1-yl)phenyl)-7-methyl-1H-indole-2-carboxamide |
| 1222 | 4-fluoro-N-(3-fluoro-5-((R)-3-((R)-2-(hydroxymethyl)morpholino)pyrrolidin-1-yl)phenyl)-7-methyl-1H-indole-2-carboxamide |
| 1223 | 4-fluoro-N-(3-fluoro-5-((R)-3-((S)-2-(hydroxymethyl)morpholino)pyrrolidin-1-yl)phenyl)-7-methyl-1H-indole-2-carboxamide |
| 1224 | (R)-4-fluoro-N-(3-fluoro-5-(3-(4-methyl-3-oxopiperazin-1-yl)pyrrolidin-1-yl)phenyl)-7-methyl-1H-indole-2-carboxamide |
| 1225 | (S)-4-fluoro-N-(3-fluoro-5-(3-(4-methyl-3-oxopiperazin-1-yl)pyrrolidin-1-yl)phenyl)-7-methyl-1H-indole-2-carboxamide |
| 1226 | (S)-4-fluoro-N-(3-fluoro-5-(2-oxo-[1,3'-bipyrrolidin]-1'-yl)phenyl)-7-methyl-1H-indole-2-carboxamide |
| 1227 | (R)-4-fluoro-N-(3-fluoro-5-(2-oxo-[1,3'-bipyrrolidin]-1'-yl)phenyl)-7-methyl-1H-indole-2-carboxamide |
| 1228 | 4-fluoro-7-methyl-N-((1R,3S)-3-((3aS,6aS)-1-methyl-2-oxohexahydropyrrolo[3,4-b]pyrrol-5(1H)-yl)cyclohexyl)-1H-indole-2-carboxamide |
| 1229 | 4-fluoro-7-methyl-N-((1R,3R)-3-((3aS,6aS)-1-methyl-2-oxohexahydropyrrolo[3,4-b]pyrrol-5(1H)-yl)cyclohexyl)-1H-indole-2-carboxamide |
| 1230 | 4-fluoro-7-methyl-N-((1R,3S)-3-((3aR,6aR)-1-methyl-2-oxohexahydropyrrolo[3,4-b]pyrrol-5(1H)-yl)cyclohexyl)-1H-indole-2-carboxamide |
| 1231 | 4-fluoro-7-methyl-N-((1R,3R)-3-((3aR,6aR)-1-methyl-2-oxohexahydropyrrolo[3,4-b]pyrrol-5(1H)-yl)cyclohexyl)-1H-indole-2-carboxamide |
| 1232 | 4-fluoro-7-methyl-N-((1R,3S)-3-((3aS,6aS)-4-methyl-5-oxohexahydropyrrolo[3,2-b]pyrrol-1(2H)-yl)cyclohexyl)-1H-indole-2-carboxamide |
| 1233 | 4-fluoro-7-methyl-N-((1R,3S)-3-((3aR,6aR)-4-methyl-5-oxohexahydropyrrolo[3,2-b]pyrrol-1(2H)-yl)cyclohexyl)-1H-indole-2-carboxamide |
| 1234 | 4-fluoro-7-methyl-N-((1R,3R)-3-((3aS,6aS)-4-methyl-5-oxohexahydropyrrolo[3,2-b]pyrrol-1(2H)-yl)cyclohexyl)-1H-indole-2-carboxamide |
| 1235 | 4-fluoro-7-methyl-N-((1R,3R)-3-((3aR,6aR)-4-methyl-5-oxohexahydropyrrolo[3,2-b]pyrrol-1(2H)-yl)cyclohexyl)-1H-indole-2-carboxamide |

TABLE 1B
| Cpd. No. | STRUCTURE | SETD2 (1434-1711) | SETD2 A549 |
| --- | --- | --- | --- |
| 15 | 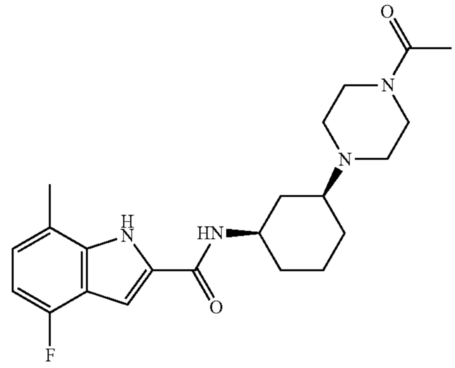 [SMILES: CC(=O)N1CCN([C@H]2CCC[C@@H](NC(=O)c3cc4c(F)ccc(C)c4[nH]3)C2)CC1] | 0.02 | 0.05 |
| 1228 | 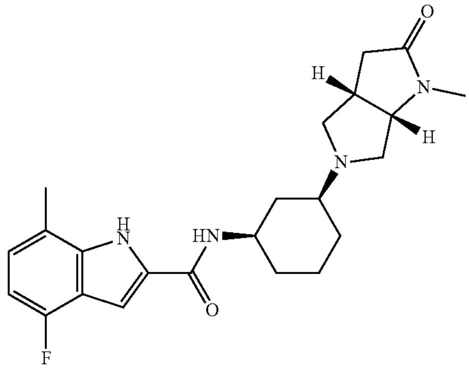 [SMILES: Cc1ccc(F)c2cc(C(=O)N[C@@H]3CCC[C@H](N4C[C@@H]5CC(=O)N(C)[C@@H]5C4)C3)[nH]c12] | 0.04 | 0.09 |
| 1229 | 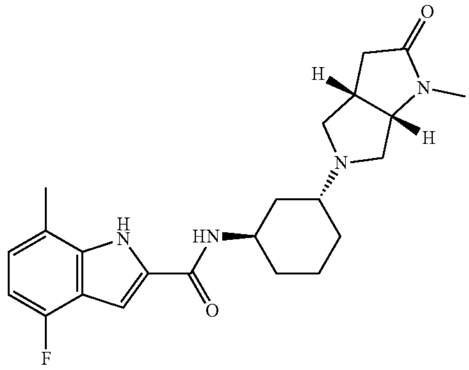 [SMILES: Cc1ccc(F)c2cc(C(=O)N[C@@H]3CCC[C@@H](N4C[C@@H]5CC(=O)N(C)[C@@H]5C4)C3)[nH]c12] | 8.8 | 2 |
| 1230 | 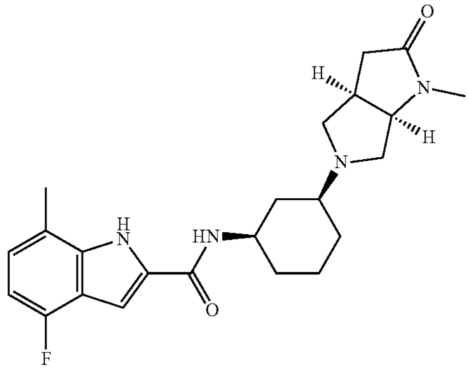 [SMILES: Cc1ccc(F)c2cc(C(=O)N[C@@H]3CCC[C@H](N4C[C@H]5CC(=O)N(C)[C@H]5C4)C3)[nH]c12] | 0.04 | 0.09 |

TABLE 1B-continued
| Cpd. No. | STRUCTURE | SETD2 (1434-1711) | SETD2 A549 |
| --- | --- | --- | --- |
| 1231 | 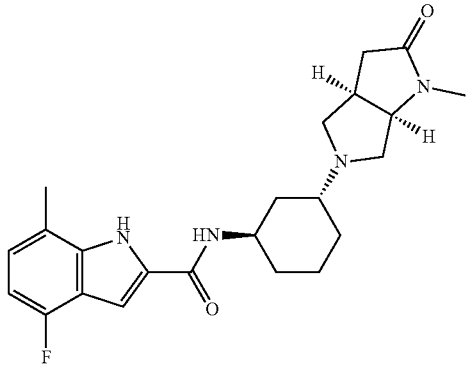 [SMILES: Cc1ccc(F)c2cc(C(=O)N[C@@H]3CCC[C@@H](N4C[C@H]5CC(=O)N(C)[C@H]5C4)C3)[nH]c12] | 9.8 | 2 |
| 1232 | 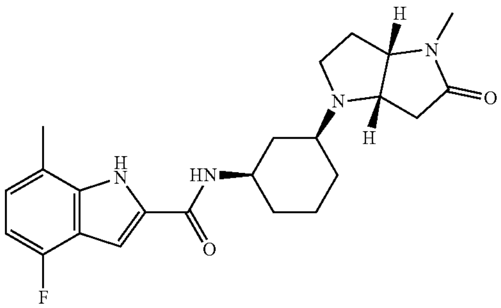 [SMILES: Cc1ccc(F)c2cc(C(=O)N[C@@H]3CCC[C@H](N4CC[C@H]5[C@@H]4CC(=O)N5C)C3)[nH]c12] | 0.008 | 0.01 |
| 1233 | 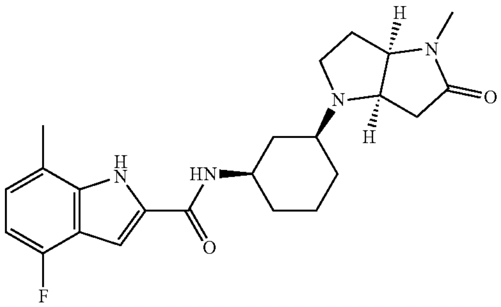 [SMILES: Cc1ccc(F)c2cc(C(=O)N[C@@H]3CCC[C@H](N4CC[C@@H]5[C@H]4CC(=O)N5C)C3)[nH]c12] | 0.04 | 0.04 |
| 1234 | 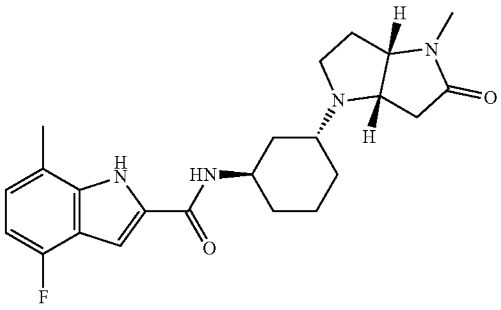 [SMILES: Cc1ccc(F)c2cc(C(=O)N[C@@H]3CCC[C@@H](N4CC[C@H]5[C@@H]4CC(=O)N5C)C3)[nH]c12] | 4.2 | 2 |

TABLE 1B-continued

| Cpd. No. | STRUCTURE | SETD2 (1434-1711) | SETD2 A549 |
|---|---|---|---|
| 1235 | 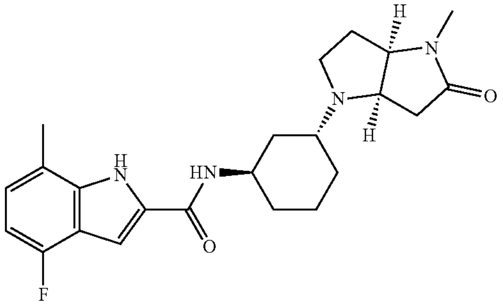 [SMILES: Cc1ccc(F)c2cc(C(=O)N[C@@H]3CCC[C@@H](N4CC[C@@H]5[C@H]4CC(=O)N5C)C3)[nH]c12] | 10 | 2 |

The present disclosure encompasses the preparation and use of salts of the Compounds of the Disclosure, including non-toxic pharmaceutically acceptable salts. Examples of pharmaceutically acceptable addition salts include inorganic and organic acid addition salts and basic salts. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, asparginate, glutamate and the like. The term "pharmaceutically acceptable salt" as used herein, refers to any salt, e.g., obtained by reaction with an acid or a base, of a Compound of the Disclosure that is physiologically tolerated in the target subject (e.g., a mammal, e.g., a human).

Acid addition salts can be formed by mixing a solution of the particular Compound of the Disclosure with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, or the like. Basic salts can be formed by mixing a solution of the compound of the present disclosure with a solution of a pharmaceutically acceptable non-toxic base such as sodium hydroxide, potassium hydroxide, choline hydroxide, sodium carbonate and the like.

The present disclosure encompasses the preparation and use of solvates of Compounds of the Disclosure. Solvates typically do not significantly alter the physiological activity or toxicity of the compounds, and as such may function as pharmacological equivalents. The term "solvate" as used herein is a combination, physical association and/or solvation of a compound of the present disclosure with a solvent molecule such as, e.g. a disolvate, monosolvate or hemisolvate, where the ratio of solvent molecule to compound of the present disclosure is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of the Disclosure can be present as solvated forms with a pharmaceutically acceptable solvent, such as water, methanol, ethanol, and the like, and it is intended that the disclosure includes both solvated and unsolvated forms of Compounds of the Disclosure. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al, *J. Pharmaceut. Sci.,* 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.,* 5(1):Article 12 (2004), and A. L. Bingham et al., *Chem. Commun.* 603-604 (2001). A typical, non-limiting, process of preparing a solvate would involve dissolving a Compound of the Disclosure in a desired solvent (organic, water, or a mixture thereof) at temperatures above 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

II. Second Therapeutic Agents

In some embodiments, the therapeutic methods of the present disclosure comprise administering a therapeutically effective amount of a Compound of the Disclosure in combination with a therapeutically effective amount of a Second Therapeutic Agent.

The term "Second Therapeutic Agent" as used herein comprises one or more glucocorticoid receptor agonists, one or more immunomodulatory drugs, one or more proteasome inhibitors, one or more Bcl-2 inhibitors, one or more pleiotropic pathway modulators, one or more XPO1 inhibitors, one or more histone deacetylase inhibitors, or one or more EZH2 inhibitors, or a combination thereof. In one embodiment, the Second Therapeutic Agent comprises one compound from one drug class, i.e., one glucocorticoid receptor agonist, one immunomodulatory drug, one proteasome inhibitor, one Bcl-2 inhibitor, one pleiotropic pathway modulator, one XPO1 inhibitor, one histone deacetylase inhibitor, or one EZH2 inhibitor. In another embodiment, the Second Therapeutic Agent comprises two different compounds from one drug class, e.g., two different glucocorticoid receptor agonists, e.g., dexamethasone and prednisone, two different immunomodulatory drugs, two different proteasome inhibitors, two different Bcl-2 inhibitors, two different pleiotropic pathway modulators, two different XPO1 inhibitors, two different histone deacetylase inhibitors, or two different EZH2 inhibitors. In another embodiment, the Second Therapeutic Agent comprises three different compounds from one drug class, e.g., three different glucocorticoid receptor agonists, e.g., dexamethasone, prednisone, and methylprednisolone, three different immunomodulatory drugs, three different proteasome inhibitors, three different Bcl-2 inhibitors, three different pleiotropic pathway modulators, three different XPO1 inhibitors, three different histone deacetylase inhibitors, or three different EZH2 inhibitors. In another embodiment, the Second Therapeutic Agent comprises three different compounds from two drug classes, e.g., two different glucocorticoid receptor agonists, e.g., dexamethasone and prednisone, and one immunomodulatory drug; two different glucocorticoid receptor agonists and one proteasome inhibitor; and so on.

In another embodiment, the Second Therapeutic Agent comprises compounds from different drug classes, for example, a first compound from a first drug class and second compound from a second drug class, wherein the first drug class and the second drug class are different. As a specific non-limiting example, the Second Therapeutic agent comprises an EZH2 inhibitor, e.g., tazemetostat, and an immunomodulatory drug, e.g., lenoliminide. Non-limiting examples of combinations of drug classes are provide in the following table:

| No. | Drug Class # 1 | Drug Class # 2 |
|---|---|---|
| 1 | GR agonist | IMiD |
| 2 | GR agonist | Proteasome inhibitor |
| 3 | GR agonist | Bcl-2 inhibitor |
| 4 | GR agonist | Pleiotropic pathway modulator |
| 5 | GR agonist | XPO1 inhibitor |
| 6 | GR agonist | HD inhibitor |
| 7 | GR agonist | EZH2 inhibitor |
| 8 | IMiD | Proteasome inhibitor |
| 9 | IMiD | Bcl-2 inhibitor |
| 10 | IMiD | Pleiotropic pathway modulator |
| 11 | IMiD | XPO1 inhibitor |
| 12 | IMiD | HD inhibitor |
| 13 | IMiD | EZH2 inhibitor |
| 14 | Proteasome inhibitor | Bcl-2 inhibitor |
| 15 | Proteasome inhibitor | Pleiotropic pathway modulator |
| 16 | Proteasome inhibitor | XPO1 inhibitor |
| 17 | Proteasome inhibitor | HD inhibitor |
| 18 | Proteasome inhibitor | EZH2 inhibitor |
| 19 | Bcl-2 inhibitor | Pleiotropic pathway modulator |
| 20 | Bcl-2 inhibitor | XPO1 inhibitor |
| 21 | Bcl-2 inhibitor | HD inhibitor |
| 22 | Bcl-2 inhibitor | EZH2 inhibitor |
| 23 | Pleiotropic pathway modulator | XPO1 inhibitor |
| 24 | Pleiotropic pathway modulator | HD inhibitor |
| 25 | Pleiotropic pathway modulator | EZH2 inhibitor |
| 26 | XPO1 inhibitor | HD inhibitor |
| 27 | XPO1 inhibitor | EZH2 inhibitor |
| 28 | HD inhibitor | EZH2 inhibitor |

In another embodiment, the Second Therapeutic Agent comprises three compounds from three different drug classes. For example, in one embodiment, the Second Therapeutic Agent comprises a first compound from a first drug class, and a second compound from a second drug class, and a third compound from a third drug class, wherein the first drug class, the second drug class, and the third drug class are different. Non-limiting examples of combinations of drug classes are provide in the following table:

| No. | Drug Class # 1 | Drug Class # 2 | Drug Class # 3 |
|---|---|---|---|
| 1 | GR agonist | IMiD | Proteasome inhibitor |
| 2 | GR agonist | IMiD | Bcl-2 inhibitor |
| 3 | GR agonist | IMiD | Pleiotropic pathway modulator |
| 4 | GR agonist | IMiD | XPO1 inhibitor |
| 5 | GR agonist | IMiD | HD inhibitor |
| 6 | GR agonist | IMiD | EZH2 inhibitor |
| 7 | GR agonist | Proteasome inhibitor | Bcl-2 inhibitor |
| 8 | GR agonist | Proteasome inhibitor | Pleiotropic pathway modulator |
| 9 | GR agonist | Proteasome inhibitor | XPO1 inhibitor |
| 10 | GR agonist | Proteasome inhibitor | HD inhibitor |
| 11 | GR agonist | Proteasome inhibitor | EZH2 inhibitor |
| 12 | GR agonist | Bcl-2 inhibitor | Pleiotropic pathway modulator |
| 13 | GR agonist | Bcl-2 inhibitor | XPO1 inhibitor |
| 14 | GR agonist | Bcl-2 inhibitor | HD inhibitor |
| 15 | GR agonist | Bcl-2 inhibitor | EZH2 inhibitor |
| 16 | GR agonist | Pleiotropic pathway modulator | XPO1 inhibitor |
| 17 | GR agonist | Pleiotropic pathway modulator | HD inhibitor |
| 18 | GR agonist | Pleiotropic pathway modulator | EZH2 inhibitor |
| 19 | GR agonist | XPO1 inhibitor | HD inhibitor |
| 20 | GR agonist | XPO1 inhibitor | EZH2 inhibitor |
| 21 | GR agonist | HD inhibitor | EZH2 inhibitor |
| 22 | IMiD | Proteasome inhibitor | Bcl-2 inhibitor |
| 23 | IMiD | Proteasome inhibitor | Pleiotropic pathway modulator |
| 24 | IMiD | Proteasome inhibitor | XPO1 inhibitor |
| 25 | IMiD | Proteasome inhibitor | HD inhibitor |
| 26 | IMiD | Proteasome inhibitor | EZH2 inhibitor |
| 27 | IMiD | Bcl-2 inhibitor | Pleiotropic pathway modulator |
| 28 | IMiD | Bcl-2 inhibitor | XPO1 inhibitor |
| 29 | IMiD | Bcl-2 inhibitor | HD inhibitor |
| 30 | IMiD | Bcl-2 inhibitor | EZH2 inhibitor |
| 31 | IMiD | Pleiotropic pathway modulator | XPO1 inhibitor |
| 32 | IMiD | Pleiotropic pathway modulator | HD inhibitor |
| 33 | IMiD | Pleiotropic pathway modulator | EZH2 inhibitor |
| 34 | IMiD | XPO1 inhibitor | HD inhibitor |
| 35 | IMiD | XPO1 inhibitor | EZH2 inhibitor |
| 36 | IMiD | HD inhibitor | EZH2 inhibitor |
| 37 | Proteasome inhibitor | Bcl-2 inhibitor | Pleiotropic pathway modulator |
| 38 | Proteasome inhibitor | Bcl-2 inhibitor | XPO1 inhibitor |
| 39 | Proteasome inhibitor | Bcl-2 inhibitor | HD inhibitor |
| 40 | Proteasome inhibitor | Bcl-2 inhibitor | EZH2 inhibitor |
| 41 | Proteasome inhibitor | Pleiotropic pathway modulator | XPO1 inhibitor |
| 42 | Proteasome inhibitor | Pleiotropic pathway modulator | HD inhibitor |
| 43 | Proteasome inhibitor | Pleiotropic pathway modulator | EZH2 inhibitor |
| 44 | Proteasome inhibitor | XPO1 inhibitor | HD inhibitor |
| 45 | Proteasome inhibitor | XPO1 inhibitor | EZH2 inhibitor |
| 46 | Proteasome inhibitor | HD inhibitor | EZH2 inhibitor |
| 47 | Bcl-2 inhibitor | Pleiotropic pathway modulator | XPO1 inhibitor |
| 48 | Bcl-2 inhibitor | Pleiotropic pathway modulator | HD inhibitor |
| 49 | Bcl-2 inhibitor | Pleiotropic pathway modulator | EZH2 inhibitor |
| 50 | Bcl-2 inhibitor | XPO1 inhibitor | HD inhibitor |
| 51 | Bcl-2 inhibitor | XPO1 inhibitor | EZH2 inhibitor |
| 52 | Bcl-2 inhibitor | HD inhibitor | EZH2 inhibitor |
| 53 | Pleiotropic pathway modulator | XPO1 inhibitor | HD inhibitor |
| 54 | Pleiotropic pathway modulator | XPO1 inhibitor | EZH2 inhibitor |
| 55 | Pleiotropic pathway modulator | HD inhibitor | EZH2 inhibitor |
| 56 | XPO1 inhibitor | HD inhibitor | EZH2 inhibitor |

The term "glucocorticoid receptor agonist" or "GR agonist" as used herein refers to a compound that activates the glucocorticoid receptor. Glucocorticoid receptor agonists and methods of administering glucocorticoid receptor agonists to a subject are known in the art. See, e.g., Pufall, M. A., *Adv Exp Med Biol.* 872:315-333 (2015). Exemplary glucocorticoid receptor agonists include, but are not limited to, dexamethasone, hydrocortisone, corticosterone, prednisolone, methylprednisolone, prednisone, triamcinolone, mapracorat, ciclesonide, and (20S)-protopanaxatriol. In one embodiment, the glucocorticoid receptor agonist is prednisone. In another embodiment, the glucocorticoid receptor agonist is dexamethasone.

The term "immunomodulatory drug" or "IMiD" as used herein refers to a compound that inhibits the production of tumour necrosis factor, interleukin 6, immunoglobulin G, and/or VEGF, andand/or co-stimulates T cells and NK cells, and/or increases interferon gamma and interleukin 2 production. Immunomodulatory drugs and methods of administering immunomodulatory drugs to a subject are known in the art. Exemplary immunomodulatory drugs include, but art not limited to, thalidomide, lenalidomide, and pomalidomide. In one embodiment, the immunomodulatory drug is pomalidomide.

The term "proteasome inhibitor" as used herein refers to a compound that blocks the action of proteasomes and thus prevents the degredation of pro-apoptotic factors such as p53 protein. Proteasome inhibitors and methods of administering proteasome inhibitors to a subject are known in the art. Exemplary proteasome inhibitors include, but art not limited to, bortezomib, carfilzomib, and ixazomib. In one embodiment, the proteasome inhibitor inhibitor is bortezomib.

The term "Bcl-2 inhibitor" as used herein refers to a compound that inhibits the anti-apoptotic Bcl-2 protein. Bcl-2 inhibitors and methods of administering Bcl-2 inhibitors to a subject are known in the art. Examplary Bcl-2 inhibitors include but are not limited to, navitoclax (ABT-263), ABT-737, Sabutoclax, AT-1019 (Gossypol), TW-37, venetoclax (ABT-199), obatoclax, HA14-1, A-1155463, A-1331852, and WEHI-539. In one embodiment, the Bcl-2 inhibitor is venetoclax.

The term "pleiotropic pathway modulator" as used herein refers to compound that binds to cereblon to promote protein degredation. Pleiotropic pathway modulators and methods of administering pleiotropic pathway modulators to a subject are known in the art are known in the art. See, e.g., Hagner et al., *Blood* 126:779-789 (2017). A non-limiting exemplary pleiotropic pathway modulator is CC-122.

The term "XPO1 inhibitor" as used herein refers to an inhibitor of exportin-1 (also known as chromosome region maintenance 1 protein homolog; CRM1). XPO1 inhibitors and methods of administering XPO1 inhibitors to a subject are known in the art. See, e.g., Wang and Liu, *Stem Cell Invest* 6:6 (2019). A non-limiting exemplary XPO1 inhibitor is selinexor.

The term "histone deacetylase inhibitor" or "HD inhibitor" as used herein refers to a compound that inhibit histone deactylase enzymes. Histone deacetylase inhibitors and methods of administering histone deacetylase inhibitors to a subject are known in the art. See, e.g., Eckschlager et al., *Int. J. Mol. Sci.* 18:1414 (2017) doi: 10.3390/ijms18071414. Exemplary histone deacetylase inhibitors include, but are not limited to, romidepsin, belinostat, panobinostat, and vorinostate. In one embodiment, the histone deacetylase inhibitor is panobinostat.

The term "EZH2 inhibitor" as used herein refers to a compound that inhibits the enhancer of zeste homolog 2 enzyme. EZH2 inhibitors and methods of administering EZH2 inhibitors to a subject are known in the art. See, e.g., Lue and Amengual, *Curr Hematol Malig Rep* 13:369-382 (2018). Exemplary EZH2 inhibitors include, but are not limited to, tazemetostat, EPZ011989, EPZ005687, GSK126, PF-06821497, and valemetostat. In one embodiment, the EZH2 inhibitor is tazemetostat.

The disclosure provides the following particular embodiments relating to combination therapy (CT):

CT Embodiment I. A method of treating a subject in need thereof, the method comprising administering to the subject: (a) a therapeutically effective amount of a Compound of the Disclosure; and (b) a therapeutically effective amount of a Second Therapeutic Agent, wherein the Second Therapeutic Agent comprises a glucocorticoid receptor agonist, an immunomodulatory drug, a proteasome inhibitor, a Bcl-2 inhibitor, a pleiotropic pathway modulator, a XPO1 inhibitor, a histone deacetylase inhibitor, or an EZH2 inhibitor, or a combination thereof; and the subject has cancer.

CT Embodiment II. The method of CT Embodiment I, wherein the Second Therapeutic Agent comprises a glucocorticoid receptor agonist.

CT Embodiment III. The method of CT Embodiment II, wherein the glucocorticoid receptor agonist is dexamethasone.

CT Embodiment IV. The method of any one of CT Embodiments I-III, wherein the Second Therapeutic Agent comprises an immunomodulatory drug.

CT Embodiment V. The method of CT Embodiment IV, wherein the immunomodulatory drug is pomalidomide or lenalidomide.

CT Embodiment VI. The method of any one of CT Embodiments I-V, wherein the Second Therapeutic Agent comprises a proteasome inhibitor.

CT Embodiment VII. The method of CT Embodiment VI, wherein the proteasome inhibitor is bortezomib.

CT Embodiment VIII. The method of any one of CT Embodiment I-VII, wherein the Second Therapeutic Agent comprises a Bcl-2 inhibitor.

CT Embodiment IX. The method of CT Embodiment VIII, wherein the Bcl-2 inhibitor is venetoclax.

CT Embodiment X. The method of any one of CT Embodiments I-IX, wherein the Second Therapeutic Agent comprises a pleiotropic pathway modulator.

CT Embodiment XI. The method of CT Embodiment X, wherein the pleiotropic pathway modulator is CC-122.

CT Embodiment XII. The method of any one of CT Embodiments I-XI, wherein the Second Therapeutic Agent comprises a XPO1 inhibitor.

CT Embodiment XIII. The method of CT Embodiment XII, wherein the XPO1 inhibitor is selinexor CT Embodiment XIV.The method of any one of CT Embodiments I-XIII, wherein the Second Therapeutic Agent comprises a histone deacetylase inhibitor.

CT Embodiment XV. The method of CT Embodiment XIV, wherein the histone deacetylase inhibitor is panobinostat.

CT Embodiment XVI. The method of any one of CT Embodiments I-XV, wherein the Second Therapeutic Agent is an EZH2 inhibitor.

CT Embodiment XVII. The method of CT Embodiment XVI, wherein the EZH2 inhibitor is tazemetostat.

III. Therapeutic Methods

The present disclosure is directed generally to a method for treating a disease, condition, or disorder in a subject suffering from, or at risk of suffering from, the disease, condition, or disorder, the method comprising administering to the subject an effective amount of a Compound of the Disclosure and, optionally, a Second Therapeutic Agent. In one embodiment, the disease, condition, or disorder is responsive to or mediated by the inhibition of SETD2 protein by a Compound of the Disclosure.

In the therapeutic methods provided herein, a Compound of the Disclosure can be administered to a subject having cancer as a single agent. A Compound of the Disclosure can also be administered to a subject having cancer in combination with a Second Therapeutic Agent. A Compound of the Disclosure and the Second Therapeutic Agent can be administered in combination under one or more of the following conditions: as separate pharmaceutical compositions, at different periodicities, e.g., simultaneously or sequentially, at different durations, at different concentrations, by different administration routes, etc. Additional optional therapeutic, e.g., anticancer, agents may also be administered to the cancer patient.

The present disclosure is also directed to a method of inhibiting SETD2 protein in subject in need thereof, the method comprising administering to the subject a therapeutically effective amount of a Compound of the Disclosure.

In one aspect, the present disclosure provides a method of treating a disease, disorder, or condition in a subject comprising administering a therapeutically effective amount of a Compound of the Disclosure.

In another aspect, the present disclosure provides a method of treating a disease, disorder, or condition in a subject comprising administering a therapeutically effective amount of a Compound of the Disclosure in combination with a Second Therapeutic Agent.

In another aspect, the present disclosure provides a method of treating cancer in a subject comprising administering a therapeutically effective amount of a Compound of the Disclosure. In another aspect, the present disclosure provides a method of treating cancer in a subject comprising administering a therapeutically effective amount of a Compound of the Disclosure in combination with a Second Therapeutic Agent. While not being limited to a specific mechanism, in some embodiments, Compounds of the Disclosure treat cancer by inhibiting SETD2 protein. Examples of treatable cancers include, but are not limited to, the cancers listed in Table 2.

TABLE 2

| | |
|---|---|
| adrenal cancer | lymphoepithelioma |
| acinic cell carcinoma | lymphoma |
| acoustic neuroma | acute lymphocytic leukemia |
| acral lentigious melanoma | acute myelogeous leukemia |
| acrospiroma | chronic lymphocytic leukemia |
| acute eosinophilic leukemia | liver cancer |
| acute erythroid leukemia | small cell lung cancer |
| acute lymphoblastic leukemia | non-small cell lung cancer |
| acute megakaryoblastic leukemia | MALT lymphoma |
| acute monocytic leukemia | malignant fibrous histiocytoma |
| acute promyelocytic leukemia | malignant peripheral nerve sheath tumor |
| adenocarcinoma | malignant triton tumor |
| adenoid cystic carcinoma | mantle cell lymphoma |
| adenoma | marginal zone B-cell lymphoma |
| adenomatoid odontogenic tumor | mast cell leukemia |
| adenosquamous carcinoma | mediastinal germ cell tumor |
| adipose tissue neoplasm | medullary carcinoma of the breast |
| adrenocortical carcinoma | medullary thyroid cancer |
| adult T-cell leukemia/lymphoma | medulloblastoma |
| aggressive NK-cell leukemia | melanoma |
| AIDS-related lymphoma | meningioma |

TABLE 2-continued

| | |
|---|---|
| alveolar rhabdomyosarcoma | merkel cell cancer |
| alveolar soft part sarcoma | mesothelioma |
| ameloblastic fibroma | metastatic urothelial carcinoma |
| anaplastic large cell lymphoma | mixed Mullerian tumor |
| anaplastic thyroid cancer | mucinous tumor |
| angioimmunoblastic T-cell lymphoma | multiple myeloma |
| angiomyolipoma | muscle tissue neoplasm |
| angiosarcoma | mycosis fungoides |
| astrocytoma | myxoid liposarcoma |
| atypical teratoid rhabdoid tumor | myxoma |
| B-cell chronic lymphocytic leukemia | myxosarcoma |
| B-cell prolymphocytic leukemia | nasopharyngeal carcinoma |
| B-cell lymphoma | neurinoma |
| basal cell carcinoma | neuroblastoma |
| biliary tract cancer | neurofibroma |
| bladder cancer | neuroma |
| blastoma | nodular melanoma |
| bone cancer | ocular cancer |
| Brenner tumor | oligoastrocytoma |
| Brown tumor | oligodendroglioma |
| Burkitt's lymphoma | oncocytoma |
| breast cancer | optic nerve sheath meningioma |
| brain cancer | optic nerve tumor |
| carcinoma | oral cancer |
| carcinoma in situ | osteosarcoma |
| carcinosarcoma | ovarian cancer |
| cartilage tumor | Pancoast tumor |
| cementoma | papillary thyroid cancer |
| myeloid sarcoma | paraganglioma |
| chondroma | pinealoblastoma |
| chordoma | pineocytoma |
| choriocarcinoma | pituicytoma |
| choroid plexus papilloma | pituitary adenoma |
| clear-cell sarcoma of the kidney | pituitary tumor |
| craniopharyngioma | plasmacytoma |
| cutaneous T-cell lymphoma | polyembryoma |
| cervical cancer | precursor T-lymphoblastic lymphoma |
| colorectal cancer | primary central nervous system lymphoma |
| Degos disease | primary effusion lymphoma |
| desmoplastic small round cell tumor | preimary peritoneal cancer |
| diffuse large B-cell lymphoma | prostate cancer |
| dysembryoplastic neuroepithelial tumor | pancreatic cancer |
| dysgerminoma | pharyngeal cancer |
| embryonal carcinoma | pseudomyxoma periotonei |
| endocrine gland neoplasm | renal cell carcinoma |
| endodermal sinus tumor | renal medullary carcinoma |
| enteropathy-associated T-cell lymphoma | retinoblastoma |
| esophageal cancer | rhabdomyoma |
| fetus in fetu | rhabdomyosarcoma |
| fibroma | Richter's transformation |
| fibrosarcoma | rectal cancer |
| follicular lymphoma | sarcoma |
| follicular thyroid cancer | Schwannomatosis |
| ganglioneuroma | seminoma |
| gastrointestinal cancer | Sertoli cell tumor |
| germ cell tumor | sex cord-gonadal stromal tumor |
| gestational choriocarcinoma | signet ring cell carcinoma |
| giant cell fibroblastoma | skin cancer |
| giant cell tumor of the bone | small blue round cell tumors |
| glial tumor | small cell carcinoma |
| glioblastoma multiforme | soft tissue sarcoma |
| glioma | somatostatinoma |
| gliomatosis cerebri | soot wart |
| glucagonoma | spinal tumor |
| gonadoblastoma | splenic marginal zone lymphoma |
| granulosa cell tumor | squamous cell carcinoma |
| gynandroblastoma | synovial sarcoma |
| gallbladder cancer | Sezary's disease |
| gastric cancer | small intestine cancer |
| hairy cell leukemia | squamous carcinoma |
| hemangioblastoma | stomach cancer |
| head and neck cancer | T-cell lymphoma |
| hemangiopericytoma | testicular cancer |
| hematological malignancy | thecoma |

TABLE 2-continued

| | |
|---|---|
| hepatoblastoma | thyroid cancer |
| hepatosplenic T-cell lymphoma | transitional cell carcinoma |
| Hodgkin's lymphoma | throat cancer |
| non-Hodgkin's lymphoma | urachal cancer |
| invasive lobular carcinoma | urogenital cancer |
| intestinal cancer | urothelial carcinoma |
| kidney cancer | uveal melanoma |
| laryngeal cancer | uterine cancer |
| lentigo maligna | verrucous carcinoma |
| lethal midline carcinoma | visual pathway glioma |
| leukemia | vulvar cancer |
| leydig cell tumor | vaginal cancer |
| liposarcoma | Waldenstrom's macroglobulinemia |
| lung cancer | Warthin's tumor |
| lymphangioma | Wilms' tumor. |
| lymphangiosarcoma | |

In another embodiment, the cancer is pancreatic cancer or esophageal cancer.

In another embodiment, the cancer is selected from the group consisting of esophageal cancer, kidney cancer, stomach cancer, hepatocellular carcinoma, glioblastoma, central nervous system (CNS) cancer, soft tissue cancer, lung cancer, breast cancer, bladder/urinary tract cancer, head and neck cancer, prostate cancer, hematological cancer, pancreatic cancer, skin cancer, endometrial cancer, ovarian cancer, and colorectal cancer.

In another embodiment, the cancer or cancer cell is a hematological cancer. Exemplary hematological cancers include, but are not limited to, the cancers listed in Table 3.

TABLE 3

| | |
|---|---|
| acute lymphocytic leukemia (ALL) | acute eosinophilic leukemia |
| acute myeloid leukemia (AML) | acute erythroid leukemia |
| chronic lymphocytic leukemia (CLL) | acute lymphoblastic leukemia |
| small lymphocytic lymphoma (SLL) | acute megakaryoblastic leukemia |
| multiple myeloma (MM) | acute monocytic leukemia |
| Hodgkins lymphoma (HL) | acute promyelocytic leukemia |
| non-Hodgkin's lymphoma (NHL) | acute myelogeous leukemia |
| mantle cell lymphoma (MCL) | B-cell prolymphocytic leukemia |
| marginal zone B-cell lymphoma | B-cell lymphoma |
| splenic marginal zone lymphoma | MALT lymphoma |
| follicular lymphoma (FL) | precursor T-lymphoblastic lymphoma |
| Waldenstrom's macroglobulinemia (WM) | T-cell lymphoma |
| diffuse large B-cell lymphoma (DLBCL) | mast cell leukemia |
| marginal zone lymphoma (MZL) | adult T cell leukemia/lymphoma |
| hairy cell leukemia (HCL) | aggressive NK-cell leukemia |
| Burkitt's lymphoma (BL) | angioimmunoblastic T-cell lymphoma |
| Richter's transformation | |

In another embodiment, the cancer is multiple myeloma.

In another embodiment, the multiple myeloma is characterized as having chromosomal translocations involving the immunoglobulin heavy chain locus at 14q32. In another embodiment, the chromosomal translocation is a t(4;14) translocation, i.e., the multiple myeloma is t(4;14) multiple myeloma.

In another embodiment, the cancer is mantle cell lymphoma.

In another embodiment, the cancer is diffuse large B-cell lymphoma.

In another embodiment, the present disclosure provides a therapeutic method of modulating protein methylation, gene expression, cell proliferation, cell differentiation and/or apoptosis in vivo in the cancers mentioned above by administering a therapeutically effective amount of a Compound of the Disclosure to a subject in need of such therapy and, optionally, a Second Therapeutic Agent.

The present disclosure provides the following particular embodiments relating to Compounds of the Disclosure, methods of treating cancer with a Compound of the Disclosure, and methods of treating cancer with a Compound of the Disclosure in combination with a Second Therapeutic Agent.

Embodiment I. A method of treating a subject in need thereof, the method comprising administering to the subject a therapeutically effective amount of a Compound of the Disclosure and, optionally, a Second Therapeutic Agent, wherein the subject has cancer, and the Second Therapeutic Agent is selected from the group consisting of a glucocorticoid receptor agonist, an immunomodulatory drug, a proteasome inhibitor, a Bcl-2 inhibitor, a pleiotropic pathway modulator, a XPO1 inhibitor, a histone deacetylase inhibitor, and an EZH2 inhibitor, or a combination thereof.

Embodiment II. The method of Embodiment I, wherein the cancer is any one or more of the cancers of Table 2.

Embodiment III. The method of Embodiment I, wherein the cancer is a hematological cancer.

Embodiment IV. The method of Embodiment III, wherein the hematological cancer is any one or more of the cancers of Table 3, e.g., multiple myeloma.

Embodiment V. The method of Embodiment IV, wherein the hematological cancer is t(4;14) multiple myeloma.

Embodiment VI. The method of any one of Embodiments I-V further comprising administering a therapeutically effective amount of a Second Therapeutic Agent.

Embodiment VII. A pharmaceutical composition comprising a Compound of the Disclosure and a pharmaceutically acceptable carrier for use in treating cancer, wherein the pharmaceutical composition comprising a Compound of the Disclosure is, optionally, to be administered in combination with a Second Therapeutic Agent, wherein the Second Therapeutic Agent is selected from the group consisting of a glucocorticoid receptor agonist, an immunomodulatory drug, a proteasome inhibitor, a Bcl-2 inhibitor, a pleiotropic pathway modulator, a XPO1 inhibitor, a histone deacetylase inhibitor, and an EZH2 inhibitor, or a combination thereof.

Embodiment VIII. The pharmaceutical composition of Embodiment VII, wherein the cancer is any one or more of the cancers of Table 2.

Embodiment IX. The pharmaceutical composition of Embodiment VII, wherein the cancer is a hematological cancer.

Embodiment X. The pharmaceutical composition of Embodiment IX, wherein the hematological cancer is any one or more of the cancers of Table 3, e.g., multiple myeloma.

Embodiment XI. The pharmaceutical composition of Embodiment X, wherein the hematological cancer is t(4;14) multiple myeloma.

Embodiment XII. A Compound of the Disclosure for use in treatment of cancer, wherein the Compound of the Disclosure is, optionally, to be administered in combination with a Second Therapeutic Agent, wherein the Second Therapeutic Agent is selected from the group consisting of a glucocorticoid receptor agonist, an immunomodulatory drug, a proteasome inhibitor, a Bcl-2 inhibitor, a pleiotropic pathway modulator, a XPO1 inhibitor, a histone deacetylase inhibitor, and an EZH2 inhibitor, or a combination thereof.

Embodiment XIII. The compound for use of Embodiment XII, wherein the cancer is any one or more of the cancers of Table 2.

Embodiment XIV. The compound for use of Embodiment XII, wherein the cancer is a hematological cancer.

Embodiment XV. The compound for use of Embodiment XIV, wherein the hematological cancer is any one or more of the cancers of Table 3, e.g., multiple myeloma.

Embodiment XVI. The compound for use of Embodiment XV, wherein the hematological cancer is t(4;14) multiple myeloma.

Embodiment XVII. Use of a Compound of the Disclosure for the manufacture of a medicament for treatment of cancer, wherein the medicament is, optionally, to be administered in combination with a Second Therapeutic Agent, wherein the Second Therapeutic Agent is selected from the group consisting of a glucocorticoid receptor agonist, an immunomodulatory drug, a proteasome inhibitor, a Bcl-2 inhibitor, a pleiotropic pathway modulator, a XPO1 inhibitor, a histone deacetylase inhibitor, and an EZH2 inhibitor, or a combination thereof.

Embodiment XVIII. The use of Embodiment XVII, wherein the cancer is any one or more of the cancers of Table 2.

Embodiment XVIII. The use of Embodiment XVII, wherein the cancer is a hematological cancer.

Embodiment XIX. The use of Embodiment XVII, wherein the hematological cancer is any one or more of the cancers of Table 3, e.g., multiple myeloma.

Embodiment XX. The use of Embodiment XIX, wherein the hematological cancer is t(4;14) multiple myeloma.

Embodiment XXI The use of any one of Embodiments XVII-XX for comprising a Secondary Therapeutic Agent.

Embodiment XXII. A kit comprising a Compound of the Disclosure and, optionally, a Second Therapeutic Agent, and instructions for administering the Compound of the Disclosure to a subject having cancer.

Embodiment XXIII. The kit of Embodiment XXII, wherein the cancer is any one or more of the cancers of Table 2.

Embodiment XXIV. The kit of Embodiment XXII, wherein the cancer is a hematological cancer.

Embodiment XXV. The kit of Embodiment XXIV, wherein the hematological cancer is any one or more of the cancers of Table 3, e.g., multiple myeloma.

Embodiment XXVI. The kit of Embodiment XXV, wherein the hematological cancer is t(4;14) multiple myeloma.

Embodiment XXVII. The kit of any one of Embodiments XXII-XXVI further comprising a Secondary Therapeutic Agent.

Embodiment XXVIII. The method of Embodiment VI, wherein the Compound of the Disclosure and the Second Therapeutic agent are administered simultaneously.

Embodiment XXIX. The method of Embodiment VI, wherein the Compound of the Disclosure and the Second Therapeutic agent are administered sequentially.

Embodiment XXX. The pharmaceutical composition of any one of Embodiments VII-XI, wherein the pharmaceutical composition is formulated for simultaneous administration of the Compound of the Disclosure and the Second Therapeutic Agent.

Embodiment XXXI. The pharmaceutical composition of any one of Embodiments VII-XI, wherein the pharmaceutical composition is formulated for sequential administration of the Compound of the Disclosure and the Second Therapeutic Agent.

Embodiment XXXII. The compound for use of any one of Embodiments XII-XVI, wherein the combination of the Compound of the Disclosure and the Second Therapeutic Agent is administered simultaneously.

Embodiment XXXIII. The compound for use of any one of Embodiments XII-XVI, wherein the combination of the Compound of the Disclosure and the Second Therapeutic Agent are administered sequentially.

Embodiment XXXIV. The use of any one of Embodiments XVII-XX, wherein the combination of the Compound of the Disclosure and the Second Therapeutic Agent is administered simultaneously.

Embodiment XXXV. The use of any one of Embodiments XVII-XX, wherein the combination of the Compound of the Disclosure and the Second Therapeutic Agent is administered sequentially.

The present disclosure also provides the following particular embodiments.

Embodiment 1. A method of treating a subject in need thereof, the method comprising administering to the subject a therapeutically effective amount of:

(a) compound of Formula I:

I

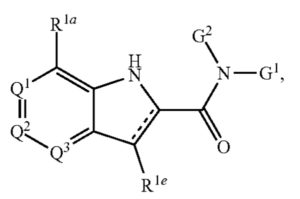

wherein:

$R^{1a}$ is selected from the group consisting of halogen, alkyl, alkoxy, cycloalkyl, (hydroxy)alkyl, and (cycloalkyl)alkyl;

$Q^1$ is selected from the group consisting of —C($R^{1b}$)= and —N=;

$Q^2$ is selected from the group consisting of —C($R^{1c}$)= and —N=;

$Q^3$ is selected from the group consisting of —C($R^{1d}$)= and —N=;

provided that at least one of $Q^1$, $Q^2$, or $Q^3$ is —C($R^{1b}$)=, —C($R^{1c}$)=, or —C($R^{1d}$)=, respectively;

$R^{1b}$, $R^{1c}$, and $R^{1d}$ are each independently selected from the group consisting of hydrogen, halogen, alkyl, alkenyl, (hydroxy)alkyl, and alkoxy;

$R^{1e}$ is selected from the group consisting of hydrogen, halogen, alkyl, cycloalkyl, (hydroxy)alkyl, and (cycloalkyl)alkyl;

⎓ is a single or double bond;

$G^1$ is selected from the group consisting of: optionally substituted aryl;

optionally substituted heteroaryl; optionally substituted heterocyclo; optionally substituted cycloalkyl; (aryl)alkyl; (heteroaryl)alkyl; (heterocyclo)alkyl; (amino)(aryl)alkyl; (heteroaryl)(aryl)alkyl; (heteroaryl)(heterocyclo)alkyl; (heteroaryl)(carboxamido)alkyl; (heteroaryl)(cycloalkyl)alkyl; (aryl)(alkoxycarbonyl)alkyl; (cycloalkyl)alkyl; (heteroaryl)(amino)alkyl; (cycloalkyl)(alkoxycarbonyl)alkyl; (heteroaryl)(alkoxycarbonyl)alkyl; (heterocyclo)(cycloalkyl)alkyl; (aryl)(cycloalkyl)alkyl; (aryl)(hydroxy)alkyl; (cycloalkyl)(hydroxy)alkyl; (hydroxy)alkyl; optionally substituted alkyl; (aryl)(haloalkyl)alkyl; (cycloalkyl)(haloalkyl)alkyl; (hydroxy)(haloalkyl)alkyl; and (alkoxycarbonyl)(haloalkyl)alkyl; and $G^2$ is selected from the group consisting of hydrogen and alkyl; or $G^1$ and $G^2$ taken together with the nitrogen atom to which they are attached form an optionally substituted heterocyclo, provided that the compound of Formula I is not N-(1-(1-(L-alanyl)piperidin-4-yl)ethyl)-7-methyl-1H-indole-2-carboxamide; N-((1r,4r)-4-(3-aminopropanamido) cyclohexyl)-7-methyl-1H-indole-2-carboxamide; or N-((1r,4r)-4-aminocyclohexyl)-7-methyl-1H-indole-2-carboxamide, or a pharmaceutically acceptable salt or solvate thereof; and (b) a Second Therapeutic Agent, wherein:

the Second Therapeutic Agent comprises one or more glucocorticoid receptor agonists, one or more immunomodulatory drugs, one or more proteasome inhibitors, one or more Bcl-2 inhibitors, one or more pleiotropic pathway modulators, one or more XPO1 inhibitors, one or morehistone deacetylase inhibitors, or one or more EZH2 inhibitors, or a combination thereof.

Embodiment 2. The method of Embodiment 1, wherein the compound is a compound of Formula II:

II

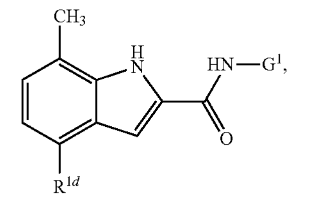

or a pharmaceutically acceptable salt or solvate thereof.

Embodiment 3. The method of Embodiments 1 or 2, wherein $G^1$ is selected from the group consisting of: optionally substituted $C_6$-$C_{10}$ aryl; optionally substituted 5- to 9-membered heteroaryl; optionally substituted 3- to 10-membered heterocyclo; optionally substituted $C_6$-$C_8$ cycloalkyl; (5- to 9-membered heteroaryl) $C_1$-$C_6$ alkyl; (5- to 9-membered heteroaryl)($C_{6-10}$ aryl)$C_1$-$C_4$ alkyl; (5- to 9-membered heteroaryl heteroaryl)($C_3$-$C_6$ cycloalkyl)$C_1$-$C_4$ alkyl; and ($C_3$-$C_6$ cycloalkyl)$C_1$-$C_4$ alkyl, or a pharmaceutically acceptable salt or solvate thereof.

Embodiment 4. The method of Embodiment 3, wherein the compound is a compound of of Formula IV:

IV

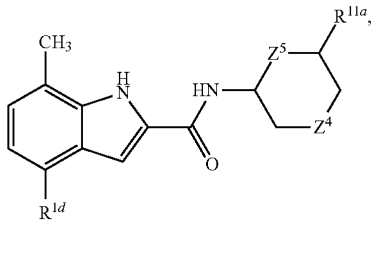

wherein:

$Z^4$ is selected from the group consisting of —O—, —C($R^{28a}$)($R^{28b}$)—, and —N($R^{23}$)—; or $Z^4$ is absent;

$Z^5$ is selected from the group consisting of —$CH_2$— and —$CH_2CH_2$—;

$R^{11a}$ is selected from the group consisting of optionally substituted alkyl, optionally substituted heterocyclo, optionally substituted heteroaryl, and —N($R^{12b}$)C(═O)$R^{13c}$;

$R^{12b}$ is selected from the group consisting of hydrogen, alkyl, cycloalkyl, and heterocyclo, ($C_1$-$C_4$ alkoxy)$C_1$-$C_4$ alkyl, and (hydroxy)$C_1$-$C_4$ alkyl; and $R^{13c}$ is selected from the group consisting of alkyl, haloalkyl, alkoxy, (alkoxy)alkyl, (hydroxy)alkyl, (cyano)alkyl, optionally substituted aryl, optionally substituted heteroaryl, optionally substituted cycloalkyl, and optionally substituted heterocycle, amino, (amino)alkyl, ($C_3$-$C_6$ cycloalkyl)oxy, and (4- to 8-membered heterocyclo)oxy;

$R^{23}$ is selected from the group consisting of hydrogen and $C_1$-$C_4$ alkyl; and $R^{28a}$ and $R^{28b}$ are independently selected from the group consisting of hydrogen, alkyl, and halo;

or a pharmaceutically acceptable salt or solvate thereof.

Embodiment 5. The method of Embodiment 4, wherein the compound is a compound of Formula IV-A:

IV-A

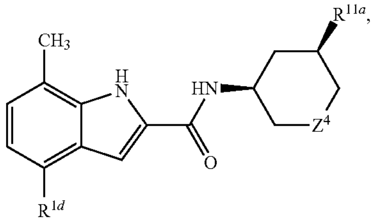

or a pharmaceutically acceptable salt or solvate thereof.

Embodiment 6. The method of Embodiment 4, wherein the compound is a compound of Formula IV-B:

IV-B

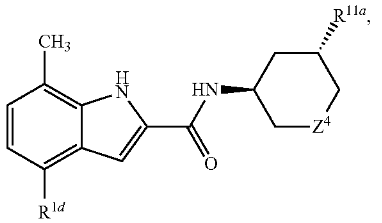

or a pharmaceutically acceptable salt or solvate thereof.

Embodiment 7. The method of Embodiment 4, wherein the compound is a compound of Formula IV-C:

IV-C

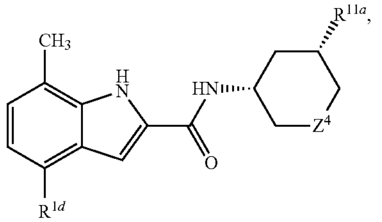

or a pharmaceutically acceptable salt or solvate thereof.

Embodiment 8. The method of Embodiment 4, wherein the compound is a compound of Formula IV-D:

IV-D

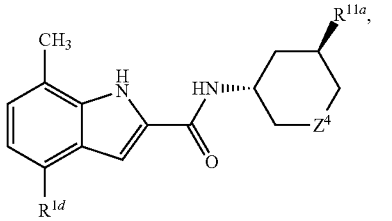

or a pharmaceutically acceptable salt or solvate thereof.

Embodiment 9. The method of any one of Embodiments 4-8, wherein:

$R^{11a}$ is selected from the group consisting of:

(A) unsubstituted 4- to 14-membered heterocyclo;

(B) substituted 4- to 14-membered heterocyclo having one, two or three substituents independently selected from the group consisting of:

—$N(R^{12a})C(=O)R^{13a}$; (ii) —$C(=O)R^{13b}$; (iv) $C_1$-$C_4$ alkyl; (iv) ($C_1$-$C_4$ alkoxy)$C_1$-$C_4$ alkyl; (v) (hydroxy)$C_1$-$C_4$ alkyl; (vi) $C_1$-$C_4$ haloalkyl; (vii) amino; (vii) hydroxy; (viii) —$N(R^{12a})S(=O)_2R^{24}$; (ix) —$S(=O)_2R^{24}$; (x) unsubstituted $C_3$-$C_6$ cycloalkyl; (xi) substituted $C_3$-$C_6$ cycloalkyl having one or two substituents independently selected from the group consisting of halo, hydroxy, $C_1$-$C_4$ alkyl, amino, and (amino)$C_1$-$C_4$ alkyl; (xii) unsubstituted 4- to 14-membered heterocyclo; and substituted 4- to 14-membered heterocyclo having one or two substituents independently selected from the group consisting of amino, hydroxy, and $C_1$-$C_4$ alkyl; (xiii)—$C(=N—R^{60})R^{61}$; and(xiv) —$C(=C—NO_2)R^{64}$;

(C) unsubstituted 5- to 10-membered heteroaryl;

(D) substituted 5- or 6-membered heteroaryl having one, two, three, or four substituents independently selected from the group consisting of halo and $C_1$-$C_4$ alkyl;

(E) $C_1$-$C_6$ alkyl; and (F) —$N(R^{12b})C(=O)R^{13c}$;

$R^{12a}$ and $R^{12b}$ are each independently selected from the group consisting of hydrogen, $C_1$-$C_4$ alkyl, ($C_1$-$C_4$ alkoxy) $C_1$-$C_4$ alkyl, and (hydroxy)$C_1$-$C_4$ alkyl;

$R^{13a}$, $R^{13b}$, and $R^{13c}$ are each independently selected from the group consisting of (A) $C_1$-$C_6$ alkyl; (B) $C_1$-$C_6$ haloalkyl; (C) unsubstituted $C_3$-$C_6$ cycloalkyl; (D) $C_1$-$C_6$ alkoxy; (E) ($C_1$-$C_4$ alkoxy)$C_1$-$C_4$ alkyl; (F) (hydroxy)$C_1$-$C_4$ alkyl; (G) (cyano)alkyl; (H) unsubstituted $C_6$-$C_{10}$ aryl; (I) substituted $C_6$-$C_{10}$ aryl, having one, two, three, or four substituents independently selected from the group consisting of halo, amino, hydroxy, and $C_1$-$C_4$ alkyl; (J) unsubstituted 5- or 6-membered heteroaryl; (K) substituted 5- or 6-membered heteroaryl having one, two, three, or four substituents independently selected from the group consisting of halo, amino, hydroxy, and $C_1$-$C_4$ alkyl; (L) unsubstituted 4- to 14-membered heterocyclo; (M) substituted 4- to 14-membered heterocyclo having one or two substituents independently selected from the group consisting of amino, hydroxy, and $C_1$-$C_4$ alkyl; (N) amino; (O) (amino)alkyl; (P) ($C_3$-$C_6$ cycloalkyl)oxy; and (Q) (4- to 8-membered heterocyclo) oxy; and $R^{24}$ is selected from the group consisting of $C_1$-$C_4$ alkyl and (hydroxy)$C_1$-$C_4$ alkyl;

$R^{60}$ is selected from the group consisting of cyano, nitro, hydroxy, $C_1$-$C_6$ alkoxy, —$C(=O)R^{62}$, and —$S(=O)_2R^{62}$;

$R^{61}$ is selected from the group consisting of $C_1$-$C_6$ alkyl, $C_3$-$C_6$ cycloalkyl, and —$NR^{63a}R^{63b}$;

$R^{62}$ is selected from the group consisting of $C_1$-$C_6$ alkyl, $C_3$-$C_6$ cycloalkyl, and —$NR^{63a}R^{63b}$;

$R^{63a}$ is selected from the group consisting of hydrogen, $C_1$-$C_6$ alkyl, and $C_3$-$C_6$ cycloalkyl;

$R^{63b}$ is selected from the group consisting of hydrogen, $C_1$-$C_6$ alkyl, and $C_3$-$C_6$ cycloalkyl; or $R^{63a}$ and $R^{63b}$ taken together with the nitrogen atom to which they are attached form a 4- to 6-membered optionally substituted heterocyclo;

$R^{64}$ is selected from the group consisting of $C_1$-$C_6$ alkyl, $C_3$-$C_6$ cycloalkyl, and —$NR^{63c}R^{63d}$;

$R^{63c}$ is selected from the group consisting of hydrogen, $C_1$-$C_6$ alkyl, and $C_3$-$C_6$ cycloalkyl;

$R^{63d}$ is selected from the group consisting of hydrogen, $C_1$-$C_6$ alkyl, and $C_3$-$C_6$ cycloalkyl; or $R^{63c}$ and $R^{63d}$ taken together with the nitrogen atom to which they are attached form a 4- to 6-membered optionally substituted heterocyclo, or a pharmaceutically acceptable salt or solvate thereof.

Embodiment 10. The method of Embodiment 9, wherein $R^{11a}$ is a substituted 4- to 14-membered heterocyclo selected from the group consisting of:

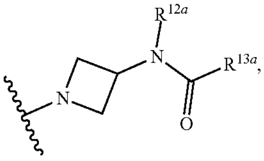
,
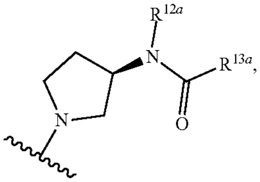
,
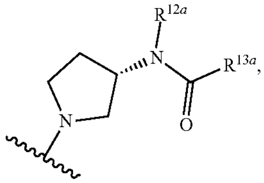
,
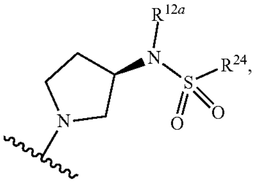
,
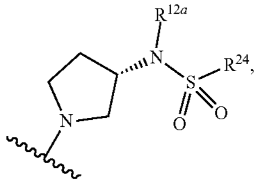
,
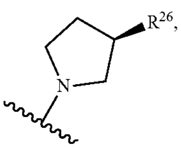
,
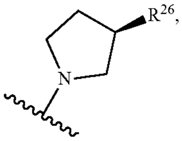
,
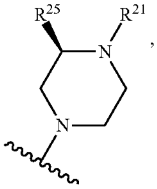
,
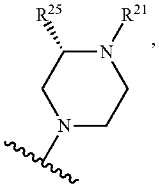
,
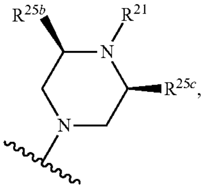
,
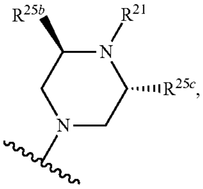
,
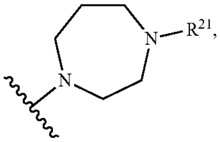
,
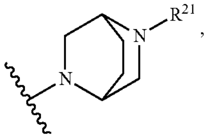
, -continued

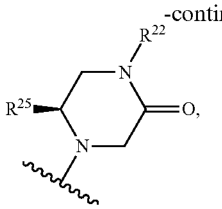

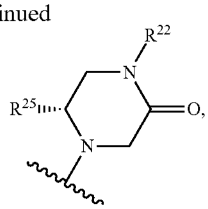

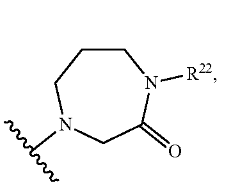

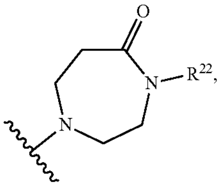

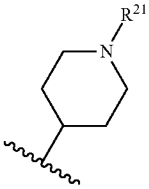

,

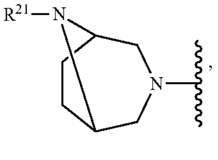

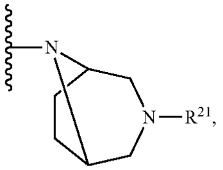

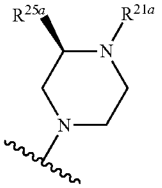

and

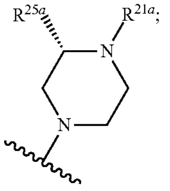

$R^{12a}$ is selected from the group consisting of hydrogen, $C_1$-$C_3$ alkyl, ($C_1$-$C_4$ alkoxy)$C_1$-$C_4$ alkyl; and (hydroxy)$C_1$-$C_4$ alkyl;

$R^{13a}$ is selected from the group consisting of $C_1$-$C_4$ alkyl; amino; unsubstituted $C_3$-$C_6$ cycloalkyl; substituted $C_3$-$C_6$ cycloalkyl having one or two substituents independently selected from the group consisting of halo, hydroxy, $C_1$-$C_4$ alkyl, amino, and (amino)$C_1$-$C_4$ alkyl; ($C_1$-$C_4$ alkoxy)$C_1$-$C_4$ alkyl; (hydroxy)$C_1$-$C_4$ alkyl; unsubstituted 4- to 14-membered heterocyclo; and substituted 4- to 14-membered heterocyclo having one or two substituents independently selected from the group consisting of amino, hydroxy, and $C_1$-$C_4$ alkyl;

$R^{13b}$ is selected from the group consisting of $C_1$-$C_4$ alkyl; amino; $C_1$-$C_4$ haloalkyl; $C_1$-$C_4$ alkoxy; (hydroxy)$C_1$-$C_4$ alkyl; ($C_1$-$C_4$ alkoxy)$C_1$-$C_4$ alkyl; (amino)alkyl; unsubstituted $C_3$-$C_6$ cycloalkyl; substituted $C_3$-$C_6$ cycloalkyl having one or two substituents independently selected from the group consisting of halo, hydroxy, $C_1$-$C_4$ alkyl, amino, and (amino)$C_1$-$C_4$ alkyl; unsubstituted 4- to 14-membered heterocyclo; and substituted 4- to 14-membered heterocyclo having one or two substituents independently selected from the group consisting of amino, hydroxy, and $C_1$-$C_4$ alkyl; ($C_3$-$C_6$ cycloalkyl)oxy; and (4- to 8-membered heterocyclo) oxy;

$R^{21}$ is selected from the group consisting of hydrogen, —C(═O)$R^{13b}$, $C_1$-$C_4$ alkyl, $C_1$-$C_4$ haloalkyl, unsubstituted 4- to 14-membered heterocyclo, and —S(═O)$_2$$R^{24}$;

$R^{22}$ is $C_1$-$C_4$ alkyl; unsubstituted $C_3$-$C_6$ cycloalkyl; substituted $C_3$-$C_6$ cycloalkyl having one or two substituents independently selected from the group consisting of halo, hydroxy, $C_1$-$C_4$ alkyl, amino, and (amino)$C_1$-$C_4$ alkyl; unsubstituted 4- to 14-membered heterocyclo; and substituted 4- to 14-membered heterocyclo having one or two substituents independently selected from the group consisting of amino, hydroxy, and $C_1$-$C_4$ alkyl;

$R^{24}$ is selected from the group consisting of $C_1$-$C_4$ alkyl and (hydroxy)$C_1$-$C_4$ alkyl;

$R^{25}$ is selected from the group consisting of hydrogen, $C_1$-$C_4$ alkyl, and $C_1$-$C_4$ haloalkyl;

$R^{25b}$ and $R^{25c}$ are independently selected from the group consisting of $C_1$-$C_4$ alkyl and $C_1$-$C_4$ haloalkyl;

$R^{26}$ is selected from the group consisting of unsubstituted 4- to 14-membered heterocyclo; and substituted 4- to 14-membered heterocyclo having one or two substituents independently selected from the group consisting of amino, hydroxy, and $C_1$-$C_4$ alkyl; and $R^{21a}$ and $R^{25a}$ taken together with the atoms to which they are attached form an optionally substituted 4- to 8-membered heterocyclo, or a pharmaceutically acceptable salt or solvate thereof.

Embodiment 11. The method of Embodiment 9, wherein $R^{11a}$ is a substituted 4- to 14-membered heterocyclo selected from the group consisting of:

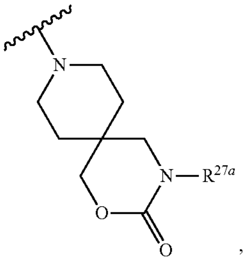

,

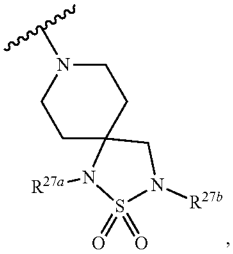

,

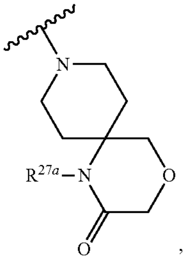

,

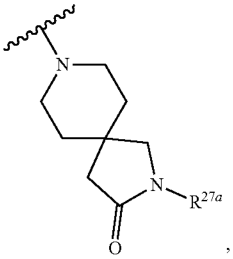

,

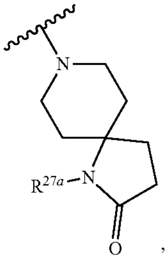

,

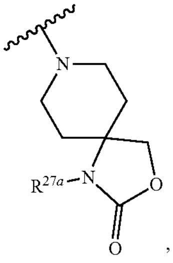

,

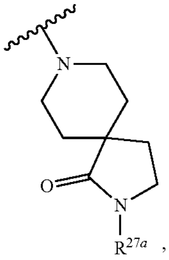

,

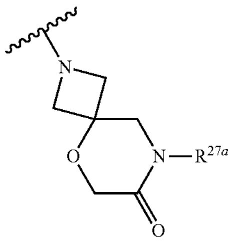

,

-continued
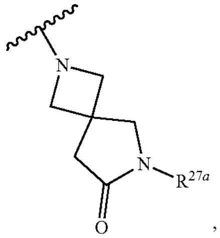,
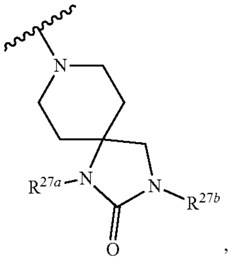,
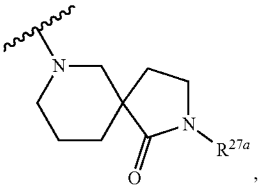,
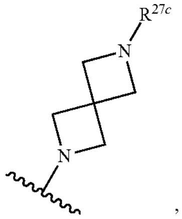,
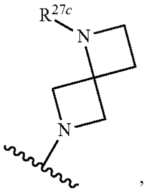,
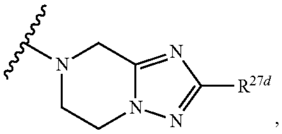,
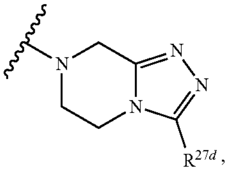,
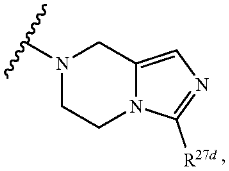,
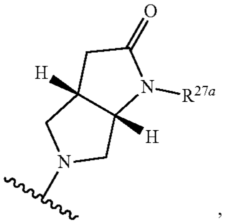,
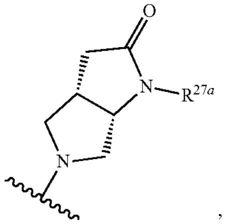,
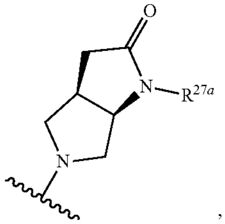,
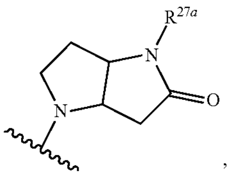,
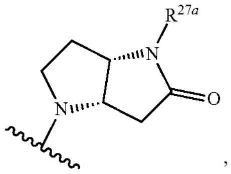,
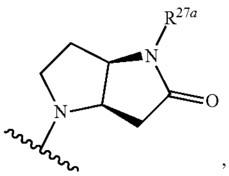,
-continued
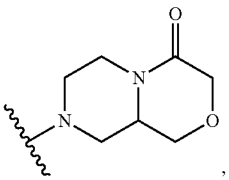,
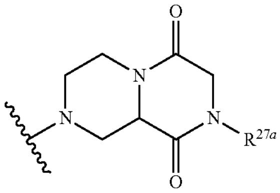,
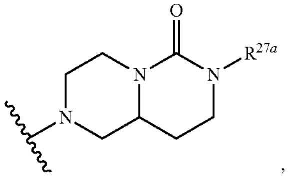,
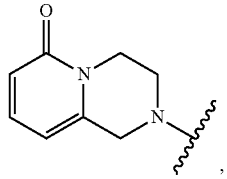,
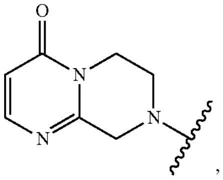,
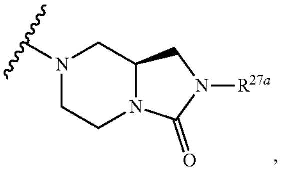,
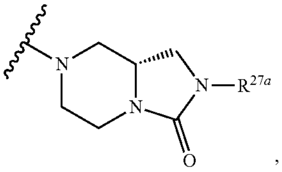,
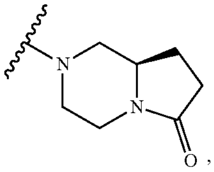,
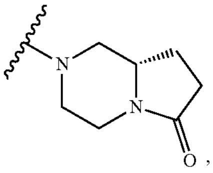,
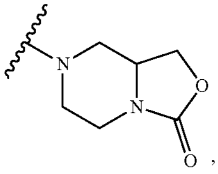,
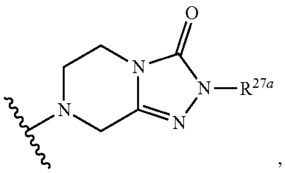,
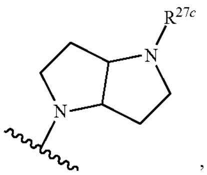,
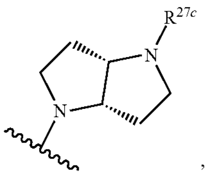,
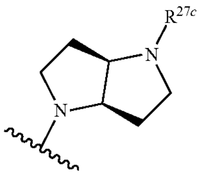,
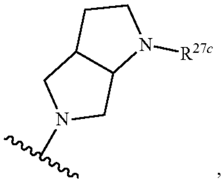,
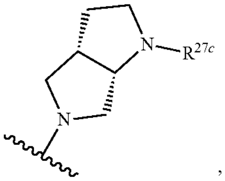,
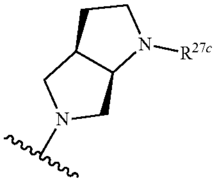
and -continued

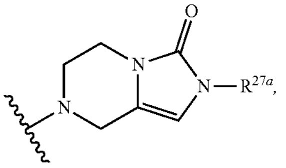

$R^{27a}$ and $R^{27b}$ are each independently selected from the group consisting of hydrogen, $C_1$-$C_4$ alkyl, $C_1$-$C_4$ haloalkyl, ($C_1$-$C_4$ alkoxy)$C_1$-$C_4$ alkyl; and (hydroxy)$C_1$-$C_4$ alkyl;

$R^{27c}$ is selected from the group consisting of hydrogen; —C(═O)$R^{13b}$; $C_1$-$C_4$ alkyl; $C_1$-$C_4$ haloalkyl; unsubstituted 4- to 14-membered heterocyclo; and substituted 4- to 14-membered heterocyclo having one or two substituents independently selected from the group consisting of amino, hydroxy, and $C_1$-$C_4$ alkyl; and —S(═O)$_2R^{24}$;

$R^{27d}$ is selected from the group consisting of hydrogen; $C_1$-$C_4$ alkyl; and $C_1$-$C_4$ haloalkyl;

$R^{13b}$ is selected from the group consisting of $C_1$-$C_4$ alkyl; amino$C_1$-$C_4$ haloalkyl; $C_1$-$C_4$ alkoxy; (hydroxy)$C_1$-$C_4$ alkyl; ($C_1$-$C_4$ alkoxy)$C_1$-$C_4$ alkyl; (amino)alkyl; unsubstituted $C_3$-$C_6$ cycloalkyl; substituted $C_3$-$C_6$ cycloalkyl having one or two substituents independently selected from the group consisting of halo, hydroxy, $C_1$-$C_4$ alkyl, amino, and (amino) $C_1$-$C_4$ alkyl; unsubstituted 4- to 14-membered heterocyclo; substituted 4- to 14-membered heterocyclo having one or two substituents independently selected from the group consisting of amino, hydroxy, and $C_1$-$C_4$ alkyl; ($C_3$-$C_6$ cycloalkyl)oxy; and (4- to 8-membered heterocyclo)oxy; and $R^{24}$ is selected from the group consisting of $C_1$-$C_4$ alkyl and (hydroxy)$C_1$-$C_4$ alkyl, or a pharmaceutically acceptable salt or solvate thereof.

Embodiment 12. The method of Embodiment 11, wherein $R^{11a}$ is a substituted 4- to 14-membered heterocyclo selected from the group consisting of:

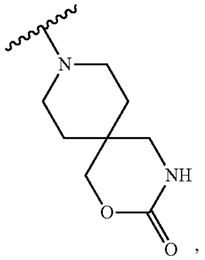
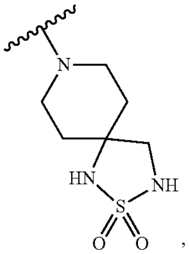
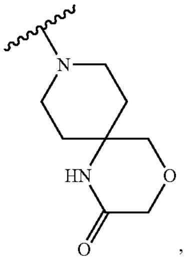
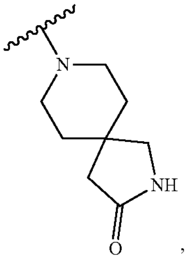

-continued

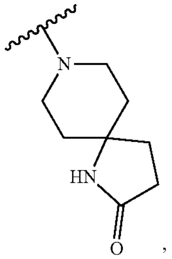
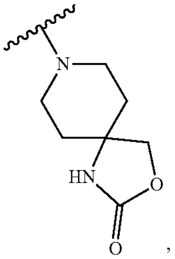
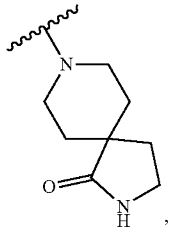
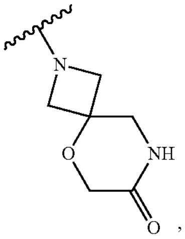
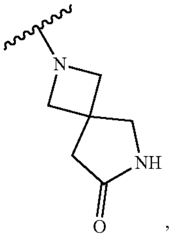
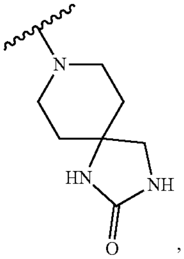
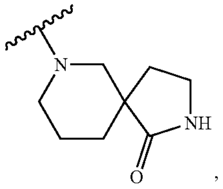
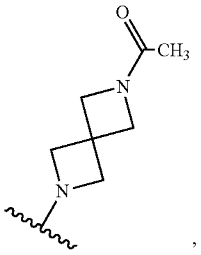
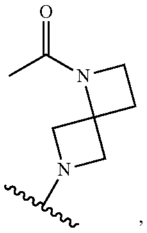
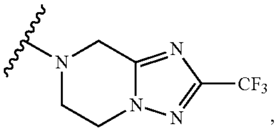
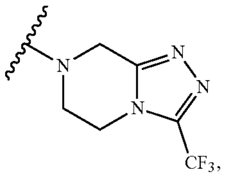
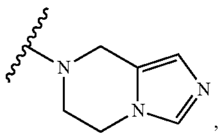
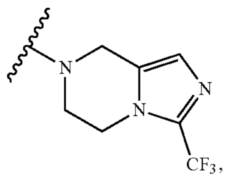
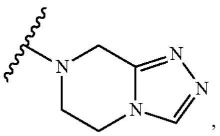

-continued
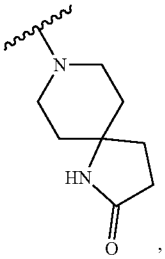 , 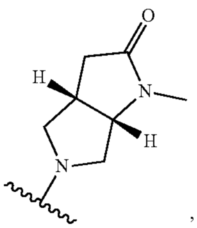 ,
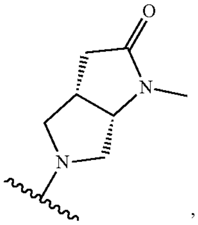 , 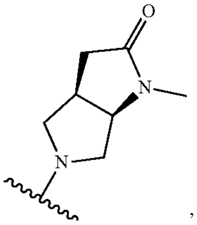 ,
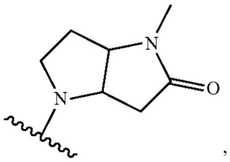 , 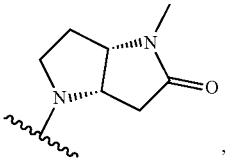 ,
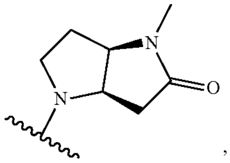 , 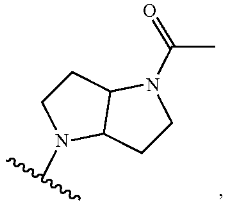 ,
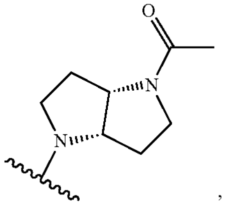 , 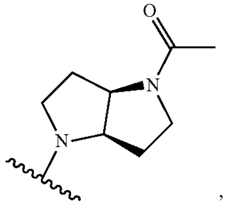 ,
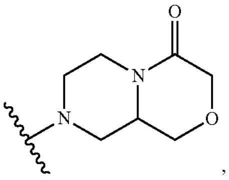 , 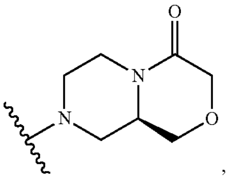 ,
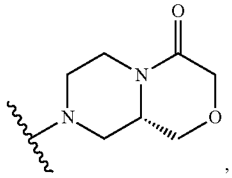 , 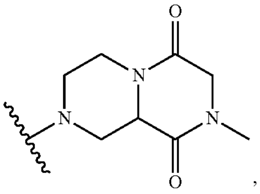 ,
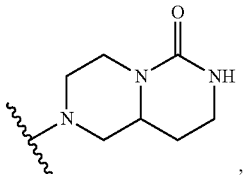 , 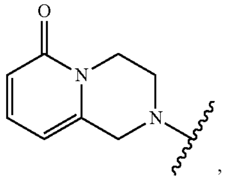 ,
-continued
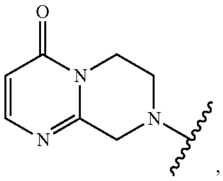 , 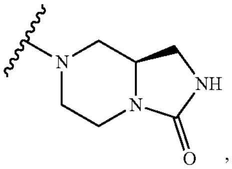 ,
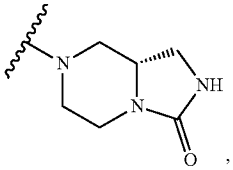 , 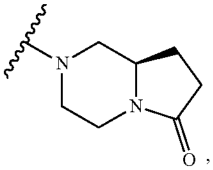 ,
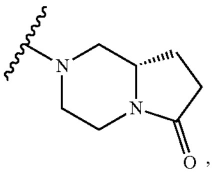 , 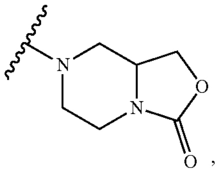 ,
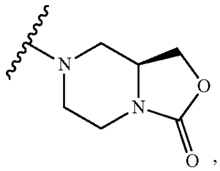 , 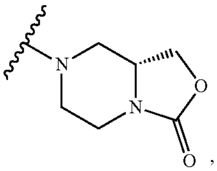 ,
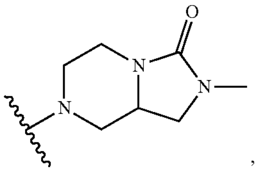 , 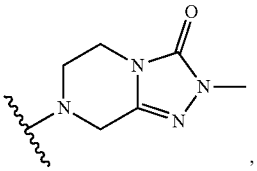 ,
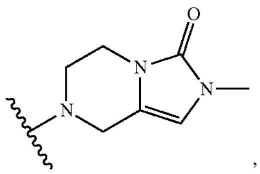 , 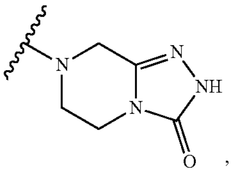 ,
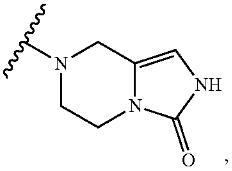 , 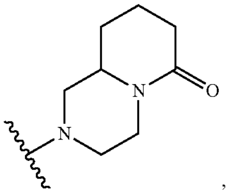 ,
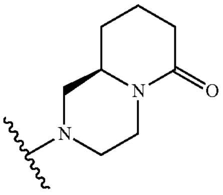 and 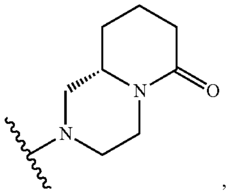 ,
or a pharmaceutically acceptable salt or solvate thereof.
Embodiment 13. The method of Embodiment 9, wherein $R^{11a}$ is a substituted 4- to 14-membered heterocyclo selected from the group consisting of:

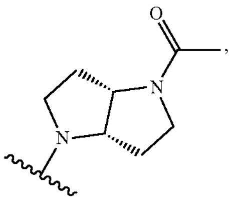

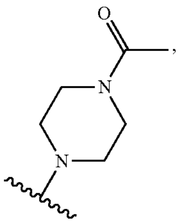

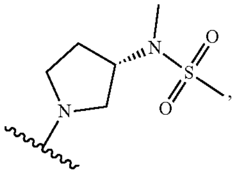

and

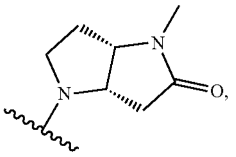

or a pharmaceutically acceptable salt or solvate thereof.

Embodiment 14. The method of any one of Embodiments 4-13, wherein $Z^4$ is —$CH_2$—, or a pharmaceutically acceptable salt or solvate thereof.

Embodiment 15. The method of any one of Embodiments 1-14, wherein $R^{1d}$ is fluoro, or a pharmaceutically acceptable salt or solvate thereof.

Embodiment 16. The method of Embodiment 1, wherein the compound is a compound of Table 1, or a pharmaceutically acceptable salt or solvate thereof.

Embodiment 17. The method of Embodiment 1, wherein the compound is a compound of Table 1B, or a pharmaceutically acceptable salt or solvate thereof.

Embodiment 18. The method of any one of Embodiments 1-17, wherein the second therapeutic agent comprises a glucocorticoid receptor agonist.

Embodiment 19. The method of Embodiment 18, wherein the glucocorticoid receptor agonist is dexamethasone.

Embodiment 20. The method of any one of Embodiments 1-19, wherein the second therapeutic agent comprises an immunomodulatory drug.

Embodiment 21. The method of Embodiment 20, wherein the immunomodulatory drug is pomalidomide or lenalidomide.

Embodiment 22. The method of any one of Embodiments 1-21, wherein the second therapeutic agent comprises a proteasome inhibitor.

Embodiment 23. The method of Embodiment 22, wherein the proteasome inhibitor is bortezomib.

Embodiment 24. The method of any one of Embodiments 1-23, wherein the second therapeutic agent comprises a Bcl-2 inhibitor.

Embodiment 25. The method of Embodiment 24, wherein the Bcl-2 inhibitor is venetoclax.

Embodiment 26. The method of any one of Embodiments 1-25, wherein the second therapeutic agent comprises a pleiotropic pathway modulator.

Embodiment 27. The method of Embodiment 26, wherein the pleiotropic pathway modulator is CC-122.

Embodiment 28. The method of any one of Embodiments 1-27, wherein the second therapeutic agent comprises a XPO1 inhibitor.

Embodiment 29. The method of Embodiment 28, wherein the XPO1 inhibitor is selinexor.

Embodiment 30. The method of any one of Embodiments 1-29, wherein the second therapeutic agent comprises a histone deacetylase inhibitor.

Embodiment 31. The method of Embodiment 30, wherein the histone deacetylase inhibitor is panobinostat.

Embodiment 32. The method of any one of Embodiments 1-31, wherein the second therapeutic agent is an EZH2 inhibitor.

Embodiment 33. The method of Embodiment 32, wherein the EZH2 inhibitor is tazemetostat.

Embodiment 34. The method of any one of Embodiments 1-33, wherein the compound of Formula I and the Second Therapeutic Agent are administered to the subject separately.

Embodiment 35. The method of any one of Embodiments 1-34, wherein the subject in need thereof has cancer.

Embodiment 36. The method of Embodiment 35, wherein the cancer is any one or more of the cancers of Table 2.

Embodiment 37. The method of Embodiment 38, wherein the cancer is a hematological cancer.

Embodiment 38. The method of Embodiment 37, wherein the hematological cancer is any one or more of the cancers of Table 3.

Embodiment 39. A kit comprising:

(a) compound of Formula I:

I

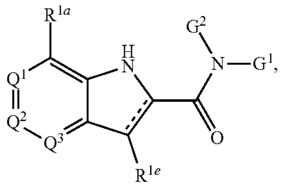

wherein:

$R^{1a}$ is selected from the group consisting of halogen, alkyl, alkoxy, cycloalkyl, (hydroxy)alkyl, and (cycloalkyl) alkyl;

$Q^1$ is selected from the group consisting of —C($R^{1b}$)= and —N=;

$Q^2$ is selected from the group consisting of —C($R^{1c}$)= and —N=;

$Q^3$ is selected from the group consisting of —C($R^{1d}$)= and —N=;

provided that at least one of $Q^1$, $Q^2$, or $Q^3$ is —C($R^{1b}$)=, —C($R^{1c}$)=, or —C($R^{1d}$)=, respectively;

$R^{1b}$, $R^{1c}$, and $R^{1d}$ are each independently selected from the group consisting of hydrogen, halogen, alkyl, alkenyl, (hydroxy)alkyl, and alkoxy;

$R^{1e}$ is selected from the group consisting of hydrogen, halogen, alkyl, cycloalkyl, (hydroxy)alkyl, and (cycloalkyl) alkyl;

⎓ is a single or double bond;

$G^1$ is selected from the group consisting of: optionally substituted aryl;

optionally substituted heteroaryl; optionally substituted heterocyclo; optionally substituted cycloalkyl; (aryl)alkyl; (heteroaryl)alkyl; (heterocyclo)alkyl; (amino)(aryl)alkyl; (heteroaryl)(aryl)alkyl; (heteroaryl)(heterocyclo)alkyl; (heteroaryl)(carboxamido)alkyl; (heteroaryl)(cycloalkyl)alkyl; (aryl)(alkoxycarbonyl)alkyl; (cycloalkyl)alkyl; (heteroaryl)(amino)alkyl; (cycloalkyl)(alkoxycarbonyl)alkyl; (heteroaryl)(alkoxycarbonyl)alkyl; (heterocyclo)(cycloalkyl)alkyl; (aryl)(cycloalkyl)alkyl; (aryl)(hydroxy)alkyl; (cycloalkyl)(hydroxy)alkyl; (hydroxy)alkyl; optionally substituted alkyl; (aryl)(haloalkyl)alkyl; (cycloalkyl)(haloalkyl) alkyl; (hydroxy)(haloalkyl)alkyl; and (alkoxycarbonyl)(haloalkyl)alkyl; and $G^2$ is selected from the group consisting of hydrogen and alkyl; or $G^1$ and $G^2$ taken together with the nitrogen atom to which they are attached form an optionally substituted heterocyclo, provided that the compound of Formula I is not N-(1-(1-(L-alanyl)piperidin-4-yl)ethyl)-7-methyl-1H-indole-2-carboxamide; N-((1r,4r)-4-(3-aminopropanamido) cyclohexyl)-7-methyl-1H-indole-2-carboxamide; or N-((1r,4r)-4-aminocyclohexyl)-7-methyl-1H-indole-2-carboxamide, or a pharmaceutically acceptable salt or solvate thereof; and (b) a Second Therapeutic Agent, wherein:

the Second Therapeutic Agent comprises one or more glucocorticoid receptor agonists, one or more immunomodulatory drugs, one or more proteasome inhibitors, one or more Bcl-2 inhibitors, one or more pleiotropic pathway modulators, one or more XPO1 inhibitor, one or more histone deacetylase inhibitors, or one or more EZH2 inhibitors, or a combination thereof.

Embodiment 40. The kit of Embodiment 39 further comprising instructions for administering the compound of Formula I and the Second Therapeutic Agent to a subject having cancer.

Embodiment 41. A compound selected from the group consisting of:

4-fluoro-7-methyl-N-((1R,3S)-3-((3aS,6aS)-1-methyl-2-oxohexahydropyrrolo[3,4-b]pyrrol-5(1H)-yl)cyclohexyl)-1H-indole-2-carboxamide;

4-fluoro-7-methyl-N-((1R,3R)-3-((3aS,6aS)-1-methyl-2-oxohexahydropyrrolo[3,4-b]pyrrol-5(1H)-yl)cyclohexyl)-1H-indole-2-carboxamide;

4-fluoro-7-methyl-N-((1R,3S)-3-((3aR,6aR)-1-methyl-2-oxohexahydropyrrolo[3,4-b]pyrrol-5(1H)-yl)cyclohexyl)-1H-indole-2-carboxamide;

4-fluoro-7-methyl-N-((1R,3R)-3-((3aR,6aR)-1-methyl-2-oxohexahydropyrrolo[3,4-b]pyrrol-5(1H)-yl)cyclohexyl)-1H-indole-2-carboxamide;

4-fluoro-7-methyl-N-((1R,3S)-3-((3aS,6aS)-4-methyl-5-oxohexahydropyrrolo[3,2-b]pyrrol-1(2H)-yl)cyclohexyl)-1H-indole-2-carboxamide;

4-fluoro-7-methyl-N-((1R,3S)-3-((3aR,6aR)-4-methyl-5-oxohexahydropyrrolo[3,2-b]pyrrol-1(2H)-yl)cyclohexyl)-1H-indole-2-carboxamide;

4-fluoro-7-methyl-N-((1R,3R)-3-((3aS,6aS)-4-methyl-5-oxohexahydropyrrolo[3,2-b]pyrrol-1(2H)-yl)cyclohexyl)-1H-indole-2-carboxamide; and 4-fluoro-7-methyl-N-((1R,3R)-3-((3aR,6aR)-4-methyl-5-oxohexahydropyrrolo[3,2-b]pyrrol-1(2H)-yl)cyclohexyl)-1H-indole-2-carboxamide, or a pharmaceutically acceptable salt or solvate thereof.

Embodiment 42. A pharmaceutical composition comprising the compound of Embodiment 41, or a pharmaceutically acceptable salt or solvate thereof, and a pharmaceutically acceptable carrier.

Embodiment 43. A method of treating a subject in need thereof, the method comprising administering to the subject a therapeutically effective amount of the compound of Embodiment 41, or a pharmaceutically acceptable salt or solvate thereof.

Embodiment 44. The method of Embodiment 43, wherein the subject in need thereof has cancer.

Embodiment 45. The method of Embodiment 44, wherein the cancer is any one or more of the cancers of Table 2.

Embodiment 46. The method of Embodiment 44, wherein the cancer is a hematological cancer.

Embodiment 47. The method of Embodiment 46, wherein the hematological cancer is any one or more of the cancers of Table 3.

Embodiment 48. The pharmaceutical composition of Embodiment 43 for use in treating a subject.

Embodiment 49. The pharmaceutical composition of Embodiment 48, wherein the subject has cancer.

Embodiment 50. The pharmaceutical composition of Embodiment 49, wherein the cancer is any one or more of the cancers of Table 2.

Embodiment 51. The pharmaceutical composition of Embodiment 49, wherein the cancer is a hematological cancer.

Embodiment 52. The method of Embodiment 51, wherein the hematological cancer is any one or more of the cancers of Table 3.

Embodiment 53. The compound of Embodiment 41 for use in treating a subject.

Embodiment 54. The compound for use of Embodiment 53, wherein the subject has cancer.

Embodiment 55. The compound for use of Embodiment 54, wherein the cancer is any one or more of the cancers of Table 2.

Embodiment 56. The compound for use of Embodiment 54, wherein the cancer is a hematological cancer.

Embodiment 57. The method of Embodiment 56, wherein the hematological cancer is any one or more of the cancers of Table 3.

Embodiment 58. Use of a compound of Embodiment 21 in the manufacture of a medicament for treating a subject.

Embodiment 59. The use of Embodiment 58, wherein the subject has cancer.

Embodiment 60. The use of Embodiment 59, wherein the cancer is any one or more of the cancers of Table 2.

Embodiment 61. The use of Embodiment 59, wherein the cancer is a hematological cancer.

Embodiment 62. The use of Embodiment 61, wherein the hematological cancer is any one or more of the cancers of Table 3.

Embodiment 63. A kit comprising the compound of Embodiment 41 and instructions for administering the compound to a subject.

Embodiment 64. The kit of Embodiment 63, wherein the subject cancer.

Compounds of the Disclosure can be administered to a subject in the form of a raw chemical without any other components present. Compounds of the Disclosure can also be administered to a subject as part of a pharmaceutical composition containing the compound combined with a suitable pharmaceutically acceptable carrier. Such a carrier can be selected from pharmaceutically acceptable excipients and auxiliaries. The term "pharmaceutically acceptable carrier" or "pharmaceutically acceptable vehicle" encompasses any of the standard pharmaceutical carriers, solvents, surfactants, or vehicles. Suitable pharmaceutically acceptable vehicles include aqueous vehicles and nonaqueous vehicles. Standard pharmaceutical carriers and their formulations are described in Remington's Pharmaceutical Sciences, Mack Publishing Co., Easton, PA, 19th ed. 1995.

Pharmaceutical compositions within the scope of the present disclosure include all compositions where a Compound of the Disclosure is combined with one or more pharmaceutically acceptable carriers. In one embodiment, the Compound of the Disclosure is present in the composition in an amount that is effective to achieve its intended therapeutic purpose. While individual needs may vary, a determination of optimal ranges of effective amounts of each compound is within the skill of the art. Typically, a Compound of the Disclosure can be administered to a mammal, e.g., a human, orally at a dose of from about 0.0025 to about 1500 mg per kg body weight of the mammal, or an equivalent amount of a pharmaceutically acceptable salt or solvate thereof, per day to treat the particular disorder. A useful oral dose of a Compound of the Disclosure administered to a mammal is from about 0.0025 to about 50 mg per kg body weight of the mammal, or an equivalent amount of the pharmaceutically acceptable salt or solvate thereof. For intramuscular injection, the dose is typically about one-half of the oral dose.

A unit oral dose may comprise from about 0.01 mg to about 1 g of the Compound of the Disclosure, e.g., about 0.01 mg to about 500 mg, about 0.01 mg to about 250 mg, about 0.01 mg to about 100 mg, 0.01 mg to about 50 mg, e.g., about 0.1 mg to about 10 mg, of the compound. The unit dose can be administered one or more times daily, e.g., as one or more tablets or capsules, each containing from about 0.01 mg to about 1 g of the compound, or an equivalent amount of a pharmaceutically acceptable salt or solvate thereof.

A Compound of Disclosure or pharmaceutical composition comprising a Compound of the Disclosure and, optionally a Second Therapeutic Agent can be administered to any subject, e.g., a cancer patient in need thereof, that may experience the beneficial effects of a Compound of the Disclosure. Foremost among such subject are mammals, e.g., humans and companion animals, although the disclosure is not intended to be so limited. In one embodiment, the subject is a human.

A pharmaceutical composition of the present disclosure can be administered by any means that achieves its intended purpose. For example, administration can be by the oral, parenteral, subcutaneous, intravenous, intramuscular, intraperitoneal, transdermal, intranasal, transmucosal, rectal, intravaginal or buccal route, or by inhalation. The dosage administered and route of administration will vary, depending upon the circumstances of the particular subject, and taking into account such factors as age, gender, health, and weight of the recipient, condition or disorder to be treated, kind of concurrent treatment, if any, frequency of treatment, and the nature of the effect desired.

In one embodiment, a pharmaceutical composition of the present disclosure can be administered orally. In another embodiment, a pharmaceutical composition of the present disclosure can be administered orally and is formulated into tablets, dragees, capsules, or an oral liquid preparation. In one embodiment, the oral formulation comprises extruded multiparticulates comprising the Compound of the Disclosure.

Alternatively, a pharmaceutical composition of the present disclosure can be administered rectally, and is formulated in suppositories.

Alternatively, a pharmaceutical composition of the present disclosure can be administered by injection.

Alternatively, a pharmaceutical composition of the present disclosure can be administered transdermally.

Alternatively, a pharmaceutical composition of the present disclosure can be administered by inhalation or by intranasal or transmucosal administration.

Alternatively, a pharmaceutical composition of the present disclosure can be administered by the intravaginal route.

A pharmaceutical composition of the present disclosure can contain from about 0.01 to 99 percent by weight, e.g., from about 0.25 to 75 percent by weight, of a Compound of the Disclosure, e.g., about 1%, about 5%, about 10%, about 15%, about 20%, about 25%, about 30%, about 35%, about 40%, about 45%, about 50%, about 55%, about 60%, about 65%, about 70%, or about 75% by weight of a Compound of the Disclosure.

A pharmaceutical composition of the present disclosure is manufactured in a manner which itself will be known in view of the instant disclosure, for example, by means of conventional mixing, granulating, dragee-making, dissolving, extrusion, or lyophilizing processes. Thus, pharmaceutical compositions for oral use can be obtained by combining the active compound with solid excipients, optionally grinding the resulting mixture and processing the mixture of granules, after adding suitable auxiliaries, if desired or necessary, to obtain tablets or dragee cores.

Suitable excipients include fillers such as saccharides (for example, lactose, sucrose, mannitol or sorbitol), cellulose preparations, calcium phosphates (for example, tricalcium phosphate or calcium hydrogen phosphate), as well as binders such as starch paste (using, for example, maize starch, wheat starch, rice starch, or potato starch), gelatin, tragacanth, methyl cellulose, hydroxypropylmethylcellulose, sodium carboxymethylcellulose, and/or polyvinyl pyrrolidone. If desired, one or more disintegrating agents can be added, such as the above-mentioned starches and also carboxymethyl-starch, cross-linked polyvinyl pyrrolidone, agar, or alginic acid or a salt thereof, such as sodium alginate.

Auxiliaries are typically flow-regulating agents and lubricants such as, for example, silica, talc, stearic acid or salts thereof (e.g., magnesium stearate or calcium stearate), and polyethylene glycol. Dragee cores are provided with suitable coatings that are resistant to gastric juices. For this purpose, concentrated saccharide solutions can be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate can be used. Dye stuffs or pigments can be added to the tablets or dragee coatings, for example, for identification or in order to characterize combinations of active compound doses.

Examples of other pharmaceutical preparations that can be used orally include push-fit capsules made of gelatin, or soft, sealed capsules made of gelatin and a plasticizer such as glycerol or sorbitol. The push-fit capsules can contain a compound in the form of granules, which can be mixed with fillers such as lactose, binders such as starches, and/or lubricants such as talc or magnesium stearate and, optionally, stabilizers, or in the form of extruded multiparticulates. In soft capsules, the active compounds are preferably dissolved or suspended in suitable liquids, such as fatty oils or liquid paraffin. In addition, stabilizers can be added.

Possible pharmaceutical preparations for rectal administration include, for example, suppositories, which consist of a combination of one or more active compounds with a suppository base. Suitable suppository bases include natural and synthetic triglycerides, and paraffin hydrocarbons, among others. It is also possible to use gelatin rectal capsules consisting of a combination of active compound with a base material such as, for example, a liquid triglyceride, polyethylene glycol, or paraffin hydrocarbon.

Suitable formulations for parenteral administration include aqueous solutions of the active compound in a water-soluble form such as, for example, a water-soluble salt, alkaline solution, or acidic solution. Alternatively, a suspension of the active compound can be prepared as an oily suspension. Suitable lipophilic solvents or vehicles for such as suspension may include fatty oils (for example, sesame oil), synthetic fatty acid esters (for example, ethyl oleate), triglycerides, or a polyethylene glycol such as polyethylene glycol-400 (PEG-400). An aqueous suspension may contain one or more substances to increase the viscosity of the suspension, including, for example, sodium carboxymethyl cellulose, sorbitol, and/or dextran. The suspension may optionally contain stabilizers.

In some embodiments, the Compound of the Disclosure and the Second Therapeutic Agent are administered in combination to a subject as part of a single pharmaceutical composition.

In some embodiments, the Compound of the Disclosure and the Second Therapeutic Agent are administered in combination to a subject separately, e.g., as two or more separate pharmaceutical compositions. For example, the Second Therapeutic Agent may comprise one of a glucocorticoid receptor agonist, an immunomodulatory drug, a proteasome inhibitor, a Bcl-2 inhibitor, a pleiotropic pathway modulator, a XPO1 inhibitor, a histone deacetylase inhibitor, or an EZH2 inhibitor. In this case, two separate pharmaceutical compositions—one comprising the Compound of the Disclosure and one comprising the Second Therapeutic Agent—are administered to a subject. The Second Therapeutic Agent may comprise a combination of two of a glucocorticoid receptor agonist, an immunomodulatory drug, a proteasome inhibitor, a Bcl-2 inhibitor, a pleiotropic pathway modulator, a XPO1 inhibitor, a histone deacetylase inhibitor, or an EZH2 inhibitor. In this case, three separate pharmaceutical compositions—one comprising the Compound of the Disclosure, one comprising the first Second Therapeutic Agent, and one comprising the second Second Therapeutic Agent—are administered to a subject. Likewise, if the Second Therapeutic Agent comprises a combination of three or more of a glucocorticoid receptor agonist, an immunomodulatory drug, a proteasome inhibitor, a Bcl-2 inhibitor, a pleiotropic pathway modulator, a XPO1 inhibitor, a histone deacetylase inhibitor, or an EZH2 inhibitor. The separate pharmaceutical compositions can be administered to the subject, for example, at different periodicities, at different durations, or by different administration routes.

In some embodiments, a Compound of the Disclosure is administered to the patient prior to the Second Therapeutic Agent, e.g., 0.5, 1, 2, 3, 4, 5, 10, 12, or 18 hours, 1, 2, 3, 4, 5, or 6 days, or 1, 2, 3, or 4 weeks prior to the administration of the Second Therapeutic Agent.

In some embodiments, a Compound of the Disclosure is administered after the Second Therapeutic Agent, e.g., 0.5, 1, 2, 3, 4, 5, 10, 12, or 18 hours, 1, 2, 3, 4, 5, or 6 days, or 1, 2, 3, or 4 weeks after the administration of the Second Therapeutic Agent.

In some embodiments, a Compound of the Disclosure and the Second Therapeutic Agent are administered concurrently.

In some embodiments, a Compound of the Disclosure and the Second Therapeutic Agent are administered concurrently but on different schedules, e.g., a Compound of the Disclosure is administered daily while the Second Therapeutic Agent is administered once a week, once every two weeks, once every three weeks, or once every four weeks.

In practice, a physician determines the actual dosing regimen that is most suitable for an individual patient, which can vary with the age, weight, and response of the particular patient.

In another embodiment, the present disclosure provides kits which comprise a Compound of the Disclosure (or a composition comprising a Compound of the Disclosure) packaged in a manner that facilitates their use to practice methods of the present disclosure. In one embodiment, the kit includes a Compound of the Disclosure (or a composition comprising a Compound of the Disclosure) packaged in a container, such as a sealed bottle or vessel, with a label affixed to the container or included in the kit that describes use of the compound or composition to practice the method of the disclosure. In one embodiment, the compound or composition is packaged in a unit dosage form. The kit further can include a device suitable for administering the composition according to the intended route of administration. The kit further can include a Second Therapeutic Agent. In some embodiments, the kit comprises a Compound of the Disclosure and a Second Therapeutic Agent as separate pharmaceutical compositions.

IV. Biomarkers

In another embodiment, present disclosure provides methods of treating a subject having cancer, e.g., multiple myeloma, comprising (a) determining whether a biomarker is present or absent in a biological sample taken from the subject; and (b) administering a therapeutically effective amount of a Compound of the Disclosure and, optionally, a Second Therapeutic Agent to the subject if the biomarker is present in the biological sample. See, e.g., Goossens et al., *Transl Cancer Res.* 4:256-269 (2015); Kamel and Al-Amodi, *Genomics Proteomics Bioinformatics* 15:220-235 (2017); and Konikova and Kusenda, Neoplasma 50:31-40 (2003).

Biomarkers include, but are not limited to, chromosomal translocations in a cancer, e.g., mulitple myeloma, cell and WHSC1/NSD2/MMSET expression. In one embodiment, the measurable aspect of the biomarker is its expression status. In one embodiment, the measurable aspect of the biomarker is its mutation status.

In one embodiment, the biomarker is WHSC1/NSD2/MMSET expression which is differentially present in a subject of one phenotypic status, e.g., a subject having a hematological cancer, as compared with another phenotypic status, e.g., a normal undiseased subject or a patient having cancer without overexpression WHSC1/NSD2/MMSET. In one embodiment, the biomarker is overexpression of WHSC1/NSD2/MMSET.

Biomarker standards can be predetermined, determined concurrently, or determined after a biological sample is obtained from the subject. Biomarker standards for use with the methods described herein can, for example, include data from samples from subjects without cancer; data from samples from subjects with cancer, e.g., breast cancer, that is not metastatic; and data from samples from subjects with cancer, e.g., breast cancer, that metastatic. Comparisons can be made to establish predetermined threshold biomarker standards for different classes of subjects, e.g., diseased vs. non-diseased subjects. The standards can be run in the same assay or can be known standards from a previous assay.

A biomarker is differentially present between different phenotypic status groups if the mean or median expression or mutation levels of the biomarker is calculated to be different, i.e., higher or lower, between the groups. Thus, biomarkers provide an indication that a subject, e.g., a cancer patient, belongs to one phenotypic status or another.

The determination of the expression level or mutation status of a biomarker in a patient can be performed using any of the many methods known in the art. Any method known in the art for quantitating specific proteins and/or detecting WHSC1/NSD2/MMSET expression and/or chromosomal translocations, or the expression or mutation levels of any other biomarker in a patient or a biological sample may be used in the methods of the disclosure. Examples include, but are not limited to, PCR (polymerase chain reaction), or RT-PCR, flow cytometry, Northern blot, Western blot, ELISA (enzyme linked immunosorbent assay), RIA (radioimmunoassay), gene chip analysis of RNA expression, immunohistochemistry or immunofluorescence. See, e.g., Slagle et al. Cancer 83: 1401 (1998); Hudlebusch et al., *Clin Cancer Res* 17: 2919-2933 (2011). Certain embodiments of the disclosure include methods wherein biomarker RNA expression (transcription) is determined. Other embodiments of the disclosure include methods wherein protein expression in the biological sample is determined. See, e.g., Harlow et al., Antibodies: A Laboratory Manual, Cold Spring Harbor Laboratory, Cold Spring Harbor, NY, (1988); Ausubel et al., Current Protocols in Molecular Biology, John Wiley & Sons, New York 3rd Edition, (1995); Kamel and Al-Amodi, *Genomics Proteomics Bioinformatics* 15:220-235 (2017). For northern blot or RT-PCR analysis, RNA is isolated from the tumor tissue sample using RNAse free techniques. Such techniques are commonly known in the art.

In one embodiment of the disclosure, a biological sample is obtained from the patient and the biological sample is assayed for determination of a biomarker expression or mutation status.

In one embodiment, the present disclosure provides a method of treating a subject having cancer, e.g., multiple myeloma, the method comprising: (a) determining whether a chromosomal translocation is present or absent in a biological sample taken from the subject; and (b) administering a therapeutically effective amount of a Compound of the Disclosure and, optionally, a Second Theraputic Agent to the subject if a chromosomal translocation is present in the biological sample.

In another embodiment, the present disclosure provides a method of treating a subject having cancer, e.g., multiple myeloma, the method comprising administering a therapeutically effective amount of a Compound of the Disclosure and, optionally, a Second Therapetuic Agent to the subject having a chromosomal translocation.

In another embodiment, the present disclosure provides a method, comprising administering a therapeutically effective amount of a Compound of the Disclosure and, optionally, a Second Therapeutic Agent, to a subject in need thereof, wherein: (a) the subject has multiple myeloma; and (b) the multiple myeloma is characterized as having a chromosomal translocation.

In any of the above embodiments, the chromosomal translocation is a t(4;14) translocation.

In one embodiment, the present disclosure provides a method of treating a subject having multiple myeloma, the method comprising: (a) determining whether an overexpression of WHSC1/NSD2/MMSET is present or absent in a biological sample taken from the subject; and (b) administering a therapeutically effective amount of a Compound of the Disclosure and, optionally, a Second Therapeutic Agent, to the subject if an overexpression of WHSC1/NSD2/MMSET is present in the biological sample.

In one embodiment, the present disclosure provides a method of treating a subject having multiple myeloma, the method comprising administering a therapeutically effective amount of a Compound of the Disclosure and, optionally, a Second Therapeutic Agent, to the subject if an overexpression of WHSC1/NSD2/MMSET is present in subject.

In another embodiment, the present disclosure provides a method, comprising administering a therapeutically effective amount of a Compound of the Disclosure and, optionally, a Second Therapeutic Agent, to a subject in need thereof, wherein: (a) the subject has multiple myeloma; and (b) the multiple myeloma is characterized as having an overexpression of WHSC1/NSD2/MMSET.

V. Definitions

The term "halo" as used herein by itself or as part of another group refers to —Cl, —F, —Br, or —I.

The term "nitro" as used herein by itself or as part of another group refers to $—NO_2$.

The term "cyano" as used herein by itself or as part of another group refers to —CN.

The term "hydroxy" as herein used by itself or as part of another group refers to —OH.

The term "alkyl" as used herein by itself or as part of another group refers to a straight- or branched-chain aliphatic hydrocarbon containing one to twelve carbon atoms, i.e., a $C_1$-$C_{12}$ alkyl, or the number of carbon atoms designated, e.g., a $C_1$ alkyl such as methyl, a $C_2$ alkyl such as ethyl, etc. In one embodiment, the alkyl is a $C_1$-$C_{10}$ alkyl. In another embodiment, the alkyl is a $C_1$-$C_6$ alkyl. In another embodiment, the alkyl is a $C_1$-$C_4$ alkyl. In another embodiment, the alkyl is a $C_1$-$C_3$ alkyl, i.e., methyl, ethyl, propyl, or isopropyl. Non-limiting exemplary $C_1$-$C_{12}$ alkyl groups include methyl, ethyl, propyl, isopropyl, butyl, sec-butyl, tent-butyl, iso-butyl, 3-pentyl, hexyl, heptyl, octyl, nonyl, and decyl.

The term "optionally substituted alkyl" as used herein by itself or as part of another group refers to an alkyl group that is either unsubstituted or substituted with one, two, or three substituents, wherein each substituent is independently nitro, haloalkoxy, aryloxy, aralkyloxy, alkylthio, sulfonamido, alkylcarbonyl, arylcarbonyl, alkyl sulfonyl, aryl sulfonyl, ureido, guanidino, carbamate, carboxy, alkoxycarbonyl, carboxyalkyl, $—N(R^{56a})C(=O)R^{56b}$, $—N(R^{56c})S(=O)_2R^{56d}$, $—C(=O)R^{57}$, $—S(=O)R^{56e}$, $—S(=O)_2R^{58}$, $—N(R^{56a})C(=N—R^{60})R^{61}$, $—N(R^{56a})C(=C—NO_2)R^{64}$, $—C(—N—R^{60})R^{61}$, or $—C(=C—NO_2)R^{64}$; wherein:

$R^{56a}$ is hydrogen or alkyl;

$R^{56b}$ is alkyl, haloalkyl, optionally substituted cycloalkyl, alkoxy, (alkoxy)alkyl, (aryl)alkyl, (heteroaryl)alkyl, (amino) alkyl, (hydroxy)alkyl, (cyano)alkyl, optionally substituted alkenyl, optionally substituted alkynyl, optionally substituted cycloalkyl, optionally substituted heterocycle, optionally substituted $C_6$-$C_{10}$ aryl, or optionally substituted heteroaryl;

$R^{56c}$ is hydrogen or alkyl;

$R^{56d}$ is alkyl, haloalkyl, optionally substituted cycloalkyl, alkoxy, (alkoxy)alkyl, (aryl)alkyl, (heteroaryl)alkyl, (amino) alkyl, (hydroxy)alkyl, (cyano)alkyl, optionally substituted alkenyl, optionally substituted alkynyl, optionally substituted cycloalkyl, optionally substituted heterocycle, optionally substituted $C_6$-$C_{10}$ aryl, or optionally substituted heteroaryl;

$R^{56e}$ is alkyl, haloalkyl, optionally substituted cycloalkyl, alkoxy, (alkoxy)alkyl, (aryl)alkyl, (heteroaryl)alkyl, (amino) alkyl, (hydroxy)alkyl, (cyano)alkyl, optionally substituted alkenyl, optionally substituted alkynyl, optionally substituted cycloalkyl, optionally substituted heterocycle, optionally substituted $C_6$-$C_{10}$ aryl, or optionally substituted heteroaryl;

$R^{57}$ is haloalkyl, amino, optionally substituted cycloalkyl, alkoxy, (alkoxy)alkyl, (aryl)alkyl, (heteroaryl)alkyl, (amino) alkyl, (hydroxy)alkyl, (cyano)alkyl, optionally substituted alkenyl, optionally substituted alkynyl, optionally substituted cycloalkyl, optionally substituted heterocycle, optionally substituted heteroaryl, ($C_3$-$C_6$ cycloalkyl)oxy, or (4- to 8-membered heterocyclo)oxy;

$R^{58}$ is haloalkyl, optionally substituted cycloalkyl, alkoxy, (alkoxy)alkyl, (aryl)alkyl, (heteroaryl)alkyl, (amino)alkyl, (hydroxy)alkyl, (cyano)alkyl, optionally substituted alkenyl, optionally substituted alkynyl, optionally substituted cycloalkyl, optionally substituted heterocycle, or optionally substituted heteroaryl;

$R^{60}$ is selected from the group consisting of cyano, nitro, hydroxy, $C_1$-$C_6$ alkoxy, —C(═O)$R^{62}$, and —S(═O)$_2R^{62}$;

$R^{61}$ is selected from the group consisting of $C_1$-$C_6$ alkyl, $C_3$-$C_6$ cycloalkyl, and —$NR^{63a}R^{63b}$;

$R^{62}$ is selected from the group consisting of $C_1$-$C_6$ alkyl, $C_3$-$C_6$ cycloalkyl, and —$NR^{63a}R^{63b}$;

$R^{63a}$ is selected from the group consisting of hydrogen, $C_1$-$C_6$ alkyl, and $C_3$-$C_6$ cycloalkyl;

$R^{63b}$ is selected from the group consisting of hydrogen, $C_1$-$C_6$ alkyl, and $C_3$-$C_6$ cycloalkyl; or $R^{63a}$ and $R^{63b}$ taken together with the nitrogen atom to which they are attached form a 4- to 6-membered optionally substituted heterocyclo;

$R^{64}$ is selected from the group consisting of $C_1$-$C_6$ alkyl, $C_3$-$C_6$ cycloalkyl, and —$NR^{63c}R^{63d}$; and $R^{63c}$ is selected from the group consisting of hydrogen, $C_1$-$C_6$ alkyl, and $C_3$-$C_6$ cycloalkyl;

$R^{63d}$ is selected from the group consisting of hydrogen, $C_1$-$C_6$ alkyl, and $C_3$-$C_6$ cycloalkyl; or $R^{63c}$ and $R^{63d}$ taken together with the nitrogen atom to which they are attached form a 4- to 6-membered optionally substituted heterocyclo.

In one embodiment, the optionally substituted alkyl is either unsubstituted or substituted with one, two, or three substituents, wherein each substituent is independently nitro, haloalkoxy, aryloxy, aralkyloxy, alkylthio, sulfonamido, alkylcarbonyl, arylcarbonyl, alkyl sulfonyl, aryl sulfonyl, ureido, guanidino, carbamate, carboxy, alkoxycarbonyl, carboxyalkyl, —N($R^{56a}$)C(═O)$R^{56b}$, —N($R^{56c}$)S(═O)$_2$ $R^{56d}$, —C(═O)$R^{57}$, —S(═O)$R^{56e}$, or —S(═O)$_2R^{58}$.

In another embodiment, the optionally substituted alkyl is substituted with two substituents. In another embodiment, the optionally substituted alkyl is substituted with one substituent. In another embodiment, the optionally substituted alkyl is an optionally substituted $C_1$-$C_6$ alkyl. In another embodiment, the optionally substituted alkyl is an optionally substituted $C_1$-$C_4$ alkyl. In one embodiment, the optionally substituted alkyl is an optionally substituted is a $C_1$ or $C_2$ alkyl. Non-limiting exemplary optionally substituted alkyl groups include —CH($CO_2$Me)$CH_2CO_2$Me and —CH($CH_3$)$CH_2$N(H)C(═O)O($CH_3$)$_3$.

The term "alkenyl" as used herein by itself or as part of another group refers to an alkyl group containing one, two, or three carbon-to-carbon double bonds. In one embodiment, the alkenyl group is a $C_2$-$C_6$ alkenyl group. In another embodiment, the alkenyl group is a $C_2$-$C_4$ alkenyl group. In another embodiment, the alkenyl group has one carbon-to-carbon double bond. Non-limiting exemplary alkenyl groups include ethenyl, propenyl, isopropenyl, butenyl, sec-butenyl, pentenyl, and hexenyl.

The term "optionally substituted alkenyl" as used herein by itself or as part of another refers to an alkenyl group that is either unsubstituted or substituted with one, two or three substituents, wherein each substituent is independently halo, nitro, cyano, hydroxy, amino (e.g., alkylamino, dialkylamino), haloalkyl, hydroxyalkyl, alkoxy, haloalkoxy, aryloxy, aralkyloxy, alkylthio, carboxamido, sulfonamido, alkylcarbonyl, arylcarbonyl, alkyl sulfonyl, aryl sulfonyl, ureido, guanidino, carboxy, carboxyalkyl, optionally substituted cycloalkyl, alkenyl, alkynyl, optionally substituted aryl, optionally substituted heteroaryl, or optionally substituted heterocyclo. Non-limiting exemplary optionally substituted alkenyl groups include —CH═CHPh.

The term "alkynyl" as used herein by itself or as part of another group refers to an alkyl group containing one, two, or three carbon-to-carbon triple bonds. In one embodiment, the alkynyl has one carbon-to-carbon triple bond. In another embodiment, the alkynyl is a $C_1$-$C_6$ alkynyl. In another embodiment, the alkynyl is a $C_2$-$C_4$ alkynyl. In another embodiment, the alkynyl has one carbon-to-carbon triple bond. Non-limiting exemplary alkynyl groups include ethynyl, propynyl, butynyl, 2-butynyl, pentynyl, and hexynyl groups.

The term "optionally substituted alkynyl" as used herein by itself or as part of another group refers to an alkynyl group that is either unsubstituted or substituted with one, two or three substituents, wherein each substituent is independently halo, nitro, cyano, hydroxy, amino (e.g., alkylamino, dialkylamino), haloalkyl, hydroxyalkyl, alkoxy, haloalkoxy, aryloxy, aralkyloxy, alkylthio, carboxamido, sulfonamido, alkylcarbonyl, arylcarbonyl, alkyl sulfonyl, aryl sulfonyl, ureido, guanidino, carboxy, carboxyalkyl, optionally substituted cycloalkyl, alkenyl, alkynyl, optionally substituted aryl, optionally substituted heteroaryl, or optionally substituted heterocyclo. Non-limiting exemplary optionally substituted alkynyl groups include —CH≡CHPh.

The term "haloalkyl" as used herein by itself or as part of another group refers to an alkyl group substituted by one or more fluorine, chlorine, bromine, and/or iodine atoms. In one embodiment, the alkyl is substituted by one, two, or three fluorine and/or chlorine atoms. In another embodiment, the alkyl is substituted by one, two, or three fluorine atoms. In another embodiment, the alkyl is a $C_1$-$C_6$ alkyl. In another embodiment, the alkyl is a $C_1$-$C_4$ alkyl. In another embodiment, the alkyl group is a $C_1$ or $C_2$ alkyl. Non-limiting exemplary haloalkyl groups include fluoromethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups.

The terms "hydroxyalkyl" or "(hydroxy)alkyl" as used herein by themselves or as part of another group refer to an alkyl group substituted with one, two, or three hydroxy groups. In one embodiment, the alkyl is a $C_1$-$C_6$ alkyl. In another embodiment, the alkyl is a $C_1$-$C_4$ alkyl. In another embodiment, the alkyl is a $C_1$ or $C_2$ alkyl. In another embodiment, the hydroxyalkyl is a monohydroxyalkyl group, i.e., substituted with one hydroxy group. In another embodiment, the hydroxyalkyl group is a dihydroxyalkyl group, i.e., substituted with two hydroxy groups. Non-limiting exemplary (hydroxyl)alkyl groups include hydroxymethyl, hydroxyethyl, hydroxypropyl and hydroxybutyl groups, such as 1-hydroxyethyl, 2-hydroxyethyl, 1,2-dihydroxyethyl, 2-hydroxypropyl, 3-hydroxypropyl, 3-hydroxybutyl, 4-hydroxybutyl, 2-hydroxy-1-methylpropyl, and 1,3-dihydroxyprop-2-yl.

The term "alkoxy" as used herein by itself or as part of another group refers to an alkyl group attached to a terminal oxygen atom. In one embodiment, the alkyl is a $C_1$-$C_6$ alkyl.

In another embodiment, the alkyl is a $C_1$-$C_4$ alkyl group. Non-limiting exemplary alkoxy groups include methoxy, ethoxy, and tert-butoxy.

The term "haloalkoxy" as used herein by itself or as part of another group refers to a haloalkyl group attached to a terminal oxygen atom. In one embodiment, the haloalkyl is a $C_1$-$C_6$ alkyl. In another embodiment, the haloalkyl group is a $C_1$-$C_4$ haloalkyl group. Non-limiting exemplary haloalkoxy groups include fluoromethoxy, difluoromethoxy, trifluoromethoxy, and 2,2,2-trifluoroethoxy.

The term "alkylthio" as used herein by itself or as part of another group refers to an alkyl group attached to a terminal sulfur atom. In one embodiment, the alkyl group is a $C_1$-$C_4$ alkyl group. Non-limiting exemplary alkylthio groups include $—SCH_3$, and $—SCH_2CH_3$.

The terms "alkoxyalkyl" or "(alkoxy)alkyl" as used herein by themselves or as part of another group refers to an alkyl group substituted with one alkoxy group. In one embodiment, the alkoxy is a $C_1$-$C_6$ alkoxy. In another embodiment, the alkoxy is a $C_1$-$C_4$ alkoxy. In another embodiment, the alkyl is a $C_1$-$C_6$ alkyl. In another embodiment, the alkyl is a $C_1$-$C_4$ alkyl. Non-limiting exemplary alkoxyalkyl groups include methoxymethyl, methoxyethyl, methoxypropyl, methoxybutyl, ethoxymethyl, ethoxyethyl, ethoxypropyl, ethoxybutyl, propoxymethyl, iso-propoxymethyl, propoxyethyl, propoxypropyl, butoxymethyl, tert-butoxymethyl, isobutoxymethyl, sec-butoxymethyl, and pentyloxymethyl.

The term "heteroalkyl" as used herein by itself or part of another group refers to a stable straight or branched chain hydrocarbon radical containing 1 to 10 carbon atoms and at least two heteroatoms, which can be the same or different, selected from O, N, or S, wherein the sulfur atom(s) can optionally be oxidized. The heteroatoms can be placed at any interior position of the heteroalkyl group or at a position at which the heteroalkyl group is attached to the remainder of the molecule. In one embodiment, the heteroalkyl contains two oxygen atoms. In another embodiment, the heteroalkyl contains one oxygen and one nitrogen atom. In another embodiment, the heteroalkyl contains two nitrogen atoms. Non-limiting exemplary heteroalkyl groups include $—OCH_2CH_2NH_2$, $—NHCH_2CH_2OCH_3$, and $—OCH_2CH_2OCH_3$.

The term "cycloalkyl" as used herein by itself or as part of another group refers to saturated and partially unsaturated, e.g., containing one or two double bonds, monocyclic, bicyclic, or tricyclic aliphatic hydrocarbons containing three to twelve carbon atoms, i.e., a $C_{3-12}$ cycloalkyl, or the number of carbons designated, e.g., a $C_3$ cycloalkyl such a cyclopropyl, a $C_4$ cycloalkyl such as cyclobutyl, etc. In one embodiment, the cycloalkyl is bicyclic, i.e., it has two rings. In another embodiment, the cycloalkyl is monocyclic, i.e., it has one ring. In another embodiment, the cycloalkyl is a $C_{3-8}$ cycloalkyl. In another embodiment, the cycloalkyl is a $C_{3-6}$ cycloalkyl, i.e., cyclopropyl, cyclobutyl, cyclopentyl, or cyclohexyl. In another embodiment, the cycloalkyl is a $C_5$ cycloalkyl, i.e., cyclopentyl. In another embodiment, the cycloalkyl is a $C_6$ cycloalkyl, i.e., cyclohexyl. Non-limiting exemplary $C_{3-12}$ cycloalkyl groups include cyclopropyl, cyclobutyl, cyclopentyl, cyclohexyl, cycloheptyl, cyclooctyl, norbornyl, decalin, adamantyl, cyclohexenyl, and spiro [3.3]heptane.

The term "optionally substituted cycloalkyl" as used herein by itself or as part of another group refers to a cycloalkyl group is either unsubstituted or substituted with one, two, or three substituents, wherein each substituent is independently halo, nitro, cyano, hydroxy, amino (e.g., $—NH_2$, alkylamino, dialkylamino, aralkylamino, hydroxyalkylamino, or (heterocyclo)alkylamino), heteroalkyl, haloalkyl, hydroxyalkyl, alkoxy, haloalkoxy, aryloxy, aralkyl, aralkyloxy, alkylthio, carboxamido, sulfonamido, alkylcarbonyl, arylcarbonyl, alkyl sulfonyl, aryl sulfonyl, ureido, guanidino, carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (cyano)alkyl, (carboxamido)alkyl, mercaptoalkyl, (heterocyclo)alkyl, (heteroaryl)alkyl, $—N(R^{56a})C(=O)R^{56b}$, $—N(R^{56c})S(=O)_2R^{56d}$, $—C(=O)R^{57}$, $—S(=O)R^{56e}$, $—S(=O)_2R^{58}$, $—OR^{59}$, $—N(R^{56a})C(=N—R^{60})R^{61}$, $—N(R^{56a})C(=C—NO_2)R^{64}$, $—C(=N—R^{60})R^{61}$, or $—C(=C—NO_2)R^{64}$; wherein $R^{56a}$, $R^{56b}$, $R^{56c}$, $R^{56d}$, $R^{56e}$, $R^{57}$, $R^{58}$, $R^{60}$, $R^{61}$, and $R^{64}$ are as defined in connection with the term "optionally substituted alkyl" and $R^{59}$ is (hydroxy) alkyl or (amino)alkyl. Non-limiting exemplary optionally substituted cycloalkyl groups include 3-(4-acetylpiperazin-1-yl)cyclohexyl, 3-(3-(N-methylacetamido)pyrrolidin-1-yl) cyclohexyl, 3-morpholinocyclohexyl, and 3-(pyrimidin-5-yl)cyclohexyl. In one embodiment, the optionally substituted cycloalkyl is either unsubstituted or substituted with one, two, or three substituents, wherein each substituent is independently halo, nitro, cyano, hydroxy, amino (e.g., $—NH_2$, alkylamino, dialkylamino, aralkylamino, hydroxyalkylamino, or (heterocyclo)alkylamino), heteroalkyl, haloalkyl, hydroxyalkyl, alkoxy, haloalkoxy, aryloxy, aralkyl, aralkyloxy, alkylthio, carboxamido, sulfonami do, alkylcarbonyl, arylcarbonyl, alkyl sulfonyl, aryl sulfonyl, ureido, guanidino, carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (cyano)alkyl, (carboxamido)alkyl, mercaptoalkyl, (heterocyclo)alkyl, (heteroaryl)alkyl, $—N(R^{56a})C(=O)R^{56b}$, $—N(R^{56c})S(=O)_2R^{56d}$, $—C(=O)R^{57}$, $—S(=O)R^{56e}$, $—S(=O)_2R^{58}$, and $—OR^{59}$.

The term "heterocyclo" as used herein by itself or as part of another group refers to saturated and partially unsaturated, e.g., containing one or two double bonds, monocyclic, bicyclic, or tricyclic groups containing three to fourteen ring members, i.e., a 3- to 14-membered heterocyclo, comprising one, two, three, or four heteroatoms. Each heteroatom is independently oxygen, sulfur, or nitrogen. Each sulfur atom is independently oxidized to give a sulfoxide, i.e., S(=O), or sulfone, i.e., $S(=O)_2$.

The term heterocyclo includes groups wherein one or more $—CH_2—$ groups is replaced with one or more —C(=O)— groups, including cyclic ureido groups such as imidazolidinyl-2-one, cyclic amide groups such as pyrrolidin-2-one or piperidin-2-one, and cyclic carbamate groups such as oxazolidinyl-2-one.

The term heterocyclo also includes groups having fused optionally substituted aryl or optionally substituted heteroaryl groups such as indoline, indolin-2-one, 2,3-dihydro-1H-pyrrolo[2,3-c]pyridine, 2,3,4,5-tetrahydro-1H-benzo[d] azepine, or 1,3,4,5-tetrahydro-2H-benzo[d]azepin-2-one.

In one embodiment, the heterocyclo group is a 4- to 8-membered cyclic group containing one ring and one or two oxygen atoms, e.g., tetrahydrofuran or tetrahydropyran, or one or two nitrogen atoms, e.g., pyrrolidine, piperidine, or piperazine, or one oxygen and one nitrogen atom, e.g., morpholine, and, optionally, one $—CH_2—$ group is replaced with one —C(=O)— group, e.g., pyrrolidin-2-one or piperazin-2-one. In another embodiment, the heterocyclo group is a 5- to 8-membered cyclic group containing one ring and one or two nitrogen atoms and, optionally, one $-CH_2-$ group is replaced with one $-C(=O)-$ group. In another embodiment, the heterocyclo group is a 5- or 6-membered cyclic group containing one ring and one or two nitrogen atoms and, optionally, one $-CH_2-$ group is replaced with one $-C(=O)-$ group. In another embodiment, the heterocyclo group is a 8- to 12-membered cyclic group containing two rings and one or two nitrogen atoms. The heterocyclo can be linked to the rest of the molecule through any available carbon or nitrogen atom. Non-limiting exemplary heterocyclo groups include:

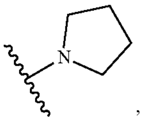 ,
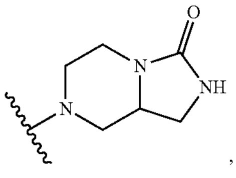 ,
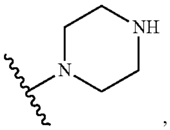 ,
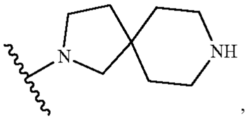 ,
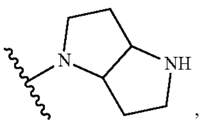 ,
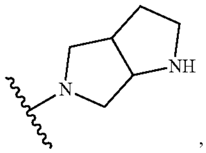 ,
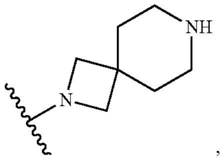 ,
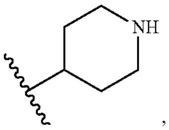 ,
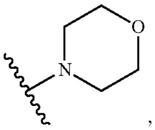 ,
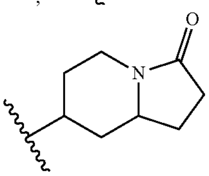 ,
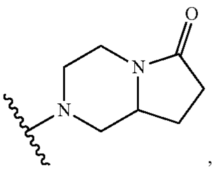 ,
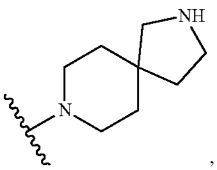 ,
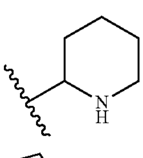 ,
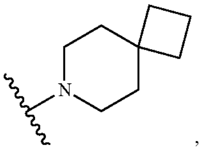 ,
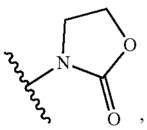 ,
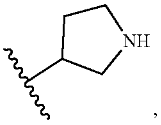 ,
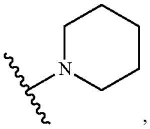 ,
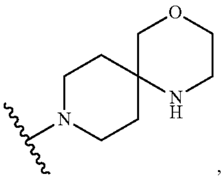 ,
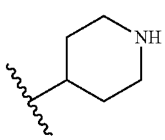 , -continued

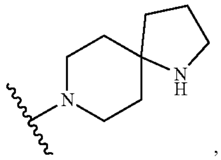 ,
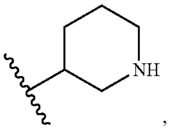 ,
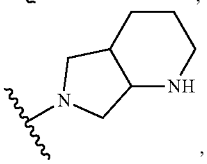 ,
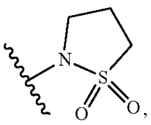 ,
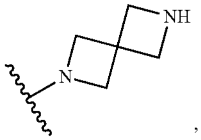 ,
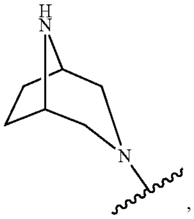 ,
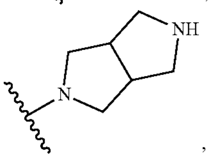 ,
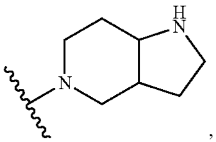 ,
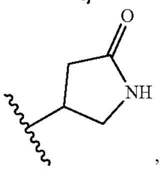 ,
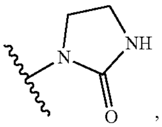 ,
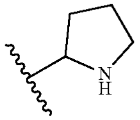 and
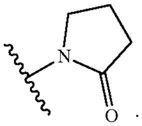 .

The term "optionally substituted heterocyclo" as used herein by itself or part of another group refers to a heterocyclo group that is either unsubstituted or substituted with one to four substituents, wherein each substituent is independently halo, nitro, cyano, hydroxy, amino, (e.g., $-NH_2$, alkylamino, dialkylamino, aralkylamino, hydroxyalkylamino, or (heterocyclo)alkylamino), heteroalkyl, haloalkyl, hydroxyalkyl, alkoxy, haloalkoxy, aryloxy, aralkyl, aralkyloxy, alkylthio, carboxamido, sulfonamido, alkylcarbonyl, arylcarbonyl, alkyl sulfonyl, aryl sulfonyl, ureido, guanidino, carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (cyano)alkyl, (carboxamido)alkyl, mercaptoalkyl, (heterocyclo)alkyl, (heteroaryl)alkyl, $-N(R^{56a})C(=O)R^{56b}$, $-N(R^{56c})S(=O)_2R^{56d}$, $-C(=O)R^{57}$, $-S(=O)R^{56e}$, $-S(=O)_2R^{58}$, $-OR^{59}$, $-N(R^{56a})C(=N-R^{60})R^{61}$, $-N(R^{56a})C(=C-NO_2)R^{64}$, $-C(=N-R^{60})R^{61}$, or $-C(=C-NO_2)R^{64}$; wherein $R^{56a}$, $R^{56b}$, $R^{56c}$, $R^{56d}$, $R^{56e}$, $R^{57}$, $R^{58}$, $R^{59}$, $R^{60}$, $R^{61}$, and $R^{64}$ are as defined in connection with the term "optionally substituted cycloalkyl." Substitution may occur on any available carbon or nitrogen atom of the heterocyclo group. In one embodiment, the optionally substituted heterocyclo is either unsubstituted or substituted with one to four substituents, wherein each substituent is independently halo, nitro, cyano, hydroxy, amino, (e.g., $-NH_2$, alkylamino, dialkylamino, aralkylamino, hydroxy alkyl amino, or (heterocyclo)alkylamino), heteroalkyl, haloalkyl, hydroxyalkyl, alkoxy, haloalkoxy, aryloxy, aralkyl, aralkyloxy, alkylthio, carboxamido, sulfonami do, alkylcarbonyl, arylcarbonyl, alkyl sulfonyl, aryl sulfonyl, ureido, guanidino, carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (cyano)alkyl, (carboxamido)alkyl, mercaptoalkyl, (heterocyclo)alkyl, (heteroaryl)alkyl, —N($R^{56a}$)C(=O)$R^{56b}$, —N($R^{56c}$)S(=O)$_2R^{56d}$, —C(=O)$R^{57}$, —S(=O)$R^{56e}$, —S(=O)$_2R^{58}$, or —O$R^{59}$.

Non-limiting exemplary optionally substituted heterocyclo groups include:

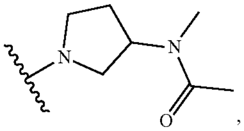,
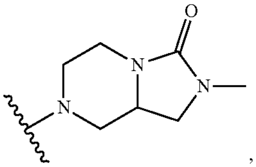,
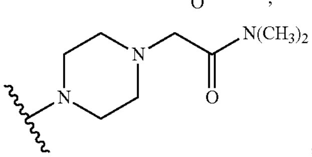,
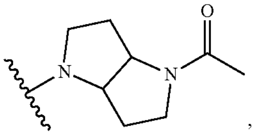,
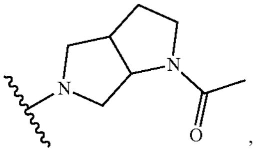,
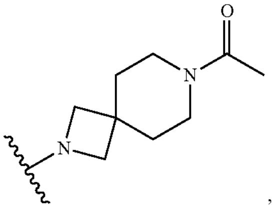,
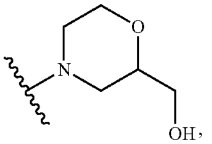,
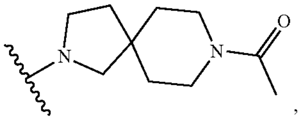,
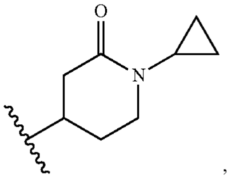,
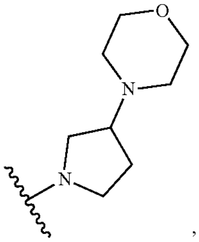,
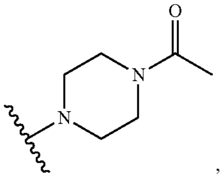,
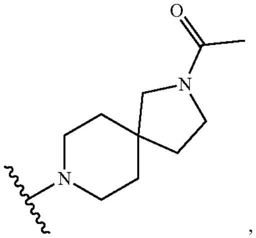, -continued

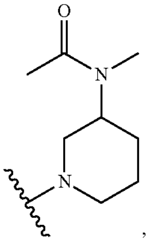,
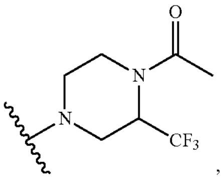,
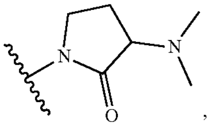,
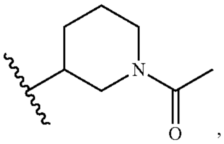,
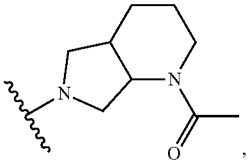,
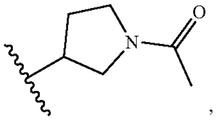,
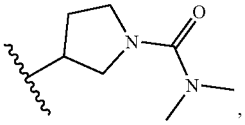,
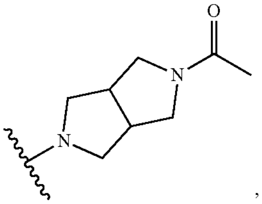,
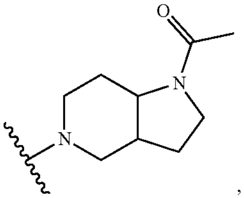,
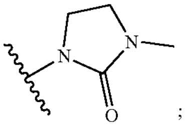;
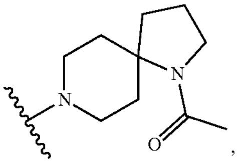, and
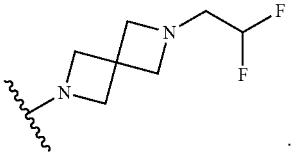.

The term "aryl" as used herein by itself or as part of another group refers to an aromatic ring system having six to fourteen carbon atoms, i.e., $C_6$-$C_{14}$ aryl. Non-limiting exemplary aryl groups include phenyl (abbreviated as "Ph"), naphthyl, phenanthryl, anthracyl, indenyl, azulenyl, biphenyl, biphenylenyl, and fluorenyl groups. In one embodiment, the aryl group is phenyl or naphthyl. In another embodiment, the aryl group is phenyl.

The term "optionally substituted aryl" as used herein by itself or as part of another group refers to aryl that is either unsubstituted or substituted with one to five substituents, wherein the substituents are each independently halo, nitro, cyano, hydroxy, amino, (e.g., —$NH_2$, alkylamino, dialkylamino, aralkylamino, hydroxy alkyl amino, or (heterocyclo) alkylamino), heteroalkyl, haloalkyl, hydroxyalkyl, alkoxy, haloalkoxy, aryloxy, aralkyl, aralkyloxy, alkylthio, carboxamido, sulfonami do, alkylcarbonyl, arylcarbonyl, alkyl sulfonyl, aryl sulfonyl, ureido, guanidino, carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (cyano)alkyl, (carboxamido)alkyl, mercaptoalkyl, (heterocyclo)alkyl, (heteroaryl) alkyl, —N($R^{56a}$)C(═O)$R^{56b}$, —N($R^{56c}$)S(═O)$_2R^{56d}$, —C(═O)$R^{57}$, —S(═O)$R^{56e}$, —S(═O)$_2R^{58}$, —O$R^{59}$, —N($R^{56a}$)C(═N—$R^{60}$)$R^{61}$, —N($R^{56a}$)C(═C—$NO_2$)$R^{64}$, —C(═N—$R^{60}$)$R^{61}$, or —C(═C—$NO_2$)$R^{64}$; wherein $R^{56a}$, $R^{56b}$, $R^{56c}$, $R^{56d}$, $R^{56e}$, $R^{57}$, $R^{58}$, $R^{59}$, $R^{60}$, $R^{61}$, and $R^{64}$ are as defined in connection with the term "optionally substituted cycloalkyl." In one embodiment, the optionally substituted aryl is either unsubstituted or substituted with one to five substituents, wherein the substituents are each independently halo, nitro, cyano, hydroxy, amino, (e.g., —$NH_2$, alkylamino, dialkylamino, aralkylamino, hydroxyalkylamino, or (heterocyclo)alkylamino), heteroalkyl, haloalkyl, hydroxyalkyl, alkoxy, haloalkoxy, aryloxy, aralkyl, aralkyloxy, alkylthio, carboxamido, sulfonamido, alkylcarbonyl, arylcarbonyl, alkyl sulfonyl, aryl sulfonyl, ureido, guanidino, carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (cyano)alkyl, (carboxamido)alkyl, mercaptoalkyl, (heterocyclo)alkyl, (heteroaryl)alkyl, —N($R^{56a}$)C(═O)$R^{56b}$, —N($R^{56c}$)S(═O)$_2R^{56d}$, —C(═O)$R^{57}$, —S(═O)$R^{56e}$, —S(═O)$_2R^{58}$, or —O$R^{59}$.

In one embodiment, the optionally substituted aryl is an optionally substituted phenyl. In another embodiment, the optionally substituted phenyl has four substituents. In another embodiment, the optionally substituted phenyl has three substituents. In another embodiment, the optionally substituted phenyl has two substituents. In another embodiment, the optionally substituted phenyl has one substituent. Non-limiting exemplary optionally substituted aryl groups include 2-methylphenyl, 2-methoxyphenyl, 2-fluorophenyl, 2-chlorophenyl, 2-bromophenyl, 3-methylphenyl, 3-methoxyphenyl, 3-fluorophenyl, 3-chlorophenyl, 4-methylphenyl, 4-ethylphenyl, 4-methoxyphenyl, 4-fluorophenyl, 4-chlorophenyl, 2,6-di-fluorophenyl, 2,6-di-chlorophenyl, 2-methyl, 3-methoxyphenyl, 2-ethyl, 3-methoxyphenyl, 3,4-di-methoxyphenyl, 3,5-di-fluorophenyl 3,5-di-methylphenyl, 3,5-dimethoxy, 4-methylphenyl, 2-fluoro-3-chlorophenyl, 3-chloro-4-fluorophenyl, and 2-phenylpropan-2-amine. The term optionally substituted aryl includes aryl groups having fused optionally substituted cycloalkyl groups and fused optionally substituted heterocyclo groups. Non-limiting examples include: 2,3-dihydro-1H-inden-1-yl, 1,2,3,4-tetrahydronaphthalen-1-yl, 1,3,4,5-tetrahydro-2H-benzo[c]azepin-2-yl, 1,2,3,4-tetrahydroisoquinolin-1-yl, and 2-oxo-2,3,4,5-tetrahydro-1H-benzo[d]azepin-1-yl.

The term "heteroaryl" as used herein by itself or as part of another group refers to monocyclic and bicyclic aromatic ring systems having five to 14 fourteen ring members, i.e., a 5- to 14-membered heteroaryl, comprising one, two, three, or four heteroatoms. Each heteroatom is independently oxygen, sulfur, or nitrogen. In one embodiment, the heteroaryl has three heteroatoms. In another embodiment, the heteroaryl has two heteroatoms. In another embodiment, the heteroaryl has one heteroatom. In another embodiment, the heteroaryl is a 5- to 10-membered heteroaryl. In another embodiment, the heteroaryl has 5 ring atoms, e.g., thienyl, a 5-membered heteroaryl having four carbon atoms and one sulfur atom. In another embodiment, the heteroaryl has 6 ring atoms, e.g., pyridyl, a 6-membered heteroaryl having five carbon atoms and one nitrogen atom. Non-limiting exemplary heteroaryl groups include thienyl, benzo[b]thienyl, naphtho[2,3-b]thienyl, thianthrenyl, furyl, benzofuryl, pyranyl, i sobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, β-carbolinyl, phenanthridinyl, acridinyl, pyrimidinyl, phenanthrolinyl, phenazinyl, thiazolyl, isothiazolyl, phenothiazolyl, isoxazolyl, furazanyl, and phenoxazinyl. In one embodiment, the heteroaryl is chosen from thienyl (e.g., thien-2-yl and thien-3-yl), furyl (e.g., 2-furyl and 3-furyl), pyrrolyl (e.g., 1H-pyrrol-2-yl and 1H-pyrrol-3-yl), imidazolyl (e.g., 2H-imidazol-2-yl and 2H-imidazol-4-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl) and isoxazolyl (e.g., isoxazol-3-yl, isoxazol-4-yl, and isoxazol-5-yl). The term heteroaryl also includes N-oxides. A non-limiting exemplary N-oxide is pyridyl N-oxide.

The term "optionally substituted heteroaryl" as used herein by itself or as part of another group refers to a heteroaryl that is either unsubstituted or substituted with one to four substituents, wherein the substituents are independently halo, nitro, cyano, hydroxy, amino, (e.g., —$NH_2$, alkylamino, dialkylamino, aralkylamino, hydroxyalkylamino, or (heterocyclo)alkylamino), heteroalkyl, haloalkyl, hydroxyalkyl, alkoxy, haloalkoxy, aryloxy, aralkyl, aralkyloxy, alkylthio, carboxamido, sulfonamido, alkylcarbonyl, arylcarbonyl, alkyl sulfonyl, aryl sulfonyl, ureido, guanidino, carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (cyano)alkyl, (carboxamido)alkyl, mercaptoalkyl, (heterocyclo)alkyl, (heteroaryl)alkyl, —N($R^{56a}$)C(═O)$R^{56b}$, —N($R^{56c}$)S(═O)$_2R^{56d}$, —C(═O)$R^{57}$, —S(═O)$R^{56e}$, —S(═O)$_2R^{58}$, —O$R^{59}$, —N($R^{56a}$)C(═N—$R^{60}$)$R^{61}$, —N($R^{56a}$)C(═C—$NO_2$)$R^{64}$, —C(═N—$R^{60}$)$R^{61}$, or —C(═C—$NO_2$)$R^{64}$; wherein $R^{56a}$, $R^{56b}$, $R^{56c}$, $R^{56d}$, $R^{56e}$, $R^{57}$, $R^{58}$, $R^{59}$, $R^{60}$, $R^{61}$, and $R^{64}$ are as defined in connection with the term "optionally substituted cycloalkyl." In one embodiment, optionally substituted heteroaryl is either unsubstituted or substituted with one to four substituents, wherein the substituents are independently halo, nitro, cyano, hydroxy, amino, (e.g., —$NH_2$, alkylamino, dialkylamino, aralkylamino, hydroxyalkylamino, or (heterocyclo) alkylamino), heteroalkyl, haloalkyl, hydroxyalkyl, alkoxy, haloalkoxy, aryloxy, aralkyl, aralkyloxy, alkylthio, carboxamido, sulfonamido, alkylcarbonyl, arylcarbonyl, alkyl sulfonyl, aryl sulfonyl, ureido, guanidino, carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (cyano)alkyl, (carboxamido)alkyl, mercaptoalkyl, (heterocyclo)alkyl, (heteroaryl) alkyl, —N($R^{56a}$)C(═O)$R^{56b}$, —N($R^{56c}$)S(═O)$_2R^{56d}$, —C(═O)$R^{57}$, —S(═O)$R^{56e}$, —S(═O)$_2R^{58}$, or —O$R^{59}$.

In one embodiment, the optionally substituted heteroaryl has two substituents. In another embodiment, the optionally substituted heteroaryl has one substituent. Any available carbon or nitrogen atom can be substituted.

The term "aryloxy" as used herein by itself or as part of another group refers to an optionally substituted aryl attached to a terminal oxygen atom. A non-limiting exemplary aryloxy group is PhO—.

The term “heteroaryloxy” as used herein by itself or as part of another group refers to an optionally substituted heteroaryl attached to a terminal oxygen atom. A non-limiting exemplary aryloxy group is pyridyl-O—.

The term “aralkyloxy” as used herein by itself or as part of another group refers to an aralkyl attached to a terminal oxygen atom. A non-limiting exemplary aralkyloxy group is $PhCH_2O$—.

The term “(cycloalkyl)oxy” as used herein by itself or as part of another group refers to a cycloalkyl group attached to a terminal oxygen atom. A non-limiting exemplary cycloalkyloxy group is:

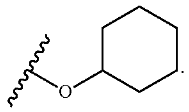 [SMILES: *OC1CCCCC1]

The term “(heterocyclo)oxy” as used herein by itself or as part of another group refers to a heterocyclo group attached to a terminal oxygen atom. A non-limiting exemplary (heterocyclo)oxy group is:

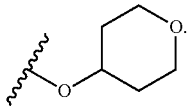 [SMILES: *OC1CCOCC1]

The term “(cyano)alkyl” as used herein by itself or as part of another group refers to an alkyl substituted with one, two, or three cyano groups. In one embodiment, the alkyl is substituted with one cyano group. In another embodiment, the alkyl is a $C_1$-$C_6$ alkyl In another embodiment, the alkyl is a $C_1$-$C_4$ alkyl. Non-limiting exemplary (cyano)alkyl groups include —$CH_2CH_2CN$ and —$CH_2CH_2CH_2CN$.

The term “(cycloalkyl)alkyl” as used herein by itself or as part of another group refers to an alkyl substituted with one optionally substituted cycloalkyl group. In one embodiment, the cycloalkyl group is an optionally substituted $C_3$-$C_6$ cycloalkyl. In another embodiment, the alkyl is a $C_1$-$C_6$ alkyl. In another embodiment, the alkyl is a $C_1$-$C_4$ alkyl. In another embodiment, the alkyl is a $C_1$ or $C_2$ alkyl. Non-limiting exemplary (cycloalkyl)alkyl groups include:

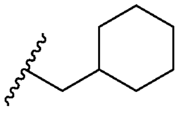
and
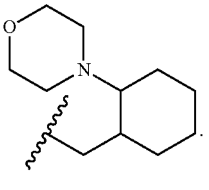

The term “sulfonamido” as used herein by itself or as part of another group refers to a radical of the formula —$SO_2NR^{50a}R^{50b}$, wherein $R^{50a}$ and $R^{50b}$ are each independently hydrogen, alkyl, optionally substituted cycloalkyl, optionally substituted heterocyclo, optionally substituted aryl, or optionally substituted heteroaryl; or $R^{50a}$ and $R^{50b}$ taken together with the nitrogen to which they are attached form a 3- to 8-membered optionally substituted heterocyclo group. Non-limiting exemplary sulfonamido groups include —$SO_2NH_2$, —$SO_2N(H)CH_3$, and —$SO_2N(H)Ph$.

The term “alkylcarbonyl” as used herein by itself or as part of another group refers to a carbonyl group, i.e., —C(═O)—, substituted by an alkyl group. In one embodiment, the alkyl is a $C_1$-$C_4$ alkyl. A non-limiting exemplary alkylcarbonyl group is —$COCH_3$.

The term “arylcarbonyl” as used herein by itself or as part of another group refers to a carbonyl group, i.e., —C(═O)—, substituted by an optionally substituted aryl group. A non-limiting exemplary arylcarbonyl group is —COPh.

The term “alkylsulfonyl” as used herein by itself or as part of another group refers to a sulfonyl group, i.e., —$SO_2$—, substituted by an alkyl group. A non-limiting exemplary alkylsulfonyl group is —$SO_2CH_3$.

The term “arylsulfonyl” as used herein by itself or as part of another group refers to a sulfonyl group, i.e., —$SO_2$—, substituted by an optionally substituted aryl group. A non-limiting exemplary arylsulfonyl group is —$SO_2Ph$.

The term “mercaptoalkyl” as used herein by itself or as part of another group refers to an alkyl substituted by a —SH group.

The term “carboxy” as used by itself or as part of another group refers to a radical of the formula —C(═O)OH.

The term “ureido” as used herein by itself or as part of another group refers to a radical of the formula —$NR^{51a}$—C(═O)—$NR^{51b}R^{51c}$, wherein $R^{51a}$ is hydrogen or alkyl; and $R^{51b}$ and $R^{51c}$ are each independently hydrogen, alkyl, optionally substituted cycloalkyl, optionally substituted heterocyclo, optionally substituted aryl, or optionally substituted heteroaryl, or $R^{51b}$ and $R^{51c}$ taken together with the nitrogen to which they are attached form a 4- to 8-membered optionally substituted heterocyclo group. Non-limiting exemplary ureido groups include —NH—C(C═O)—$NH_2$ and —NH—C(C═O)—$NHCH_3$.

The term “guanidino” as used herein by itself or as part of another group refers to a radical of the formula —$NR^{52a}$—C(═$NR^{53}$)—$NR^{52b}R^{52c}$, wherein $R^{52a}$ is hydrogen or alkyl; $R^{52b}$ and $R^{53c}$ are each independently hydrogen, alkyl, optionally substituted cycloalkyl, optionally substituted heterocyclo, optionally substituted aryl, or optionally substituted heteroaryl; or $R^{52b}$ and $R^{52c}$ taken together with the nitrogen to which they are attached form a 4- to 8-membered optionally substituted heterocyclo group; and $R^{53}$ is hydrogen, alkyl, cyano, alkylsulfonyl, alkylcarbonyl, carboxamido, or sulfonamido. Non-limiting exemplary guanidino groups include —NH—C(C═NH)—$NH_2$, —NH—C(C═NCN)—$NH_2$, and —NH—C(C═NH)—$NHCH_3$.

The term “(heterocyclo)alkyl” as used herein by itself or as part of another group refers to an alkyl substituted with one, two, or three optionally substituted heterocyclo groups. In one embodiment, the alkyl is substituted with one optionally substituted 5- to 8-membered heterocyclo group. In another embodiment, alkyl is a $C_1$-$C_6$ alkyl. In another embodiment, alkyl is a $C_1$-$C_4$ alkyl. The heterocyclo group can be linked to the alkyl group through a carbon or nitrogen atom. Non-limiting exemplary (heterocyclo)alkyl groups include:

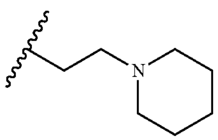
,
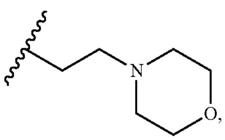
,

-continued

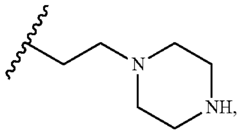

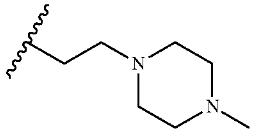
,

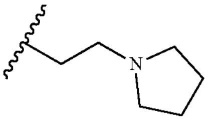
,

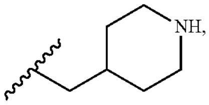

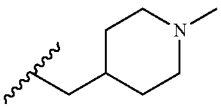
,

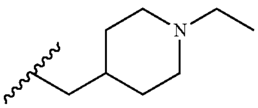
,

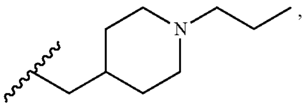
,

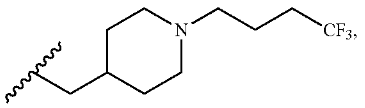

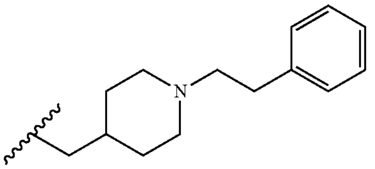
,

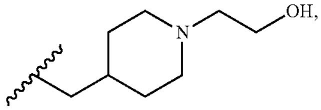

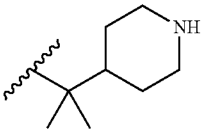
and

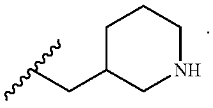
.

The term "carbamate" as used herein by itself or as part of another group refers to a radical of the formula $—NR^{54a}—C(=O)—OR^{54b}$, wherein $R^{54a}$ is hydrogen or alkyl, and $R^{54b}$ is hydrogen, alkyl, optionally substituted cycloalkyl, optionally substituted heterocyclo, optionally substituted aryl, or optionally substituted heteroaryl. A non-limiting exemplary carbamate group is —NH—(C=O)—OtBu.

The term "(heteroaryl)alkyl" as used herein by itself or as part of another group refers to an alkyl substituted with one or two optionally substituted heteroaryl groups. In one embodiment, the alkyl group is substituted with one optionally substituted 5- to 14-membered heteroaryl group. In another embodiment, the alkyl group is substituted with two optionally substituted 5- to 14-membered heteroaryl groups. In another embodiment, the alkyl group is substituted with one optionally substituted 5- to 9-membered heteroaryl group. In another embodiment, the alkyl group is substituted with two optionally substituted 5- to 9-membered heteroaryl groups. In another embodiment, the alkyl group is substituted with one optionally substituted 5- or 6-membered heteroaryl group. In another embodiment, the alkyl group is substituted with two optionally substituted 5- or 6-membered heteroaryl groups. In one embodiment, the alkyl group is a $C_1$-$C_6$ alkyl. In another embodiment, the alkyl group is a $C_1$-$C_4$ alkyl. In another embodiment, the alkyl group is a $C_1$ or $C_2$ alkyl. Non-limiting exemplary (heteroaryl)alkyl groups include:

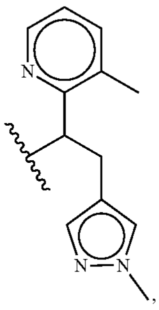
,

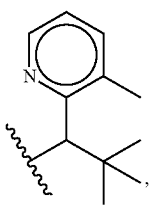
,

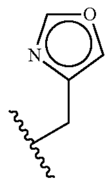
and

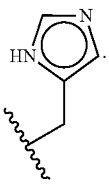
.

The term "(heteroaryl)(aryl)alkyl" as used herein by itself or as part of another group refers to an alkyl group substituted with one optionally substituted heteroaryl group and one optionally substituted aryl group. In one embodiment, the heteroaryl is an optionally substituted 5- to 9-membered heteroaryl group. In another embodiment, the heteroaryl is an optionally substituted 5- or 6-membered heteroaryl group. In one embodiment, the aryl is an optionally substituted phenyl group or optionally substituted naphthyl group. In one embodiment, the alkyl is a $C_1$-$C_6$ alkyl. In another embodiment, the alkyl is a $C_1$-$C_4$ alkyl. In another embodiment, the alkyl is a $C_1$ or $C_2$ alkyl. Non-limiting exemplary (heteroaryl)(aryl)alkyl groups include:

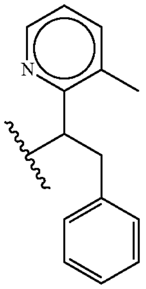
and

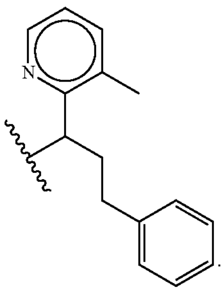
.

The term "(heteroaryl)(heterocyclo)alkyl" as used herein by itself or as part of another group refers to an alkyl group substituted with one optionally substituted heteroaryl group and one optionally substituted heterocyclo group. In one embodiment, the heteroaryl is an optionally substituted 5- to 9-membered heteroaryl group. In another embodiment, the heteroaryl is an optionally substituted 5- or 6-membered heteroaryl group. In one embodiment, the heterocyclo is an optionally substituted 5- to 8-membered heterocyclo. In another embodiment, the heterocyclo is an optionally substituted 5- or 6-membered heterocyclo. In one embodiment, the alkyl is a $C_1$-$C_6$ alkyl. In another embodiment, the alkyl is a $C_1$-$C_4$ alkyl. In another embodiment, the alkyl is a $C_1$ or $C_2$ alkyl. A non-limiting exemplary (heteroaryl)(heterocyclo)alkyl group is:

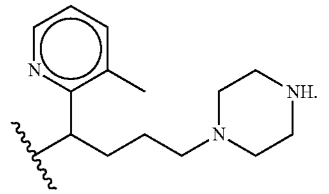

The term "(heteroaryl)(carboxamido)alkyl" as used herein by itself or as part of another group refers to an alkyl group substituted with one optionally substituted heteroaryl group and one carboxamido group. In one embodiment, the heteroaryl is an optionally substituted 5- to 9-membered heteroaryl group. In another embodiment, the heteroaryl is an optionally substituted 5- or 6-membered heteroaryl group. In one embodiment, the alkyl is a $C_1$-$C_6$ alkyl. In another embodiment, the alkyl is a $C_1$-$C_4$ alkyl. In another embodiment, the alkyl is a $C_1$-$C_3$ alkyl. Non-limiting exemplary (heteroaryl)(carboxamido)alkyl groups include:

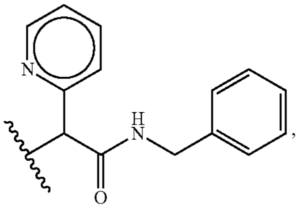
,

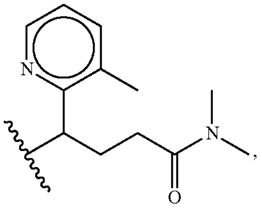
, and

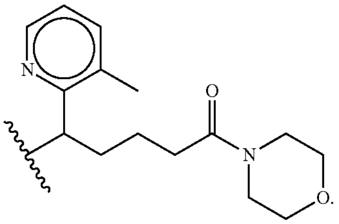

The term "carboxamido" as used herein by itself or as part of another group refers to a radical of formula —C(═O)NR$^{55a}$R$^{55b}$, wherein R$^{55a}$ and R$^{55b}$ are each independently hydrogen, optionally substituted alkyl, optionally substituted alkenyl, optionally substituted alkynyl, haloalkyl, (alkoxy)alkyl, (hydroxy)alkyl, (cyano)alkyl, optionally substituted cycloalkyl, optionally substituted heterocyclo, optionally substituted aryl, optionally substituted heteroaryl, (aryl)alkyl, (cycloalkyl)alkyl, (heterocyclo)alkyl, or (heteroaryl)alkyl; or R$^{55a}$ and R$^{55b}$ taken together with the nitrogen to which they are attached from a 4- to 8-membered optionally substituted heterocyclo group. Non-limiting exemplary carboxamido groups include: morpholine-4-carbonyl, N,N-dimethylaminocarbonyl, N-(1-methylpiperidin-4-yl)aminocarbonyl, 4-methylpiperazine-1-carbonyl, N-(3-aminocyclopentyl)aminocarbonyl, N-(pyridin-3-yl)aminocarbonyl, and N-(tetrahydrofuran-3-yl)aminocarbonyl.

The term "(heteroaryl)(cycloalkyl)alkyl" as used herein by itself or as part of another group refers to an alkyl group substituted with one optionally substituted heteroaryl group and one optionally substituted cycloalkyl group. In one embodiment, the heteroaryl is an optionally substituted 5- to 9-membered heteroaryl group. In another embodiment, the heteroaryl is an optionally substituted 5- or 6-membered heteroaryl group. In one embodiment, the cycloalkyl is an optionally substituted $C_3$-$C_6$ cycloalkyl. In one embodiment, the alkyl is a $C_1$-$C_6$ alkyl. In another embodiment, the alkyl is a $C_1$-$C_4$ alkyl. In another embodiment, the alkyl is a $C_1$-$C_3$ alkyl. A non-limiting exemplary (heteroaryl)($C_3$-$C_6$ cycloalkyl) alkyl group is:

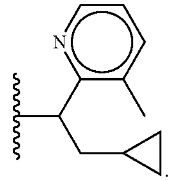

The term "(aryl)(alkoxycarbonyl)alkyl" as used herein by itself or as part of another group refers to an alkyl group substituted with one optionally substituted aryl group and one alkoxycarbonyl group. In one embodiment, the aryl is an optionally substituted phenyl group or optionally substituted naphthyl group. In another embodiment, the aryl is an optionally substituted phenyl group. In one embodiment, the alkyl is a $C_1$-$C_6$ alkyl. In another embodiment, the alkyl is a $C_1$-$C_4$ alkyl. In another embodiment, the alkyl is a $C_1$ or $C_2$ alkyl. A non-limiting exemplary (aryl)(alkoxycarbonyl)alkyl group is:

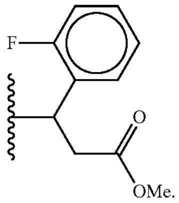

The term "alkoxycarbonyl" as used herein by itself or as part of another group refers to a carbonyl group, i.e., —C(═O)—, substituted by a $C_1$-$C_6$ alkoxy group. In one embodiment, the alkoxy group is a $C_1$-$C_4$ alkoxy. In another embodiment, the alkoxy group is a $C_1$-$C_3$ alkoxy. Non-limiting exemplary alkoxycarbonyl groups include —$CO_2$-Me and —$CO_2$Et.

The term "(heteroaryl)(amino)alkyl" as used herein by itself or as part of another group refers to an alkyl group substituted with one optionally substituted heteroaryl group and one amino group. In one embodiment, the heteroaryl is an optionally substituted 5- to 9-membered heteroaryl group. In another embodiment, the heteroaryl is an optionally substituted 5- or 6-membered heteroaryl group. In one embodiment, the alkyl is a $C_1$-$C_6$ alkyl. In another embodiment, the alkyl is a $C_1$-$C_4$ alkyl. In another embodiment, the alkyl is a $C_1$ or $C_2$ alkyl. A non-limiting exemplary (heteroaryl)(amino)alkyl group is:

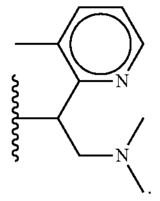

The term "(cycloalkyl)(alkoxycarbonyl)alkyl" as used herein by itself or as part of another group refers to an alkyl group substituted with one optionally substituted cycloalkyl group and one alkoxycarbonyl group. In one embodiment, the cycloalkyl is an optionally substituted $C_3$-$C_6$ cycloalkyl. In one embodiment, the alkyl is a $C_1$-$C_6$ alkyl. In another embodiment, the alkyl is a $C_1$-$C_4$ alkyl. In another embodiment, the alkyl is a $C_1$ or $C_2$ alkyl. A non-limiting exemplary (cycloalkyl)(alkoxycarbonyl)alkyl group is:

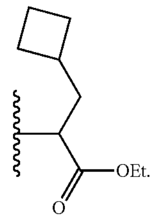 [SMILES: *C(CC1CCC1)C(=O)OCC]

The term "(heteroaryl)(alkoxycarbonyl)alkyl" as used herein by itself or as part of another group refers to an alkyl group substituted with one optionally substituted heteroaryl group and one alkoxycarbonyl group. In one embodiment, the heteroaryl is an optionally substituted 5- to 9-membered heteroaryl group. In another embodiment, the heteroaryl is an optionally substituted 5- or 6-membered heteroaryl group. In one embodiment, the alkyl is a $C_1$-$C_6$ alkyl. In another embodiment, the alkyl is a $C_1$-$C_4$ alkyl. In another embodiment, the alkyl is a $C_1$ or $C_2$ alkyl. Non-limiting exemplary (heteroaryl)(alkoxycarbonyl)alkyl groups include:

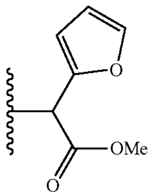
and
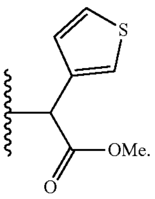

The term "(heterocyclo)(cycloalkyl)alkyl" as used herein by itself or as part of another group refers to an alkyl group substituted with one optionally substituted heterocyclo group and one optionally substituted cycloalkyl group. In one embodiment, the heterocyclo is an optionally substituted 5- to 8-membered heterocyclo. In another embodiment, the heterocyclo is an optionally substituted 5- or 6-membered heterocyclo. In one embodiment, the cycloalkyl is an optionally substituted $C_3$-$C_6$ cycloalkyl. In one embodiment, the alkyl is a $C_1$-$C_6$ alkyl. In another embodiment, the alkyl is a $C_1$-$C_4$ alkyl. In another embodiment, the alkyl is a $C_1$ or $C_2$ alkyl. A non-limiting exemplary (heterocyclo)(cycloalkyl) alkyl group is:

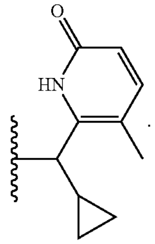 [SMILES: *C(c1[nH]c(=O)ccc1C)C1CC1]

The term "(aryl)(cycloalkyl)alkyl" as used herein by itself or as part of another group refers to an alkyl group substituted with one optionally substituted aryl group and one optionally substituted cycloalkyl group. In one embodiment, the aryl is an optionally substituted phenyl group or optionally substituted naphthyl group. In another embodiment, the aryl is an optionally substituted phenyl group. In one embodiment, the cycloalkyl is an optionally substituted $C_3$-$C_6$ cycloalkyl. In one embodiment, the alkyl is a $C_1$-$C_6$ alkyl. In another embodiment, the alkyl is a $C_1$-$C_4$ alkyl. In another embodiment, the alkyl is a $C_1$ or $C_2$ alkyl. A non-limiting exemplary (aryl)(cycloalkyl)alkyl group is:

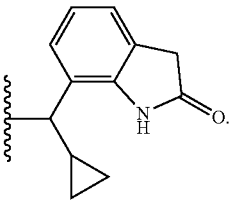 [SMILES: *C(c1cccc2c1NC(=O)C2)C1CC1]

The terms "aralkyl" or "(aryl)alkyl" as used herein by themselves or as part of another group refers to an alkyl substituted with one, two, or three optionally substituted aryl groups. In one embodiment, the alkyl is substituted with one optionally substituted aryl group. In another embodiment, the alkyl is substituted with two optionally substituted aryl groups. In one embodiment, the aryl is an optionally substituted phenyl or optionally substituted naphthyl. In another embodiment, the aryl is an optionally substituted phenyl. In one embodiment, the alkyl is a $C_1$-$C_6$ alkyl. In another embodiment, the alkyl is a $C_1$-$C_4$ alkyl. In another embodiment, the alkyl is a $C_1$ or $C_2$ alkyl. Non-limiting exemplary (aryl)alkyl groups include benzyl, phenethyl, —$CHPh_2$, and —$CH(4\text{-}F\text{-}Ph)_2$.

The term "(aryl)(hydroxy)alkyl" as used herein by itself or as part of another group refers to an alkyl substituted with one optionally substituted aryl group and one hydroxyl group. In one embodiment, the aryl is an optionally substituted phenyl group or optionally substituted naphthyl group. In another embodiment, the aryl is an optionally substituted phenyl group. In one embodiment, the alkyl is a $C_1$-$C_6$ alkyl. In another embodiment, the alkyl is a $C_1$-$C_4$ alkyl. In another embodiment, the alkyl is a $C_1$ or $C_2$ alkyl. Non-limiting exemplary (aryl)(hydroxy)alkyl groups include:

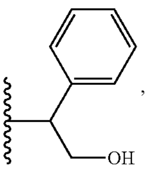
,
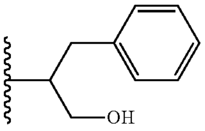
and

-continued

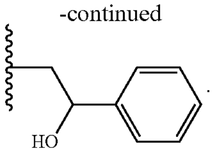

The term "(cycloalkyl)(hydroxy)alkyl" as used herein by itself or as part of another group refers to an alkyl group substituted with one optionally substituted cycloalkyl group and one hydroxyl group. In one embodiment, the cycloalkyl group is an optionally substituted $C_3$-$C_6$ cycloalkyl group. In one embodiment, the alkyl is a $C_1$-$C_6$ alkyl. In another embodiment, the alkyl is a $C_1$-$C_4$ alkyl. In another embodiment, the alkyl is a $C_1$ or $C_2$ alkyl. A non-limiting exemplary (cycloalkyl)(hydroxy)alkyl group is:

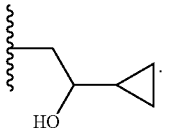 [SMILES: *CC(O)C1CC1]

The term "(alkoxycarbonyl)alkyl" as used herein by itself or as part of another group refers to an alkyl substituted with one or two alkoxycarbonyl groups. In one embodiment, the alkyl is a $C_1$-$C_4$ alkyl. In another embodiment, the alkyl is a $C_1$ or $C_2$ alkyl. A non-limiting exemplary (alkoxycarbonyl) alkyl groups is:

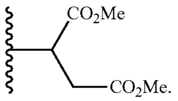

The term "(aryl)(haloalkyl)alkyl" as used herein by itself or as part of another group refers to an alkyl substituted with one optionally substituted aryl group and one haloalkyl group. In one embodiment, the aryl is an optionally substituted group or optionally substituted naphthyl. In another embodiment, the aryl is an optionally substituted phenyl. In one embodiment, the haloalkyl is a $C_1$-$C_4$ haloalkyl. In one embodiment, the alkyl is a $C_1$-$C_4$ alkyl. In another embodiment, the alkyl is a $C_1$ or $C_2$ alkyl. A non-limiting exemplary (aryl)(haloalkyl)alkyl groups is:

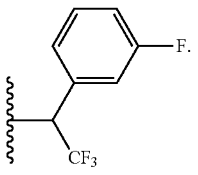

The term "(cycloalkyl)(haloalkyl)alkyl" as used herein by itself or as part of another group refers to an alkyl substituted with one optionally substituted cycloalkyl group and one haloalkyl group. In one embodiment, the cycloalkyl is an optionally substituted $C_3$-$C_6$ cycloalkyl. In one embodiment, the haloalkyl is a $C_1$-$C_4$ haloalkyl. In one embodiment, the alkyl is a $C_1$-$C_4$ alkyl. In another embodiment, the alkyl is a $C_1$ or $C_2$ alkyl. A non-limiting exemplary (cycloalkyl)(haloalkyl) alkyl groups is:

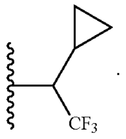 [SMILES: *C(C1CC1)C(F)(F)F]

The term "(hydroxy)(haloalkyl)alkyl" as used herein by itself or as part of another group refers to an alkyl substituted with one hydroxy group and one haloalkyl group. In one embodiment, the haloalkyl is a $C_1$-$C_4$ haloalkyl. In one embodiment, the alkyl is a $C_1$-$C_4$ alkyl. In another embodiment, the alkyl is a $C_1$ or $C_2$ alkyl. A non-limiting exemplary (hydroxy)(haloalkyl)alkyl groups is:

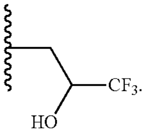 [SMILES: *CC(O)C(F)(F)F]

The term "(alkoxycarbonyl)(haloalkyl)alkyl" as used herein by itself or as part of another group refers to an alkyl substituted with one alkoxycarbonyl group and one haloalkyl group. In one embodiment, the haloalkyl is a $C_1$-$C_4$ haloalkyl. In one embodiment, the alkyl is a $C_1$-$C_4$ alkyl. In another embodiment, the alkyl is a $C_1$ or $C_2$ alkyl. A non-limiting exemplary (alkoxycarbonyl)(haloalkyl)alkyl groups is:

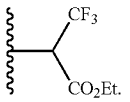

The term "(carboxamido)alkyl" as used herein by itself or as part of another group refers to an alkyl substituted with a carboxamido group. In one embodiment, the alkyl is a $C_1$-$C_4$ alkyl. In another embodiment, the alkyl is a $C_1$ or $C_2$ alkyl. Non-limiting exemplary (carboxamido)alkyl groups include $-CH_2C(=O)NH_2$, $-C(H)(CH_3)C(=O)NH_2$, $-CH_2C(=O)N(H)CH_3$, and $-CH_2C(=O)N(CH_3)_2$.

The term "(carboxy)alkyl" as used herein by itself or as part of another group refers to an alkyl substituted with $-C(=O)OH$. In one embodiment, the alkyl is a $C_1$-$C_4$ alkyl. In another embodiment, the alkyl is a $C_1$ or $C_2$ alkyl. A non-limiting exemplary (carboxy)alkyl group is $-CH_2CO_2H$.

The term "(amino)(hydroxy)alkyl" as used herein by itself or as part of another group refers to an alkyl substituted with one hydroxy group and one amino group. In one embodiment, the alkyl is a $C_1$-$C_4$ alkyl. A non-limiting exemplary "(amino)(hydroxy)alkyl" group is:

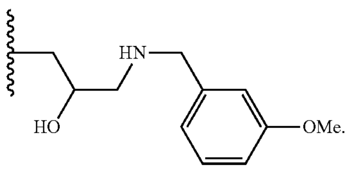 [SMILES: *CC(O)CNCc1cccc(OC)c1]

The term “(amino)(aryl)alkyl” as used herein by itself or as part of another group refers to an alkyl group substituted with one amino group and one optionally substituted aryl group. In one embodiment, the amino group is —$NH_2$, alkylamino, or dialkylamino. In one embodiment, the aryl group is an optionally substituted phenyl. In one embodiment, the alkyl is a $C_1$-$C_6$ alkyl. In another embodiment, the alkyl is a $C_1$-$C_4$ alkyl. Non-limiting exemplary (amino)(aryl) alkyl groups include:

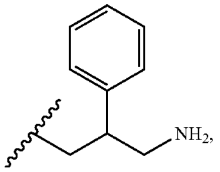
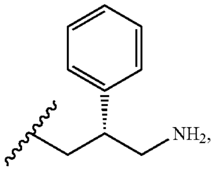
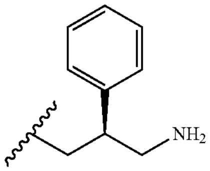
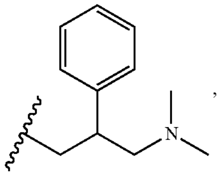
,
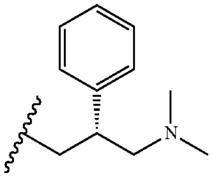
and
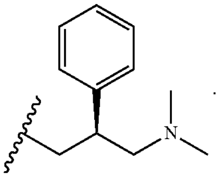
.

The term “amino” as used by itself or as part of another group refers to a radical of the formula —$NR^{55a}R^{55b}$, wherein $R^{55a}$ and $R^{55b}$ are independently hydrogen, optionally substituted alkyl, haloalkyl, (hydroxy)alkyl, (alkoxy) alkyl, (amino)alkyl, heteroalkyl, optionally substituted cycloalkyl, optionally substituted heterocyclo, optionally substituted aryl, optionally substituted heteroaryl, (aryl) alkyl, (cycloalkyl)alkyl, (heterocyclo)alkyl, or (heteroaryl) alkyl.

In one embodiment, the amino is —$NH_2$.

In another embodiment, the amino is an “alkylamino,” i.e., an amino group wherein $R^{55a}$ is $C_{1-6}$ alkyl and $R^{55b}$ is hydrogen. In one embodiment, $R^{55a}$ is $C_1$-$C_4$ alkyl. Non-limiting exemplary alkylamino groups include —$N(H)CH_3$ and —$N(H)CH_2CH_3$.

In another embodiment, the amino is a “dialkylamino,” i.e., an amino group wherein $R^{55a}$ and $R^{55b}$ are each independently $C_{1-6}$ alkyl. In one embodiment, $R^{55a}$ and $R^{55b}$ are each independently $C_1$-$C_4$ alkyl. Non-limiting exemplary dialkylamino groups include —$N(CH_3)_2$ and —$N(CH_3)CH_2CH(CH_3)_2$.

In another embodiment, the amino is a “hydroxyalkylamino,” i.e., an amino group wherein $R^{55a}$ is (hydroxyl) alkyl and $R^{55b}$ is hydrogen or $C_1$-$C_4$ alkyl.

In another embodiment, the amino is a “cycloalkylamino,” i.e., an amino group wherein $R^{55a}$ is optionally substituted cycloalkyl and $R^{55b}$ is hydrogen or $C_1$-$C_4$ alkyl.

In another embodiment, the amino is a “aralkylamino,” i.e., an amino group wherein $R^{55a}$ is aralkyl and $R^{55b}$ is hydrogen or $C_1$-$C_4$ alkyl. Non-limiting exemplary aralkylamino groups include —$N(H)CH_2Ph$, —$N(H)CHPh_2$, and —$N(CH_3)CH_2Ph$.

In another embodiment, the amino is a “(cycloalkyl) alkylamino,” i.e., an amino group wherein$R^{55a}$ is (cycloalkyl)alkyl and $R^{55b}$ is hydrogen or $C_1$-$C_4$ alkyl. Non-limiting exemplary (cycloalkyl)alkylamino groups include:

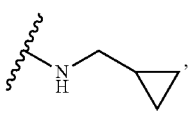
,
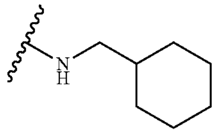
and
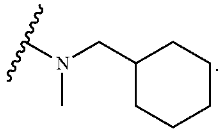
.

In another embodiment, the amino is a “(heterocyclo) alkylamino,” i.e., an amino group wherein $R^{55a}$ is (heterocyclo)alkyl and $R^{55b}$ is hydrogen or $C_1$-$C_4$ alkyl. Non-limiting exemplary (heterocyclo)alkylamino groups include:

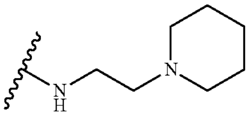
and
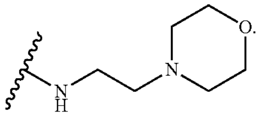
.

The term “(amino)alkyl” as used herein by itself or as part of another group refers to an alkyl substituted with one amino group. In one embodiment, the amino group is —$NH_2$. In one embodiment, the amino group is an alkylamino. In another embodiment, the amino group is a dialkylamino. In another embodiment, the alkyl is a $C_1$-$C_6$ alkyl. In another embodiment, the alkyl is a $C_1$-$C_4$ alkyl. Non-limiting exemplary (amino)alkyl groups include —$CH_2NH_2$, $CH_2CH_2N(H)CH_3$, —$CH_2CH_2N(CH_3)_2$, $CH_2N(H)$cyclopropyl, —$CH_2N(H)$cyclobutyl, and —$CH_2N(H)$cyclohexyl, and —$CH_2CH_2CH_2N(H)CH_2Ph$ and —$CH_2CH_2CH_2N(H)CH_2(4\text{-}CF_3\text{-}Ph)$.

The present disclosure encompasses any of the Compounds of the Disclosure being isotopically-labelled (i.e., radiolabeled) by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^2H$ (or deuterium (D)), $^3H$, $^{11}C$, $^{13}C$, $^{14}C$, $^{15}N$, $^{18}O$, $^{17}O$, $^{31}P$, $^{32}P$, $^{35}S$, $^{18}F$, and $^{36}Cl$, respectively, e.g., $^3H$, $^{11}C$, and $^{14}C$. In one embodiment, provided is a composition wherein substantially all of the atoms at a position within the Compound of the Disclosure are replaced by an atom having a different atomic mass or mass number. In another embodiment, provided is a composition wherein a portion of the atoms at a position within the Compound of the disclosure are replaced, i.e., the Compound of the Disclosure is enriched at a position with an atom having a different atomic mass or mass number.” Isotopically-labelled Compounds of the Disclosure can be prepared by methods known in the art.

Compounds of the Disclosure may contain one or more asymmetric centers and may thus give rise to enantiomers, diastereomers, and other stereoisomeric forms. The present disclosure encompasses the use of all such possible forms, as well as their racemic and resolved forms and mixtures thereof. The individual enantiomers can be separated according to methods known in the art in view of the present disclosure. When the compounds described herein contain olefinic double bonds or other centers of geometric asymmetry, and unless specified otherwise, it is intended that they include both E and Z geometric isomers. All tautomers are also encompassed by the present disclosure.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" or "asymmetric carbon atom" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive. In one embodiment, Compounds of the Disclosure are racemic.

The term "absolute configuration" refers to the spatial arrangement of the atoms of a chiral molecular entity (or group) and its stereochemical description, e.g., R or S.

The stereochemical terms and conventions used in the specification are meant to be consistent with those described in *Pure & Appl. Chem* 68:2193 (1996), unless otherwise indicated.

The term "enantiomeric excess" or "ee" refers to a measure for how much of one enantiomer is present compared to the other. For a mixture of R and S enantiomers, the percent enantiomeric excess is defined as $|R-S|*100$, where R and S are the respective mole or weight fractions of enantiomers in a mixture such that $R+S=1$. With knowledge of the optical rotation of a chiral substance, the percent enantiomeric excess is defined as $([\alpha]_{obs}/[\alpha]_{max})*100$, where $[\alpha]_{obs}$ is the optical rotation of the mixture of enantiomers and $[\alpha]_{max}$ is the optical rotation of the pure enantiomer. Determination of enantiomeric excess is possible using a variety of analytical techniques, including NMR spectroscopy, chiral column chromatography or optical polarimetry.

In one embodiment, Compounds of the Disclosure having one or more chiral centers are enantiomerically enriched, e.g., the ee is about 5% or more. In another embodiment, the ee is about 10%. In another embodiment, the ee is about 20%. In another embodiment, the ee is about 30%. In another embodiment, the ee is about 40%. In another embodiment, the ee is about 50%. In another embodiment, the ee is about 60%. In another embodiment, the ee is about 70%. In another embodiment, the ee is about 80%. In another embodiment, the ee is about 85%. In another embodiment, the ee is about 90%. In another embodiment, the ee is about 91%. In another embodiment, the ee is about 92%. In another embodiment, the ee is about 93%. In another embodiment, the ee is about 94%. In another embodiment, the ee is about 95%. In another embodiment, the ee is about 96%. In another embodiment, the ee is about 97%. In another embodiment, the ee is about 98%. In another embodiment, the ee is about 99%.

The terms "a" and "an" refer to one or more.

The term "about," as used herein, includes the recited number ±10%. Thus, "about 10" means 9 to 11.

The terms "treat," "treating," "treatment," and the like as used herein refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a Compound of the Disclosure to an individual in need of such treatment.

Within the meaning of the disclosure, "treatment" also includes relapse prophylaxis or phase prophylaxis, as well as the treatment of acute or chronic signs, symptoms and/or malfunctions. The treatment can be orientated symptomatically, for example, to suppress symptoms. It can be effected over a short period, be oriented over a medium term, or can be a long-term treatment, for example within the context of a maintenance therapy.

The term "therapeutically effective amount" or "effective dose" as used herein refers to an amount of the active ingredient(s) that is(are) sufficient, when administered by a method of the disclosure, to efficaciously deliver the active ingredient(s) for the treatment of condition or disease of interest to an individual in need thereof. In the case of a cancer or other proliferation disorder, the therapeutically effective amount of the agent may reduce (i.e., retard to some extent and preferably stop) unwanted cellular proliferation; reduce the number of cancer cells; reduce the tumor size; inhibit (i.e., retard to some extent and preferably stop) cancer cell infiltration into peripheral organs; inhibit (i.e., retard to some extent and preferably stop) tumor metastasis; inhibit, to some extent, tumor growth; modulate protein methylation in the target cells; and/or relieve, to some extent, one or more of the symptoms associated with the cancer. To the extent the administered compound or composition prevents growth and/or kills existing cancer cells, it may be cytostatic and/or cytotoxic.

The term "container" means any receptacle and closure therefore suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

The term "disease" or "condition" or "disorder" denotes disturbances and/or anomalies that as a rule are regarded as being pathological conditions or functions, and that can manifest themselves in the form of particular signs, symptoms, and/or malfunctions. Compounds of the Disclosure inhibit SETD2 protein and can be used in treating diseases and conditions such as proliferative diseases, wherein inhibition of SETD2 protein provides a benefit. See, e.g., U.S. Provisional Appl. No. 62/545,353.

In some embodiments, the Compounds of the Disclosure can be used to treat a "SETD2 protein mediated disorder" A SETD2 protein mediated disorder is any pathological condition in which a SETD2 protein is known to play a role. In some embodiments, a SETD2 mediated disorder is a proliferative disease.

In some embodiments inhibiting SETD2 protein is the inhibition of the activity of one or more activities of SETD2 protein. In some embodiments, the activity of the SETD2 protein is the ability of the SETD2 protein to transfer a methyl group to a target protein, e.g., histone. It should be appreciated that the activity of SETD2 may be inhibited in vitro or in vivo. Exemplary levels of inhibition of the activity of SETD2 include at least 5% inhibition at least 10% inhibition, at least 20% inhibition, at least 30% inhibition, at least 40% inhibition, at least 50% inhibition, at least 60% inhibition, at least 70% inhibition, at least 80% inhibition, at least 90% inhibition, and up to about 100% inhibition.

The term "biological sample" as used herein refers any tissue or fluid from a subject that is suitable for detecting chromosomal translocations. Examples of useful biological samples include, but are not limited to, biopsied tissues and/or cells, e.g., solid tumor, lymph gland, inflamed tissue, tissue and/or cells involved in a condition or disease, blood, plasma, serous fluid, cerebrospinal fluid, saliva, urine, lymph, cerebral spinal fluid, and the like. Other suitable biological samples will be familiar to those of ordinary skill in the relevant arts. A biological sample can be analyzed for chromosomal translocations using any technique known in the art. Such techniques include, but are not limited to, polymerase chain reaction (PCR) methodology, reverse transcription-polymerase chain reaction (RT-PCR) methodology, or cytoplasmic light chain immunofluorescence combined with fluorescence in situ hybridization (cIg-FISH). A biological sample can be obtained using techniques that are well within the scope of ordinary knowledge of a clinical practioner. In one embodiment of the disclosure, the biological sample comprises blood cells.

The phrase "in combination" as used in connection with the administration of a Compound of the Disclosure and a Second Therapeutic Agent to a subject means that the Compound of the Disclosure and the Second Therapeutic Agent can be administered to the subject together, e.g., as part of a single pharmaceutical composition or formulation, or separately, e.g., as part of two or more separate pharmaceutical compositions or formulations. The phrase "in combination" as used in connection with the administration of a Compound of the Disclosure and a Second Therapeutic Agent to a subject is thus intended to embrace administration of a Compound of the Disclosure and a Second Therapeutic Agent in a sequential manner, wherein the Compound of the Disclosure and the Second Therapeutic Agent are administered to the subject at a different time, as well as administration concurrently, or in a substantially simultaneous manner. Simultaneous administration can be accomplished, for example, by administering to the subject a single capsule having a fixed ratio of each of the Compound of the Disclosure and the Second Therapeutic Agent or in multiple, single capsules for each of the Compound of the Disclosure and the Second Therapeutic Agent. Sequential or substantially simultaneous administration of the Compound of the Disclosure and the Second Therapeutic Agent agent can be accomplished by any appropriate route including, but not limited to, oral routes, intravenous routes, intramuscular routes, and direct absorption through mucous membrane tissues. The Compound of the Disclosure and the Second Therapeutic Agent can be administered by the same route or by different routes. For example, the Second Therapeutic Agent of the combination may be administered by intravenous injection while the Compound of the Disclosure of the combination may be administered orally. Alternatively, for example, both the Compound of the Disclosure and the Second Therapeutic Agent may be administered orally or both the Compound of the Disclosure and the Second Therapeutic Agent may be administered by intravenous injection. The Compound of the Disclosure and the Second Therapeutic Agent may also be administered in alternation. In one embodiment, the Compound of the Disclosure and the Second Therapeutic Agent are administered to a subject separately, e.g., as part of two or more separate pharmaceutical compositions or formulations.

General Synthesis of Compounds

Compounds of the Disclosure are prepared using methods disclosed in PCT/US2019/046569, or by the illustrative methods shown in the General Schemes below. In the General Schemes, $R^{1d}$, $R^{2b}$, $R^{2d}$, $R^{2e}$, $A^1$, $A^2$, $R^{11a}$, $R^{14a}$, $R^{14b}$, $R^{19}$, $R^{20}$, G, $Z^4$, and q are as defined in connection with Formulae II, III, IV, V, or VI, unless otherwise indicated. In any of the General Schemes, suitable protecting groups can be employed in the synthesis, for example, when Z is (amino)alkyl or any other group that may group that may require protection, or when $R^8$ is amino, (amino)alkyl, or any other group that may require protection. (See, Wuts, P. G. M.; Greene, T. W., "Greene's Protective Groups in Organic Synthesis", 4th Ed., J. Wiley & Sons, NY, 2007) unless otherwise indicated.

In General Scheme 1, the aryl hydrazine of Formula (1) is reacted with ethyl 2-oxopropanoate to give a compound of Formula (2). In step 2, the compound of Formula (2) is converted to the indole of Formula (3) under acidic conditions. In step 3, the compound of Formula (3) is hydrolyzed to give the indole-2-carboxylic acid of Formula (4). In step 4, a compound of Formula (4) is reacted with $G^1NH_2$ under standard coupling conditions to give a compound of Formula II.

General Scheme 1

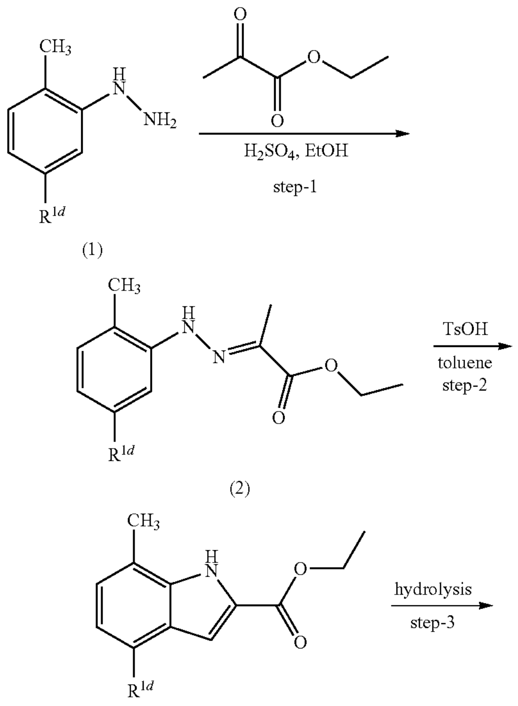

(1)

(2)

(3)

-continued

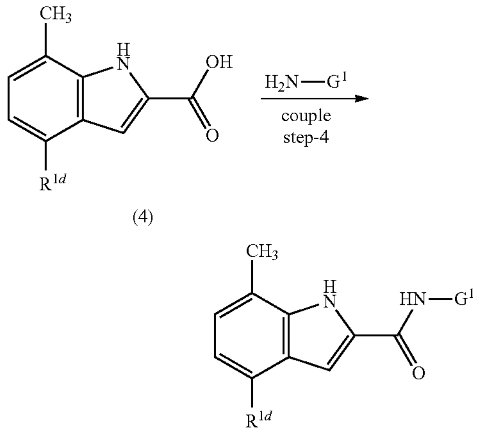

(4)

Formula II

In General Scheme 2, a compound of Formula (5) is reacted with $R^{2b}$—H wherein $R^{2b}$ is a heterocyclo, e.g., $R^{2b}$—H is piperidine, or an amine, e.g., $R^{2b}$—H is dimethyl amine, to give a compound of Formula (6). The nitro group of the compound of Formula (6) is reduced to give a compound of Formula (7). In step 3, the compound of Formula (7) is reacted with a compound of Formula (4), see General Scheme 1, under standard coupling conditions to give a compound of Formula III, wherein $A^1$ and $A^2$ are CH and $R^{2b}$ is an optionally substituted heterocyclo or an amino group.

General Scheme 2

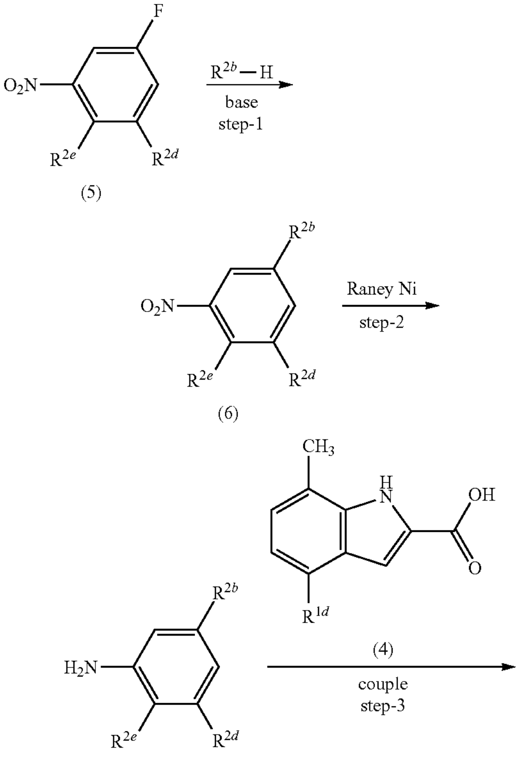

(5)

(6)

(7)

-continued

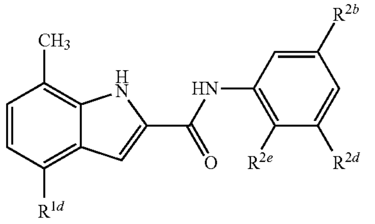

Formula III
(wherein $A^1$ and $A^2$ are CH; and
$R^{2b}$ is optionally substituted heterocyclo or amino)

In General Scheme 3, a compound of Formula (8) is reacted with $R^{2b}$—H wherein $R^{2b}$ is a heterocyclo, e.g., $R^{2b}$—H is piperidine, or an amine, e.g., $R^{2b}$—H is dimethyl amine, to give a compound of Formula (9). In step 2, the compound of Formula (9) is reacted with a compound of Formula (10) to give a compound of Formula III, wherein $A^1$ and/or $A^2$ are N and $R^{2b}$ is an optionally substituted heterocyclo or an amino group.

General Scheme 3

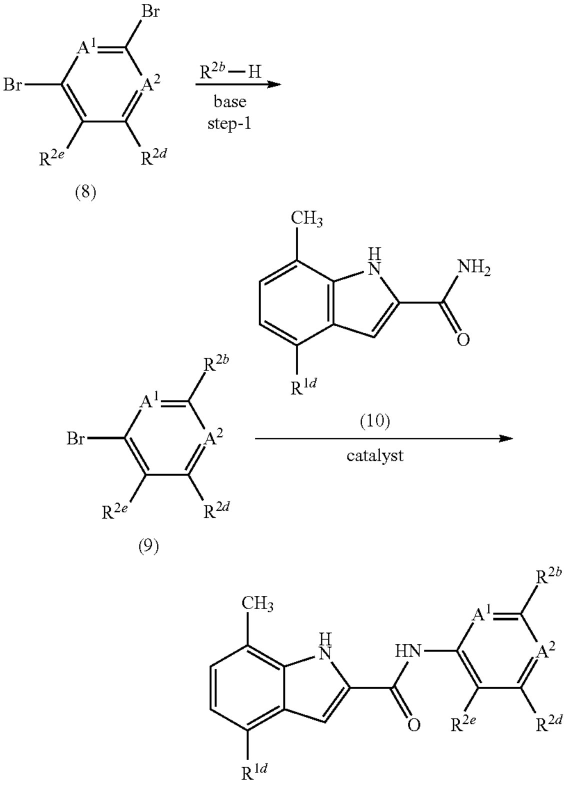

(8)

(9)

Formula III
(wherein $A^1$ and/or $A^2$ are N; and
$R^{2b}$ is optionally substituted heterocyclo or amino)

In General Scheme 4, a compound of Formula (11) is reacted with $R^{11a}$—H, wherein $R^{11a}$ is a heterocyclo, e.g., $R^{11a}$—H is piperidine, to give a compound of Formula (12). In step 2, the Cbz group is removed to give a compound of Formula (13). The compound of Formula (13) is coupled with a compound of Formula (4) to give a compound of Formula IV, wherein $R^{11a}$ is optionally substituted heterocyclo and $Z^5$ is —$CH_2$—.

General Scheme 4

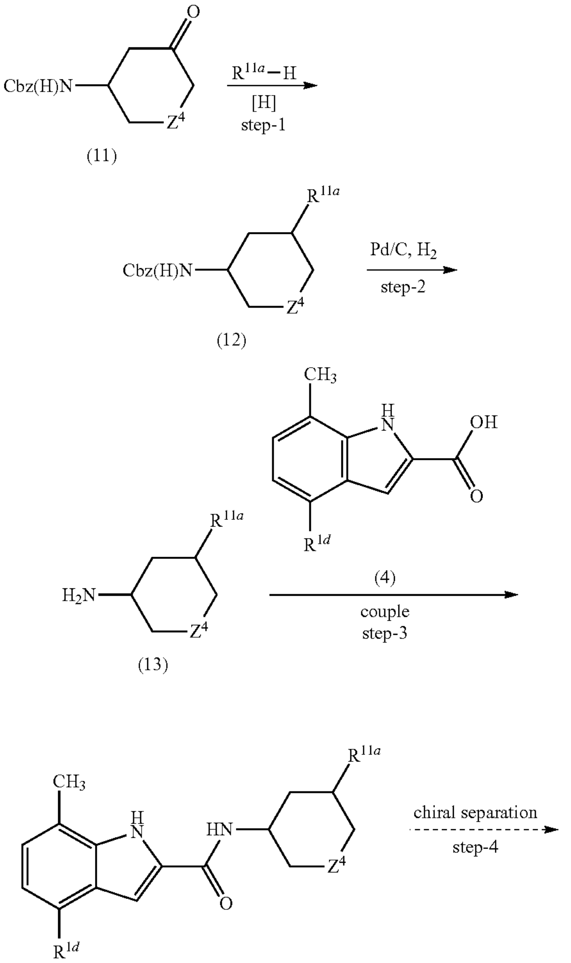

Formula IV
(wherein $R^{11a}$ is optionally substituted heterocyclo; and $Z^5$ is $CH_2$)

Formula IV-A
Formula IV-B
Formula IV-C
Formula IV-D

In step 1 of General Scheme 5, a nitrile of Formula (14) is reacted with a Grignard reagent ($R^{14a}$—MgBr) and the resulting product is reduced to give a compound of Formula (15). The compound of Formula (15) is coupled with a compound of Formula (4) to give a compound of Formula V, wherein p is 0.

General Scheme 5

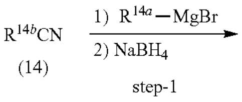

-continued

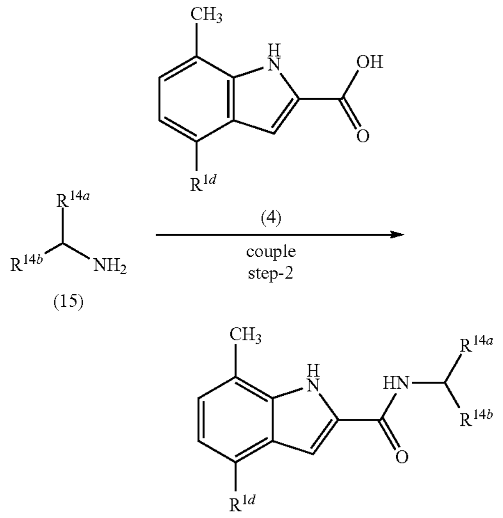

Formula V
(wherein p is 0)

In General Scheme 6, an aldehyde of Formula (16) is reacted with an ester of Formula (17) to give a compound of Formula (18). In step 2, the compound of Formula (18) hydrolyzed to give a compound of Formula (19). In step 3, the compound of Formula (19) is converted to the isocyanate of Formula (20). The compound of Formula (20) is reacted with benzyl alcohol to give a compound of Formula (21). Hydrogenation of a compound of Formula (21) and removal of the Cbz groups gives an amine of Formula (23). Coupling a compound of Formula (23) with a compound of Formula (4) gives a compound of Formula V, wherein p is 1.

General Scheme 6

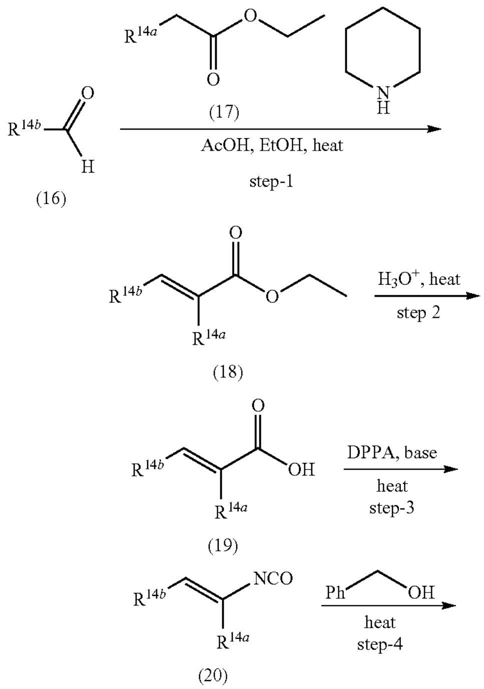

-continued

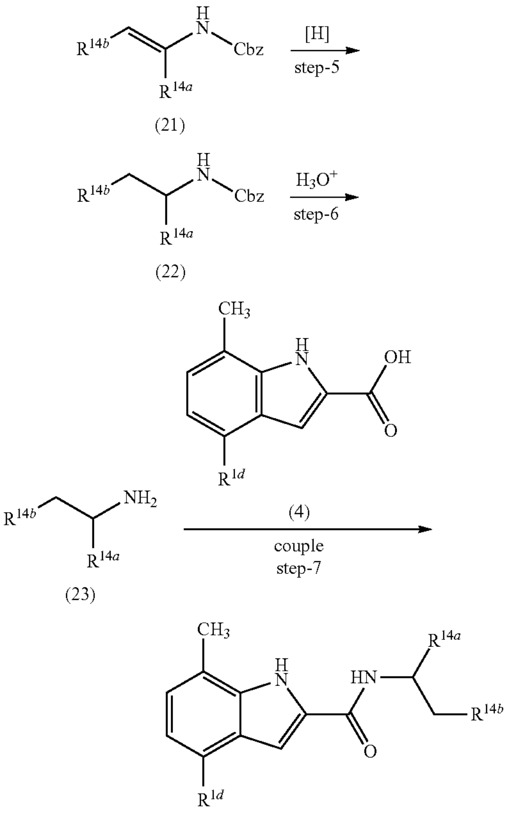

(21)

(22)

(23)

Formula V
(wherein p is 1)

In General Scheme 7, the nitrile of Formula (24) is reduced to give an amine of Formula (25). The compound of Formula (25) is coupled with a compound of Formula (4) to give a compound of Formula VI.

General Scheme 7

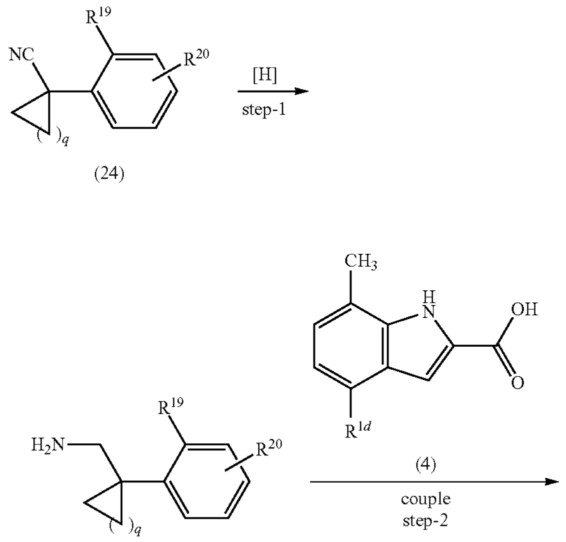

(24)

(25)

-continued

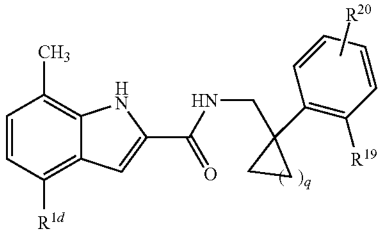

Formula VI

EXAMPLES

Example 1

Synthesis of N-((1R,3S)-3-(4-acetylpiperazin-1-yl) cyclohexyl)-4-fluoro-7-methyl-1H-indole-2-carboxamide (Cpd. No. 15)

Step 1. Synthesis of ethyl (2E)-2-[2-(5-fluoro-2-methylphenyl)hydrazin-1-ylidene]propanoate

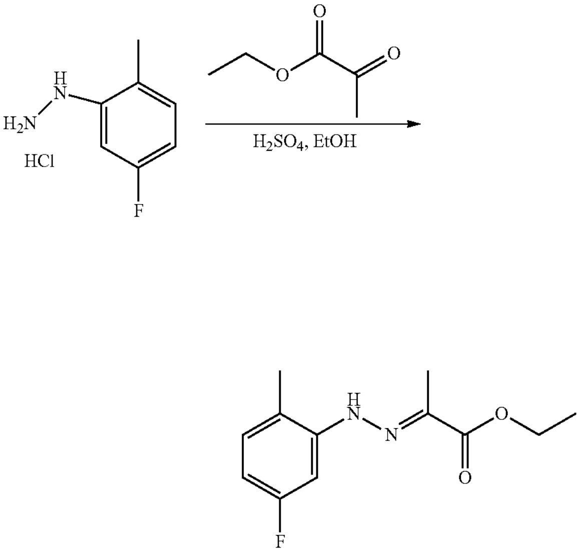

Into a 1000-mL round-bottom flask, was placed a solution of (5-fluoro-2-methylphenyl)hydrazine hydrochloride (100 g, 572.73 mmol, 1.00 equiv) in ethanol (400 mL), ethyl 2-oxopropanoate (66 g, 1.20 equiv), sulfuric acid (10 mL). The resulting solution was stirred for 2 h at 25° C. The reaction progress was monitored by LCMS. The resulting mixture was concentrated under vacuum. The solids were collected by filtration. This resulted in 120 g (yield=88%) of ethyl (2E)-2-[2-(5-fluoro-2-methylphenyl) hydrazin-1-ylidene]propanoate as a yellow solid. LCMS (Method A: ESI): RT=1.399 min, m/z=239.0 $[M+H]^+$. $^1H$ NMR (400 MHz, DMSO-$d_6$) δ 11.96 (d, J=2.0 Hz, 1H), 7.15 (m, 2H), 6.62 (m, 1H), 4.25 (q, J=7.1 Hz, 2H), 2.12 (d, J=9.3 Hz, 6H), 1.29 (t, J=7.1 Hz, 3H) ppm.

Step 2. Synthesis of ethyl 4-fluoro-7-methyl-1H-indole-2-carboxylate

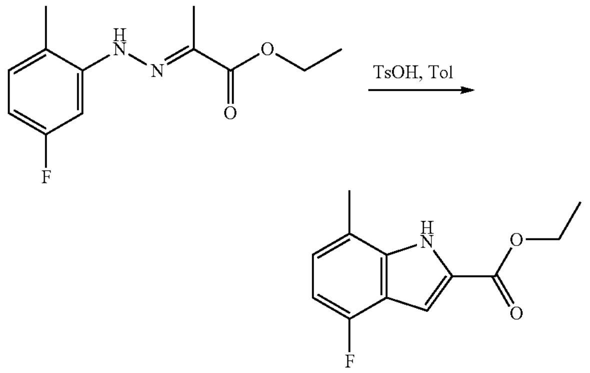

Into a 1000-mL round-bottom flask, was placed a solution of ethyl (2E)-2-[2-(5-fluoro-2-methylphenyl)hydrazin-1-ylidene]propanoate (40 g, 167.89 mmol, 1.00 equiv) in Toluene (400 mL), 4-methylbenzene-1-sulfonic acid (50 g, 290.36 mmol, 1.70 equiv). The resulting solution was stirred for 18 h at 100° C. The reaction progress was monitored by LCMS. The resulting solution was concentrated under vacuum, and the residue was dissolved by 100 ml of ethyl acetate. The resulting mixture was washed with 3×200 mL of saturated aqueous $NaHCO_3$. The residue was applied onto a silica gel column with ethyl acetate/petroleum ether (1:5). The resulting mixture was concentrated under vacuum. The solid was purified by recrystalization from ethanol. This resulted in 9.0 g (yield=24%) of ethyl 4-fluoro-7-methyl-1H-indole-2-carboxylate as a yellow solid. LCMS (Method A, ESI): RT=1.354 min,: m/z=222.0 $[M+H]^+$. $^1$H NMR (400 MHz, DMSO-$d_6$) δ 12.07 (s, 1H), 7.17 (d, J=2.1 Hz, 1H), 7.00 (m, 1H), 6.77 (m, 7.8 Hz, 1H), 4.36 (q, J=7.1 Hz, 2H), 2.49 (d, J=1.0 Hz, 3H), 1.35 (t, J=7.1 Hz, 3H) ppm.

Step 3. Synthesis of 4-fluoro-7-methyl-1H-indole-2-carboxylic acid

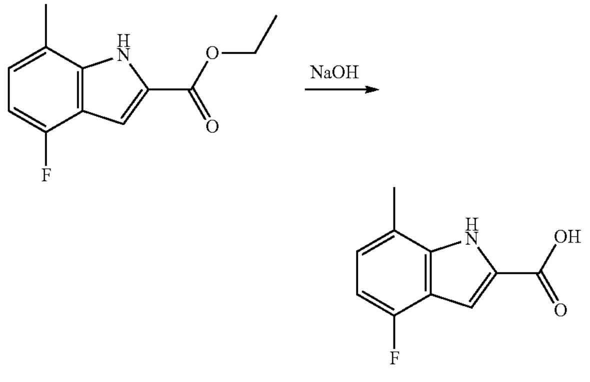

Into a 500-mL round-bottom flask, was placed a solution of ethyl 4-fluoro-7-methyl-1H-indole-2-carboxylate (9.1 g, 41.13 mmol, 1.00 equiv) in tetrahydrofuran (150 mL), sodium hydroxide (8 g, 200.00 mmol, 5.00 equiv), water (50 mL), methanol (2 mL). The resulting solution was stirred for 6 h at 25° C. The resulting mixture was concentrated under vacuum. The residue was diluted with water 50 ml, then adjusted to pH 5 with hydrogen chloride (3.0 mol/L). The resulting solution was extracted with 3×50 mL of ethyl acetate. The solid was collected by filtration. This resulted in 8.0 (yield=81%) g of 4-fluoro-7-methyl-1H-indole-2-carboxylic acid as a brown solid. LCMS (Method C, ESI): RT=0.989 min, m/z=192.0 $[M-H]^+$. $^1$H NMR (300 MHz, DMSO-$d_6$) δ 13.10 (s, 1H), 11.94 (s, 1H), 7.09 (d, J=2.1 Hz, 1H), 6.96 (m, 1H), 6.73 (m, 1H), 2.46 (d, J=1.1 Hz, 3H) ppm.

Step 4. Synthesis of tert-butyl N-[3-(4-acetylpiperazin-1-yl)cyclohexyl]carbamate

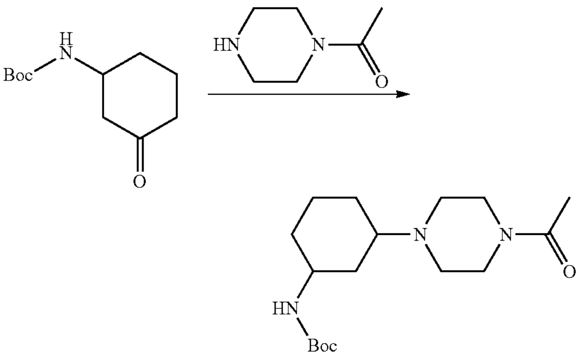

Into a 100-mL round-bottom flask, was placed tert-butyl N-(3-oxocyclohexyl)carbamate (800 mg, 3.75 mmol, 1.00 equiv), 1-(piperazin-1-yl)ethan-1-one (800 mg, 6.24 mmol, 1.66 equiv), methanol (10 mL), Pd/C (0.2 g), and to the above mixture, hydrogen was introduced. The resulting solution was stirred for 2 h at 25° C. The reaction progress was monitored by LCMS. The solids were filtered out. The resulting mixture was concentrated under vacuum. The crude product (900 mg) was purified by Flash-Prep-HPLC with the following conditions: Column, C18 silica gel; mobile phase; Detector, UV 254/220 nm. This resulted in 700 mg (yield=57%) of tert butyl N-[3-(4-acetylpiperazin-1-yl)cyclohexyl] carbamate as colorless oil. LCMS (Method A, ESI): RT=1.361 min, m/z=325.9 $[M+H]^+$.

Step 5. Synthesis of 1-[4-(3-aminocyclohexyl)piperazin-1-yl]ethan-1-one

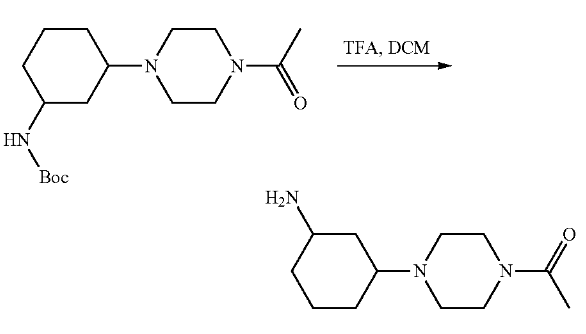

Into a 100-mL round-bottom flask, was placed tert-butyl N-[3-(4-acetylpiperazin-1-yl)cyclohexyl]carbamate (700 mg, 2.15 mmol, 1.00 equiv), dichloromethane (3 mL), trifluoroacetic acid (2 mL) was added by dropwise. The resulting solution was stirred for 2 h at 25° C. The reaction progress was monitored by LCMS. The resulting mixture was concentrated under vacuum. This resulted in 700 mg of 1-[4-(3-aminocyclohexyl)piperazin-1-yl]ethan-1-one as a brown oil. LCMS (Method A, ES): RT=0.647 min, m/z=225.95 $[M+H]^+$.

Step 6. Synthesis of N-[(1R,3S)-3-(4-acetylpiperazin-1-yl)cyclohexyl]-4-fluoro-7-methyl-1H-indole-2-carboxamide (as the TFA salt)

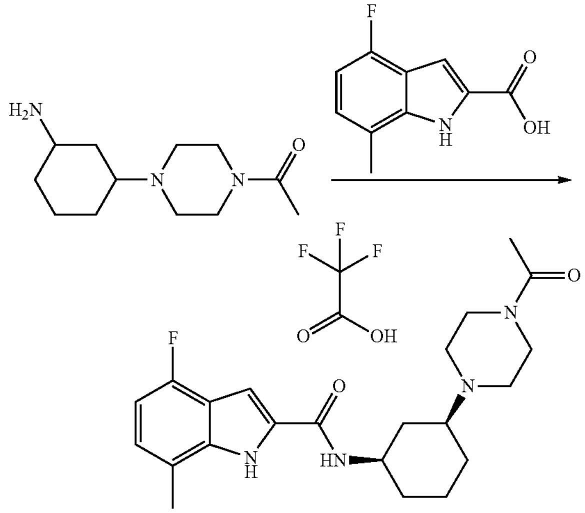

Cpd. No. 15

Into a 100-mL round-bottom flask, was placed 4-fluoro-7-methyl-1H-indole-2-carboxylic acid (100 mg, 0.52 mmol, 1.00 equiv), 1-[4-(3-aminocyclohexyl)piperazin-1-yl]ethan-1-one (110 mg, 0.49 mmol, 0.94 equiv), N,N-dimethylformamide (4 mL), DIEA (200 mg, 1.55 mmol, 2.99 equiv), HATU (260 mg, 0.68 mmol, 1.32 equiv) was added batchwise. The resulting solution was stirred for 2 h at 25° C. The reaction progress was monitored by LCMS, and the reaction solution was quenched by 10 ml of water. The resulting solution was extracted with 3×15 ml of ethyl acetate and the organic layers combined and concentrated under vacuum. The residue was applied onto a silica gel column with ethyl acetate/petroleum ether (1:1). The crude product was purified by Chiral-Prep-HPLC with the following conditions: Column, (R,R)-WHELK-014.6*50 mm, 3.5 μm: 1-78220-30056749; mobile phase, Hexane (0.1%DEA):EtOH=85:15; Detector, UV 254 nm/220 nm. The product thus obtained was further purified by Prep-HPLC with the following conditions: Column,)(Bridge Prep Phenyl OBD Column, 5 μm, 19*150 mm; mobile phase, Water with 10 mmol TFA and MeCN (20.0% MeCN up to 30.0% in 10 min, up to 95.0% in 1 min, hold 95.0% in 1 min, down to 20.0% in 2 min); Detector, UV 254/220 nm. This resulted in 30.5 mg (yield=11%) of N-[(1R,3S)-3-(4-acetylpiperazin-1-yl)cyclohexyl]-4-fluoro-7-methyl-1H-indole-2-carboxamide trifluoroacetic acid salt as a white solid. LCMS (Method B, ES): RT=1.138 min, m/z=401.0 $[M-TFA]^+$. $^1H$ NMR (300 MHz, Methanol-d4) δ 7.18 (s, 1H), 6.94-6.92 (m, 1H), 6.64-6.62 (m, 1H), 4.03-3.88 (m, 1H), 3.57-3.55 (m, 4H), 2.65 (t, J=16.4 Hz, 5H), 2.48 (t, J=1.0 Hz, 3H), 2.23 (d, J=12.0 Hz, 1H), 2.09 (s, 3H), 1.93 (d, J=12.2 Hz, 3H), 1.53-1.18 (m, 4H) ppm.

Example 2

Combination Studies

Multiple myeloma (MM) and mantle cell lymphoma (MCL) Cell line cultures in log-linear growth rate were treated with combinations of Cpd. No. 15 and combination partners according to a co-treatment model. Assay-ready plates were prepared by dispensing the compounds with the HP-D300 nanoliter dispenser (Tecan, Mannedorf, Switzerland) onto 384-well white opaque plates (CulturPlate-384, White Opaque 384-well Microplate, Sterile and Tissue Culture Treated) to achieve either 2-fold or 3-fold serial dilutions in a concentration range bracketed around the $IC_{50}$ of Cpd. No. 15 and the combination partner. Concentrations were matrixed in an 8×9 array (8 concentrations of Cpd. No. 15 and 9 concentrations of its combination partner). Each combination was tested in quadruplicate wells. The final concentration of DMSO (vehicle) in the assay was 0.1% v/v. Fifty microliters of cell line suspension were directly dispensed to the assay-ready plates with an automated multichannel dispenser on to 384-well assay-ready plates. Assay plates were incubated for seven days in a humidified atmosphere of 5% $CO_2$ at 37° C. Quantification of the effect of single agents or combinations on cell viability was performed through measurement of cellular adenosine triphosphate (ATP) using a CellTiter-Glo® (Promega, MadisonWIs.) Luminescent Cell Viability Assay. Luminescence was detected using a SpectraMax M5 microplate reader (Molecular Devices, Sunnyvale, CA). Concentration response plots were generated in GraphPad Prism version 7.0 for Windows, GraphPad Software, (La Jolla, CA) and curves fitted to a four-parameter logistic model with variable slope. Percent of inhibition was calculated at each treatment concentration. Quantification of synergy was performed using the Loewe Additivity model and by calculating the Loewe Volume (VLoewe) with the CHALICE software (Horizon Discovery, Cambridge, UK) (Lehar 2007) (VLoewe>1: synergy, between 1 and −1: additivity, and <−1: antagonistic; if neither of the agents or the combination reached 50 percent inhibition of prolferationit is deemed as "No Effect." See Loewe, *Arzneimittelforschung* 3(6): 285-290 (1953) and Lehar et al., *Mol Syst Biol* 3:80 (2007). The cell lines used in these studies were purchased from commercial suppliers. For example, NCI-H929, MM1. S, MINO, REC1, MAVER1, Z138, JEKO1, JVM2, and RPMI-8226 cell lines were purchased from the American Type Culture Collection (ATCC, Manassas VA); KMS-11, KMS34, and KMS-28-BM were purchased from the Japanese Collection of Research Bioresourres (JCRB, Osaka, Japan); and L-363 and GRANTA519 were purchased from Leibniz Institute DSMZ-German Collection of Microorganisms and Cell Cultures.

The results of these combinations are summarized in Tables A and B (multiple myeloma cell lines), and Tables C and D (mantle cell lymphoma cell lines).

Figure 3:
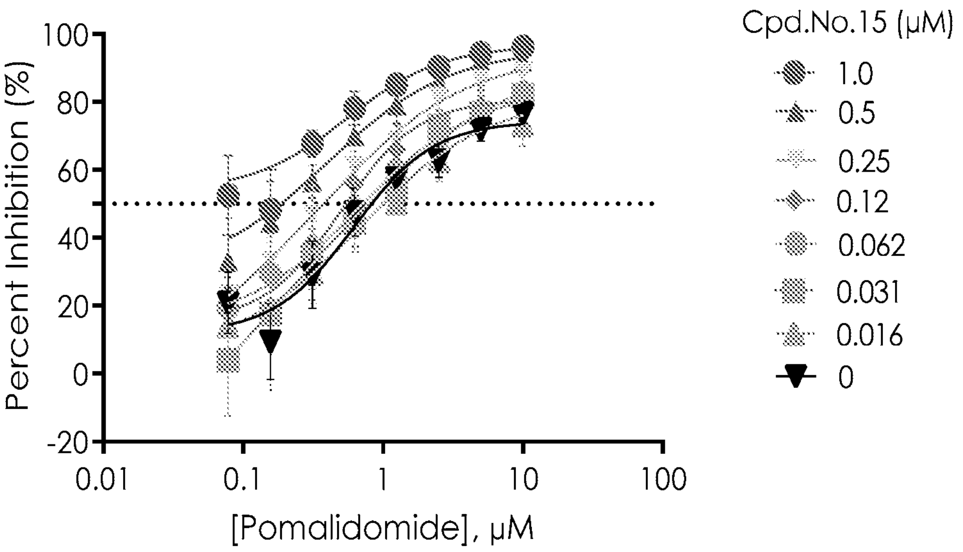
FIG. 3 is a line graph showing the synergistic anti-proliferative activity of Cpd. No. 15 in combination with pomalidomide in KMS-11 cells in 7-day co-treatment study.
Figure 4:
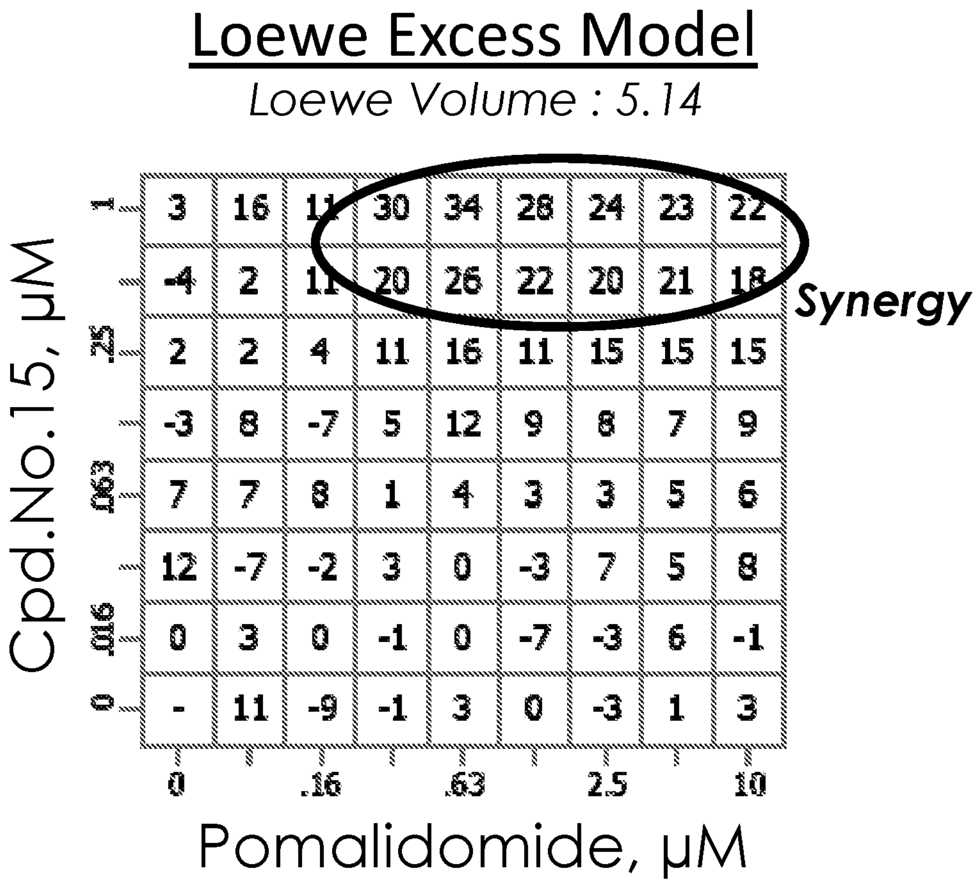
FIG. 4 is a table showing the Loewe Excess Model analysis of the Cpd. No. 15 plus pomalidomide combination in KMS-11 cells in 7-day co-treatment study.

By way of example, FIG. 3 shows the synergistic anti-proliferative activity of Cpd. No. 15 combined with pomalidomide in KMS-11 cells in a 7-day co-treatment study. FIG. 4 shows the Loewe Model analysis of the Cpd. No. 15/pomalidomide combination studies in KMS-11 cells.

Diffuse large B-cell lymphoma cells were seeded into flasks and pre-treated with several concentrations of Cpd. No. 15 or DMSO. Cells were then split adjusted to initial density, replated and co-treated Cpd. No. 15 and a second agent of interest using the HP D300 digital dispenser (Tecan Group, Mannedorf, Switzerland) in tissue culture treated solid white 384-well plates for additional 3 days. Both agents were serially diluted and combined in a matrix format with constant ratios diagonally across the plate with a final DMSO content of 0.11% (v/v). After 3 days cotreatment, cell viability was measured via ATP content using CellTiter-Glo® (Promega, Madison, WI) and luminescence was detected using a SpectraMax M5 microplate reader (Molecular Devices, Sunnyvale, CA).

Example 3

Combination Studies

Diffuse large B-cell lymphoma (DLBCL) cell line cultures in log-linear growth rate were treated with combinations of Cpd. No. 15 and combination partners according to a pre-treatment model. Cells were seeded first into 8 flasks and pre-treated with 7 different concentrations of Cpd. No. 15 (concentrations were bracketed around the $IC_{50}$ of Cpd. No. 15 in a 3-fold dilution range) and DMSO for four days. On Day 4, assay-ready plates were prepared by dispensing the compounds with the HP-D300 nanoliter dispenser (Tecan, Mannedorf, Switzerland) onto 384-well white opaque plates (CulturPlate-384, White Opaque 384-well Microplate, Sterile and Tissue Culture Treated) to achieve 3-fold serial dilutions in a concentration range bracketed around the IC50 of the combination partner. Cells were harvested from each flask and re-seeded onto the corresponding 384-well plate with the same concentration of Cpd. No. 15. and 9 concentrations of its combination partner in triplicate wells. The final concentration of DMSO (vehicle) in the assay was 0.1% v/v. Fifty microliters of cell line(s) suspension were directly dispensed to the assay-ready plates with an automated multichannel dispenser on to 384-well assay-ready plates. Assay plates were incubated for three days in a humidified atmosphere of 5% CO2 at 37° C. Quantification of the effect of single agents or combinations on cell viability was performed through measurement of cellular adenosine triphosphate (ATP) using CellTiter-Glo® (Promega, Madison, WI). Luminescence was detected using a SpectraMax M5 microplate reader (Molecular Devices, Sunnyvale, CA). Concentration response plots were generated in GraphPad Prism version 8.0 for Windows, GraphPad Software, (La Jolla, CA) and curves fitted to a four-parameter logistic model with variable slope. Percent of inhibition was calculated at each treatment concentration. Quantification of synergy was performed using the Loewe Additivity model and by calculating the Loewe Volume (VLoewe) with the CHALICE software (Horizon Discovery, Cambridge, UK) (Lehar 2007) (VLoewe>1: synergy, between 1 and −1: additivity, and <−1: antagonistic; if neither of the agents or the combination reached 50 percent inhibition it is deemed as no effect. See Loewe, *Arzneimittelforschung* 3(6): 285-290 (1953) and Lehar et al., *Mol Syst Biol* 3:80 (2007). SUDHL6 and SUDHL2 cell lines were purchased from the American Type Culture Collection (ATCC, Manassas VA). WSUDLCL2 was purchased from Leibniz Institute DSMZ-German Collection of Microorganisms and Cell Cultures and KARPAS422 was purchased from Sigma Aldrich (St. Louis, MO). The results of these combinations are summarized in Table E (diffuse large B-cell lymphoma cell lines).

TABLE A

| Combination Partner | Drug Class | NCI-H929 Cat. No. CRL-9068 | KMS-11 Cat. No. JCRB1179 | KMS-28-BM Cat. No. JCRB1192 | RPMI-8226 Cat. No. CCL-155 |
|---|---|---|---|---|---|
| Dexamethasone | Glucocorticoid receptor agonist | Synergy | Synergy | Additivity | Synergy |
| Pomalidomide | Immunomodulatory | Synergy | Synergy | Additivity | Synergy |
| Lenalidomide | drug | Not Tested | Synergy | No Effect | Synergy |
| Bortezomib | Proteasome inhibitor | Additivity | Additivity | Additivity | Additivity |
| Venetoclax | Bcl-2 inhibitor | Synergy | Synergy | Additivity | Additivity |
| CC-122 | Pleiotropic pathway modulator | Synergy | Synergy | Additivity | Additivity |
| Selinexor | Selective inhibitor of nuclear export (SINE) or XPO1 inhibitor | Synergy | Additivity | Additivity | Additivity |
| Panobinostat | Histone deacetylase inhibitor | Synergy | Additivity | Additivity | Additivity |
| Tazemetostat | EZH2 inhibitor | Not Tested | Not Tested | Not Tested | Additivity |
| EPZ-11989 | | No Effect | Additivity | Additivity | Not Tested |

TABLE B

| Combination Partner | Drug Class | KMS34 Cat. No. CCL-155 | L363 Cat. No. JCRB1195 | MM1.S Cat. No. CRL-2974 |
|---|---|---|---|---|
| Dexamethasone | Glucocorticoid receptor agonist | Synergy | Synergy | Additivity |
| Pomalidomide | Immunomodulatory | Synergy | Additivity | Additivity |
| Lenalidomide | drug | Synergy | Additivity | Additivity |
| Bortezomib | Proteasome inhibitor | Additivity | Additivity | Additivity |
| Venetoclax | Bcl-2 inhibitor | Additivity | Additivity | Additivity |
| CC-122 | Pleiotropic pathway modulator | Synergy | Additivity | Additivity |
| Selinexor | Selective inhibitor of nuclear export (SINE) or XPO1 inhibitor | Synergy | Additivity | Additivity |
| Panobinostat | Histone deacetylase inhibitor | Synergy | Additivity | Additivity |
| Tazemetostat | EZH2 inhibitor | Synergy | Synergy | Synergy |
| EPZ-11989 | | Not tested | Not tested | Not tested |

TABLE C

| Combination Partner | Drug Class | MINO Cat. No. CRL-3000 | REC1 Cat. No. CRL-3004 | MAVER1 Cat. No. CRL-3008 | Z138 Cat. No. CRL-3001 |
|---|---|---|---|---|---|
| Prednisolone | Glucocorticoid receptor agonist | Additivity | Synergy | Synergy | Additivity |
| Lenalidomide | Immunomodulatory drug | Additivity | Additivity | Synergy | Synergy |
| Bortezomib | Proteasome inhibitor | Additivity | Additivity | Additivity | Additivity |
| Venetoclax | Bcl-2 inhibitor | Additivity | Additivity | Synergy | Synergy |
| Tazemetostat | EZH2 inhibitor | No Effect | Additivity | Additivity | No Effect |

TABLE D

| Combination Partner | Drug Class | JEKO1 Cat. No. CRL-3006 | JVM2 Cat. No. CRL-3002 | GRANTA519 Cat. No. ACC 342 |
|---|---|---|---|---|
| Prednisolone | Glucocorticoid receptor agonist | Additivity | Additivity | Synergy |
| Lenalidomide | Immunomodulatory drug | Synergy | Additivity | Additivity |
| Bortezomib | Proteasome inhibitor | Additivity | Additivity | Additivity |
| Venetoclax | Bcl-2 inhibitor | Additivity | Synergy | Synergy |
| Tazemetostat | EZH2 inhibitor | No Effect | Additivity | No Effect |

TABLE E

| Combination Partner | Drug Class | SUDHL-6 Cat. No. CRL-2956 | SUDHL-2 Cat. No. CRL-2959 | KARPAS422 Cat. No. 06101702-1VL | WSUDLCL2 Cat. No. ACC 575 |
|---|---|---|---|---|---|
| Prednisolone | Glucocorticoid receptor agonist | Synergy | Synergy | Additivity | Antagonism |
| Lenalidomide | Immunomodulatory drug | No effect | Additivity | No effect | Additivity |
| Venetoclax | Bcl-2 inhibitor | Synergy | Synergy | No effect | Synergy |
| Tazemetostat | EZH2 inhibitor | No effect | Additivity | No effect | Additivity |

Example 4

Combination Studies

Figure 2:
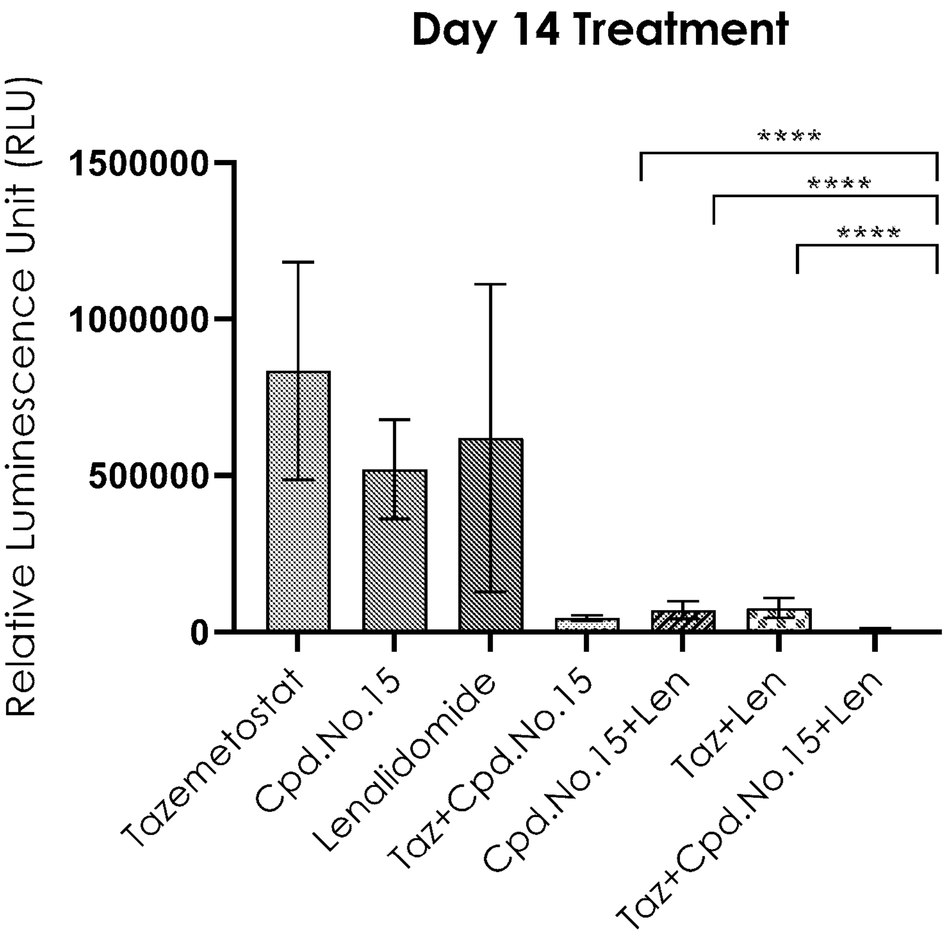
FIG. 2 is a bar graph showing the anti-proliferative activity of Cpd. No. 15, tazemetostat (Taz), and lenalidomide (Len), and combinations thereof, in KMS-11 cells at day 14 of a co-treatment study.

Long Term KMS-11 Proliferation Assay: Cells in log-linear growth rate were treated with Cpd. No. 15 (at 500 nM) and combination partners Tazemetostat (at 100 nM) and/or Lenalidomide (at 1000 nM)) over a total period of 14 days. Concentrations used were bracketed around the $IC_{50}$ values on day 14 for each of these agents. On day 0, exponentially growing cells were dispensed, in six replicate wells, into three 96-well plates. Cell cultures were incubated in the presence of DMSO, single agents and double or triple combinations of the above mentioned agents agents. for four and seven days in a humidified atmosphere of 5% $CO_2$ at 37° C. These plates were developed on days 0, 4, 7 and quantification of the effect of single agents and combinations on cell viability was performed through measurement of cellular adenosine triphosphate (ATP) using CellTiter-Glo® (Promega, Madison, WI). Luminescence was detected using a SpectraMax M5 microplate reader (Molecular Devices, Sunnyvale, CA). Additionally, on day 0, cells in log-linear growth rate were also seeded into three 6 well plates and treated with DMSO, single agents and double or triple combinations with the respective agents. These 6 well plates incubated for seven days in a humidified atmosphere of 5% $CO_2$ at 37° C. On day 7, cells from each treatment were trysinized, counted, and split back to the original plating density into three 96 well plates, in six replicate wells, to be analyzed on days 7, 11, and 14. These re-plated cells were and subjected to the same treatment as in Day 0. These plates were then developed on days 7, 11, and 14 using CellTiter-Glo® (Promega, Madison, WI). Luminescence was detected using a SpectraMax M5 microplate reader (Molecular Devices, Sunnyvale, CA). Cell viability vs time plot (with cell number split corrected) was generated in GraphPad Prism version 8.0 for Windows, GraphPad Software(La Jolla, California). Statistical analysis done using one-way ANOVA with Tukey's Multiple Comparisons (**$p<0.0001$) for triple combination compared to each of the doublets. The results of the Long Term KMS-11 Proliferation Assay are presented in FIG. 1 and FIG. 2**.

Having now fully described this invention, it will be understood by those of ordinary skill in the art that the same can be performed within a wide and equivalent range of conditions, formulations, and other parameters without affecting the scope of the invention or any embodiment thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents, patent applications, e.g., PCT/US2019/046569, and publications cited herein are fully incorporated by reference herein in their entirety.

What is claimed is:

1. A method of treating multiple myeloma or mantle cell lymphoma in a subject in need thereof, the method comprising administering to the subject:

(a) a compound of Formula IV-A:

IV-A

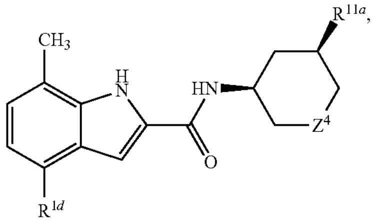

$Z^4$ is —$CH_2$—;

$R^{11a}$ is selected from the group consisting of optionally substituted alkyl, optionally substituted heterocyclo, optionally substituted heteroaryl, and —$N(R^{12b})C(=O)R^{13c}$;

$R^{12b}$ is selected from the group consisting of hydrogen, alkyl, cycloalkyl, and heterocyclo, ($C_1$-$C_4$ alkoxy) $C_1$-$C_4$ alkyl, and (hydroxy) $C_1$-$C_4$ alkyl; and $R^{13c}$ is selected from the group consisting of alkyl, haloalkyl, alkoxy, (alkoxy) alkyl, (hydroxy) alkyl, (cyano) alkyl, optionally substituted aryl, optionally substituted heteroaryl, optionally substituted cycloalkyl, and optionally substituted heterocycle, amino, (amino) alkyl, ($C_3$-$C_6$ cycloalkyl) oxy, and (4- to 8-membered heterocyclo) oxy;

$R^{1d}$ is fluoro;

or a pharmaceutically acceptable salt or solvate thereof, and (b) a Second Therapeutic Agent, wherein:

the Second Therapeutic Agent is dexamethasone, pomalidomide, lenalidomide, venetoclax, CC-122, selinexor, panobinostat, or tazmetostat.

2. The method of claim 1, wherein the compound of Formula IV-A and the Second Therapeutic Agent are administered to the subject separately.

3. The method of claim 1, wherein the compound is:

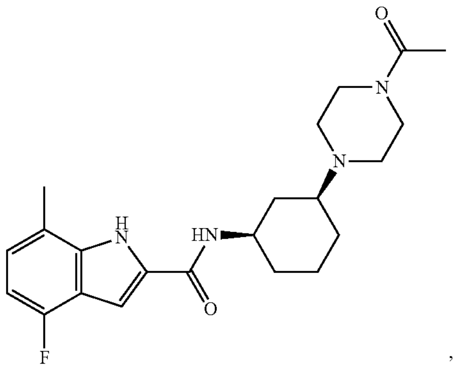

,

-continued

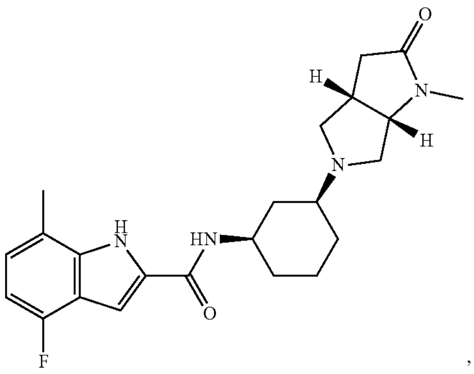

,

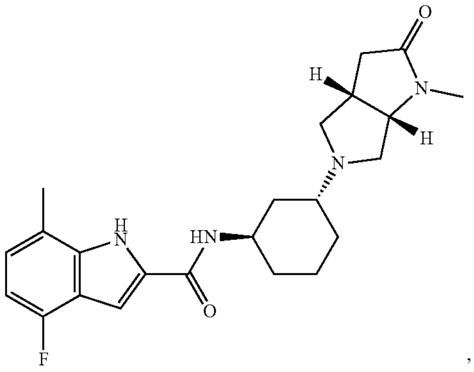

,

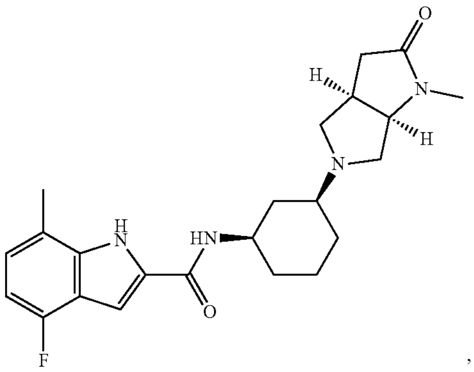

,

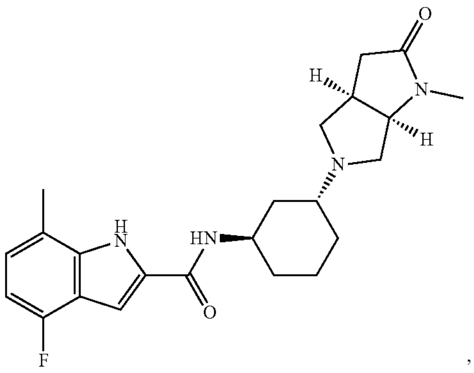

,

-continued

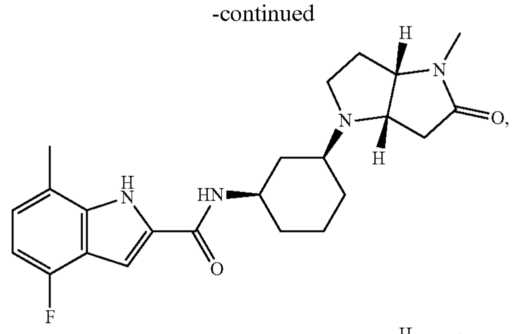

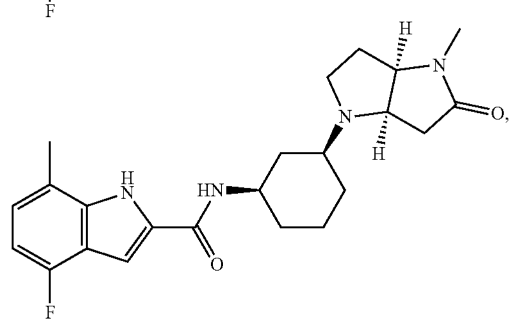

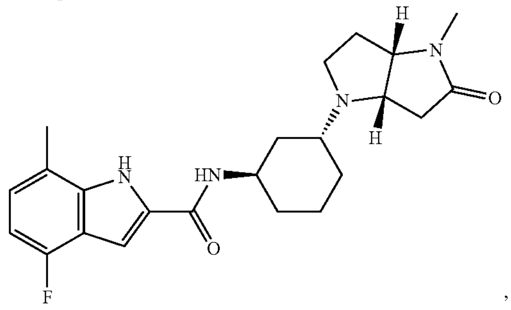

, or

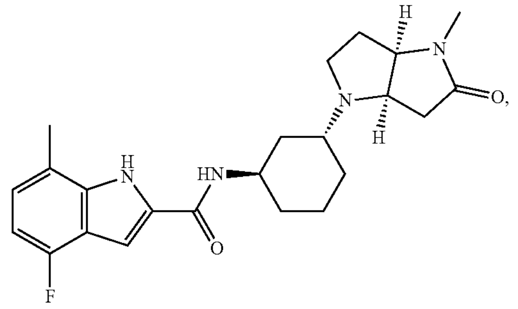 [SMILES: Cc1ccc(F)c2cc(C(=O)N[C@@H]3CCC[C@@H](N4CC[C@@H]5[C@H]4CC(=O)N5C)C3)[nH]c12]

or a pharmaceutically acceptable salt or solvate thereof.

4. The method of claim 3, wherein the compound and the second therapeutic agent are administered to the subject separately.

5. The method of claim 3, wherein the compound is:

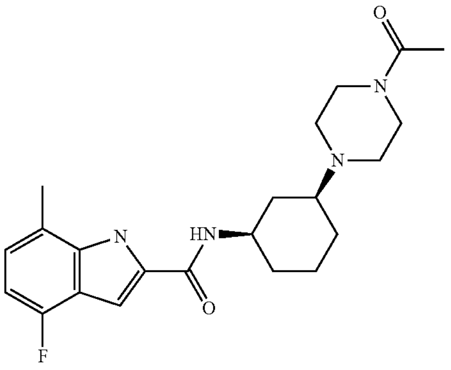 [SMILES: CC(=O)N1CCN([C@H]2CCC[C@@H](NC(=O)c3cc4c(F)ccc(C)c4[nH]3)C2)CC1]

or a pharmaceutically acceptable salt or solvate thereof.

6. The method of claim 5, wherein the Second Therapeutic Agent is dexamethasone.

7. The method of claim 5, wherein the Second Therapeutic Agent is pomalidomide or lenalidomide.

8. The method of claim 5, wherein the Second Therapeutic Agent is venetoclax.

9. The method of claim 5, wherein the Second Therapeutic Agent is CC-122.

10. The method of claim 5, wherein the Second Therapeutic Agent is selinexor.

11. The method of claim 5, wherein the Second Therapeutic Agent is panobinostat.

12. The method of claim 5, wherein the Second Therapeutic Agent is tazemetostat.

13. The method of claim 5, wherein the compound and the second therapeutic agent are administered to the subject separately.

14. The method of claim 5, wherein the cancer is multiple myeloma.

15. The method of claim 14, wherein the compound and the second therapeutic agent are administered to the subject separately.

16. The method of claim 5, wherein the cancer is mantle cell lymphoma.

17. The method of claim 16, wherein the compound and the second therapeutic agent are administered to the subject separately.

18. The method of claim 16, wherein the Second Therapeutic Agent is lenalidomide or venetoclax.

19. The method of claim 18, wherein the compound and the second therapeutic agent are administered to the subject separately.

* * * * *